US007521062B2

(12) United States Patent
Barsanti et al.

(10) Patent No.: US 7,521,062 B2
(45) Date of Patent: Apr. 21, 2009

(54) THIOSEMICARBAZONES AS ANTI-VIRALS AND IMMUNOPOTENTIATORS

(75) Inventors: Paul A. Barsanti, Pleasant Hill, CA (US); Nathan Brammeier, Walnut Creek, CA (US); Anthony Diebes, Minnetonka, MN (US); Liana Marie Lagniton, Berkeley, CA (US); Simon Ng, Walnut Creek, CA (US); Zhi-Jie Ni, Fremont, CA (US); Keith B. Pfister, San Ramon, CA (US); Casey Philbin, Columbus, OH (US); Nicholas Valiante, Walnut Creek, CA (US); Allan S. Wagman, Belmont, CA (US); Weibo Wang, Moraga, CA (US); Amy J. Weiner, Fairfield, CA (US)

(73) Assignee: Novartis Vaccines & Diagnostics, Inc., Emeryville, CA (US)

( * ) Notice: Subject to any disclaimer, the term of this patent is extended or adjusted under 35 U.S.C. 154(b) by 571 days.

(21) Appl. No.: 10/748,071

(22) Filed: Dec. 29, 2003

(65) Prior Publication Data
US 2005/0069555 A1    Mar. 31, 2005

Related U.S. Application Data

(60) Provisional application No. 60/436,472, filed on Dec. 27, 2002, provisional application No. 60/436,638, filed on Dec. 30, 2002, provisional application No. 60/438,987, filed on Jan. 10, 2003.

(51) Int. Cl.
*A61K 39/00* (2006.01)
*A61K 31/40* (2006.01)
*A61K 31/44* (2006.01)
*A61K 31/175* (2006.01)
*A61K 39/095* (2006.01)
*A61K 45/00* (2006.01)

(52) U.S. Cl. .................. 424/278.1; 514/357; 514/408; 514/582; 552/517; 424/184.1

(58) Field of Classification Search .................. None
See application file for complete search history.

(56) References Cited

U.S. PATENT DOCUMENTS 3,379,620 A    4/1968    Archer et al.

(Continued)

FOREIGN PATENT DOCUMENTS

EP            258182         3/1988

(Continued)

OTHER PUBLICATIONS

Erik De Clercq, "Vaccinia Virus Inhibitors as a Paradigm for the Chemotherapy of Poxvirus Infections" Clinical Microbiology Reviews, Apr. 2001, p. 382-397.*

(Continued)

*Primary Examiner*—Bruce Campell
*Assistant Examiner*—Stuart W Snyder
(74) *Attorney, Agent, or Firm*—Morrison & Foerster LLP

(57) ABSTRACT

The present invention is directed to novel immune potentiators, novel vaccine adjuvants, novel compounds and pharmaceutical compositions, novel methods for treating viral infections, including HCV, by administering the compounds, and novel methods for modulating an immune response by administering the compounds.

40 Claims, 4 Drawing Sheets

U.S. PATENT DOCUMENTS

| | | | | |
|---|---|---|---|---|
| 3,917,703 | A | 11/1975 | Archer et al. | 260/570.5 |
| 3,980,774 | A | 9/1976 | Hegarty et al. | 424/166 |
| 4,093,812 | A | 6/1978 | Rainer | 548/374 |
| 4,971,986 | A | 11/1990 | Stanek et al. | 514/357 |
| 5,019,560 | A | 5/1991 | Hector et al. | 514/43 |
| 5,204,352 | A | 4/1993 | Sundberg et al. | 514/258 |
| 5,278,152 | A | 1/1994 | Peyman et al. | 514/76 |
| 5,516,750 | A | 5/1996 | Willms et al. | 504/106 |
| 5,627,181 | A | 5/1997 | Riedl et al. | 514/236.8 |
| 6,329,378 | B1 | 12/2001 | Mei et al. | 514/255.05 |
| 6,350,771 | B1 | 2/2002 | Wu et al. | 514/404 |
| 6,613,803 | B1 | 9/2003 | Wang et al. | 514/583 |
| 6,638,947 | B2 | 10/2003 | Wang et al. | 514/317 |
| 2003/0045568 | A1 | 3/2003 | Altamura et al. | 514/438 |
| 2003/0176503 | A1 | 9/2003 | Altamura et al. | 514/550 |

FOREIGN PATENT DOCUMENTS

| | | |
|---|---|---|
| EP | 457727 | 11/1991 |
| GB | 1314899 | 4/1973 |
| WO | WO 98/47869 | 10/1998 |
| WO | WO 00/30683 | 6/2000 |
| WO | WO 01/34585 | 5/2001 |
| WO | WO 01/49413 | 7/2001 |
| WO | WO 02/41843 | 5/2002 |

OTHER PUBLICATIONS

Gall, D. The Adjevant Activity of Aliphatic Nitrogenous Bases. Immunology. 1966; 11:369-386.*

Blantz, et al. Carcinostatic Activity of Thiosemicarbazones of Formyl Heteroaromatic Compounds. VII. 2-Formylpyridine Derivatives Bearing Additional Ring Substititutents. J Med Cehm. 1970; 13(6)1124-1130.*

Edelman, "An Update on Vaccine Adjuvants in Clinical Trial," Aids Research and Human Retroviruses 8(8): 1409-1411 (1992).*

McElrath, "Selection of potent immunological adjuvants for vaccine construction," seminars in Cancer Biology 6:375-385 (1995).*

Aucouturier et al., "Adjuvants designed for veterinary and human vaccines," Vaccine 19:2666-2672 (2001).*

East et al., "Adjuvants for New Veterinary Vaccines," Chapter 1 in Progress in Vaccinology, vol. 4 Veterinary Vaccines, Springer Verlag, NY 1993, pp. 1-28.*

Altman et al., "Immunomodifiers iin Vaccines," Advances In Veterinary Science and Comparative Medicine 33:301-343 (1989).*

Wilson et al., "Tissue Reaction and Immunity in Swine Immunized with *Actinobacillus pleuropneumoniae* Vaccines," Can J Vet Res 59:299-305 (1995).*

Dickson and Iddon, "Condensed Thiophene Ring Systems. Part XII. Synthesis and Antiviral Activity of Some Benzo [*b*] Thiophene-2- and -3-Carbaldehyde Thiosemicarbazones" *Int. J. Sulfur Chem.* 8(2) :233-242, 1973.

Markovac et al, "4-(3-Nitrophenyl)-2-Picoline" *J. Heterocyclic Chem.* 14:147-148, 1977.

Tarasconi et al., "Synthesis, Spectorscopic Characterization and Biological Properties of New Natural Aldehydes Thiosemicarbazones" *Bioorganic and Medicinal Chemistry* 8:157-162, 2000.

* cited by examiner

THIOSEMICARBAZONES AS ANTI-VIRALS AND IMMUNOPOTENTIATORS

This application claims benefit of priority to the following US Provisional Patent Applications, Ser. No. 60/436,472, filed Dec. 27, 2002; Ser. No. 60/436,638, filed Dec. 30, 2002; and Ser. No. 60/438,987 filed Jan. 10, 2003; each of which is incorporated herein by reference in its entirety for any purpose.

FIELD OF THE INVENTION

This invention relates to compounds and compositions, as well as uses of the compounds as immunopotentiators and use of the compounds in methods for treating and preventing viral infections including HCV. More particularly, the invention relates to compounds that are used alone or combined with other agents for which the immune response is desired, in the treatment or modulation of cancer, allergic diseases, asthma, as well as amelioration of viral, bacterial, and fungal infections.

BACKGROUND OF THE INVENTION

It is known that immune response to certain antigens which are otherwise weakly immunogenic can be enhanced through the use of vaccine adjuvants. Such adjuvants potentiate the immune response to specific antigens and are therefore the subject of considerable interest and study within the medical community.

Research has permitted development of vaccines possessing antigenic epitopes that were previously impossible to produce. For example, currently available vaccine candidates include synthetic peptides mimicking streptococcal, gonococcal, and malarial antigens. These purified antigens are generally weak immunogens, however, that require adjuvants in order to evoke protective immunity. However, conventional vaccine adjuvants possess a number of drawbacks, which limit their overall use and effectiveness.

It is also common knowledge that substances, which stimulate immune cells in vitro exhibit similar immuno-stimulatory effects in vivo. These compounds, such as recombinant cytokines, pathogen products (e.g. toxins, lipids, proteins/peptides, carbohydrates and nucleic acids) and other mammalian-derived immunostimulatory molecules (e.g. heat shock proteins, complement, immune complexes and proteoglycans) all induce a measurable pro-inflammatory response both in vitro and in vivo.

Historically, the classic adjuvants have been Freund's complete or incomplete (i.e., without mycobacteria) adjuvants. Edmund Coley, the inventor of Coley's Toxin, described this potential for cancer immuno-therapy.

Other adjuvants have been compared to Freund's. However, clinical use of such adjuvants in animals or humans is precluded because they produce granulomas at the site of injection; fever and other toxic effects; and tuberculin hypersensitivity. Other materials, such as mineral oil and aluminum hydroxide, have also been used as adjuvants, but they invariably suffer from disadvantages. For example, mineral oil is known to produce tissue irritation and to be potentially oncogenic. Aluminum hydroxide, the only approved adjuvant in the United States, also induces granulomas at the inoculation site and furthermore it does not effectively induce cell-mediated immunity. Moreover, many of the adjuvants currently available have limited utility because they contain components, which are not metabolizable in humans. Additionally, most adjuvants are difficult to prepare in that they may require time consuming procedures and the use, in some cases, of elaborate and expensive equipment to formulate a vaccine and adjuvant system.

For a thorough discussion of various immunological adjuvants, see "Current Status of Immunological Adjuvants", Ann. Rev. Immunol., 1986, 4, pp. 369-388, and "Recent Advances in Vaccine Adjuvants and Delivery Systems" by Derek T O'Hagan and Nicholas M. Valiente, both of which are hereby incorporated by reference in its entirety. See also U.S. Pat. Nos. 4,806,352; 5,026,543; and 5,026,546 for disclosures of various vaccine adjuvants appearing in the patent literature all of which are hereby incorporated by reference in its entirety.

There has been an effort to find new adjuvants for vaccines that would overcome the drawbacks and deficiencies of conventional adjuvants. In particular, an adjuvant formulation which elicits potent cell-mediated and humoral immune responses to a wide range of antigens in humans and domestic animals, but lacking the side effects of conventional adjuvants, such as Freund's complete adjuvant, would be highly desirable.

It is also desirable to identify small molecules, which stimulate a proinflammatory response for use as vaccine adjuvants.

Hepatitis is a systemic disease, which predominantly affects the liver. The disease is typified by the initial onset of symptoms such as anorexia, nausea, vomiting, fatigue, malaise, arthralgias, myalgias, and headaches, followed by the onset of jaundice. The disease may also be characterized by increased serum levels of the aminotransferases AST and ALT. Quantification of these enzymes in serum indicates the extent of liver damage.

There are five general categories of viral agents which have been associated with hepatitis: the hepatitis A virus (HAV); the hepatitis B virus (HBV); two types of non-A, non-B (NANB) agents, one blood-borne (hepatitis C) and the other enterically transmitted (hepatitis E); and the HBV-associated delta agent (hepatitis D).

There are two general clinical categories of hepatitis, acute hepatitis and chronic hepatitis. Symptoms for acute hepatitis range from asymptomatic and non-apparent to fatal infections. The disease may be subclinical and persistent, or rapidly progress to chronic liver disease with cirrhosis, and in some cases, to hepatocellular carcinoma. Acute hepatitis B infection in adult Caucasians in the United States progresses to chronic hepatitis B in about 5% to 10% of the cases. In the remainder of the cases, approximately 65% are asymptomatic. In the Far East, infection is usually perinatal, and 50% to 90% progress to the chronic state. It is likely that the different rates of progression are linked to the age at infection rather than genetic differences in the hosts. In the United States, about 0.2% of the population is chronically infected, with higher percentages in high-risk groups such as physicians, drug addicts and renal dialysis patients. In countries such as Taiwan, Hong Kong and Singapore, the level in the population with hepatitis infection may be as high as 10%.

In the United States, about 20% of patients with chronic hepatitis die of liver failure, and a further 5% develop hepatitis B-associated carcinoma. In the Far East, a large percentage of the population is infected with HBV, and after a long chronic infection (20 to 40 years), approximately 25% of these will develop hepatocellular carcinoma.

After the development of serologic tests for both hepatitis A and B, investigators identified other patients with hepatitis-like symptoms, and with incubation periods and modes of transmission consistent with an infectious disease, but without serologic evidence of hepatitis A or B infection. After almost 15 years, the causative agent was identified as an RNA virus. This virus (designated "hepatitis C") has no homology with HBV, retroviruses, or other hepatitis viruses.

Hepatitis C(HCV) appears to be the major cause of post-transfusion and sporadic non-A, non-B (NANB) hepatitis worldwide, and plays a major role in the development of chronic liver disease, including hepatocellular carcinoma (Kuo et al., Science 244:362-364, 1989; Choo et al., British Medical Bulletin 46(2):423441, 1990). Of the approximately 3 million persons who receive transfusions each year, approximately 150,000 will develop acute hepatitis C (Davis et al., New Eng. J. Med. 321(22):1501-1506, 1989). In addition, of those that develop acute hepatitis C, at least one-half will develop chronic hepatitis C.

Until recently, no therapy has proven effective for treatment of acute or chronic hepatitis B or C infections, and patients infected with hepatitis must generally allow the disease to run its course. Most anti-viral drugs, such as acyclovir, as well as attempts to bolster the immune system through the use of corticosteroids have proven ineffective (Alter, "Viral hepatitis and liver disease," Zuckerman (ed.), New York: Alan R. Liss, pp. 537-42, 1988). Some anti-viral activity has been observed with adenosine arabinoside (Jacyna et al., British Med. Bull. 46:368-382, 1990), although toxic side effects, which are associated with this drug render such treatment unacceptable.

One treatment that has provided some benefit for chronic hepatitis B and C infections is the use of recombinant alpha interferon (Davis et al., New Eng. J. Med. 321(22):1501-1506, 1989; Perrillo et al., New Eng. J. Med. 323:295-301, 1990). However, for patients with hepatitis B infections only about 35% of infectees responded to such treatment, and in perinatal infectees only about 10% responded to treatment. For hepatitis C infections, despite apparent short-term success utilizing such therapy, six months after termination of treatment half of the patients who responded to therapy had relapsed. In addition, a further difficulty with alpha interferon therapy is that the composition frequently has toxic side effects such as nausea, and flu-like symptoms, which require reduced dosages for sensitive patients.

A disease related to hepatitis B and hepatitis C infections is hepatocellular carcinoma. Briefly, hepatocellular carcinoma is the most common cancer worldwide. It is responsible for approximately 1,000,000 deaths annually, most of them in China and in sub-Saharan Africa. There is strong evidence of an etiologic role for hepatitis B infection in hepatocellular carcinoma. Carriers of the HBV are at greater than 90 times higher risk for the development of hepatocellular carcinoma than noncarriers. In many cases, hepatitis B virus DNA is integrated within the cellular genome of the tumor. Similarly, hepatitis C virus has also recently been found to be associated with hepatocellular carcinoma, based upon the observation that circulating HCV antibodies can be found in some patients with hepatocellular carcinoma. At present, surgical resection offers the only treatment for hepatocellular carcinoma, as chemotherapy, radiotherapy, and immunotherapy have not shown much promise (Colombo et al., Lancet 1006-1008, 1989; Bisceglie et al., Ann. of Internal Med. 108:390401, 1988; Watanabe et al., Int. J. Cancer 48:340-343, 1991; Bisceglie et al., Amer. J. Gastro. 86:335-338, 1991).

Therefore, therapeutics that could serve to augment natural host defenses against hepatitis, or against tumor induction and progression, with reduced cytotoxicity, or that allows treatment of interferon non-responsive individuals would be very beneficial. The present invention provides such therapeutic agents, and further provides other related advantages.

BRIEF SUMMARY OF THE INVENTION

The invention provides novel immune potentiators, novel vaccine adjuvants, novel compounds and pharmaceutical compositions, novel methods for treating viral infections, including HCV, by administering the compounds, and novel methods for modulating the immune response by administering the compounds.

The compounds used in the methods and compositions of the invention are small molecules. They have greater potential for finer specificity thus providing improved efficacy and safety profiles compared to existing immuno-stimulants and antivirals.

As adjuvants, the compounds are combined with numerous antigens and delivery systems to form a final vaccine product.

As immuno-therapeutics, the compounds are used alone or combined with agents or other therapies for which the immune response is desired for treatment or modulation of cancer, allergic diseases, asthma, and chronic infections such as coronavirus, SARS-associated coronavirus (SARS-CoV), HIV, HCV, HBV, HSV, and *H. pylori*.

One embodiment of the invention is a composition comprising:

a vaccine in an amount effective to stimulate a cell-mediated immune response; and a vaccine adjuvant comprising a thiosemicarbazone or derivative thereof, in an amount effective to potentiate the cell-mediated immune response to the vaccine.

In another embodiment, the invention is an composition according to claim 1, wherein the thiosemicarbazone is a compound of formula I:

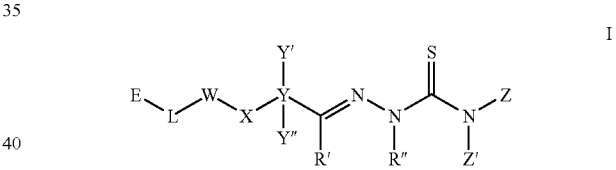

wherein:

E is absent or selected from the group consisting of alkyl, substituted alkyl, cycloalkyl, substituted cycloalkyl, aryl, substituted aryl, heterocyclyl, substituted heterocyclyl, heteroaryl, and substituted heteroaryl;

L is absent or is selected from the group consisting of oxo, amino, alkylene, substituted alkylene, alkoxy, alkylamino, aminoalkyl, heterocyclyl, carbocyclyl, and carbonyl;

W is absent or selected from the group consisting of cycloalkyl, substituted cycloalkyl, aryl, substituted aryl, heterocyclyl, substituted heterocyclyl, heteroaryl, and substituted heteroaryl;

X is absent or is selected from the group consisting of oxo, amino, alkylene, substituted alkylene, alkoxy, alkylamino, aminoalkyl, heterocyclyl, carbocyclyl, and carbonyl;

Y is selected from the group consisting of cycloalkyl, substituted cycloalkyl, aryl, substituted aryl, heterocyclyl, substituted heterocyclyl, heteroaryl, and substituted heteroaryl;

Y' is absent or is selected from the group consisting of F, Cl, Br, I, nitro, alkyl, substituted alkyl, and optionally substituted heterocyclyl, amino, alkylamino, dialkylamino;

Y" is absent or is selected from the group consisting of F, Cl, Br, I, nitro, alkyl, substituted alkyl, and optionally substituted heterocyclyl, amino, alkylamino, dialkylamino;

R' is H, alkyl, or substituted alkyl;

R" is H, or

R' and R" are taken together to form a hetercyclic ring;

Z and Z' are independently selected from the group consisting of hydrogen, alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylamino-carbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cycloamidino, cycloalkyl, cycloimido, arylsulfonyl and arylsulfonamido; or Z and Z' are taken together to form a heterocyclic group, which may be optionally substituted;

the tautomers and the pharmaceutically acceptable salts, esters, or prodrugs thereof.

Other embodiments include methods of treating a viral infection comprising the step of administering to a subject a composition as described above.

Still other embodiments include a method of treating a viral infection or potentiating a cell-mediated immune response comprising administering to a subject a compound of formula II:

wherein:

W is selected from substituted and unsubstituted aryl, or a substituted and unsubstituted heteroaryl group having one ring or two fused rings;

X is absent or is selected from the group consisting of oxo, amino, alkylene, substituted alkylene, alkoxy, alkylamino, aminoalkyl, heterocyclyl, and carbocyclyl, wherein if X is absent, Y and W together form an optionally substituted aryl or heteroaryl group having at least two fused rings;

Y is selected from substituted and unsubstituted aryl, or a substituted and unsubstituted heteroaryl group having one ring or two fused rings;

Y' is absent or is selected from the group consisting of F, Cl, Br, I, nitro, alkyl, substituted alkyl, and optionally substituted heterocyclyl, amino, alkylamino, dialkylamino;

Y" is absent or is selected from the group consisting of F, Cl, Br, I, nitro, alkyl, substituted alkyl, and optionally substituted heterocyclyl, amino, alkylamino, dialkylamino;

R' is H or $CH_3$,

Z is selected from the group consisting of hydrogen, alkyl, substituted alkyl, heterocyclyl, substituted heterocyclyl, and optionally substituted heterocyclylalkyl;

salts, prodrugs, or tautomers thereof.

Still other embodiments include compounds of formula III, wherein:

W is selected from the group consisting of substituted or unsubstituted alkyl, substituted or unsubstituted cycloalkyl, substituted or unsubstituted aryl, substituted or unsubstituted heterocyclyl, and substituted or unsubstituted heteroaryl groups;

X and L are each independently absent or independently selected from the group consisting of lower alkyl and carbonyl;

R is absent or selected from the group consisting of carbonyl, amino, alkyl, substituted alkyl, alkylamino, and dialkylamino;

Y is an aryl or heteroaryl group;

Y' is absent or selected from the group consisting of F, Cl, Br, I, alkyl, substituted alkyl, heterocyclyl, amino, alkylamino, dialkylamino, and nitro;

Y" is absent or selected from the group consisting of F, Cl, Br, I, alkyl, substituted alkyl, heterocyclyl, amino, alkylamino, dialkylamino, and nitro;

Z is hydrogen, or if Y is furanyl, then Z may be selected from the group consisting of alkyl, substituted alkyl, heterocyclyl, amino, alkylamino, dialkylamino, and nitro; and salts, prodrugs, or tautomers thereof.

Yet other embodiments include compounds of formula IV, wherein:

W is an optionally substituted phenyl or pyridinyl group;

X is alkoxy or alkylamino;

Y' is H or fluoro;

Y' is dialkylamino, fluoro, or nitro; and salts, prodrugs, or tautomers thereof.

Another embodiment includes compounds of Formula IVc wherein:

W is phenyl substituted with at least one member selected from the group consisting of —Cl; —F; —Br; —CF3; —OCH3; —NO2; —CH3; N(CH3)2; and —OCF3;

X is alkoxy; and n is an integer from 1 and 3.

Another embodiment includes compounds of Formula V

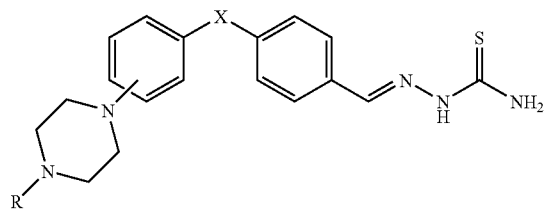

V wherein:

R is an alkyl group;

X is alkoxy; and salts, prodrugs, or tautomers thereof.

Still another embodiment includes compounds of Formula VI

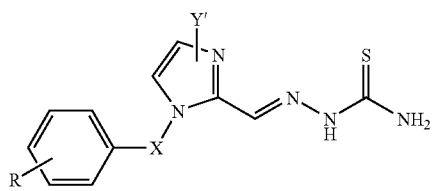

VI wherein:

X is absent or an alkylene;

Y' is absent or is an alkyl group; and

R is a halogen; and salts, prodrugs, or tautomers thereof.

Another embodiment includes compounds of Formula VII

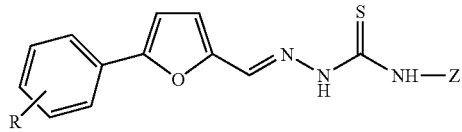

VII wherein:

R is nitro and Z is H; or

R is Cl and Z is selected from the group consisting of alkyl, pyridylalkylene, piperidinylalkylene, morpholinylalkylene, and piperizinylalkylene; and salts, prodrugs, or tautomers thereof.

Other embodiments include compounds of formula VIII and salts, prodrugs, or tautomers thereof:

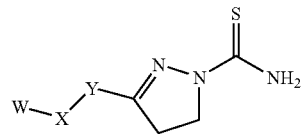

VIII wherein:

W is a phenyl, substituted phenyl, pyridinyl, or substituted pyridinyl group;

X is absent or is selected from the group consisting of oxo, amino, alkylene, and substituted alkylene; and Y is an aryl or heteroaryl group.

Another embodiment includes compounds of formula IX:

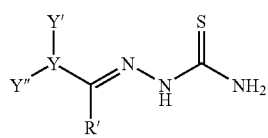

IX wherein;

Y is an aryl or heteroaryl group having one ring or two fused rings;

Y' is selected from the group consisting of halo, nitro, alkyl, substituted alkyl, alkenyl, substituted alkenyl, alkynyl, substituted alkynyl, heterocyclyl, substituted heterocyclyl, amino, alkylamino, and dialkylamino; and Y" is absent or is selected from the group consisting of halo, nitro, alkyl, substituted alkyl, heterocyclyl, substituted heterocyclyl, amino, alkylamino, and dialkylamino.

Yet another embodiment includes a pharmaceutical composition comprising a therapeutically effective amount of a compound of Formula III, IV, IVc, V, VI, VII, VIII, or IX and a pharmaceutically acceptable carrier.

Another embodiment includes a method of treating a viral infection comprising administering to a subject a pharmaceutical composition comprising a therapeutically effective amount of any of the above-mentioned compounds, salts and tautomers thereof, and a pharmaceutically suitable carrier.

In some embodiments, the viral infection is HCV.

Some embodiments involve a method of treating viral infections in a subject comprising administering to the subject any one or more of the compounds described herein or, a tautomer of the compound, a pharmaceutically acceptable salt of the compound, or a pharmaceutically acceptable salt of the tautomer.

Still other embodiments involve the methods described above wherein the infection is an HCV infection.

Some embodiments of a method of adminstering a vaccine comprise simulatneously administering a vaccine in an amount effective to stimulate a cell-mediated immune response; and a vaccine adjuvant comprising a thiosemicarbazone or derivative thereof, in an amount effective to potentiate the cell-mediated immune response to the vaccine.

Other embodiments of a method of adminstering a vaccine comprise separately administering a vaccine in an amount effective to stimulate a cell-mediated immune response; and a vaccine adjuvant comprising a thiosemicarbazone or derivative thereof, in an amount effective to potentiate the cell-mediated immune response to the vaccine, wherein the vaccine adjuvant is adminstered either prior to or subsequent to administration of the vaccine.

DETAILED DESCRIPTION OF THE INVENTION

Figure 1:
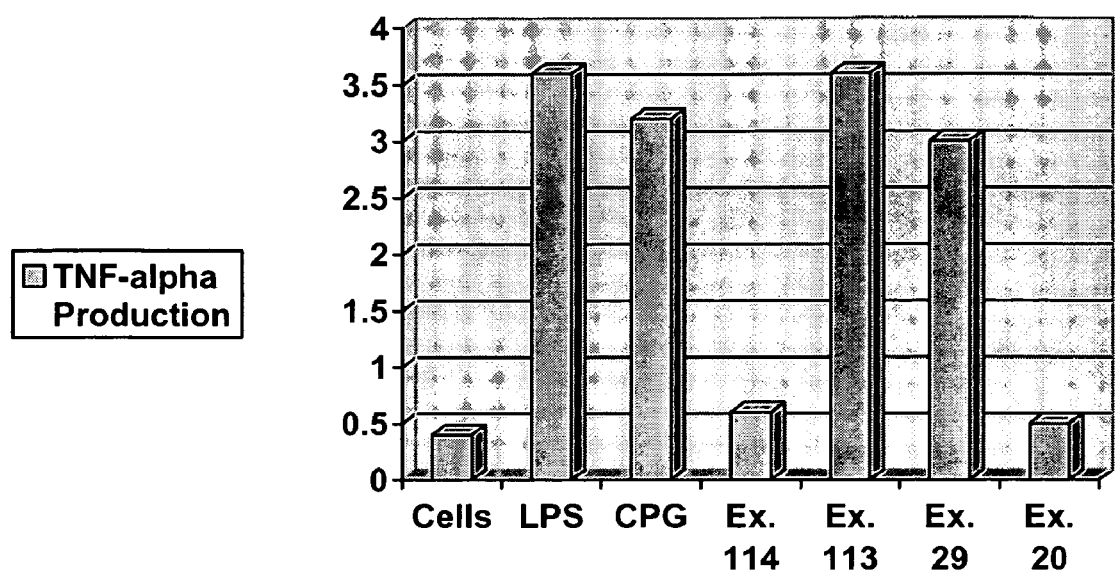
FIG. 1 shows candidate small molecule immuno-potentiators identified in vitro by measuring TNF-alpha production by human PBMC.

One embodiment of the invention is directed to a method of inducing an immunostimulatory effect in a patient comprising administering a thiosemicarbazone compound in an amount effective to stimulate a cell-mediated immune response.

One preferred embodiment of the method of inducing an immunostimulatory effect in a patient is directed to a vaccine adjuvant composition comprising a vaccine in an amount effective to stimulate a cell-mediated immune response and, as a vaccine adjuvant, a thiosemicarbazone or derivatives thereof, in an amount effective to potentiate the cell-mediated immune response to the vaccine.

As is well-understood in the art, a vaccine may be prophylactic and/or therapeutic in nature. The vaccines and vaccine compositions disclosed herein likewise may be used prophylactically or therapeutically.

When the thiosemicarbazone is administered as a vaccine adjuvant, it may be administered simultaneously with the vaccine, prior to the vaccine, and even after vaccine administration.

Preferably, the thiosemicarbazone is a compound of formula I, the tautomers thereof, and the pharmaceutically acceptable salts, esters, or prodrugs thereof:

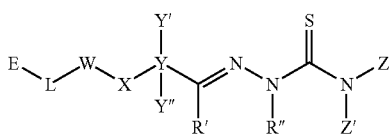

I

E is absent or selected from the group consisting of alkyl, substituted alkyl, cycloalkyl, substituted cycloalkyl, aryl, substituted aryl, heterocyclyl, substituted heterocyclyl, heteroaryl, and substituted heteroaryl;

L is absent or is selected from the group consisting of oxo, amino, alkylene, substituted alkylene, alkoxy, alkylamino, aminoalkyl, heterocyclyl, carbocyclyl, and arbonyl;

W is absent or selected from the group consisting of cycloalkyl, substituted cycloalkyl, aryl, substituted aryl, heterocyclyl, substituted heterocyclyl, heteroaryl, and substituted heteroaryl;

X is absent or is selected from the group consisting og oxo, amino, alkylene, substituted alkylene, alkoxy, alkylamino, aminoalkyl, heterocyclyl, carbocyclyl, and carbonyl;

Y is selected from the group consisting of cycloalkyl, substituted cycloalkyl, aryl, substituted aryl, heterocyclyl, substituted heterocyclyl, heteroaryl, and substituted heteroaryl;

Y' is absent or is selected from the group consisting of halo, nitro, alkyl, substituted alkyl, and optionally substituted heterocyclyl, amino, alkylamino, dialkylamino;

Y" is absent or is selected from the group consisting of halo, nitro, alkyl, substituted alkyl, and optionally substituted heterocyclyl, amino, alkylamino, dialkylamino;

R' is H, alkyl, or substituted alkyl;

R" is H, or

R' and R" are taken together to form a heterocyclic ring;

Z and Z' are independently selected from the group consisting of hydrogen, alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylamino-carbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cycloamidino, cycloalkyl, cycloimido, arylsulfonyl and arylsulfonamido.

Alternatively, Z and Z' are taken together to form a heterocyclic group or substituted heterocyclic group.

The above method of inducing an immunostimulatory effect in a patient includes the administration of the thiosemicarbazone compound to enhance the efficacy of a therapeutic treatment by stimulating a local immune response in selected cells or tissues of the patient.

The above method of stimulating a local immune response in selected cells or tissues of a patient includes the stimulation of a local immune response wherein the selected cells or tissues are infected or cancerous. In one embodiment the selected cells or tissues are infected with a fungus or bacterium. In another embodiment the selected cells are infected with an allergen. In another embodiment the selected cells are infected with a virus. In still a more particular embodiment the virus is the as coronavirus, SARS-associated coronavirus (SARS-CoV), HCV, HIV, HBV, HSV, H. pylori, HSV Type 1 or 2, or Human Papilloma Virus.

The vaccine adjuvant compositions of the invention can contain further pharmaceutically acceptable ingredients, excipients, carriers, and the like well known to those skilled in the art.

The invention is also directed to administering the vaccine adjuvant composition. The vaccine is administered in an amount effective to stimulate an immune response. The amount that constitutes an effective amount depends, inter alia, on the particular vaccine used, the particular adjuvant compound being administered and the amount thereof, the immune response that is to be enhanced (humoral or cell mediated), the state of the immune system (e.g., suppressed, compromised, stimulated), and the desired therapeutic result. Accordingly it is not practical to set forth generally the amount that constitutes an effective amount of the vaccine. Those of ordinary skill in the art, however, can readily determine the appropriate amount with due consideration of such factors.

The vaccine adjuvant compositions of the invention can be administered to animals, e.g., mammals (human and nonhuman), fowl, and the like according to conventional methods well known to those skilled in the art (e.g., orally, subcutaneously, nasally, topically).

Suitable vaccines include, but are not limited to, any material that raises either humoral or cell mediated immune response, or both. Suitable vaccines include live viral and bacterial immunogens and inactivated viral, tumor-derived, protozoal, organism-derived, fungal, and bacterial immunogens, toxoids, toxins, polysaccharides, proteins, glycoproteins, peptides, and the like. Conventional vaccines, such as those used in connection with BCG (live bacteria), cholera, plague, and typhoid (killed bacteria), hepatitis B, influenza, inactivated polio, and rabies (inactivated virus), measles, mumps, rubella, oral polio, and yellow fever (live virus), tetanus and diphtheria (toxoids), hemophilus influenzae b, meningococcal, and pneumococcal (bacterial polysaccharides) also can be used.

Furthermore, it is contemplated that certain currently experimental vaccines, especially materials such as recombinant proteins, glycoproteins, and peptides that do not raise a strong immune response, will also find use in connection with the thiosemicarbazone. Exemplary experimental subunit immunogens include those related to viral disease such as adenovirus, AIDS, chicken pox, cytomegalovirus, dengue, feline leukemia, fowl plague, hepatitis A, hepatitis B, hepatitis C, HSV-1, HSV-2, hog cholera, influenza A, influenza B, Japanese encephalitis, measles, parainfluenza, rabies, respiratory syncytial virus, rotavirus, wart, and yellow fever.

Specific antigens for use with the invention include, but are not limited to, those listed below. The number(s) in parenthesis indicate representative resources of the antigen. The resource list follows the antigen list and each resource is incorporated by reference in its entirety.

Specific antigens include: a protein antigen from *N. meningitides* serogroup B (1-7); an outer-membrane vesicle (OMV) preparation from *N. meningitides* serogroup B. (8, 9, 10, 11); a saccharide antigen from *N. meningitides* serogroup A, C W135 and/or Y, such as the oligosaccharide (12) from serogroup C (13); a saccharide antigen from *Streptocaccus pneumoniae* (14, 15, 16); an antigen from *N. gonorrhoeae* (1, 2, 3); an antigen from *Chlamydia pneumoniae* (17, 18, 19, 20, 21, 22, 23); an antigen from *Chlamydia trachomatis* (24); an antigen from hepatitis A virus, such as inactive virus (25, 26); an antigen from hepatitis B virus, such as the surface and/or core antigens [e.g. 26, 27]; an antigen from hepatitis C virus (28); an antigen from *Bordetella pertussis*, such as petussis holotoxin (PT) and filamentous haemagglutinin (FHA) from *B. pertussis*, optionally also combination with pertactin and/or agglutinogens 2 and 3 (29, 30); a diphtheria antigen, such as a diphtheria toxoid (31:chapter 3) e.g. the CRM197 mutant (32); a tetanus antigen, such as a tetanus toxioid (31:chapter 4); a protein antigen from *Helicobacter pylori* such as CagA (33), VacA (33), NAP (34), HopX (5), HopY (35) and/or urease; a saccharide antigen from *Haemophilus influenzae* B (13); an antigen from *Porphyromonas gingivalis* (36); polio antigen(s) (37, 38) such as IPV or OPV; rabies antigen(s) (39) such lyophilized inactivated virus (40, RabAvert™); measles, mumps and/or rubella antigens (31: chapters 9, 10, & 11); influenza antigen(s) (31:chapter 19), such as the haemagglutinin and/or neuraminidase surface proteins; an antigen from *Moraxella catarrhalis* (41); an antigen from *Streptococcus agalactiae* (group B *streptococcus*) (42, 43); an antigen from *Streptococcus pyogenes* (group A *streptococcus*) (43, 44, 45); and an antigen from *Staphylococcus aureus* (46).

The composition may comprise one or more of the above antigens.

Where a saccharide or carbohydrate antigen is used, it is preferably conjugated to a carrier protein in order to enhance immunogenicity (47-6). Preferred carrier proteins are bacterial toxine or toxiods, such as diphtheria or tetanus toxoids. The CRM197 diphtheria toxoid is particularly preferred. Other suitable carrier proteins include the *N. meningitides* outer membrane protein (57), synthetic peptides (58, 59), heat shock proteins (60), pertussis proteins (61, 62), protein D from *H. influenzae* (63), toxin A or B from *C. difficile* (64) etc. Where a mixture comprises capsular saccharides from both serogroups A and C, it is preferred that the ratio (w/w) of MenA saccharide:MenC saccharide is greater than 1 (e.g. 2:1, 3:1, 4:4, 5:1, 10:1 or higher). Saccharides from different serogroups of *N. meningitides* may be conjugated to the same or different carrier proteins.

Any suitable conjugation reaction can be used, with any suitable liner where necessary. Toxic protein antigens may be detoxified where necessary (e.g. detoxification of pertussis toxin by chemical and/or genetic means (30)). Where a diphtheria antigen is included in the composition it is preferred also to include tetanus antigens and pertussis antigens. Similarly, where a tetanus antigen is included it is preferred also to include diphtheria and pertussis antigens. Similar, where pertussis antigen is included it is preferred also to include diphtheria and tetanus antigens.

In another embodiment, the invention provides a method of treating a viral infection in a mammal comprising administering to the mammal a compound of formula II or its salts, prodrugs, or tautomers thereof:

II 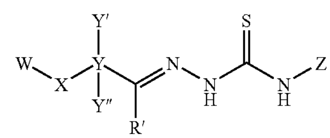 wherein:

W is an aryl, substituted aryl, heteroaryl or substituted heteroaryl group having one ring or two fused rings;

X is absent or is selected from the group consisting of oxo, amino, alkylene, substituted alkylene, alkoxy, alkylamino, aminoalkyl, heterocyclyl, and carbocyclyl. Preferably X is absent or is selected from the group consisting of piperizinyl, $—O(CH_2)_n—$; $—(CH_2)_n—O—$; —O—; —C(O)O—; $—NH—(CH_2)_m—$; $—(CH_2)_m—NH—$; $—NH—(CH_2)_m—NH—$; $—N(CH_2)_n—(CH_2)_m—NH—$; $—N(CH_2)_n—(CH_2)_m—N(CH_2)_p—$; $—NH—(CH_2)_m—N(CH_2)_n$ and $—O—(CH_2)_p—O—$, wherein n, m, and p are 1 to 3. More preferably, X is absent or is selected from the group consisting of $—CH_2—O—$; $—O—CH_2—$; $—CH_2$; —O—; —C(O)O—; $—NHCH_2—$; $—NHCH_2CH_2$; and $—OCH_2CH_2O—$;

Y is an aryl, substituted aryl, heteroaryl, or substituted heteroaryl group having one ring or two fused rings. Preferably, Y is selected from the group consisting of phenyl, furanyl, pyrrolyl, pyrazolyl, pyrazinyl, thiazolyl, pyrimidinyl, and imidazolyl;

Alternatively, X does not exist and Y and W together form an arly, substituted aryl, heteroaryl, or substituted heteroaryl group having at least two fused rings. Preferably, Y and W together form an unsubstituted or substituted nitrogen-containing fused heteroaryl group having at least two fused rings. More preferably an unsubstituted or substituted quinolinyl, indolyl, benzo[g]indolyl, benzindolyl, or benzofuranyl.

Y' is absent or is selected from the group consisting of halo, nitro, alkyl, substituted alkyl, heterocyclyl, substituted heterocyclyl, amino, alkylamino, and dialkylamino. Preferably, Y' is absent or is selected from the group consisting of halo; —CH$_3$; —OCH$_3$; —N(CH$_2$CH$_3$)$_2$; -phenyl; —Br; and —NO$_2$.

Y" is absent or is selected from the group consisting of halo, nitro, alkyl, substituted alkyl, heterocyclyl, substituted heterocyclyl, amino, alkylamino, and dialkylamino.

R' is H or CH$_3$;

Z is selected from the group consisting of hydrogen, alkyl, substituted alkyl, heterocyclyl, substituted heterocyclyl, heterocyclylalkyl, and substituted heterocyclylalkyl. In one embodiment, Z is preferably hydrogen. In another embodiment, if Y is furanyl, then Z is selected from the group consisting of pyridylalkylene, piperidinylalkylene, morpholinylalkylene, and piperizinylalkylene.

In one embodiment, W is phenyl or phenyl substituted with at least one member selected from the group consisting of halogen; nitro; alkylamino; dialkylamino; alkyl; trifluoroalkyl; and trifluoroalkylalkoxy, preferably with at least one member selected from the group consisting of —Cl; —F; —Br; —CF$_3$; —OCH$_3$; —NO$_2$; CH$_3$; —N(CH$_3$)$_2$; and —OCF$_3$.

In another embodiment, W is a heteroaryl or substituted heteroaryl selected from the group consisting of furanyl, pyridinyl, pyrrolyl, pyrazolyl, pyrazinyl, thiazolyl, and imidazolyl, preferably pyridinyl. If substituted, the heteroaryl is preferably substituted with at least one member selected from the group consisting of halogen; nitro; alkylamino; dialkylamino; alkyl; trifluoroalkyl; and trifluoroalkylalkoxy, more preferably at least one member selected from the group consisting of —Cl; —F; —Br; —CF$_3$; —OCH$_3$; —NO$_2$; CH$_3$; —N(CH$_3$)$_2$; and —OCF$_3$.

In one embodiment, if Y is pyrrol, the Y' and Y" are alkyl. In another embodiment, if Y is phenyl, and Y' is alkoxy, then Y" is a halogen. In another embodiment if Y is pyrazolyl, then Y' is aryl. In another embodiment, if Y is aryl with two fused rings, then Y' is alkoxy and Y" is alkyl.

In one preferred embodiment, Y is pyrrol and Y' and Y" are each —CH$_3$, X is absent, and W is phenyl substituted with nitro, dimethylamine, Cl, F, or CH$_3$.

In other preferred embodiments, Z is hydrogen, Y is furanyl, Y' does not exist, X is absent, and W is phenyl substituted with C$_1$ or CF$_3$; or Z is hydrogen, Y is phenyl, Y' is —OCH$_3$, X is —OCH$_2$— and W is phenyl substituted with one or two Cl; or Z is hydrogen, Y is phenyl, Y' is nitro, X is —NHCH$_2$— and W is phenyl substituted with Cl.

In another embodiment, the invention provides a method of treating a patient with an HCV infection by administering to the patient a compound of formula II, or its salts, prodrugs, or tautomers thereof as described above.

The patient is preferably a mammal, and in some embodiments, a human. The compounds may be injected or taken orally.

In another embodiment, the invention provides a method of treating a patient with an HCV infection by administering to the patient a compound of formula II, or its salts, prodrugs, or tautomers thereof.

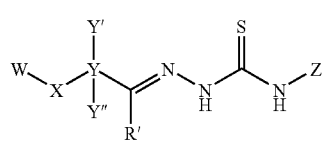

R' is H or —CH$_3$.

W is an aryl, substituted aryl, heteroaryl, or substituted heteroaryl group having one ring or two fused rings. Preferably, W is phenyl or phenyl substituted with at least one member selected from the group consisting of halogen; nitro; alkylamino; dialkylamino; alkyl; trifluoroalkyl; and trifluoroalkylalkoxy, preferably with at least one member selected from the group consisting of —Cl; —F; —Br; —CF$_3$; —OCH$_3$; —NO$_2$; CH$_3$; —N(CH$_3$)$_2$; and —OCF$_3$.

X is absent or is selected from the group consisting of oxo, amino, alkylene, substituted alkylene, alkoxy, alkylamino, aminoalkyl, heterocyclyl, and carbocyclyl.

Y is an aryl or heteroaryl group having one ring or two fused rings.

Alternatively, X does not exist and Y and W together form an aryl, substituted aryl, heteroaryl, or substituted heteroaryl group having at least two fused rings.

Y' is absent or is selected from the group consisting of nitro, alkyl, substituted alkyl, heterocyclyl, substituted heterocyclyl, amino, alkylamino, and dialkylamino;

Y" is absent or is selected from the group consisting of nitro, alkyl, substituted alkyl, heterocyclyl, substituted heterocyclyl, amino, alkylamino, and dialkylamino;

Z is selected from the group consisting of hydrogen, alkyl, substituted alkyl, heterocyclyl, substituted heterocyclyl, heterocyclylalkyl, and substituted heterocyclylalkyl.

The patient is preferably a mammal, and in some embodiments, a human. The compounds may be injected or taken orally.

The invention is also directed to novel compounds as defined below by formulas III-VII, and salts, prodrugs, or tautomers thereof, as well as pharmaceutical compositions containing the compounds and methods of treating or preventing viral infections, in particular HCV, by administering such compounds to a mammal in need thereof.

The invention is also directed to novel compounds defined by formula III and salts, prodrugs, or tautomers thereof:

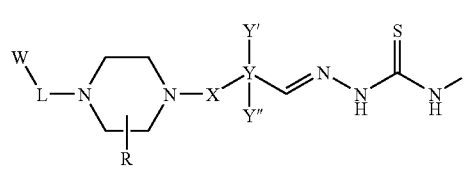

W is an aryl, substituted aryl, heteroaryl, or substituted heteroaryl group. Preferably W is phenyl or substituted phenyl. If substituted, phenyl is preferably substituted with at least one member selected from the group consisting of Br, Cl, F, and CF$_3$.

L and X are each independently absent or independently selected from the group consisting of lower alkyl and carbonyl;

R is absent or selected from the group consisting of carbonyl, amino, alkyl, substituted alkyl, alkylamino, and dialkylamino.

Y is an aryl or heteroaryl group. Y is preferably selected from the group consisting of phenyl, furanyl, pyrridinyl, pyrrolyl, pyrazolyl, pyrazinyl, thiazolyl, pyrimidinyl, and imidazolyl. More preferably, Y is phenyl, furanyl, or pyrimidinyl.

Y' is absent or selected from the group consisting of halo, alkyl, substituted alkyl, heterocyclyl, amino, alkylamino, dialkylamino, and nitro. If present, Y' is preferably fluro, nitro or piperizinyl.

Y" is absent or selected from the group consisting of halo, alkyl, substituted alkyl, heterocyclyl, amino, alkylamino, dialkylamino, and nitro. If present, Y' is preferably fluoro, nitro or piperizinyl.

Z is hydrogen, or if Y is furanyl, then Z may be selected from the group consisting of alkyl, substituted alkyl, heterocyclyl, amino, alkylamino, dialkylamino, and nitro.

In a preferred embodiment, W is phenyl or phenyl substituted with —CF$_3$ or Cl; Y is phenyl; Y' is nitro; and Z is H.

The present invention is also directed to novel compounds defined by formula IV and salts, prodrugs, or tautomers thereof:

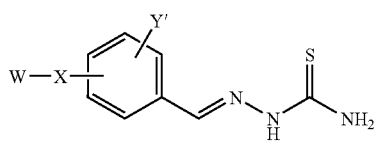

IV

W is a phenyl, substituted phenyl, pyridinyl, or substituted pyridinyl group. W is preferably substituted with at least one member selected from the group consisting of —Cl; —F; —Br; —CF$_3$; —OCH$_3$; —NO$_2$; —CH$_3$; —N(CH$_3$)$_2$; and —OCF$_3$.

X is alkoxy or alkylamino.

Y' is dialkylamino, fluro, or nitro.

In one embodiment, the compound IV is defined as IVa and salts, prodrugs, or tautomers thereof:

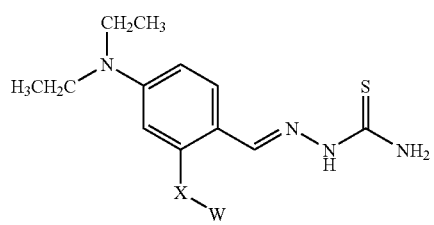

IVa

X is alkoxy, preferably —OCH$_2$—.

W is phenyl substituted with at least one member selected from the group consisting of —Cl; —F; —Br; —CF$_3$; —OCH$_3$; —NO$_2$; —CH$_3$; —N(CH$_3$)$_2$; and —OCF$_3$.

In one embodiment, the compound IV is defined as IVb and salts, prodrugs, or tautomers thereof:

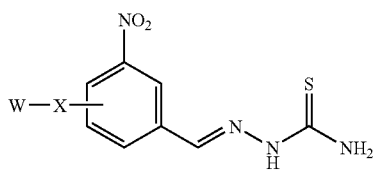

IVb

X is alkylamino, preferably —NHCH$_2$CH$_2$— or —NHCH$_2$—.

W is pyridinyl or phenyl substituted with at least one member selected from the group consisting of Cl, F, and CF$_3$, preferably pyridinyl or phenyl substituted with Cl, F, and CF$_3$.

In one embodiment, the compound IV is defined as IVc and salts, prodrugs, or tautomers thereof:

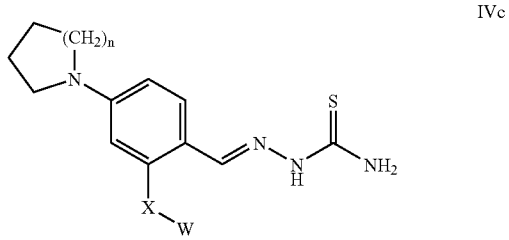

IVc

X is alkoxy, preferably —OCH$_2$—.

W is phenyl substituted with at least one member selected from the group consisting of —Cl; —F; —Br; —CF$_3$; —OCH$_3$; —NO$_2$; —CH$_3$; —N(CH$_3$)$_2$; and —OCF$_3$.

n is an integer from 1 and 3.

The invention is also directed to novel compounds defined by formula V and salts, prodrugs, or tautomers thereof

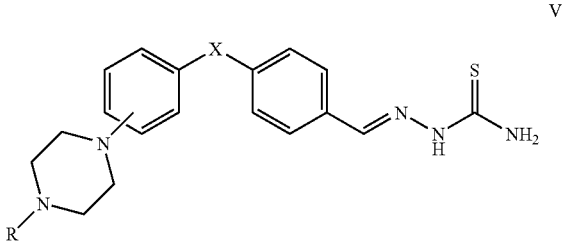

V

R is an alkyl group, preferably methyl.

X is alkoxy, preferably CH$_2$—; —OCH$_2$CH$_2$—; —CH$_2$O—; or —CH$_2$CH$_2$O—.

The invention is also directed to novel compounds defined by formula VI and salts, prodrugs, or tautomers thereof:

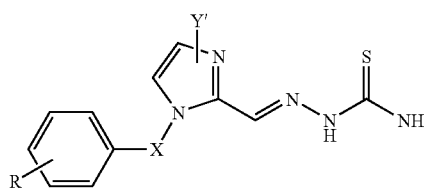

VI

X is absent or an alkylene, preferably —CH$_2$CH$_2$—.

Y' is absent or is an alkyl group, preferably Y' is absent or is methyl.

R is a halogen, preferably Cl.

The invention is also directed to novel compounds defined by formula VII and salts, prodrugs, or tautomers thereof:

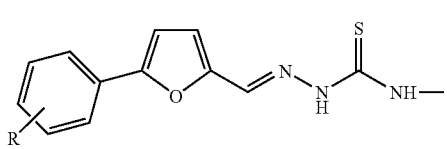

VII

R is nitro and Z is H; or R is Cl and Z is selected from the group consisting of alkyl, pyridylalkylene, piperidinylalkylene, morpholinylalkylene, and piperizinylalkylene, preferably methyl, pyridylmethylene, piperidinylethylene, morpholinylethylene, piperizinylmethylene, piperizinylethylene, and morpholinylbutylene.

The invention is also directed to a vaccine adjuvant composition comprising a vaccine in an amount effective to stimulate a cell-mediated immune response and, as a vaccine adjuvant, a a compound of formulas II through VI or derivatives thereof, in an amount effective to potentiate the cell-mediated immune response to the vaccine.

The invention is also directed to novel compounds defined by formula VIII and salts, prodrugs, or tautomers thereof:

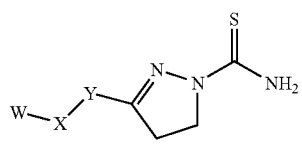

VIII wherein:

Y is an aryl or heteroaryl group. Y is preferably selected from the group consisting of phenyl, furanyl, pyrridinyl, pyrrolyl, pyrazolyl, pyrazinyl, thiazolyl, and imidazolyl. More preferably, Y is furanyl.

X is absent or is selected from the group consisting of oxo, amino, alkylene, and substituted alkylene. More preferably, X is absent.

W is a phenyl, substituted phenyl, pyridinyl, or substituted pyridinyl group. W is preferably substituted with at least one member selected from the group consisting of —Cl; —F; —Br; —CF$_3$; —OCH$_3$; —NO$_2$; —CH$_3$; —N(CH$_3$)$_2$; and —OCF$_3$.

The invention is also directed to a pharmaceutical composition comprising a therapeutically effective amount of a compound of formulas III through VIII a pharmaceutically acceptable salt of the compound, or a pharmaceutically acceptable salt of the tautomer and a pharmaceutically suitable carrier or excipient.

The invention also provides a method of treating viral infections, including HCV, in a subject comprising administering to the subject a compound of formulas III though VIII, a tautomer of the compound, a pharmaceutically acceptable salt of the compound, or a pharmaceutically acceptable salt of the tautomer.

The invention also provides a method of treating an HCV infection, in a subject comprising administering to the subject a compound of the following formula (IX), a tautomer of the compound, a pharmaceutically acceptable salt of the compound, or a pharmaceutically acceptable salt of the tautomer.

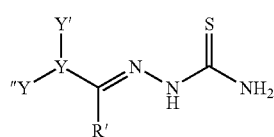

IX wherein;

R' is H or lower alkyl.

Y is an aryl or heteroaryl group having one ring or two fused rings. Preferably, Y is selected from the group consisting of phenyl, furanyl, pyrrolyl, pyrazolyl, pyrazinyl, thiazolyl, pyrimidinyl, and imidazolyl.

Y' is selected from the group consisting of nitro, alkyl, substituted alkyl, alkenyl, substituted alkenyl, alkynyl, substituted alkynyl, heterocyclyl, substituted heterocyclyl, amino, alkylamino, and dialkylamino.

Y" is absent or is selected from the group consisting of halo, nitro, alkyl, substituted alkyl, heterocyclyl, substituted heterocyclyl, amino, alkylamino, and dialkylamino.

Definitions:

As used above and elsewhere herein the following terms and abbreviations have the meanings defined below:

| | |
|---|---|
| AcOH: | Acetic Acid |
| ATP: | Adenosine triphosphate |
| BCG | Mycobacterium bovis bacillus Calmette-Guerin |
| BOC | tert-butoxycarbonyl |
| BSA: | Bovine Serum Albumin |
| DIBAL-H | diisobutylaluminum hydride |
| DCM | dichloromethane |
| DIEA | diisopropylethylamine |
| DMA: | N,N-Dimethylacetamide |
| DMF: | N,N-Dimethylformamide |
| DMSO | dimethyl sulfoxide |
| dppf: | 1,1'(diphenylphosphino)ferrocene |
| DTT: | DL-Dithiothreitol |
| EDTA: | Ethylene diamine tetraacetic acid |
| EtOAc: | Ethyl acetate |
| EtOH: | Ethanol |
| FHA | Filamentous haemaglutinin |
| GCMS | Gas Chromatography/Mass Spectroscopy |
| H. Pylori | Helicobacter Pylori |
| HAV | Hepatitis A Virus |
| HBTU: | O-Benzotriazol-1-yl-N,N,N',N'-tetramethyluronium hexafluorophosphate |
| HBV | Hepatitis B Virus |
| HCV | Hepatitis C Virus |
| HIV | Human Immunodeficiency Virus |
| HPLC | High Performance Liquid Chromatography |
| HSV | Herpes Simplex Virus |
| IC50 value: | The concentration of an inhibitor that causes a 50% reduction in a measured activity. |
| IFN | Interferon |
| IL | Interleukin |
| IMS | Immunomagnetic separation |
| IPV | Inactivated polio virus |
| LCMS | Liquid Chromatography/Mass Spectroscopy |
| LPS | Lipopolysaccharide |
| Men A | Type A meningitis |
| Men C | Type C meningitis |
| MeOH: | Methanol |
| NANB | Non-A, non-B hepatits |
| NMP: | N-methylpyrrolidone |
| NMR | Nuclear magnetic resonance |
| OMV | Outer membrane vesicle |
| PBMC | Peripheral blood mononuclear cells |
| PT | Petussis holotoxin |
| Rt | Room temperature (25° C.) |
| SARS | Severe Acute Respiratory Syndrome |
| SMIP | Small Molecule Immune Potentiator |
| THF: | Tetrahydrofuran |
| TLC | Thin-layer chromatography |
| TNF-alpha | Tumour necrosis factor-a |

Generally, reference to a certain element such as hydrogen or H is meant to include all isotopes of that element. For example, if an R group is defined to include hydrogen or H, it also includes deuterium and tritium.

The term "absent" in reference to a particular substituent means the substuent is not present or, when between two other moieties, the "absent" substituent is a covalent bond therebetween.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus alkyl groups include primary alkyl groups, secondary alkyl groups, and tertiary alkyl groups. Preferred alkyl groups include straight and branched chain alkyl groups and cyclic alkyl groups having 1 to 12 carbon atoms.

The phrase "loweralkyl" refers to an acyclic alkyl group as described above. "Lower" is about 1 to about 8 carbon atoms, preferably about 1 to about 6 carbon atoms.

The phrase "substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heterocyclyl group, or cycloalkyl group. Preferred substituted alkyl groups include, among others, alkyl groups in which one or more bonds to a carbon or hydrogen atom is/are replaced by one or more bonds to fluorine atoms. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Still other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group.

The phrase "alkenyl" refers to straight and branched chain and cyclic groups such as those described with respect to alkyl groups as defined above, except that at least one double bond exists between two carbon atoms. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others. The phrase "substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "alkynyl" refers to straight and branched chain groups such as those described with respect to alkyl groups as defined above, except that at least one triple bond exists between two carbon atoms. Examples include, but are not limited to —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others. The phrase "substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "heterocyclyl" refers to both aromatic and non-aromatic ring compounds including monocyclic, bicyclic, and polycyclic ring compounds such as, but not limited to, quinuclidinyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl groups also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to a heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "aryl" refers to aryl groups that do not contain heteroatoms. Thus the phrase includes, but is not limited to, groups such as phenyl, biphenyl, anthracenyl, naphthenyl by way of example. Although the phrase "aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, 1,3-dichlorobenzene, and hydroxyphenyl among others.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl, and the like.

The term "substituted heteroaryl" as used herein refers to a heteroaryl group as defined herein substituted by independent replacement of one, two or three of the hydrogen atoms thereon with Cl, Br, F, I, OH, CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred unsubstituted or substituted biaryl groups include: 2-(phenylamino)-N-[4-(2-phenylethynyl)phenyl]acetamide, 1,4-diphenylbenzene, 2,4-dichloro-1-(2-methylphenyl)benzene, N-[4-(2-phenylethynyl)phenyl]-2-[benzylamino]acetamide, and [4-(2-phenylethynyl)phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)furan, 3-(2,4-dichlorophenyl)$_4$-methylpyrrole, and the like. Preferred unsubstituted or substituted heteroarylaryl groups include: 4-(2,4-dichlorophenyl)-3-methylpyrazole, 5-(2-phenylethynyl)pyrimidine-2-ylamine, 1-methoxy-4-(2-thienyl)benzene, 2-(3-nitrophenyl)thiophene, (tert-butoxy)-N-[(5-phenyl(3-pyridyl))methyl]carboxamide, hydroxy-N-[(5-phenyl(3-pyridyl))methyl]-amide, 2-(phenylmethylthio) pyridine, and benzylimidazole.

The term "heteroarylheteroaryl" refers to a biaryl group where both of the aryl groups are heteroaryl groups. Exemplary heteroarylheteroaryl groups include, for example, 3-pyridylimidazole, 2-imidazolylpyrazine, and the like. Preferred unsubstituted or substituted heteroarylheteroaryl groups include: 2-(4-piperazinyl-3-pyridyl)furan, diethyl(3-pyrazin-2-yl(4-pyridyl))amine, and dimethyl {2-[2-(5-methylpyrazin-2-yl)ethynyl](4-pyridyl)}amine.

"Optionally substituted" refers to the optional replacement of hydrogen with one or more monovalent or divalent radicals. Suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

"Substituted" refers to the definite replacement of hydrogen with one or more monovalent or divalent radicals. Suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

Representative substituted amidino and heterocycloamidino groups include, for example, those shown below. These amidino and heterocycloamidino groups can be further substituted as will be apparent to those having skill in the organic and medicinal chemistry arts in conjunction with the disclosure herein.

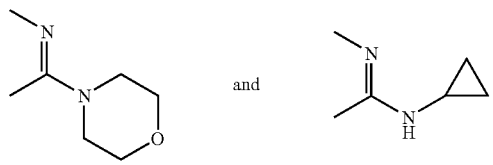

Representative substituted alkylcarbonylamino, alkyloxycarbonylamino, aminoalkyloxycarbonylamino, and arylcarbonylamino groups include, for example, those shown below. These groups can be further substituted as will be apparent to those having skill in the organic and medicinal chemistry arts in conjunction with the disclosure herein.

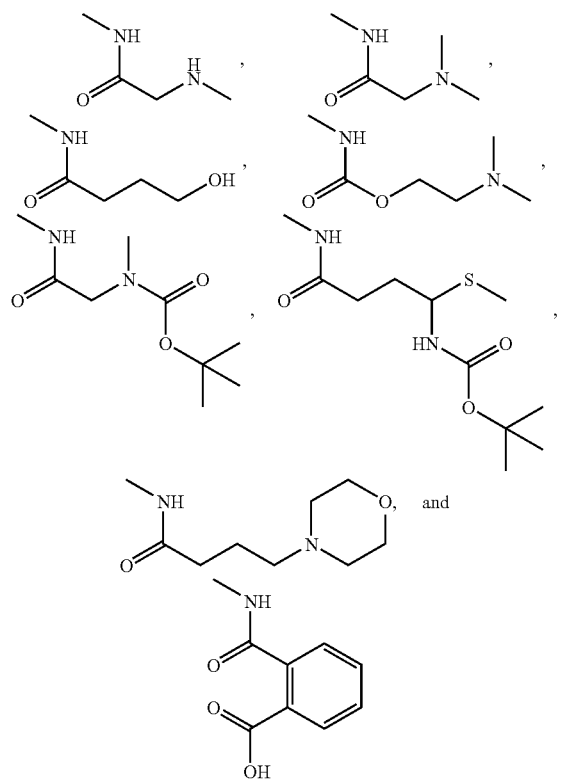

Representative substituted aminocarbonyl groups include, for example, those shown below. These can be further substituted by heterocyclo groups and heteroaryl groups as will be apparent to those having skill in the organic and medicinal chemistry arts in conjunction with the disclosure herein. Preferred aminocarbonyl groups include: N-(2-cyanoethyl)carboxamide, N-(3-methoxypropyl)carboxamide, N-cyclopropyl-carboxamide, N-(2-hydroxy-isopropyl)carboxamide, methyl 2-carbonylamino-3-hydroxypropanoate, N-(2-hydroxypropyl)carboxamide, N-(2-hydroxy-isopropyl)-carboxamide, N-[2-hydroxy-1-(hydroxymethyl)ethyl]-carboxamide, N-(2-carbonylaminoethyl)acetamide, N-(2-(2-pyridyl)ethyl)-carboxamide, N-(2-pyridylmethyl)carboxamide, N-(oxolan-2-ylmethyl)-carboxamide, N-(4-hydroxypyrrolidin-2-yl)carboxamide, N-[2-(2-hydroxyethoxy)ethyl]-carboxamide, N-(4-hydroxycyclohexyl)carboxamide, N-[2-(2-oxo-4-imidazolinyl)-ethyl]-carboxamide, N-(carbonylaminomethyl)acetamide, N-(3-pyrrolidinylpropyl)-carboxamide, N-[1-(carbonylaminomethyl)pyrrolidin-3-yl]acetamide, N-(2-morpholin-4-ylethyl)-carboxamide, N-[3-(2-oxopyrrolidinyl)propyl]carboxamide, 4-methyl-2-oxopiperazine-carbaldehyde, N-(2-hydroxy-3-pyrrolidinyl-propyl)-carboxamide, N-(2-hydroxy-3-morpholin-4-ylpropyl)carboxamide, N-{2-[(5-cyano-2-pyridyl)amino]-ethyl}carboxamide, 3-(dimethyl-amino)pyrrolidinecarbaldehyde, N-[(5-methylpyrazin-2-yl)methyl]carboxamide, 2,2,2-trifluoro-N-(1-formylpyrrolidin-3-yl)acetamide,

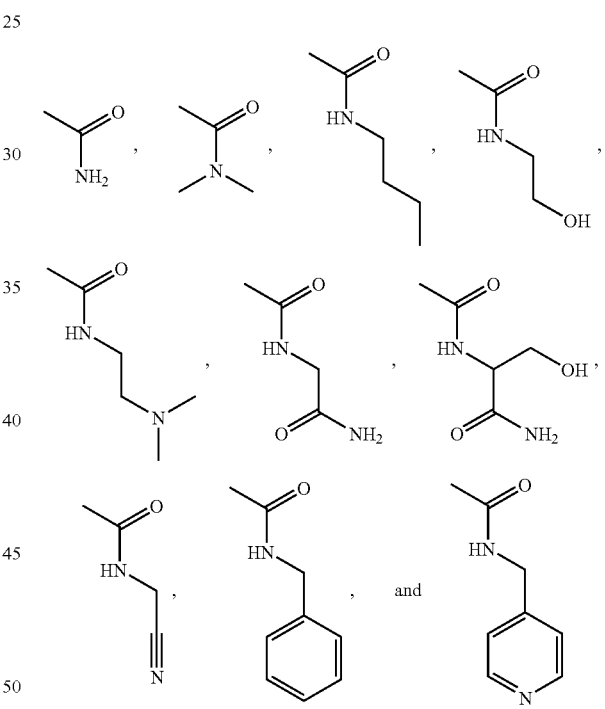

Representative substituted alkoxycarbonyl groups include, for example, those shown below. These alkoxycarbonyl groups can be further substituted as will be apparent to those having skill in the organic and medicinal chemistry arts in conjunction with the disclosure herein.

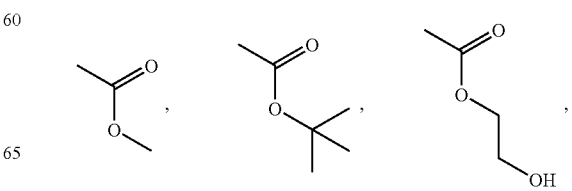

-continued

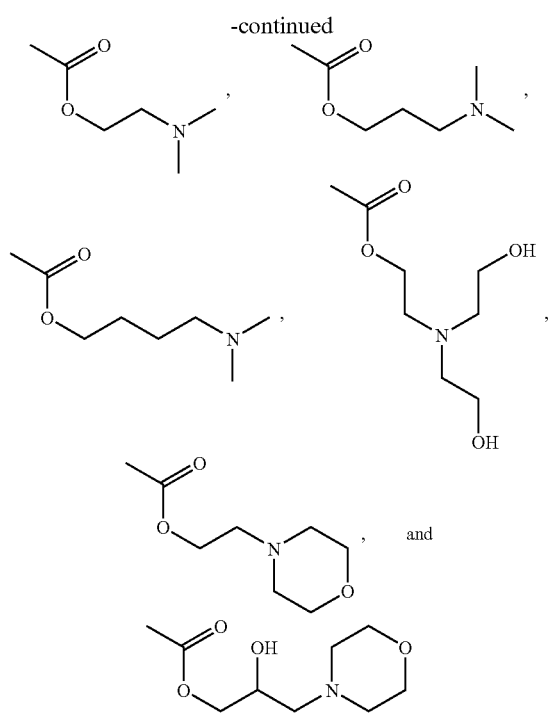

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S4-picolyl thioether; substituted S-methyl derivatives such as hemithio, dithio and aminothio acetals; and others.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The methods of the invention are useful in treating "allergic diseases," which is accomplished in the same way as other immunotherapeutic methods described herein. An "allergen" refers to a substance (antigen) that can induce an allergic or asthmatic response in a susceptible subject. The list of allergens is enormous and can include pollens, insect venoms, animal dander, dust, fungal spores, and drugs (e.g. penicillin).

"Asthma" refers to a disorder of the respiratory system characterized by inflammation, narrowing of the airways and increased reactivity of the airways to inhaled agents. Asthma is frequently, although not exclusively associated with atopic or allergic symptoms.

"Immune-stimulation" or "immune potentiation" refers to the increase in cytokine production from a dendritic cell.

A "subject" or "patient" is meant to describe a human or vertebrate animal including a dog, cat, horse, cow, pig, sheep, goat, chicken, monkey, rat, and mouse.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington: The Science and Practice of Pharmacy," Lippincott Williams and Wilkins, Baltimore, Md. (1995), incorporated herein by reference.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the invention may be administered enterally, orally, parenterally, sublingually, by inhalation spray, rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intramuscular, intraperitoneal, intranasal, subdural, rectal, and the like. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

Effective amounts of the compounds of the invention generally include any amount sufficient to detectably treat viral infections.

Successful treatment of a subject in accordance with the invention may result in the inducement of a reduction or alleviation of symptoms in a subject afflicted with a medical or biological disorder to, for example, halt the further progression of the disorder, or the prevention of the disorder.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be from about 0.1 mg/kg/day to about 1000 mg/kg/day, preferably from about 1 mg/kg/day to about 20 mg/kg/day, which may be administered in one or multiple doses with or without an antigen as described herein.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

While the compounds of the invention can be administered as the sole active pharmaceutical agent, they can also be used in combination with one or more other agents used in the treatment of disorders. Representative agents useful in combination with the compounds of the invention for the treatment of viral infections include, for example, Interferon, Ribavirin, and the like.

When additional active agents are used in combination with the compounds of the present invention, the additional active agents may generally be employed in therapeutic amounts as indicated in the Physicians' Desk Reference (PDR) 57th Edition (2003), PDR/Medical Economics Company, which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

General procedure for the preparation of thiosemicarbazones

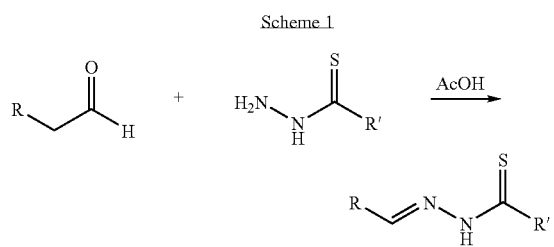

Scheme 1

A solution of aldehyde (1.0 equiv.) and thiosemicarbazide (1.05 equiv.) in acetic acid was stirred overnight. Excess of acetic acid was removed to give a residue, which was washed with ethanol, or purified by preparative-HPLC to give the thiosemicarbazone.

Scheme 2

A solution of aldehyde (1.0 equiv.), thiosemicarbazide (1.05 equiv.) and acetic acid (0.1 equiv.) in methanol was stirred overnight. Methanol was removed to give a residue, which was worked up as in Scheme 1.

Scheme 3

To a solution of {[(1E)-1-aza-2-(4-fluoro-3-nitrophenyl) vinyl]amino}-aminomethane-1-thione in ethanol was added an arylamine (2.1 equiv.). The solution was stirred at room temperature until the starting fluoride disappeared. The solution was purified to the product.

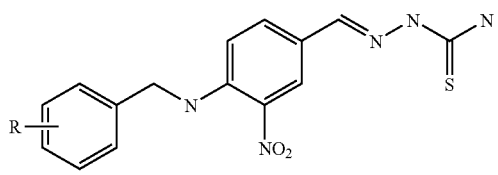

A mixture of 4-(diethylamino)-2-hydroxybenzaldehyde (1 equiv.), benzylic bromide (1.2 equiv.) and powder potassium carbonate in ethanol was stirred at room temperature for 2 days. Ethanol was removed, and the residue was dissolved in ethyl acetate and water. The organic layer was washed with aqueous NaHCO$_3$ and brine, dried over Na2SO4, and concentrated. The residue was purified on silica gel eluting with ethyl acetate/hexane to give 4-(diethylamino)-2-benzoxylic-benzaldehyde.

The aldehydes were converted to thiosemicarbazones according to Scheme 2.

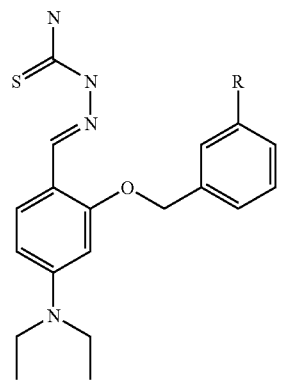

A solution of 3,4-difluorobenzenecarbonitrile (1 equiv.), amine (1.5 equiv.) and DIEA (2 equiv.) in NMP was heated in a Smith Microwave (Personal Chemistry) for 30 minutes. The reaction mixture was purified on silica gel to give 4-substituted 3-fluorobenzenecarbonitrile.

To a solution of nitrile in toluene at −78° C. was added DIBAL-H (1 M in toluene, 1.5 equiv.). The reaction mixture was warmed to rt, and stirred for 16 h, and quenched with methanol/ethyl acetate/brine (1:1:4). After being stirred at rt for 30 min, the solution was extracted with ethyl acetate (3×). The combined organic layers were washed with aqueous NaHCO$_3$, brine and concentrated. The aldehyde was purified on silica gel or directly converted to thiosemicarbazones (Scheme 2).

Scheme 6

A solution of 2,4,5-trifluorobenzenecarbonitrile (1 equiv.) and 4-arylpiperazine (1.2 equiv.) and DIEA (1.2 equiv.) in THF was heated at 80° C. for 2 hours. The mixture was purified on silica gel to give 4-substituted 2,5-difluorobenzenecarbonitrile.

Scheme 7

To an alcohol (1.0 equiv) was added potassium t-butoxide in THF (1 M, 1.1 equiv). After 5 minutes, the solution was added to a solution of 4-N-substituted-2,5-difluorobenzenecarbonitrile (1 equiv.) in THF. The reaction mixture was stirred at rt overnight and quenched with aqueous ammonium chloride. The aqueous layer was extracted with ethyl acetate (3×). The combined organic layers were washed with brine, and concentrated to give a residue, which was purified to give 4-N-substituted-2-O-substituted-5-fluorobenzenecarbonitrile.

4-N-substituted-2-O-substituted-5-fluorobenzenecarbonitrile was reduced with DIBAL-H to give a 4-N-substituted-2-O-substituted-5-fluorobenzaldehyde according to procedure in Scheme 5.

The aldehyde was converted to the corresponding thiosemicarbazone using Scheme 2.

Scheme 8

A solution of 4-N-substituted-2,5-difluorobenzenecarbonitrile (1 equiv.), amine (1.5 equiv.) and DIEA (2 equiv.) in NMP was heated in a Smith Microwave (Personal Chemistry) for 30 minutes. The reaction mixture was purified on silica gel to give 4-N-substituted-2-N-substituted-5-fluorobenzenecarbonitrile.

4-N-substituted-2-N-substituted-5-fluorobenzenecarbonitrile was reduced with DIBAL-H according to procedure described in Scheme 5 to give 4-N-substituted-2-N-substituted-5-fluorobenzaldehyde.

Preparation of amino{3-[5-(3-chlorophenyl)(2-furyl)](2-pyrazolinyl)} methane-1-thione

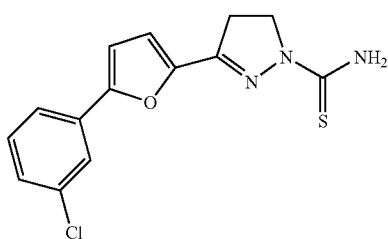

To a solution of 5-(3-chlorophenyl)furan-2-carbaldehyde (1.0 equiv.) in THF at 0° C. was added MeMgBr in ether (3.0 equiv.) and stirred for 45 min. The reaction was quenched with water, diluted with ether and filtered through Celite. The organic layer was separated and washed with brine, dried over $MgSO_4$, and concentrated to give the 1-[5-(3-chlorophenyl)-2-furyl]ethan-1-ol.

To a solution of secondary alcohol (1.0 equiv.) in $CH_2Cl_2$ was added $MnO_2$ (10 equiv.). The reaction was stirred overnight, filtered through Celite, and concentrated to give 1-[5-(3-chlorophenyl)-2-furyl]ethan-1-one.

To a mixture of ketone (1.0 equiv.), paraformaldehyde (2.0 equiv.), and dimethylamine hydrochloride (2.0 equiv) and molecular sieves in ethanol was added concentrated hydrochloric acid (cat.). The reaction was refluxed overnight under nitrogen and the concentrated. A few drops of HCl was added, and the mixture was worked up with DCM and water. The organic layer was discarded. The aqueous layer was adjusted to basic and extracted with DCM (3×). The organic layer was washed with brine, dried over $MgSO_4$, and concentrated to yield 3-(dimethylamino)-1-[5-(3-chlorophenyl)(2-furyl)]propan-1-one.

Thiosemicarbazide (1.0 equiv.) was dissolved in MeOH upon heating under nitrogen. Aqueous sodium hydroxide (6 M, 9.0 equiv.) was added to the reaction. A methanol solution of 3-(dimethylamino)-1-[5-(3-chlorophenyl)(2-furyl)]propan-1-one (1.0 equiv) was then added dropwise to the reaction mixture. The solvent was removed and the residue was dissolved in DCM and washed with water, brine, dried over $MgSO_4$, and concentrated. The final compound was purified by preparative-HPLC to give amino{3-[5-(3-chlorophenyl)(2-furyl)](2-pyrazolinyl)}methane-1-thione; LC/MS m/z 306.2 (MH+); Rt=3.06 minutes.

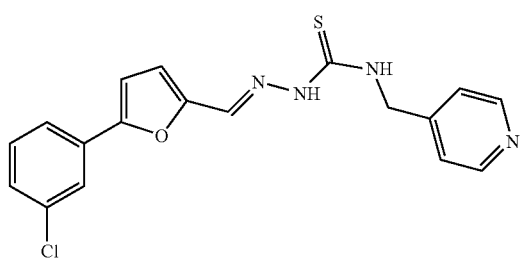

To a solution of 4-pyridylmethylamine (1.0 equiv.) and triethylamine (2.0 equiv.) in $CHCl_3$ was added $CS_2$ (1.0 equiv.)) and stirred overnight. The reaction was cooled to 0° C. and ethyl chloroformate (1.0 equiv.) was added dropwise. The reaction was stirred for 15 min at 0° C. and then stirred at room temperature for 2 hrs followed by addition of (tert-butyl)oxycarbohydrazide (1.2 equiv.). After stirring for an addition hour the mixture was washed with aqueous citric acid (5%), saturated $NaHCO_3$, brine, dried over $MgSO_4$, and concentrated. The desired Boc protected thiosemicarbazide was purified using column chromatography.

To a solution of Boc protected thiosemicarbazide (1.0 equiv.) dissolved in DCM was added HCl in dioxane (2M, 8.3 equiv.) and stirred for 15 min. MeOH is then added to dissolve the precipitate, followed by addition of the furfural, and small amount of acetic acid (0.5 mL). The mixture is stirred overnight and the solvents are removed to give a residue purified by preparative-HPLC to give the thiosemicarbazone.

Synthesis of 4-[4-(4-methylpiperazin-1-yl)phenoxymethyl]benzaldehyde

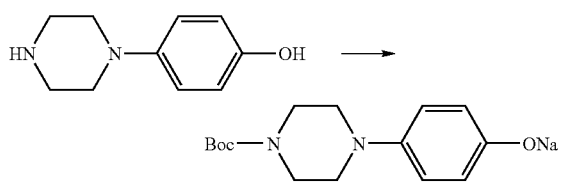

To a solution of 4-piperazin-1-yl phenol (1 equivalent) in $CHCl_3$, cooled to 0° C., was added di-t-butyl dicarbonate (1 equivalent) in $CHCl_3$ drop-wise. The solution was stirred at 0° C. for 1 hour before removing from the cold bath and stirring at ambient temperatures for 18 hours. The organic solution was washed aqueous $NaHCO_3$ and brine dried over $MgSO_4$ and concentrated the crude material was used without purification.

A solution of the resulting 4-(1-BOC-piperazin-4-yl)phenol (1 equivalent) in dry $CH_3CN$ was slowly added drop-wise to a slurry of NaH (1 equivalent) in dry $CH_3CN$ at room temperature under $N_2$. The slurry was stirred at room temperature for 2 hours before the solids were filtered and washed with $Et_2O$.

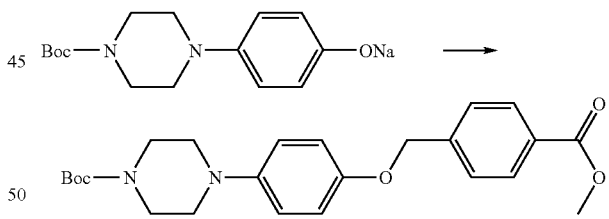

Sodium 4-(1-BOC-piperazin-4-yl)phenoxide (1 equivalent) and methyl 4-bromomethylbenzoate (1 equivalent) were combined in dry acetone and heated to reflux at 60° C. for 18 hours. The slurry was filtered and the filtrate was then concentrated to provide the crude methyl 4-[4-(1-BOC-piperazin-4-yl)phenoxymethyl]benzoate, which was used without purification.

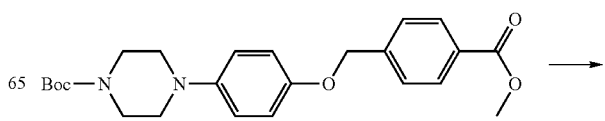

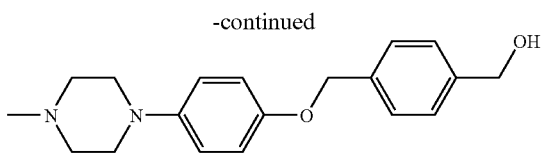

To a slurry of LiAlH$_4$ (4 equivalents) in dry THF, cooled to 0° C. under N$_2$, was slowly added drop-wise a solution of methyl 4-[4-(1-BOC-piperazin-4-yl)phenoxymethyl]benzoate (1 equivalent) in dry THF. Once the addition was complete, the slurry was heated to reflux at 80° C. for 1 hour. The slurry was subsequently cooled to 0° C. and treated with water, 10% aq. NaOH and with water again. The resulting solids were filtered, and the filtrate was diluted with chloroform, washed with brine, dried over MgSO$_4$ and concentrated, providing the crude 4-[4-(4-methylpiperazin-1-yl)phenoxymethyl]benzyl alcohol which was used without purification.

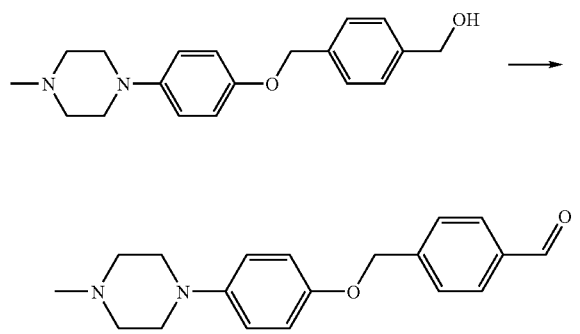

To a solution of DMSO (2.6 equivalents) in dry DCM, cooled to −78° C. under N$_2$ was added oxalyl chloride (1.1 equivalents) in DCM drop-wise. The solution was stirred at −78° C. for 5 minutes before a solution of 4-[4-(4-methylpiperazin-1-yl)phenoxymethyl]benzyl alcohol (1 equivalent) in DCM was added drop-wise, and allowed to stir at −78° C. for another 30 minutes. Triethylamine (2.5 equivalents) was slowly dripped in before allowing the solution to reach ambient temperatures. The solution was washed with aqueous NaHCO$_3$ and brine, dried over MgSO$_4$ and concentrated to provide the crude 4-[4-(4-methylpiperazin-1-yl)phenoxymethyl]benzaldehyde which was converted to thiosemicarbazones according to Scheme 2.

Characterization and Purification Methods

Referring to the examples that follow, compounds of the present invention were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburg, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses are reported as those of the protonated parent ions.

GCMS analysis was performed on a Hewlet Packard instrument (HP6890 Series gas chromatograph with a Mass Selective Detector 5973; injector volume: 1 μL; initial column temperature: 50° C.; final column temperature: 250° C.; ramp time: 20 minutes; gas flow rate: 1 mL/min; column: 5% phenyl methyl siloxane, Model #HP 190915-443, dimensions: 30.0 m×25 m×0.25 m).

Nuclear magnetic resonance (NMR) analysis was performed with a Varian 300 Mhz NMR (Palo Alto, Calif.). The spectral reference was either TMS or the known chemical shift of the solvent. Some compound samples were run at elevated temperatures (i.e. 75° C.) to promote increased sample solubility.

The purity of some of the invention compounds was assessed by elemental analysis (Desert Analytics, Tuscon, Ariz.)

Melting points were determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Compounds of the present invention can be readily synthesized using the methods described herein, or other methods, which are well known in the art. The precursors are readily recognizable by one skilled in the art and are commercially available from Aldrich (Milwaukee, Wis.), Acros Organics (Pittsburgh, Pa.), Biosynth International (Naperville, Ill.), Asymchem International, Inc. (Durham, N.C.) Maybridge Chemical Company Ltd. (Cornwall), and/or UK Peakdale Molecular (High Peak, UK).

The compounds were named using ACD/Name v. 5.04, 2001 and Nomenclator (v. 6.0) from ChemInovation Software, Inc.

The foregoing may be better understood by reference to the following examples, which are presented for illustration and not to limit the scope of the inventive concepts.

EXAMPLES

TABLE 1

| Example | Name | Structure | LC/MS (m/z) MH+ |
|---|---|---|---|
| 1 | (1E)-1-(1,1'-biphenyl-4-yl)ethan-1-one thiosemicarbazone | 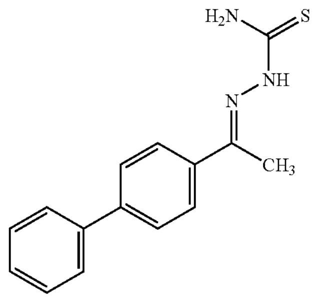 | 270.4 |
| 2 | 5-(4-chlorophenyl)furan-2-carbaldehyde N-prop-2-enylthiosemicarbazone | 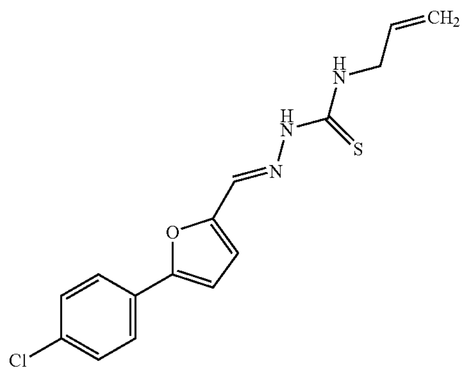 | 320.8 |
| 3 | 5-(2,4-dichlorophenyl)furan-2-carbaldehyde N-prop-2-enylthiosemicarbazone | 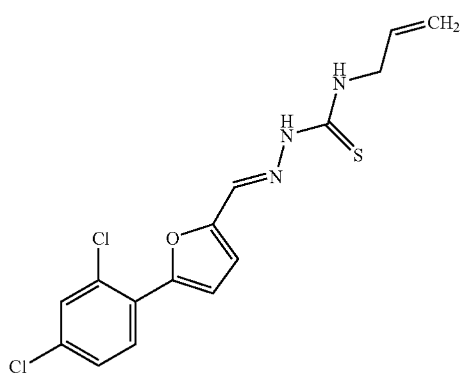 | 355.3 |
| 4 | 5-(2,5-dichlorophenyl)furan-2-carbaldehyde N-prop-2-enylthiosemicarbazone | 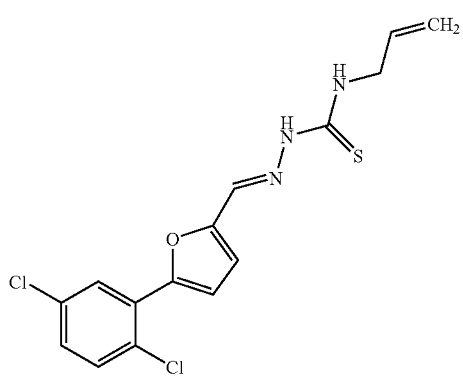 | 355.3 |

TABLE 1-continued

| Example | Name | Structure | LC/MS (m/z) MH+ |
|---|---|---|---|
| 5 | (1E)-1-(2-phenyl-1,3-thiazol-4-yl)ethan-1-one thiosemicarbazone | 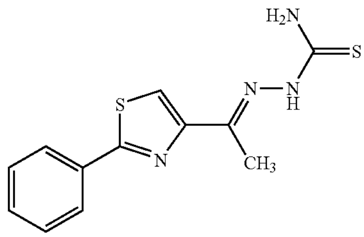 | 277.4 |
| 6 | 1-[3-(trifluoromethyl)phenyl]-1H-pyrrole-2-carbaldehyde thiosemicarbazone | 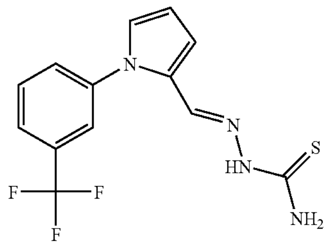 | 313.3 |
| 7 | 3-[(phenylmethyl)oxy]benzaldehyde thiosemicarbazone | 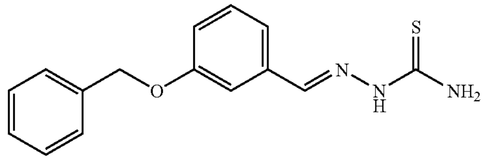 | 286.4 |
| 8 | 4-[(phenylmethyl)oxy]benzaldehyde thiosemicarbazone | 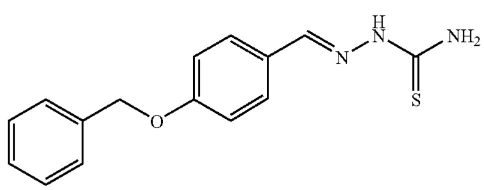 | 286.4 |
| 9 | 5-[4-(methyloxy)phenyl]furan-2-carbaldehyde thiosemicarbazone | 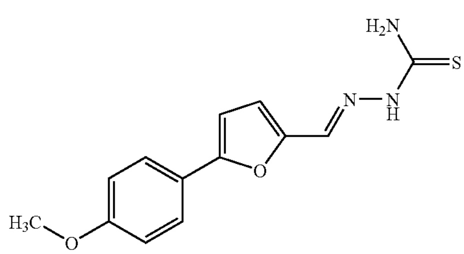 | 276.3 |
| 10 | 5-(4-fluorophenyl)furan-2-carbaldehyde thiosemicarbazone | 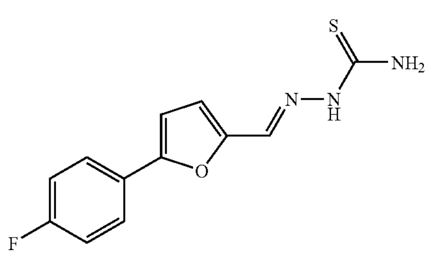 | 264.3 |

TABLE 1-continued

| Example | Name | Structure | LC/MS (m/z) MH+ |
|---|---|---|---|
| 11 | 5-(4-chlorophenyl)furan-2-carbaldehyde thiosemicarbazone | 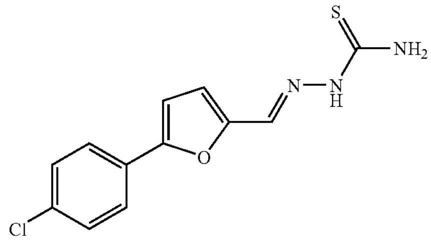 | 280.8 |
| 12 | 5-(3-chlorophenyl)furan-2-carbaldehyde thiosemicarbazone | 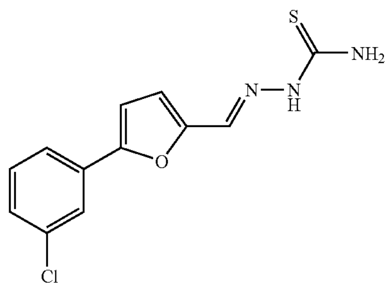 | 280.8 |
| 13 | 3H-[1,4]benzoxathiino[3,2-e]indole-1-carbaldehyde thiosemicarbazone 11,11-dioxide | 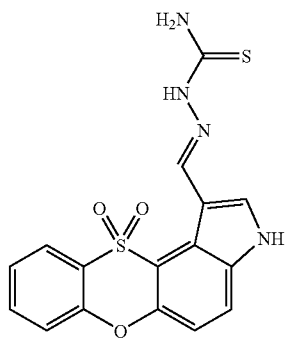 | 373.4 |
| 14 | 3-chloro-5-(methyloxy)-4-({2-[(4-methylphenyl)oxy]ethyl}oxy)benzaldehyde N-methylthiosemicarbazone | 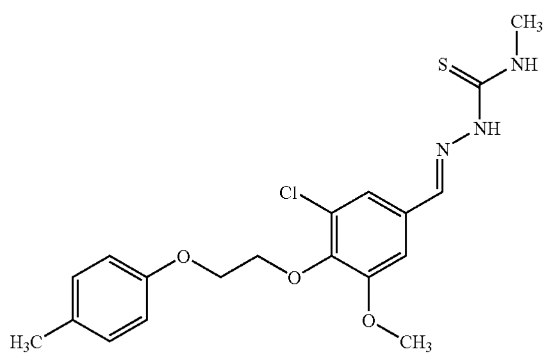 | 408.9 |
| 15 | 5-[5-chloro-2-(methyloxy)phenyl]furan-2-carbaldehyde thiosemicarbazone | 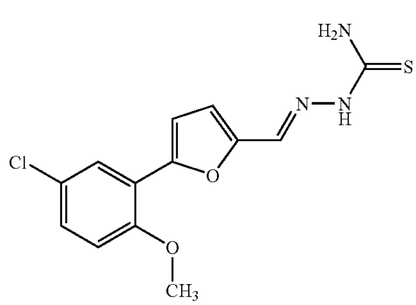 | 310.8 |

TABLE 1-continued

| Example | Name | Structure | LC/MS (m/z) MH+ |
|---|---|---|---|
| 16 | 5-(4-methylphenyl)furan-2-carbaldehyde thiosemicarbazone | 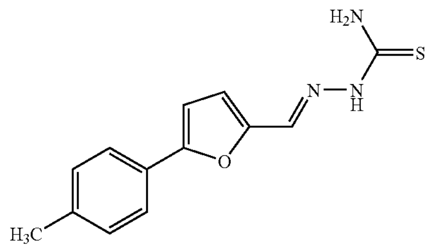 | 260.3 |
| 17 | 1H-indole-3-carbaldehyde thiosemicarbazone | 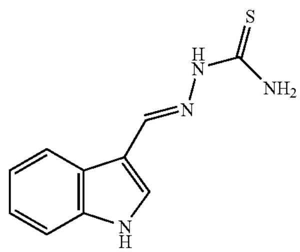 | 219.3 |
| 18 | 1-methyl-1H-indole-3-carbaldehyde thiosemicarbazone | 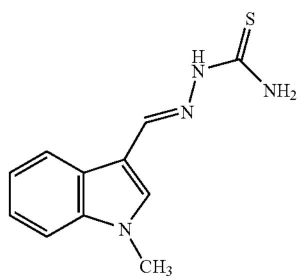 | 233.3 |
| 19 | methyl 3-{(E)-[(aminocarbonothioyl)hydrazono]methyl}-1H-indole-6-carboxylate | 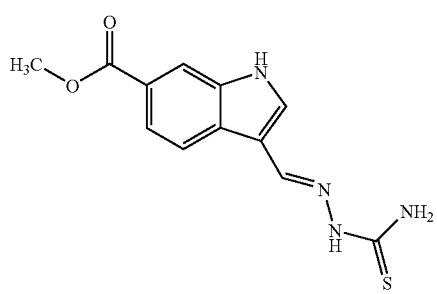 | 277.3 |
| 20 | 1-[(4-chlorophenyl)methyl]-1H-imidazole-2-carbaldehyde thiosemicarbazone | 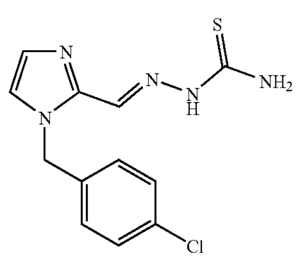 | 294.8 |

TABLE 1-continued

| Example | Name | Structure | LC/MS (m/z) MH+ |
|---|---|---|---|
| 21 | 5-(4-nitrophenyl)furan-2-carbaldehyde thiosemicarbazone | 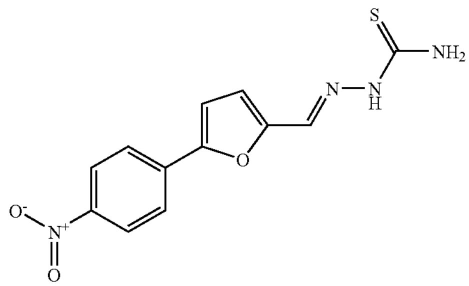 | 291.3 |
| 22 | 5-(4-methyl-2-nitrophenyl)furan-2-carbaldehyde thiosemicarbazone | 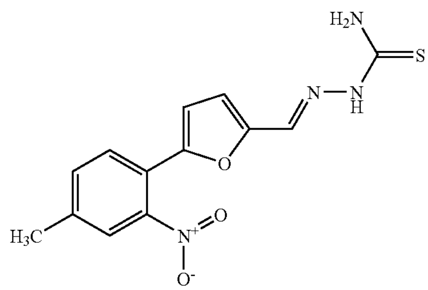 | 305.3 |
| 23 | methyl 4-(5-{(E)-[(aminocarbonothioyl)hydrazono]methyl}furan-2-yl)-2-chlorobenzoate | 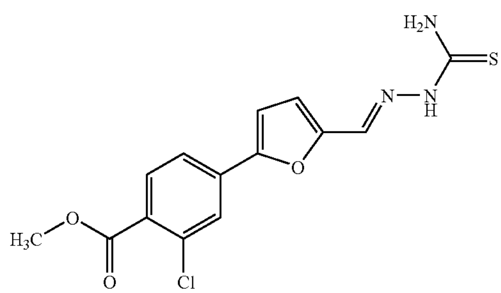 | 338.8 |
| 24 | 5-phenylfuran-2-carbaldehyde thiosemicarbazone | 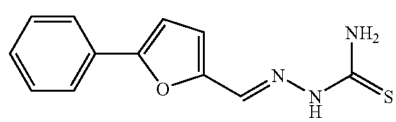 | 246.3 |
| 25 | 2-methyl-5-(methyloxy)-3-phenyl-1-benzofuran-6-carbaldehyde thiosemicarbazone | 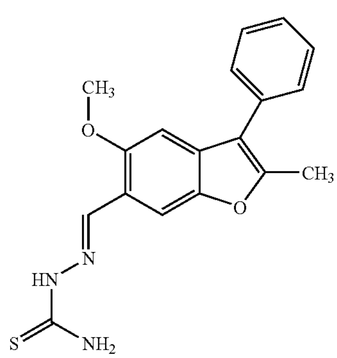 | 340.4 |

TABLE 1-continued

| Example | Name | Structure | LC/MS (m/z) MH+ |
|---|---|---|---|
| 26 | 9-ethyl-9H-carbazole-3-carbaldehyde thiosemicarbazone | 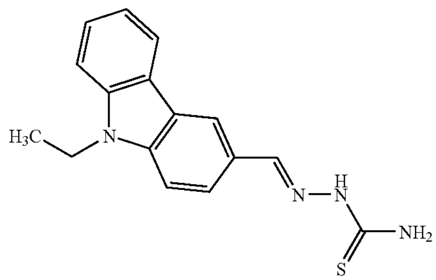 | 297.4 |
| 27 | 2-[(phenylmethyl)oxy] benzaldehyde thiosemicarbazone | 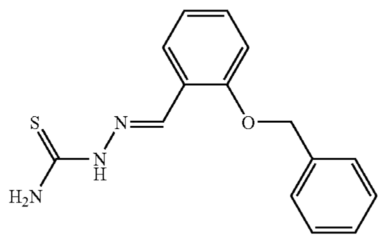 | 286.4 |
| 28 | 2-{[(2,4-dichlorophenyl)methyl] oxy}-3-(methyloxy) benzaldehyde thiosemicarbazone | 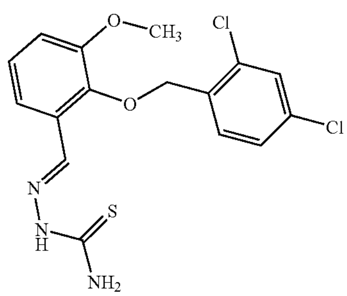 | 385.3 |
| 29 | 2-{[(4-chlorophenyl)methyl] oxy}-4-(diethylamino) benzaldehyde thiosemicarbazone | 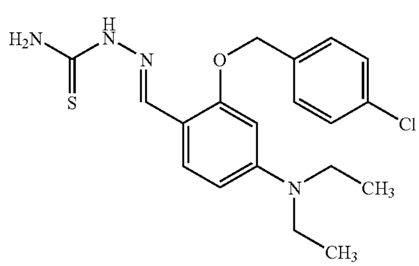 | 391.9 |
| 30 | 3-(methyloxy)-4-{[2-nitro-4-(trifluoromethyl)phenyl]oxy} benzaldehyde thiosemicarbazone | 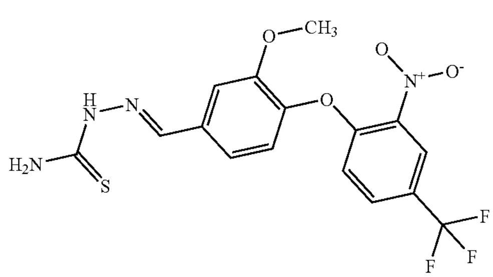 | 415.4 |

TABLE 1-continued

| Example | Name | Structure | LC/MS (m/z) MH+ |
|---|---|---|---|
| 31 | 5-(3,5-dichlorophenyl)furan-2-carbaldehyde thiosemicarbazone | 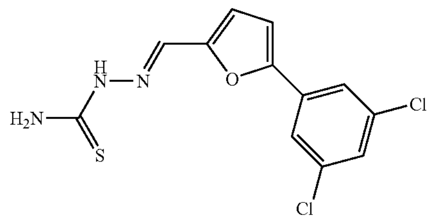 | 315.2 |
| 32 | 1-[(3,4-dichlorophenyl)methyl]-3-phenyl-1H-pyrazole-4-carbaldehyde thiosemicarbazone | 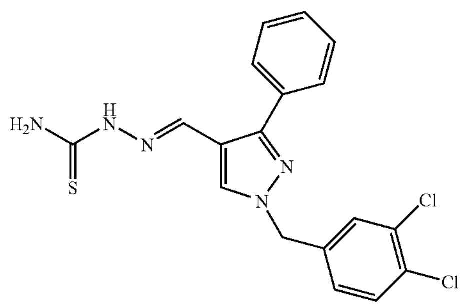 | 405.3 |
| 33 | 5-[3-(trifluoromethyl)phenyl]furan-2-carbaldehyde thiosemicarbazone | 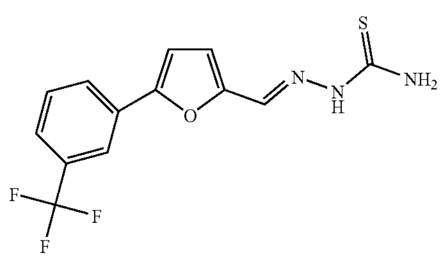 | 314.3 |
| 34 | 1-(4-fluorophenyl)-2,5-dimethyl-1H-pyrrole-3-carbaldehyde thiosemicarbazone | 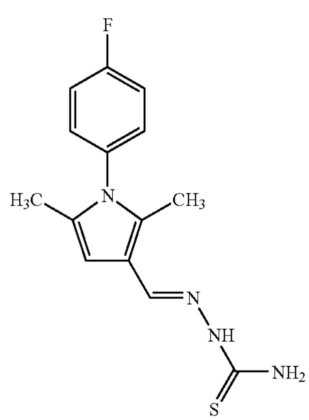 | 291.4 |

TABLE 1-continued

| Example | Name | Structure | LC/MS (m/z) MH+ |
|---|---|---|---|
| 35 | 1-(4-chlorophenyl)-2,5-dimethyl-1H-pyrrole-3-carbaldehyde thiosemicarbazone | 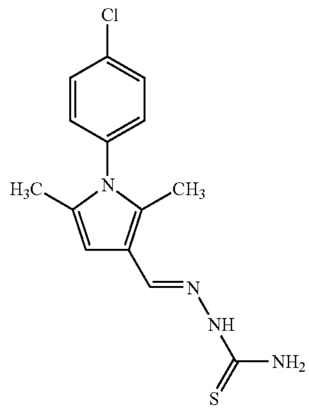 | 307.8 |
| 36 | 2,5-dimethyl-1-(4-methylphenyl)-1H-pyrrole-3-carbaldehyde thiosemicarbazone | 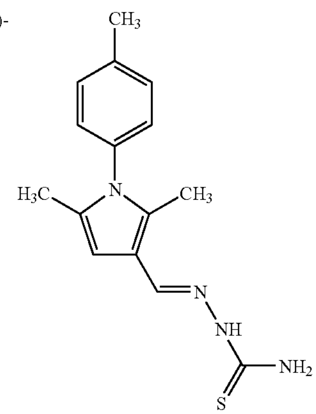 | 287.4 |
| 37 | 1-(3-chlorophenyl)-2,5-dimethyl-1H-pyrrole-3-carbaldehyde thiosemicarbazone | 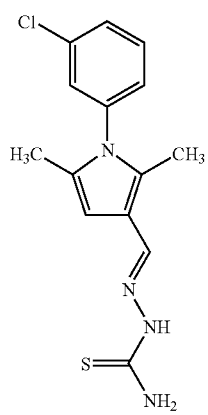 | 307.8 |
| 38 | 4-{[(2-chlorophenyl)methyl]oxy}-3-(methyloxy) benzaldehyde thiosemicarbazone | 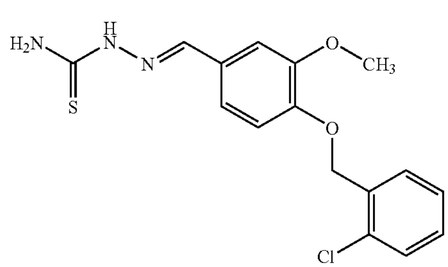 | 350.8 |

TABLE 1-continued

| Example | Name | Structure | LC/MS (m/z) MH+ |
|---|---|---|---|
| 39 | 3-bromo-4-{[(2-fluorophenyl)methyl]oxy}-5-methyloxy)benzaldehyde thiosemicarbazone | 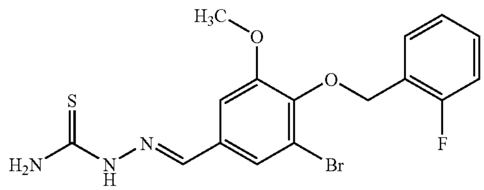 | 413.3 |
| 40 | 4-(dimethylamino) benzaldehyde thiosemicarbazone | 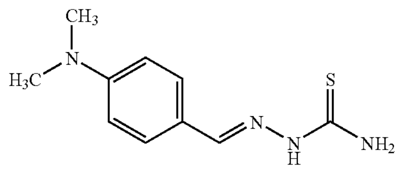 | 223.3 |
| 41 | quinoline-2-carbaldehyde thiosemicarbazone | 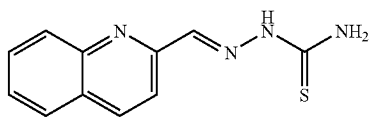 | 231.3 |
| 42 | 3-{(E)-[2-(aminocarbonothioyl) hydrazono]methyl}phenyl 3-chloro-1-benzothiophene-2-carboxylate | 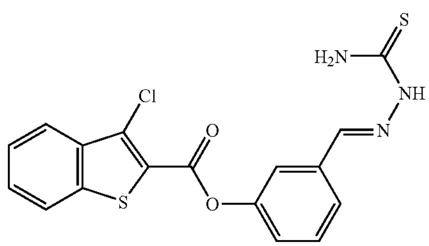 | 390.9 |
| 43 | 1-(phenylmethyl)-1H-benzimidazole-2-carbaldehyde thiosemicarbazone | 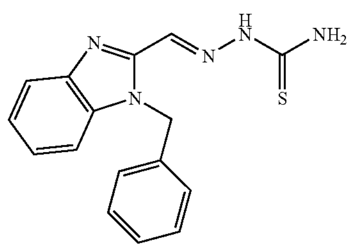 | 310.4 |
| 44 | 1-[(2,4-dichlorophenyl)methyl]-3-phenyl-1H-pyrazole-4-carbaldehyde thiosemicarbazone | 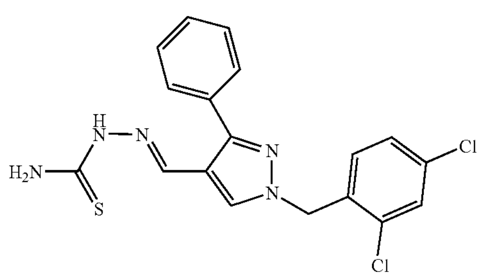 | 405.3 |
| 45 | 2,5-dimethyl-1-(3-nitrophenyl)-1H-pyrrole-3-carbaldehyde thiosemicarbazone | 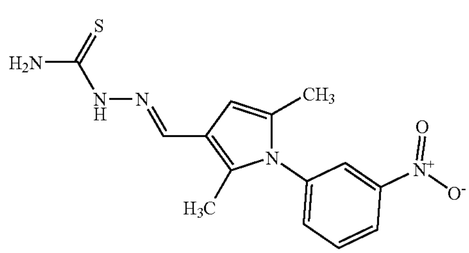 | 318.4 |

TABLE 1-continued

| Example | Name | Structure | LC/MS (m/z) MH+ |
|---|---|---|---|
| 46 | 1-[4-(dimethylamino)phenyl]-2,5-dimethyl-1H-pyrrole-3-carbaldehyde thiosemicarbazone | 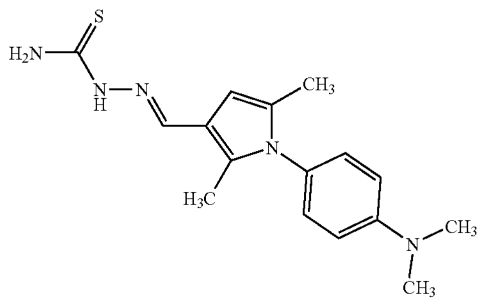 | 316.4 |
| 47 | (1Z)-1-(3-{[(2-methylphenyl)methyl]oxy}phenyl)ethan-1-one thiosemicarbazone | 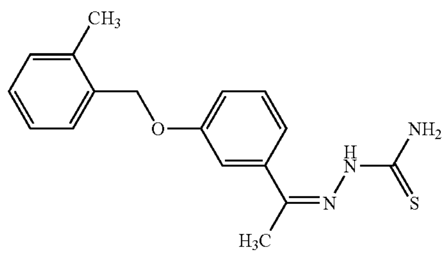 | 314.4 |
| 48 | 5-(2,5-dichlorophenyl)furan-2-carbaldehyde N-(1,1-dioxidotetrahydrothien-3-yl)thiosemicarbazone | 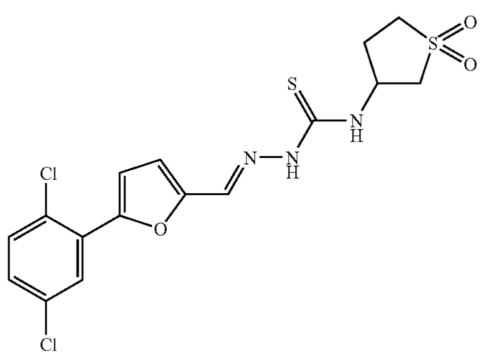 | 433.4 |
| 49 | 4-{[(2,4-dichlorophenyl)methyl]oxy}benzaldehyde thiosemicarbazone | 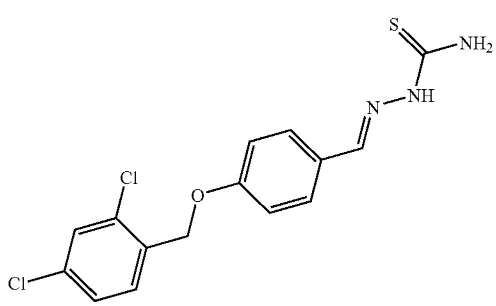 | 355.3 |
| 50 | 1-[(4-chlorophenyl)methyl]-5-methyl-1H-imidazole-4-carbaldehyde thiosemicarbazone | 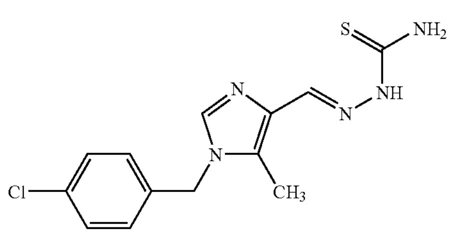 | 308.8 |

TABLE 1-continued

| Example | Name | Structure | LC/MS (m/z) MH+ |
|---|---|---|---|
| 51 | 4-(diethylamino)-2-hydroxybenzaldehyde thiosemicarbazone | 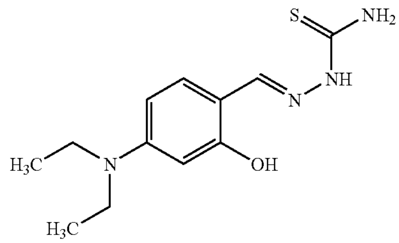 | 267.4 |
| 52 | 4-(diethylamino)-2-{[(4-fluorophenyl)methyl]oxy}benzaldehyde thiosemicarbazone | 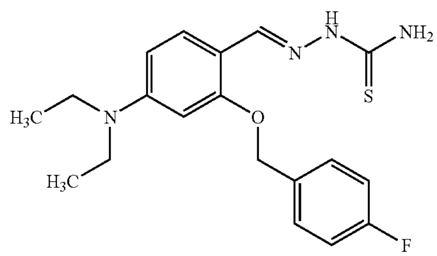 | 375.5 |
| 53 | 4-(diethylamino)-2-({[3-methyloxy)phenyl]methyl}oxy)benzaldehyde thiosemicarbazone | 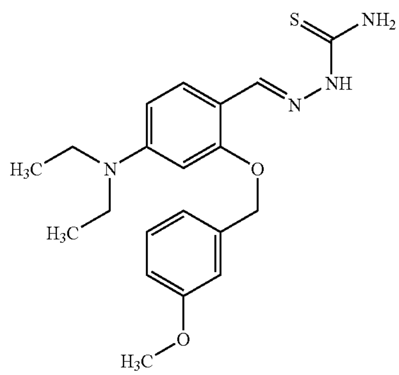 | 387.5 |
| 54 | 4-(diethylamino)-2-{[(3-methylphenyl)methyl]oxy}benzaldehyde thiosemicarbazone | 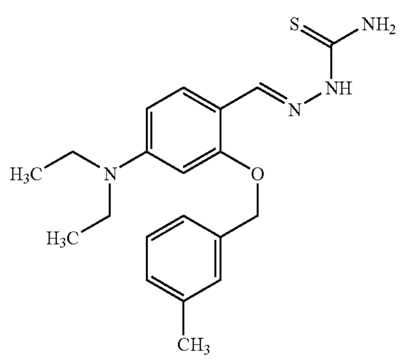 | 371.5 |
| 55 | 2-{[(2-bromophenyl)methyl]oxy}-4-(diethylamino)benzaldehyde thiosemicarbazone | 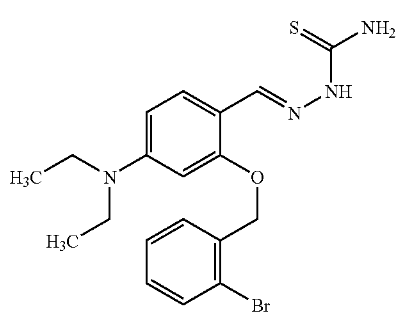 | 436.4 |

TABLE 1-continued

| Example | Name | Structure | LC/MS (m/z) MH+ |
|---|---|---|---|
| 56 | 4-(diethylamino)-2-{[(3,5-difluorophenyl)methyl]oxy}benzaldehyde thiosemicarbazone | 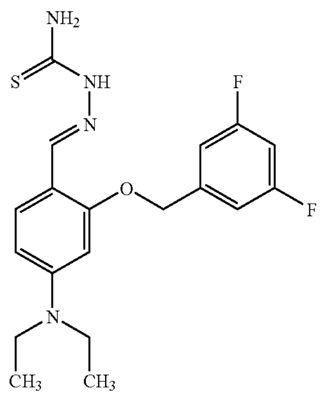 | 393.5 |
| 57 | 4-(diethylamino)-2-{[(3,5-difluorophenyl)methyl]oxy)benzaldehyde thiosemicarbazone | 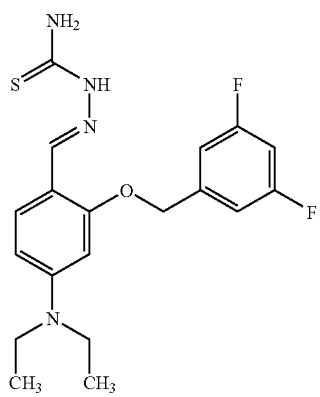 | 393.5 |
| 58 | 2-{[(2,6-dichlorophenyl)methyl]oxy}-4-(diethylamino)benzaldehyde thiosemicarbazone | 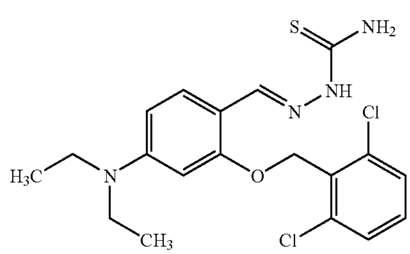 | 426.4 |
| 59 | 2-{[(3-bromophenyl)methyl]oxy}-4-(diethylamino)benzaldehyde thiosemicarbazone | 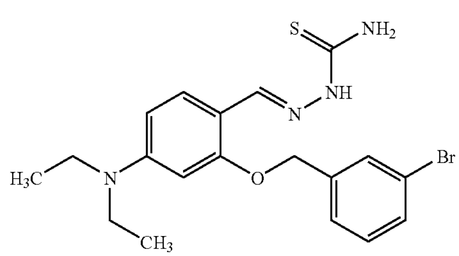 | 436.4 |

TABLE 1-continued

| Example | Name | Structure | LC/MS (m/z) MH+ |
|---|---|---|---|
| 60 | 4-{(diethylamino)-2-[({4-[(trifluoromethyl)oxy]phenyl}methyl)oxy]benzaldehyde thiosemicarbazone | 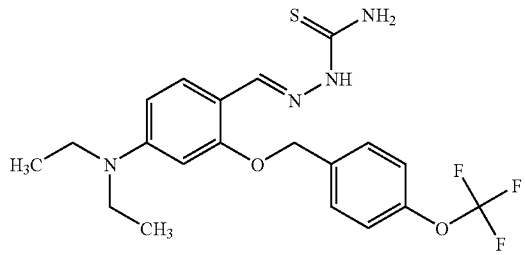 | 441.5 |
| 61 | 3-nitro-4-[(pyridin-2-ylmethyl)amino]benzaldehyde thiosemicarbazone | 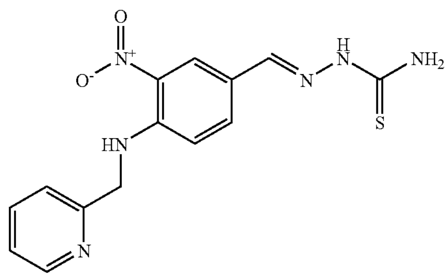 | 331.4 |
| 62 | 3-nitro-4-[(pyridin-3-ylmethyl)amino]benzaldehyde thiosemicarbazone | 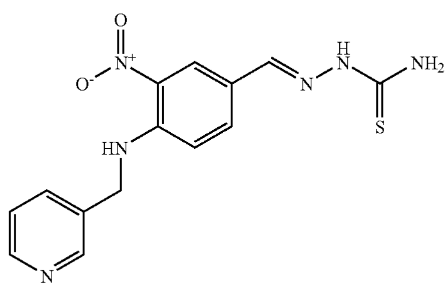 | 331.4 |
| 63 | 3-nitro-4-[(2-pyridin-2-ylethyl)amino]benzaldehyde thiosemicarbazone | 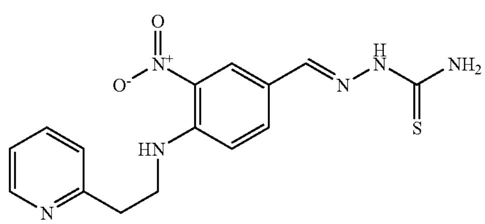 | 345.4 |
| 64 | 3-nitro-4-[(2-pyridin-3-ylethyl)amino]benzaldehyde thiosemicarbazone | 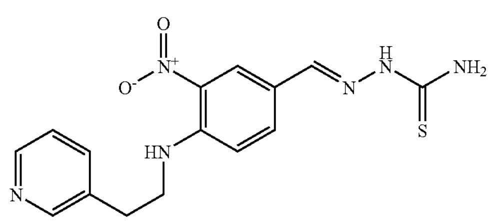 | 345.4 |
| 65 | 3-nitro-4-[(2-pyridin-4-ylethyl)amino]benzaldehyde thiosemicarbazone | 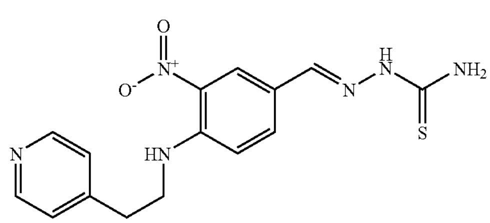 | 345.4 |

TABLE 1-continued

| Example | Name | Structure | LC/MS (m/z) MH+ |
|---|---|---|---|
| 66 | 4-{[(4-chlorophenyl)methyl]amino}-3-nitrobenzaldehyde thiosemicarbazone | 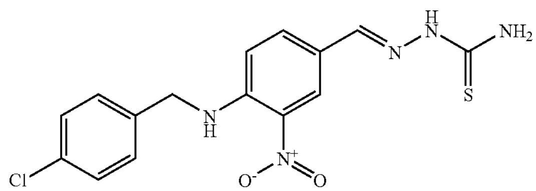 | 364.8 |
| 67 | 4-{[(3-chlorophenyl)methyl]amino}-3-nitrobenzaldehyde thiosemicarbazone | 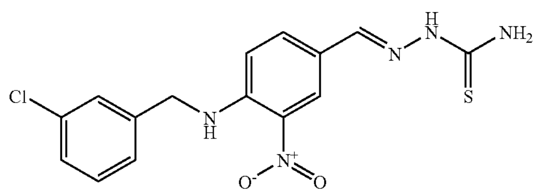 | 364.8 |
| 68 | 3-nitro-4-[(pyridin-4-ylmethyl)amino]benzaldehyde thiosemicarbazone | 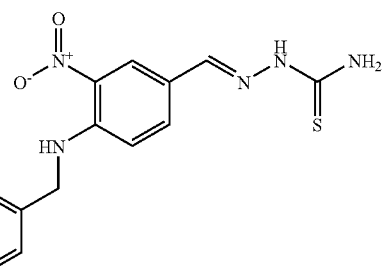 | 331.4 |
| 69 | 4-({[3-(4-methylpiperazin-1-yl)phenyl]oxy}methyl)benzaldehyde thiosemicarbazone | 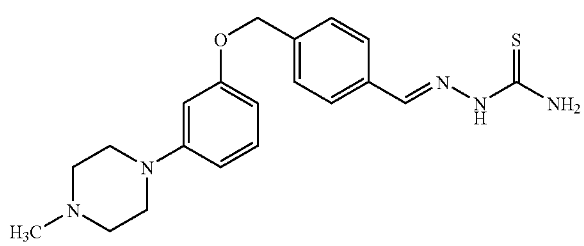 | 384.5 |
| 70 | 3-({[3-(4-methylpiperazin-1-yl)phenyl]oxy}methyl)benzaldehyde thiosemicarbazone | 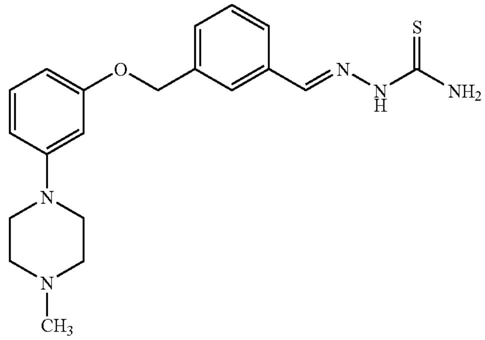 | 384.5 |

TABLE 1-continued

| Example | Name | Structure | LC/MS (m/z) MH+ |
|---|---|---|---|
| 71 | 3-({[4-(4-methylpiperazin-1-yl)phenyl]oxy}methyl)benzaldehyde thiosemicarbazone | 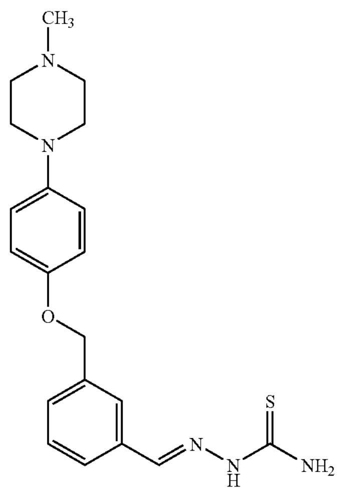 | 384.5 |
| 72 | 5-nitro-2-[(2-pyridin-3-ylethyl)amino]benzaldehyde thiosemicarbazone | 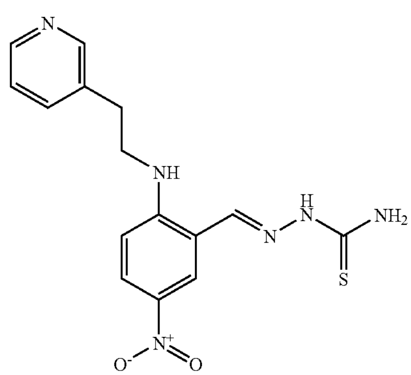 | 345.4 |
| 73 | 5-nitro-2-[(2-pyridin-4-ylethyl)amino]benzaldehyde thiosemicarbazone | 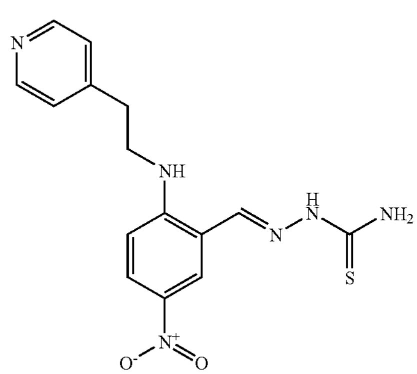 | 345.4 |

TABLE 1-continued

| Example | Name | Structure | LC/MS (m/z) MH+ |
|---|---|---|---|
| 74 | 4-{[(4-fluorophenyl)methyl]amino}-5-nitrobenzaldehyde thiosemicarbazone | 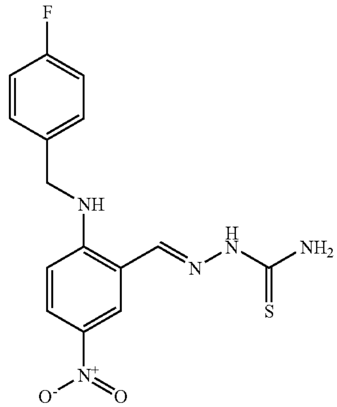 | 348.4 |
| 75 | 2-{]2-(3-chlorophenyl)methyl]amino}-5-nitrobenzaldehyde thiosemicarbazone | 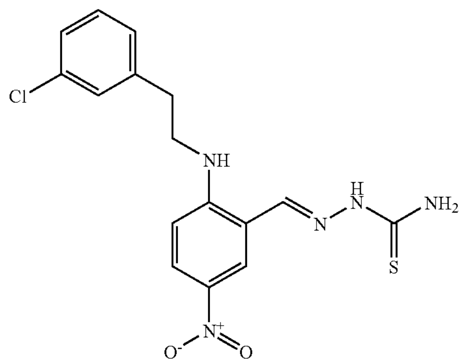 | 378.9 |
| 76 | 2-{[2-(4-chlorophenyl)ethyl]amino}-5-nitrobenzaldehyde thiosemicarbazone | 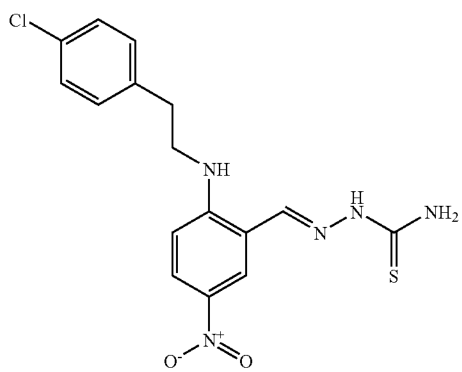 | 378.9 |
| 77 | 2-{[(2,4-dichlorophenyl)methyl]amino}-5-nitrobenzaldehyde thiosemicarbazone | 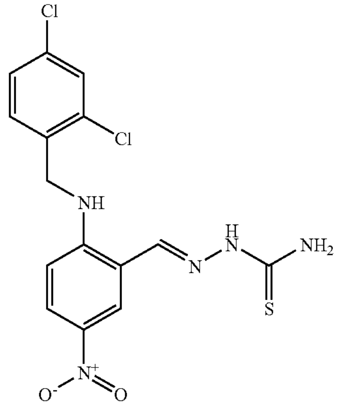 | 399.3 |

TABLE 1-continued

| Example | Name | Structure | LC/MS (m/z) MH+ |
|---|---|---|---|
| 78 | 2-{[2-(2,4-dichlorophenyl)ethyl]amino}-5-nitrobenzaldehyde thiosemicarbazone | 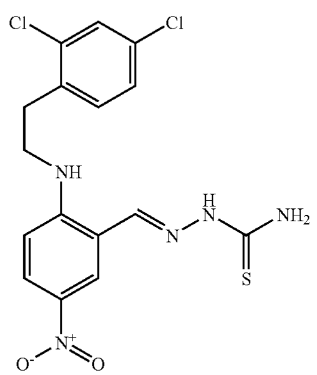 | 413.3 |
| 79 | 2-({[4-fluoro-2-(trifluoromethyl)phenyl]methyl}amino)-5-nitrobenzaldehyde thiosemicarbazone | 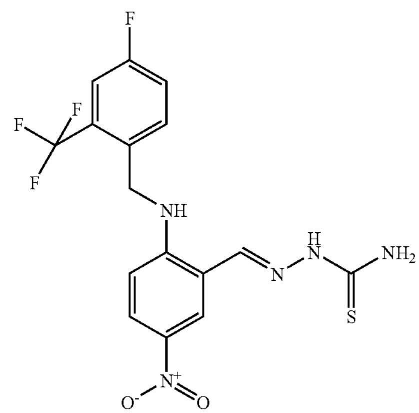 | 416.4 |
| 80 | 4-(3-chlorophenyl)furan-2-carbaldehyde N-methylthiosemicarbazone | 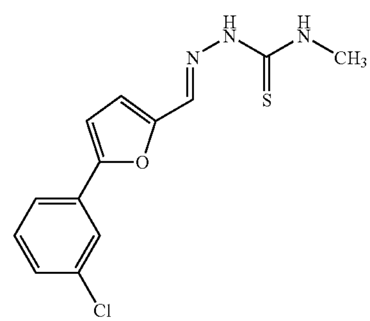 | 294.8 |
| 81 | 5-(3-chlorophenyl)furan-2-carbaldehyde N-(pyridin-3-ylmethyl)thiosemicarbazone | 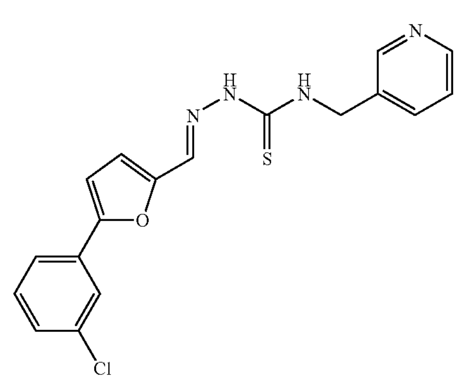 | 371.9 |

TABLE 1-continued

| Example | Name | Structure | LC/MS (m/z) MH+ |
|---|---|---|---|
| 82 | 5-(3-chlorophenyl)furan-2-carbaldehyde N-(2-morpholin-4-ylethyl)thiosemicarbazone | 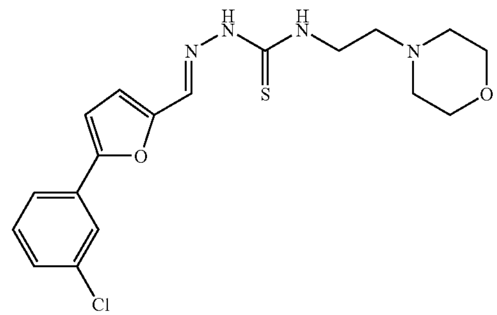 | 393.9 |
| 83 | 4-(diethylamino)-2-{[(4-fluorophenyl)methyl]oxy)benzaldehyde N-methylthiosemicarbazone | 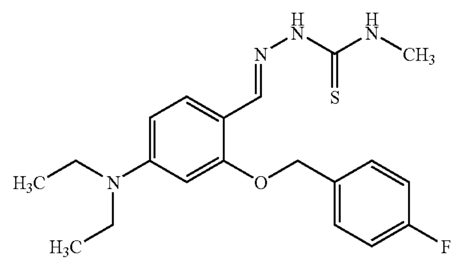 | 389.5 |
| 84 | 4-{[(4-fluorophenyl)methyl]amino}-3-nitrobenzaldehyde thiosemicarbazone | 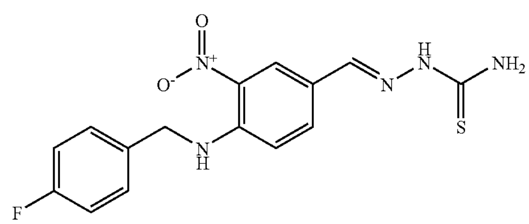 | 348.4 |
| 85 | 4-[4-(3-chlorophenyl)piperazin-1-yl]-3-nitrobenzaldehyde thiosemicarbazone | 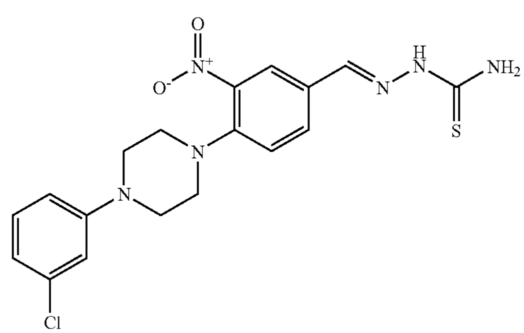 | 419.9 |
| 86 | 4-{[2-(3-chlorophenyl)ethyl]amino}-3-nitrobenzaldehyde thiosemicarbazone | 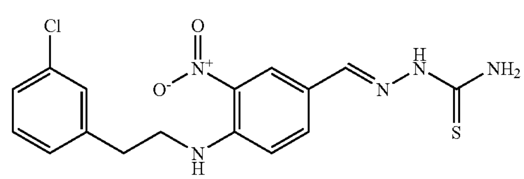 | 378.9 |
| 87 | 4-{[2-(4-chlorophenyl)ethyl]amino}-3-nitrobenzaldehyde thiosemicarbazone | 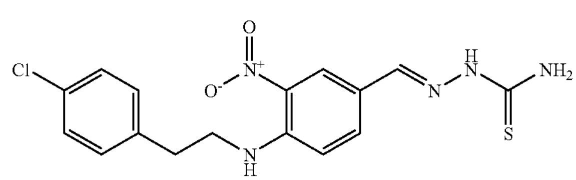 | 378.9 |

TABLE 1-continued

| Example | Name | Structure | LC/MS (m/z) MH+ |
|---|---|---|---|
| 88 | 4-{[(2,4-dichlorophenyl)methyl]amino}-3-nitrobenzaldehyde thiosemicarbazone | 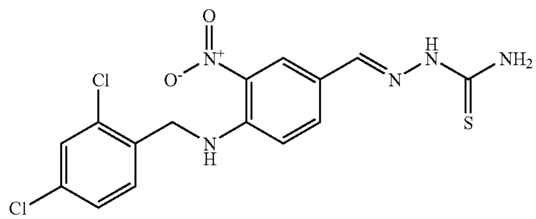 | 399.3 |
| 89 | 4-{[(3,4-dichlorophenyl)methyl]amino}-3-nitrobenzaldehyde thiosemicarbazone | 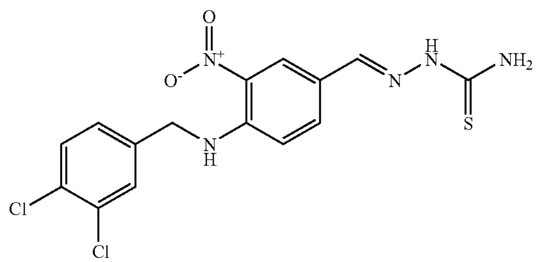 | 399.3 |
| 90 | 4-{[2-(2,4-dichlorophenyl)ethyl]amino}-3-nitrobenzaldehyde thiosemicarbazone | 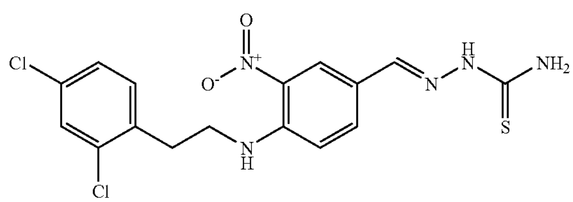 | 413.3 |
| 91 | 4-({[4-fluoro-2-(trifluoromethyl)phenyl]methyl}amino)-3-nitrobenzaldehyde thiosemicarbazone | 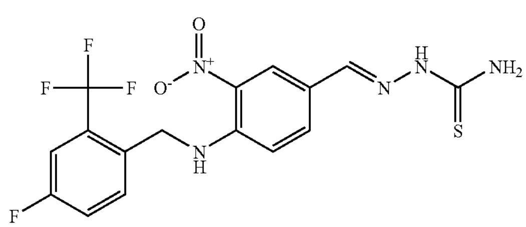 | 416.4 |
| 92 | 4-[[2-(dimethylamino)ethyl](phenylmethyl)amino]-3-nitrobenzaldehyde thiosemicarbazone | 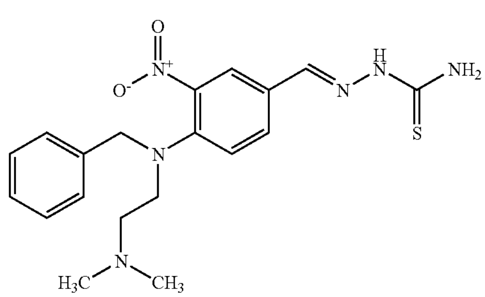 | 401.5 |

TABLE 1-continued

| Example | Name | Structure | LC/MS (m/z) MH+ |
|---|---|---|---|
| 93 | 5-fluoro-2-{[(4-fluorophenyl)methyl]oxy}-4-piperidin-1-ylbenzaldehyde thiosemicarbazone | 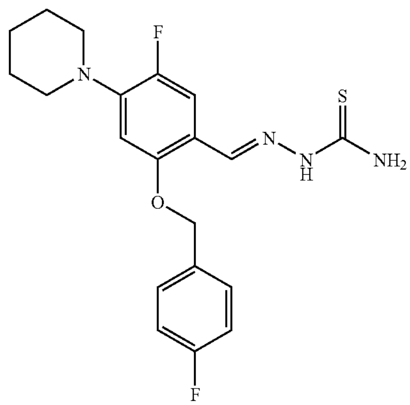 | 405.5 |
| 94 | 4-{[(4-chlorophenyl)methyl]amino}-3-fluorobenzaldehyde thiosemicarbazone | 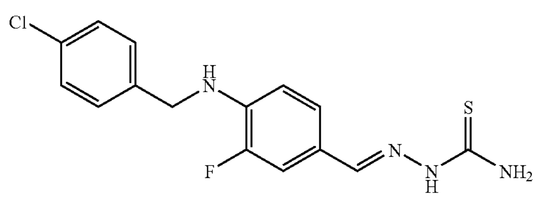 | 337.8 |
| 95 | 2,5-difluoro-4-{4-[3-(trifluoromethyl)phenyl]piperazin-1-yl}benzaldehyde thiosemicarbazone | 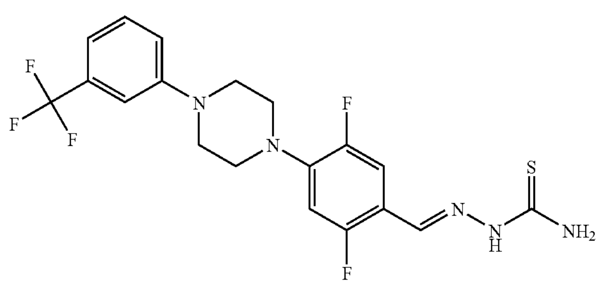 | 444.4 |
| 96 | 4-[4-(3-chlorophenyl)piperazin-1-yl]-2,5-difluorobenzaldehyde thiosemicarbazone | 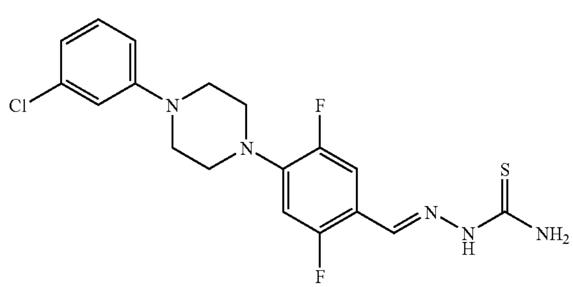 | 410.9 |
| 97 | 4-{[(3-chlorophenyl)methyl]amino}-3-fluorobenzaldehyde thiosemicarbazone | 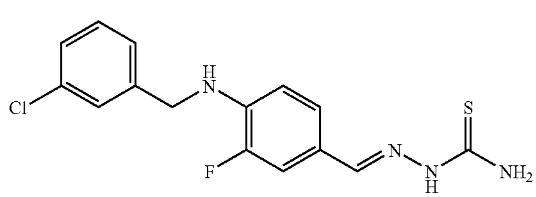 | 337.8 |

TABLE 1-continued

| Example | Name | Structure | LC/MS (m/z) MH+ |
|---|---|---|---|
| 98 | 2-{[(3,4-difluorophenyl)methyl]oxy}-5-fluoro-4-piperidin-1-ylbenzaldehyde thiosemicarbazone | 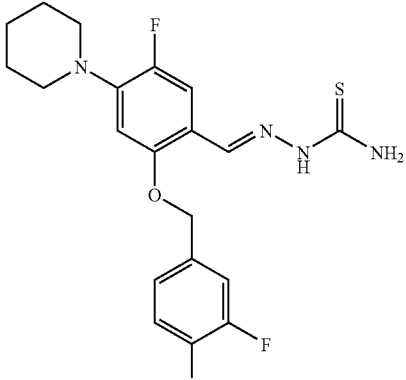 | 423.5 |
| 99 | 5-fluoro-2-(4-methylpiperazin-1-yl)-4-{4-[3-(trifluoromethyl)phenyl]piperazin-1-yl} benzaldehyde thiosemicarbazone | 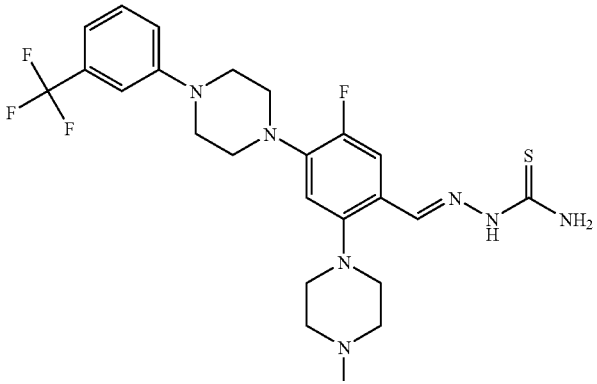 | 524.6 |
| 100 | 5-fluoro-2-(4-methylpiperazin-1-yl)-4-{4-[3-(trifluoromethyl)phenyl]piperazin-1-yl} benzaldehyde N-(pyridin-3-ylmethyl)thiosemicarbazone | 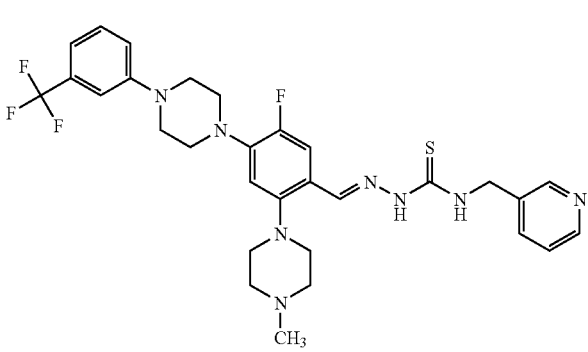 | 615.7 |
| 101 | 5-(4-chlorophenyl)furan-2-carbaldehyde N-(pyridin-3-ylmethyl)thiosemicarbazone | 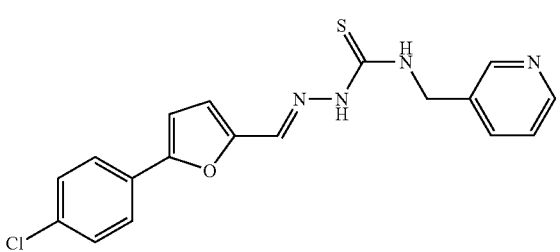 | 371.9 |

TABLE 1-continued

| Example | Name | Structure | LC/MS (m/z) MH+ |
|---|---|---|---|
| 102 | 5-(2-chlorophenyl)furan-2-carbaldehyde N-(pyridin-3-ylmethyl)thiosemicarbazone | 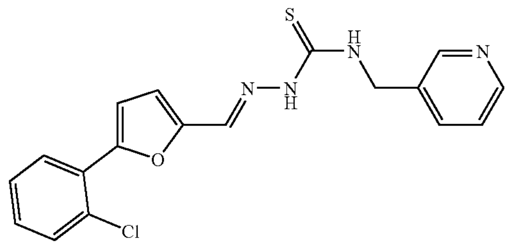 | 371.9 |
| 103 | 5-phenylfuran-2-carbaldehyde N-(pyridin-3-ylmethyl)thiosemicarbazone | 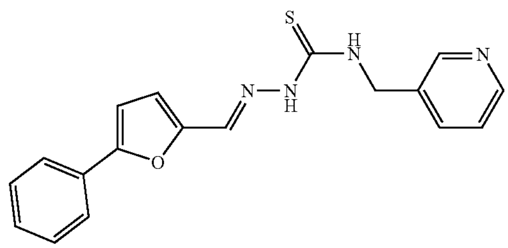 | 337.4 |
| 104 | 5-(3-(trifluoromethyl)phenyl]furan-2-carbaldehyde N-(pyridin-3-ylmethyl)thiosemicarbazone | 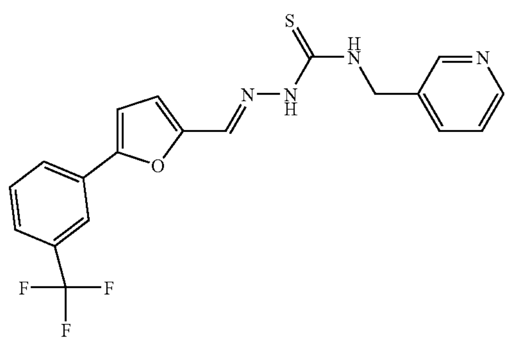 | 405.4 |
| 105 | 2-{[(3,4-dichlorophenyl)methyl]oxy}-5-fluoro-4-piperidin-1-ylbenzaldehyde thiosemicarbazone | 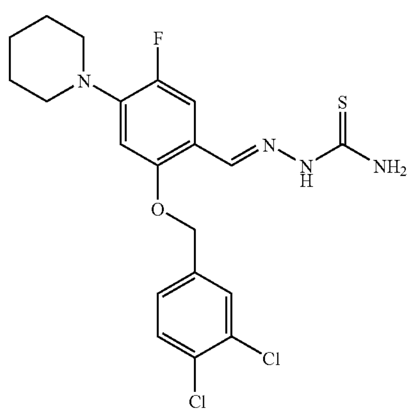 | 456.4 |
| 106 | 5-[4-fluoro-3-(trifluoromethyl)phenyl]furan-2-carbaldehyde N-(pyridin-3-ylmethyl)thiosemicarbazone | 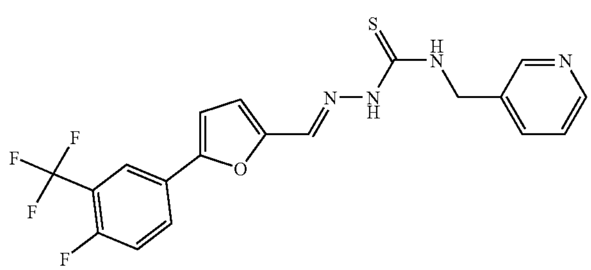 | 423.4 |

TABLE 1-continued

| Example | Name | Structure | LC/MS (m/z) MH+ |
|---|---|---|---|
| 107 | 5-(2,4-dichlorophenyl)furan-2-carbaldehyde N-(pyridin-3-ylmethyl)thiosemicarbazone | 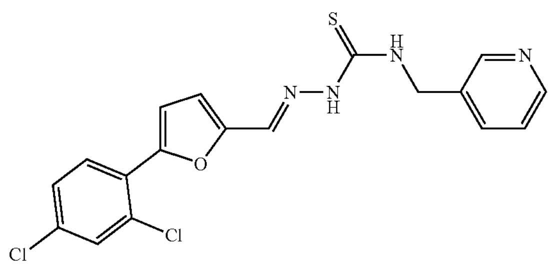 | 406.3 |
| 108 | 5-(2,4-dichlorophenyl)furan-2-carbaldehyde thiosemicarbazone | 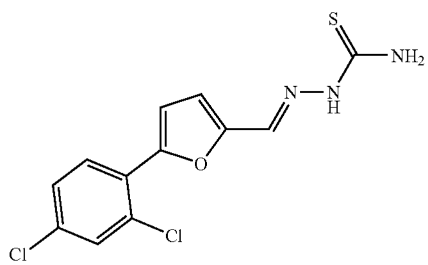 | 315.2 |
| 109 | 1,1'-biphenyl-4-carbaldehyde N-(pyridin-3-ylmethyl) thiosemicarbazone | 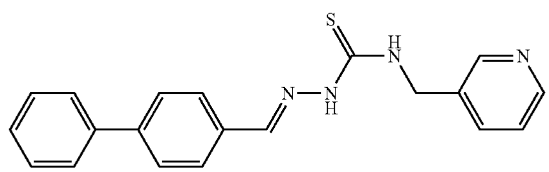 | 347.5 |
| 110 | 1,1'-biphenyl-4-carbaldehyde thiosemicarbazone | 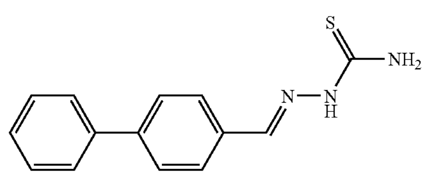 | 256.3 |

Each of the Example compounds of Table 1 was synthesized and assayed as described above. Each of these Example compounds displayed an $IC_{50}$ value of less than 10 µM with respect to HCV. Many of the compounds displayed an $IC_{50}$ value of less than or equal to 1 µM or less than or equal to 0.1 µM. Many of these compounds exhibited $IC_{50}$ values of less than or equal to 0.050 µM, less than or equal to 0.030 µM, less than or equal to 0.025 µM, or less than or equal to 0.010 µM. For this reason, each of the R groups of any of the Example compounds is preferred. Additionally, because of the excellent inhibition activity of each of the Example compounds, each of these compounds is individually preferred and is preferred as a member of a group that includes any or all of the other compounds and each Example compound is preferred in methods of inhibiting HCV and in methods of treating biological conditions mediated by HCV activity, as well as modulating immunopotentiation to be used as a vaccine adjuvant. Each of the Example compounds is also preferred for use in preparation of medicaments for vaccine adjuvants, immunopotentiation, inhibiting HCV and in treating biological conditions mediated therefrom.

Candidate small molecule immuno-potentiators can be identified in vitro. Compounds are screened in vitro for their ability to stimulate human peripheral blood mononuclear cells to produce cytokines (e.g. TNF-alpha and IL-12 p40). HCV antivirals were identified having this activity. These small molecule immuno-potentiators have potential utility as adjuvants and immuno-therapeutics.

Example 111

TNF-alpha production by human PBMC was measured using a commercial ELISA from supernatants of cells stimulated with the indicated compounds for 18 to 24 hours All test compounds were used at a final concentration of 5 µM/ml. Untreated PBMC (Cells) and LPS (0.1 ng/ml), CPG (10 ng/ml) and/or ALTTE (5 µM/ml) treated PBMC served as negative and positive controls, respectively. The following HCV antiviral compounds induced TNF and IL-12 production by human PBMC in vitro. The results are shown in FIG. 1.

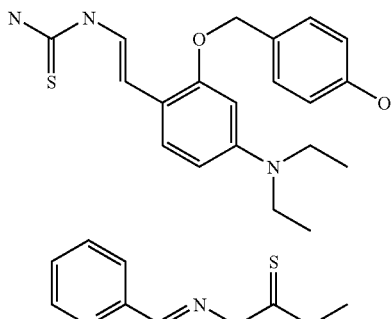

Example 112

The following thiosemicarbazone was tested at concentrations of 10 μM, 5 μM, 2.5 μM, and 1.25 μM for its ability to induce cytokines from human PBMC. Multi-cytokine analysis was performed using the Luminex system on culture supernatants following 18 h incubation with the compound. The results are presented as percent of cytokine production following stimulation with an optimal does (10 ng/ml) of LPS. The cytokines measured were: IL-6, TNF-α, IFN-γ, and IL-10.

Figure 2:
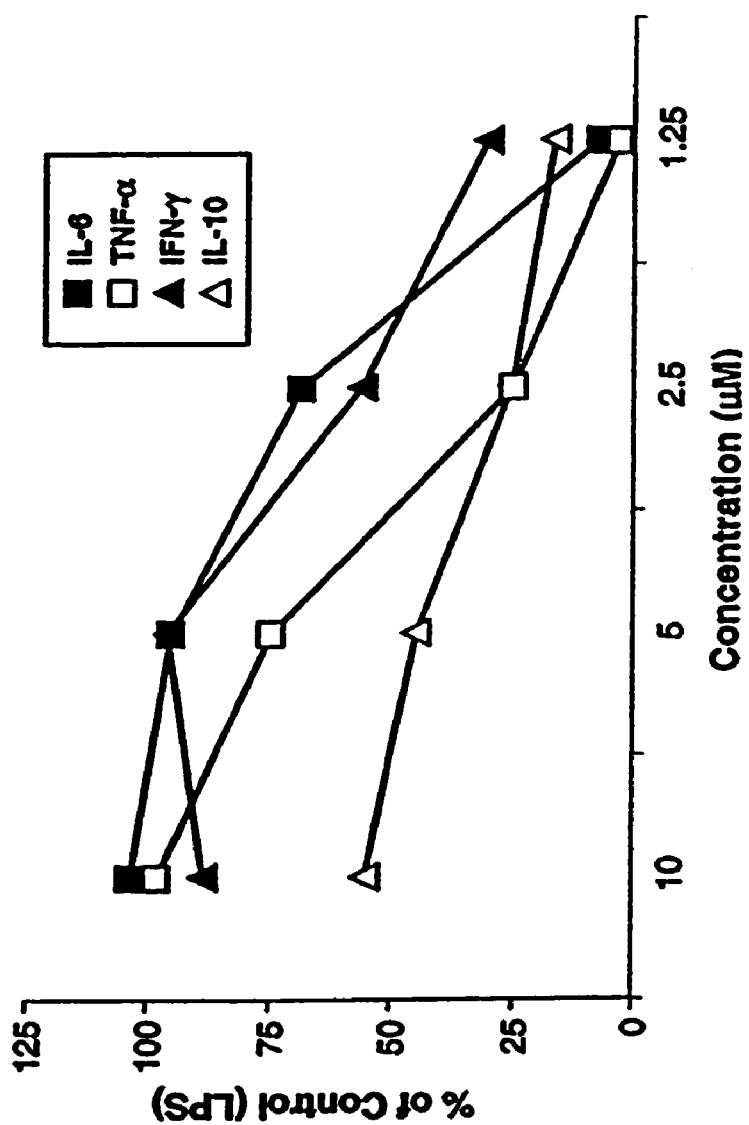
FIG. 2 shows thiosemicarbazone cytokine induction at several concentrations.

The results are shown in FIG. 2.

Table 2. Cytokine secretion of hPBMC after stimulation with thiosemicarbazone compounds.

TABLE 2

| Example | Structure | Name | LC/MS (mz) MH+ | TNFa production (ng/$10^6$ cells/ml) |
|---|---|---|---|---|
| 113 | [structure] | pyridine-2-carbaldehyde thiosemicarbazone | 181.2 | 2.34 |
| 114 | [structure] | (1E)-1-{2-[3-chloro-5-trifluoromethyl)pyridin-2-yl]-4-methyl-1,3-thiazol-5-yl}ethan-1-one thiosemicarbazone | 394.8 | 1.7 |
| 12 | [structure] | 5-(3-chlorophenyl)furan-2-carbaldehyde thiosemicarbazone | 280.8 | 2.32 |
| 7 | [structure] | 3-[(phenylmethyl)oxy] benzaldehyde thiosemicarbazone | 286.4 | 0 |

TABLE 2-continued

| Example | Structure | Name | LC/MS (mz) MH+ | TNFa production (ng/10⁶ cells/ml) |
|---|---|---|---|---|
| 39 | 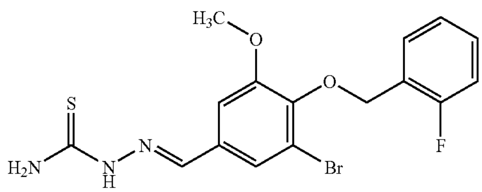 | 3-bromo-4-{[(2-fluorophenyl)methyl]oxy}-5-(methyloxy)benzaldehyde thiosemicarbazone | 413.3 | 5 |
| 115 | 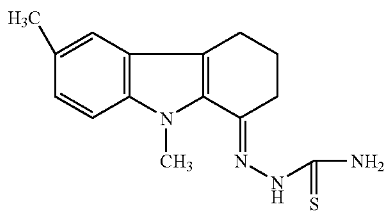 | (1E)-6,9-dimethyl-2,3,4,9-tetrahydro-1H-carbazol-1-one thiosemicarbazone | 287.4 | 1.25 |
| 86 | 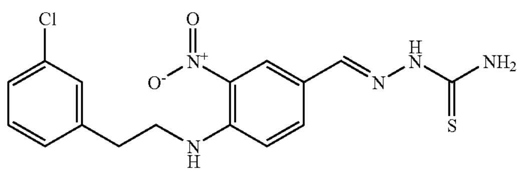 | 4-{[2-(3-chlorophenyl)ethyl]amino}-3-nitrobenzaldehyde thiosemicarbazone | 378.9 | 5 |
| 87 | 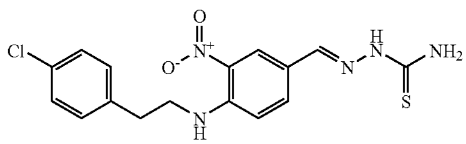 | 4-{[2-(4-chlorophenyl)ethyl]amino}-3-nitrobenzaldehyde thiosemicarbazone | 378.9 | 1.25 |

Figure 3:
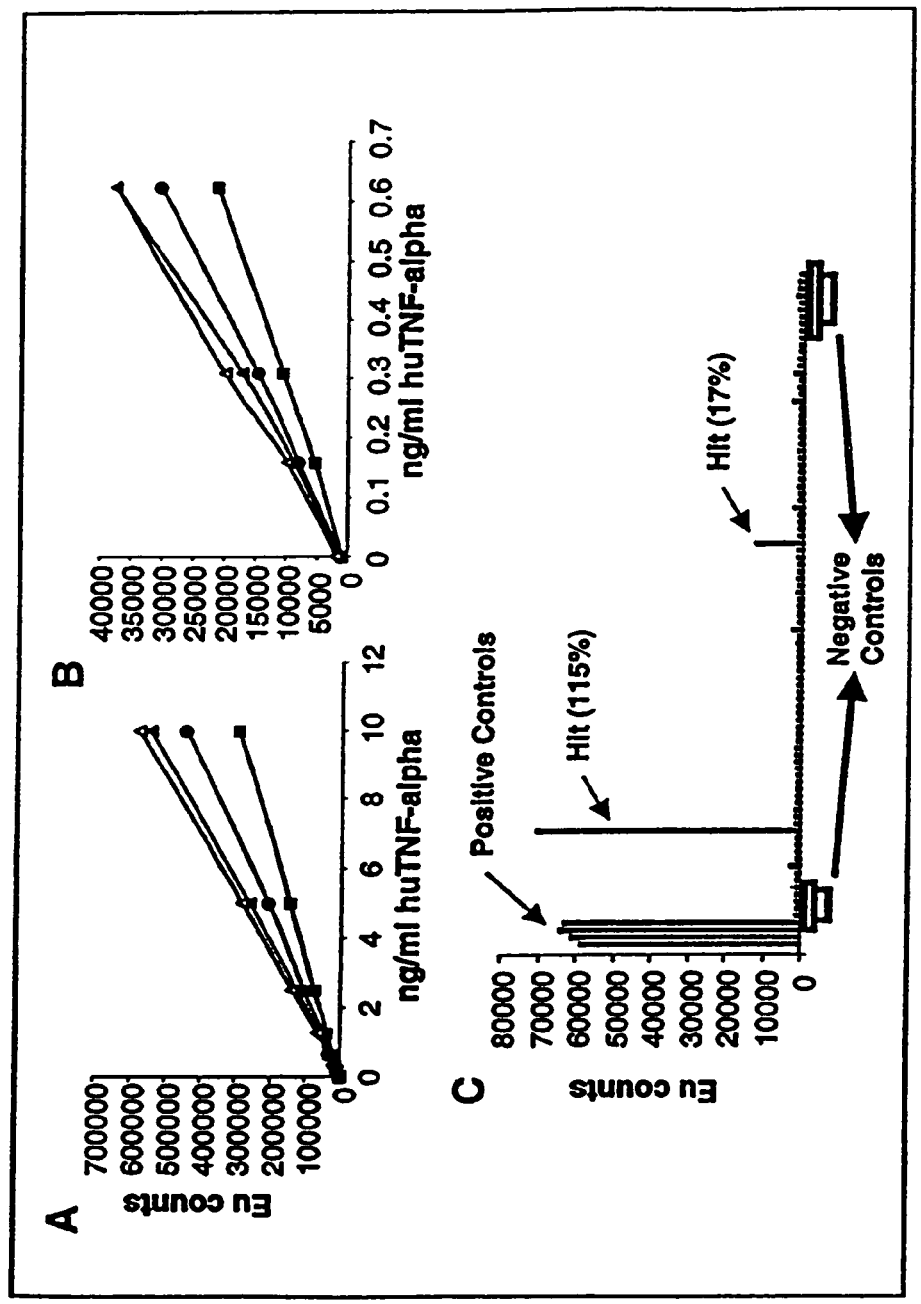
FIG. 3 depicts a high throughput assay for small molecule immune potentiator screen.

High Throughput Screening (ITS) for small molecule immune potentiators; SMIPs: Attention is drawn to FIG. 3. Various compounds were evaluated for their ability to produce cytokines in response to the small molecule compounds using a modified sandwich ELISA. Compounds are screened for their TNF inducing. "Hits" are selected based on their TNF-inducing activity relative to an optimal dose a strong TNF inducer. The robustness of the assay and low backgrounds have allowed for the routine selection of hits with ~10% of this activity which is normally between 5-10× background (cells alone). Selected hits are then subjected to confirmation for their ability to induce cytokines from multiple donors at decreasing concentrations. Those compounds with consistent activity at or below 5 μM are considered confirmed.

Figure 4:
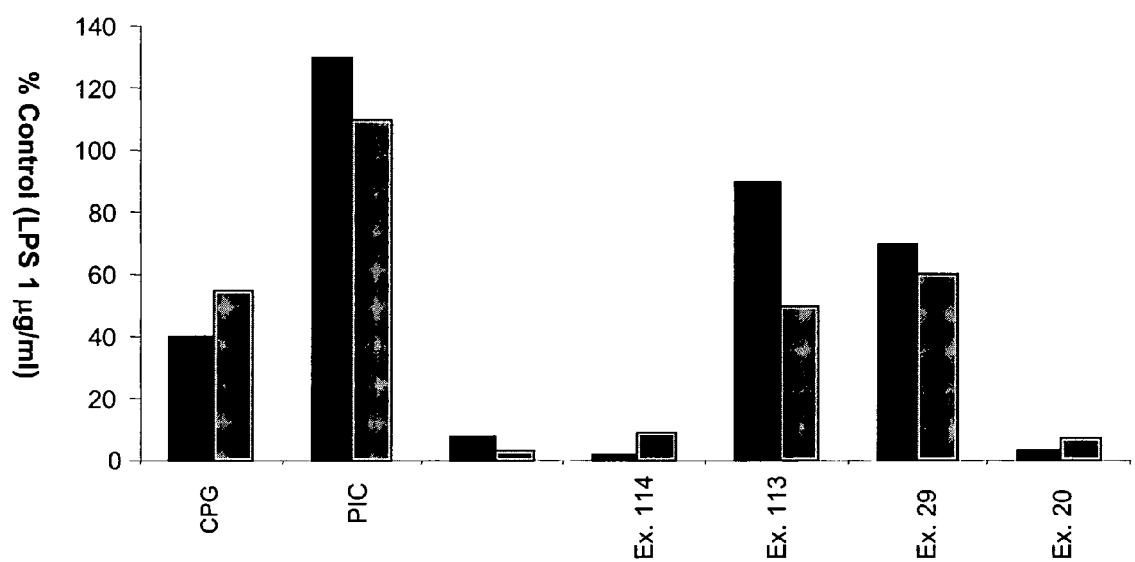
FIG. 4 depicts dual functional HCV anti-virals and immune potentiators. TNF-alpha production is represented by black bars and IL-12 p40 is represented by gray bars, presented as the % of LPS (1 mg/ml) activity.

Dual Functional HCV Anti-virals and Immune Potentiators:

Thiosemicarbazones compounds with and without anti-HCV activity were screened for their capacity to activate immune cells. Structural analogs of this scaffold have been tested for their ability to induce cytokines from human PBMC and murine splenocytes. FIG. 4 shows results from representative assays for human TNF-alpha (black bars) and IL-12 p40 (gray bars) presented as the % of LPS (1 μg/ml) activity. All compounds were tested at a final concentration of 5 μM except for poly I:C (PIC) and the 1806 oligodinucleotide (CpG) which were used at 10 μg/ml and 10 ng/ml respectively. Numerous thiosemicarbazones were tested with this approach and some of these have previously been shown to have anti-HCV acivity in separate assays but have weak or absent SMIP activity. Others (e.g. Example 113) possess potent SMIP activity but have weak or absent anti-HCV effects. Finally compounds, such as Example 29, possess both SMIP and anti-HCV activity in independent assays.

Quantification of HCV replicon RNA in Cell Lines (HCV Cell Based Assay):

Cell lines, including Huh-11-7 or Huh 9-13, harboring HCV replicons (Lohmann, et al Science 285:110-113, 1999) are seeded at 5×10³ cells/well in 96 well plates and fed media containing DMEM (high glucose), 10% fetal calf serum, penicillin-streptomycin and non-essential amino acids. Cells are incubated in a 5% CO₂ incubator at 37° C. At the end of the incubation period, total RNA is extracted and purified from cells using Qiagen Rneasy 96 Kit (Catalog No. 74182). To amplify the HCV RNA so that sufficient material can be detected by an HCV specific probe (below), primers specific for HCV (below) mediate both the reverse transcription (RT) of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

HCV Forward primer "RBNSSbfor"

5'GCTGCGGCCTGTCGAGCT:

HCV Reverse primer "RBNS5Brev":

5'CAAGGTCGTCTCCGCATAC

Detection of the RT-PCR product was accomplished using the Applied Biosystem (ABI) Prism 7700 Sequence Detection System (SDS) that detects the fluorescence that is emitted when the probe, which is labeled with a fluorescence reporter dye and a quencher dye, is processed during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

5'FAM-CGAAGCTCCAGGACTGCACGATGCT-TAMRA

FAM=Fluorescence reporter dye.
TAMRA=Quencher dye.

The RT reaction is performed at 48° C. for 30 minutes followed by PCR. Thermal cycler parameters used for the PCR reaction on the ABI Prism 7700 Sequence Detection System were: one cycle at 95° C., 10 minutes followed by 35 cycles each of which included one incubation at 95° C. for 15 seconds and a second incubation for 60° C. for 1 minute.

To normalize the data to an internal control molecule within the cellular RNA, we perform RT-PCR on the cellular messenger RNA glyceraldehydes-3-phosphate dehydrogenase (GAPDH). The GAPDH copy number is very stable in the cell lines used. GAPDH RT-PCR is performed on the same exact RNA sample from which the HCV copy number is determined. The GAPDH primers and probes, as well as the standards with which to determine copy number, is contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of compounds as inhibitors of HCV replication (Cell based Assay) in replicon containing Huh-7 cell lines: The effect of a specific anti-viral compound on HCV replicon RNA levels in Huh-11-7 or 9-13 cells, cells was determined by comparing the amount of HCV RNA normalized to GAPDH (e.g. the ratio of HCV/GAPDH) in the cells exposed to compound versus cells exposed to the 0% inhibition and the 100% inhibition controls. Specifically, cells were seeded at 5×103 cells/well in a 96 well plate and were incubated either with: 1) media containing 1% DMSO (0% inhibition control), 2) 100 international units, IU/ml Interferon-alpha 2b in media/1% DMSO or 3) media/1% DMSO containing a fixed concentration of compound. 96 well plates as described above were then incubated at 37° C. for 3 days (primary screening assay) or 4 days ($IC_{50}$ determination).

Percent Inhibition was Defined as:

% Inhibition=$[100-((S-C2)/C1-C2))] \times 100$ where:
S=the ratio of HCV RNA copy number/GAPDH RNA copy number in the sample
C1=the ratio of HCV RNA copy number/GAPDH RNA copy number in the 0% inhibition control (media/i % DMSO)
C2=the ratio of HCV RNA copy number/GAPDH RNA copy number in the 100% inhibition control (100 IU/ml Interferon-alpha 2b)

The dose-response curve of the inhibitor was generated by adding compound in serial, three-fold dilutions over three logs to wells starting with the highest concentration of a specific compound at 10 uM and ending with the lowest concentration of 0.01 uM. Further dilution series (1 uM to 0.001 uM for example) was performed if the $IC_{50}$ value was not in the linear range of the curve. $IC_{50}$ was determined based on the IDBS Activity Base program using Microsoft Excel "XL Fit" in which A=100% inhibition value (100 IU/ml Interferon-alpha 2b), B=0% inhibition control value (media/1% DMSO) and C=midpoint of the curve as defined as C=(B−A/2)+A. A, B and C values are expressed as the ratio of HCV RNA/GAPDH RNA as determined for each sample in each well of a 96 well plate as described above. For each plate the average of 4 wells were used to define the 100% and 0% inhibition values.

FURTHER EXAMPLES

Additional exemplary compounds were using the exmplary synthesis reactions set forth below. By varying starting materials and/or intermediates of the schemes below, those skilled in the art can readily synthesize the variants presented in the table 3 as well as others.

Scheme 10:
Preparation of Difluorophenyl
Thiosemicarbazone Derivatives

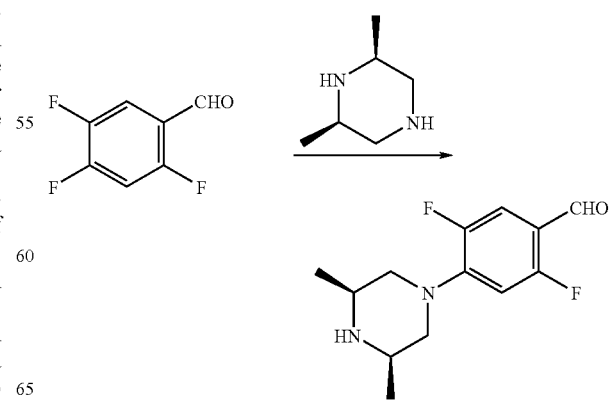

To a solution of 2,4,5-trifluorobenzaldehyde (1 eq) in ethyl acetate at room temperature was added 2,6-dimehtylpiperazine (2 eq). After being stirred overnight, the solution was washed with water, aqueous sodium bicarbonate, brine and dried, and purified on silica gel to give 4-(cis-3,5-dimethylpiperazinyl)-2,5-difluorobenzaldehyde.

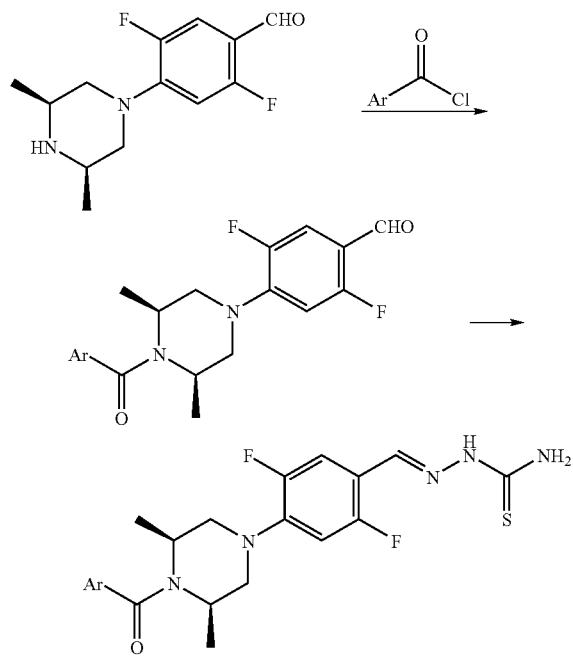

General procedure: To a solution of 4-(cis-3,5-dimethylpiperazinyl)-2,5-difluorobenzaldehyde (1 equiv) and triethylamine (1.2 eq) in DCM at room temperature was added arylcarboxylic chloride (1.1 eq). After 1 hour, acetic acid (10 equiv) and thiosemicarbazide (1.2 eq) were added. The mixture was purified with prep-HPLC to give the 4-(4-{(1E)-2-[(aminothioxomethyl)amino]-2-azavinyl}-2,5-difluorophenyl)-cis-2,6-dimethylpiperazinyl aryl ketone.

Scheme 11: Preparation Of Pyridine Thiosemicarbazone Derivatives 6-Substitution:

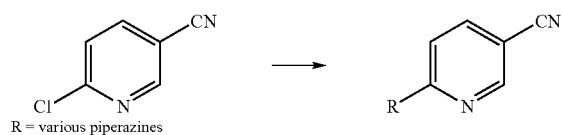

R=various piperazines

To the 6-chloro pyridine (7.2 mmol) was added ACN (15 mL) followed by DIPEA (15.9 mmol). To the solution was added the appropriate piperazine (8.0 mmol). The reaction was heated to 50° C. Once the reaction was complete, the solution was concentrated under reduced pressure and diluted with EtOAc. The organics were washed with sat. aq. NaHCO₃ (×2), H₂O (×2), brine (×1), dried (Na₂SO₄), filtered, and concentrated under reduced pressure to yield the appropriate crude pyridine.

Reduction to Alcohol:

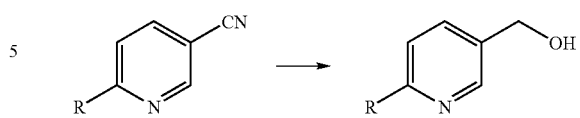

The nitrile (1.9 mmol) in DCM (5 mL) was cooled to 0° C. To the solution was added DIBAL (4.83 mmol-1.5 M soln. in toluene) dropwise. Once the reaction was complete, it was quenched with sat. aq. NH₄Cl. The solution was diluted with DCM and H₂O and filtered washing with DCM and H₂O. The separated aqueous layer was extracted with DCM (×3). The combined organics were washed with sat. aq. NH₄Cl (×2), H₂O (×1), brine (×1), dried (Na₂SO₄), filtered, and concentrated under reduced pressure to give the crude alcohol.

Oxidation to Aldehyde:

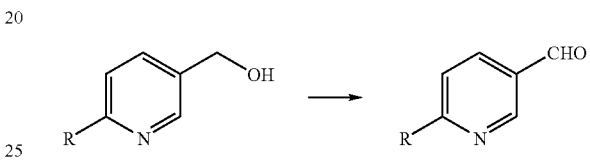

To the alcohol (0.35 mmol) in DCM (5 mL) was added MnO₂ (4.7 mmol). Once the reaction was complete, it was filtered through Celite. The filtrate was concentrated under reduced pressure to yield the crude aldehyde.

Synthesis of Thiosemicarbazone:

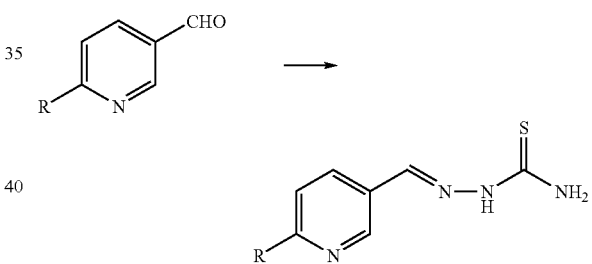

To the aldehyde (1.0 mmol) was added AcOH (5 mL) followed by thiosemicarbazide (1.0 mmol). Once the reaction was complete, the solution was concentrated under reduced pressure aided by toluene azeotrope. The remaining crude product was purified by prep LC to yield the pure thiosemicarbazone.

Scheme 12: Preparation of Pyrimidine thiosemiacarbazone derivatives

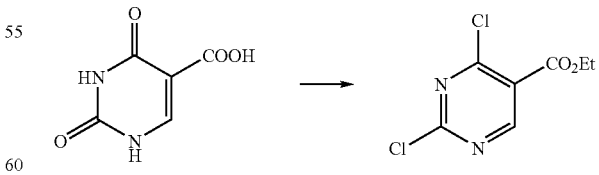

A suspension of 5-carboxyuracil (126 mmol) in POCl₃ (150 mL) and DMF (126 mmol) was refluxed until the solution became homogeneous. The POCl₃ was removed by evaporation under reduced pressure aided by toluene azeotrope. To the remaining brown tar was added DCM (200 mL). The mixture was cooled to −25° C. and absolute EtOH (200 mL) was slowly added keeping the internal temperature below −12° C. Once the reaction was complete, sat. aq. NaHCO$_3$ (200 mL) was added slowly keeping the internal temperature below −12° C. Solid NaHCO$_3$ was added portionwise to adjust pH to 7-8. Organics were separated and the aqueous layer was extracted with DCM (×2). The combined organics were washed with sat. aq. NaHCO$_3$ (×2), sat. brine (×1), then dried (Na$_2$SO$_4$), filtered, and evaporated under reduced pressure to yield the crude pyrimidine. The crude product was chromatographed using 10% EtOAc in hexanes to yield the pure pyrimidine.

4-Substitution:

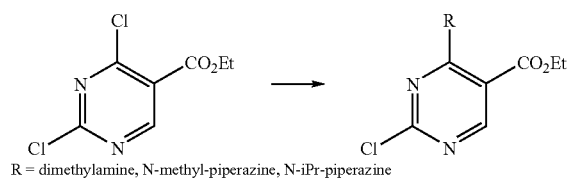

R = dimethylamine, N-methyl-piperazine, N-iPr-piperazine

R=dimethylamine, N-methyl-piperazine, N-piperazine

Ethyl 2,4-dichloropyrimidine-5-carboxylate (31.7 mmol) and triethylamine (34.9 mmol) were dissolved in DCM (150 mL) and cooled to 0° C. The amine (31.7 mmol) was added slowly keeping the internal temperature under 5° C. Once the reaction was complete, water (50 mL) was added. The separated organic layer was washed with sat. brine (×1), dried (Na$_2$SO$_4$), filtered, and concentrated under reduced pressure to yield the crude 4-substituted pyrimidine. The crude product was chromatographed using 20% EtOAc in hexanes to yield the pure pyrimidine.

4-Substition:

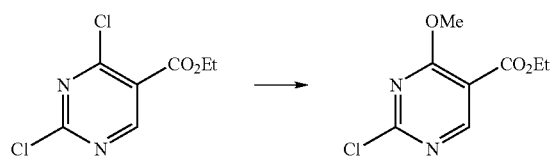

Ethyl 2,4-dichloropyrimidine-5-carboxylate (3.2 mmol) in MeOH (10 mL) was cooled to 0° C. To the cooled solution was added NaOMe (3.2 mmol-0.5 M soln. in MeOH). Once the reaction was complete, the solution was concentrated under reduced pressure and diluted with EtOAc. The organics were washed with H$_2$O (×2), sat. brine (×1), dried (Na$_2$SO$_4$), filtered, and concentrated under reduced pressure to yield the crude 4-methoxy pyrimidine.

Reduction to Alcohol:

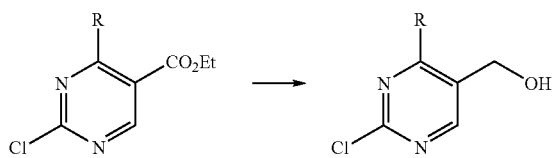

The ester (1.9 mmol) in DCM (5 mL) was cooled to 0° C. To the solution was added DIBAL (4.83 mmol-1.5 M soln. in toluene) dropwise. Once the reaction was complete, it was quenched with sat. aq. NH$_4$Cl. The solution was diluted with DCM and H$_2$O and filtered washing with DCM and H$_2$O. The separated aqueous layer was extracted with DCM (×3). The combined organics were washed with sat. aq. NH$_4$Cl (×2), H$_2$O (×1), brine (×1), dried (Na$_2$SO$_4$), filtered, and concentrated under reduced pressure to give the crude alcohol.

Oxidation to Aldehyde:

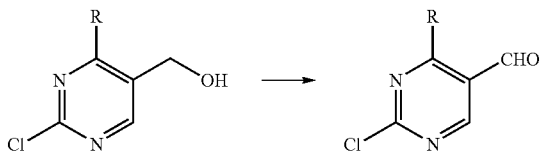

To the alcohol (0.35 mmol) in DCM (5 mL) was added MnO$_2$ (4.7 mmol). Once the reaction was complete, it was filtered through Celite. The filtrate was concentrated under reduced pressure to yield the crude aldehyde.

2-Substitution:

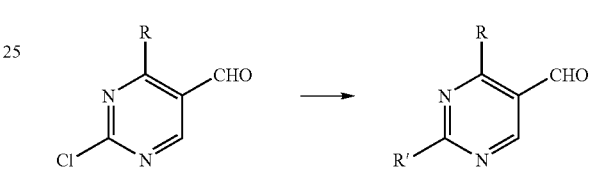

R' = various piperazine and piperidine derivatives

R=various piperazine and piperidine derivatives

To the 2-chloro pyrimidine (1.6 mmol) in ACN (5 mL) was added DIPEA (3.2 mmol) followed by the appropriate piperazine or piperidine derivative (1.7 mmol). The solution was heated to 50° C. Once the reaction was complete, the solution was concentrated under reduced pressure and diluted with EtOAc. The organics were washed with sat. aq. NaHCO3 (×2), H$_2$O (×2), brine (×1), dried (Na2SO4), filtered, and concentrated under reduced pressure to yield the appropriate crude pyrimidine.

Synthesis of Thiosemicarbazone:

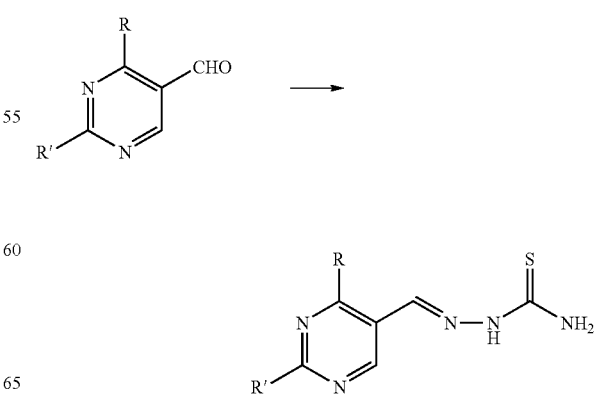

To the aldehyde (1.0 mmol) was added AcOH (5 mL) followed by thiosemicarbazide (1.0 mmol). Once the reaction was complete, the solution was concentrated under reduced pressure aided by toluene azeotrope. The remaining crude product was purified by prep LC to yield the pure thiosemicarbazone.

Scheme 13: Preparation of Furan thiosemicarbazone derivatives
Preparation of 5-(6-Chloro-pyridin-3-yl)-furan-2-carbaldehyde (3)

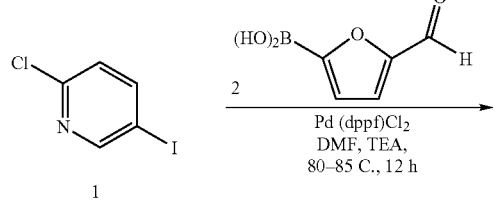

| Reagent | MW | EQ | g/ml | mmol |
|---|---|---|---|---|
| 2-Chloro-5-iodo-pyridine | 239.4 | 1.1 | 1.88 g | 7.86 |
| Boronic Acid 2 | 140 | 1.0 | 1 g | 7.15 |
| Pd(dppf)Cl$_2$ | 816.63 | 0.03 | 10 mg | 0.21 |
| TEA | 101.19 | 1.5 | 1.5 ml | 10.72 |
| DMF (dry & sparged with argon for 5 min.) | | | 14 ml | |

The 2-chloro-5-iodo-pyridine 1 (1.88 g, 7.86 mmol), furan-2-carbaldehyde-5-boronic acid 2 (1 g, 7.15 mmol) and Pd(dppf)Cl$_2$ catalyst (10 mg, 0.21 mmol) were weighted out and added to a 25 ml vial. The DMF was sparged with argon for 5-10 minutes and added to the reaction followed by TEA (1.5 ml, 10.72 mmol). The reaction was lightly bubbled with argon. The vial was flushed with argon, capped tight and shaken at 75° C. Analytical samples were taken as needed to follow the progress of the reaction. The reaction was flushed with argon as a precaution against oxygen. After 3.5 hours, the reaction had reached completion by HPLC. Immediately, the reaction was diluted with EtOAc (150-200 ml), filtered, washed with 1N NaOH (15 ml), sat. NaHCO$_3$ (2×15 ml), water (15 ml), brine (15 ml) and dried with Na$_2$SO$_4$. The organic layer was filtered through a plug of silica (1 inch high), and the silica was flushed with EtOAc (50 ml). The combined organics were concentrated under vacuum to a solid (1.54 g). The crude solid was purified by flash chromatography eluting with EtOAc/Hexane (4:6 v/v). The purified fractions were combined and evaporated under reduced pressure to give pure product (0.81 g) in 55% yield.

Preparation of 5-{6-[4-(2-Chloro-benzyl)-piperazin-1-yl]-pyridin-3-yl}-furan-2-thiosemicarbazone (5)

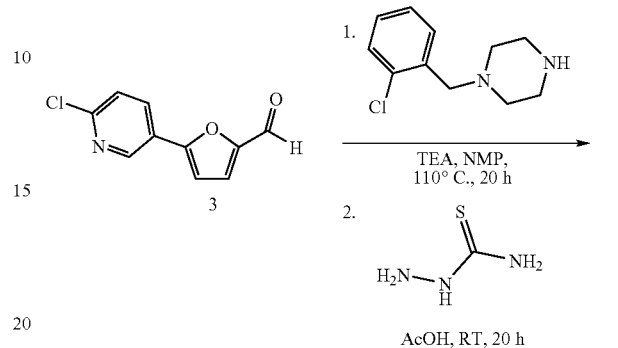

| Reagent | MW | EQ | g/ml | mmol |
|---|---|---|---|---|
| 2-Chloropyridine 3 | 207.6 | 1.0 | 20.7 mg | 0.1 |
| Piperazine 2 | 210.7 | 2.5 | 53 mg | 0.25 |
| TEA | 101.19 | 3.0 | 42 ul | 0.3 |
| NMP | | | 0.3 ml | |
| Thiosemicarbazone | 91.14 | 2.2 | 20 mg | 0.22 |
| AcOH gal. | | | 120 ul | |

The 5-(6-Chloro-pyridin-3-yl)-furan-2-carbaldehyde 3 (20.7 mg, 0.1 mmol), 1-(2-Chloro-benzyl)-piperazine 4 (53 mg, 0.25 mmol), TEA (42 ul, 0.3 mmol) and NMP (300 ul) were added to a 2 ml vial. The vial was flushed with argon, capped tight and shaken at 110° C. Analytical samples were taken as needed to follow the progress of the reaction. The reaction was flushed with argon as a precaution against oxygen. After 20 hours, the reaction had reached completion by HPLC and LCMS. Thiosemicarbazone (20 mg, 0.22 mmol) and AcOH (120 ul) were added to the reaction and shaken for 20 hours. The crude reaction was purified by prep. HPLC. The crude reaction was passed through a Teflon syringe filter, and the clear filtrate was injected on a preparative HPLC. The purification used a 20×50 mm Ultro 120 C18 column running a 22 ml/min 2% gradient (AcCN/water, 0.1% TFA) for 16 min. The purified fractions were lyophilized to dryness to give 3.2 mg of pure product as the TFA salt (14% yield and 87% purity).

TABLE 3

| Structure | | Name | MH+ |
|---|---|---|---|
| 116 | (structure) | 6-{4-[3-(trifluoromethyl)phenyl]piperazin-1-yl)nicotinaldehyde thiosemicarbazone | 409 |
| 117 | (structure) | 2-[4-(3-chlorophenyl)piperazin-1-yl]-4-(dimethylamino)pyrimidine-5-carbaldehyde thiosemicarbazone | 420 |
| 118 | (structure) | 2-[4-(2-chlorobenzyl)piperazin-1-yl]-4-(dimethylamino)pyrimidine-5-carbaldehyde thiosemicarbazone | 434 |
| 119 | (structure) | 4-(dimethylamino)-2-{4-[3-(trifluoromethyl)phenyl]piperazin-1-yl}pyrimidine-5-carbaldehyde thiosemicarbazone | 454 |

TABLE 3-continued

| Structure | Name | MH+ |
|---|---|---|
| 120 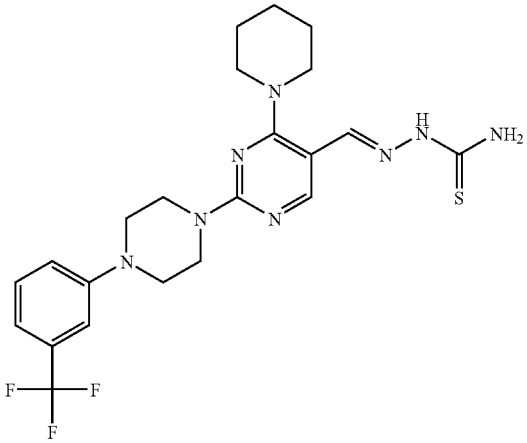 | 4-piperidin-1-yl-2-{4-(3-(trifluoromethyl)phenyl]piperazin-1-yl}pyrimidine-5-carbaldehyde thiosemicarbazone | 494 |
| 121 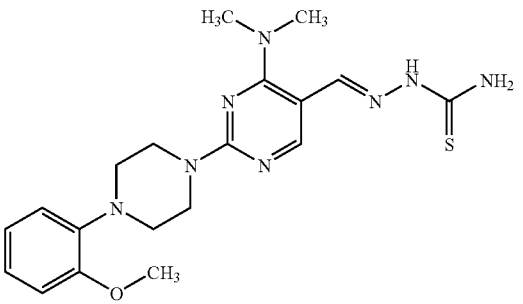 | 4-(dimethylamino)-2-[4-(2-methoxyphenyl)piperazin-1-yl]pyrimidine-5-carbaldehyde thiosemicarbazone | 416 |
| 122 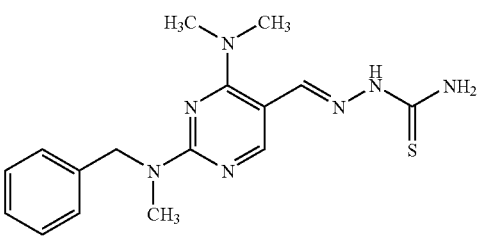 | 2-[benzyl(methyl)amino]-4-dimethylamino)pyrimidine-5-carbaldehyde thiosemicarbazone | 344 |
| 123 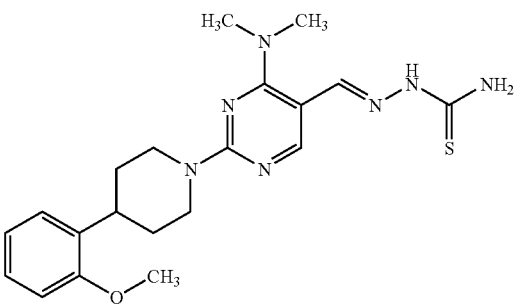 | 4-(dimethylamino)-2-[4-(2-methoxyphenyl)piperidin-1-yl]pyrimidine-5-carbaldehyde thiosemicarbazone | 415 |

TABLE 3-continued

| Structure | | Name | MH+ |
|---|---|---|---|
| 124 | | 4-(dimethylamino)-2-[4-(4-fluorophenyl)piperazin-1-yl]pyrimidine-5-carbaldehyde thiosemicarbazone | 404 |
| 125 | | 4-(dimethylamino)-2-[4-(4-fluorobenzyl)piperazin-1-yl]pyrimidine-5-carbaldehyde thiosemicarbazone | 418 |
| 126 | | 2-(4-benzylpiperazin-1-yl)-4-(dimethylamino)pyrimidine-5-carbaldehyde thiosemicarbazone | 400 |
| 127 | | 2-(dimethylamino)-2-{[2-(trifluoromethoxy)benzyl]amino}pyrimidine-5-carbaldehyde thiosemicarbazone | 414 |
| 128 | | 4-(dimethylamino)-2-(4-phenylpiperazin-1-yl)pyrimidine-5-carbaldehyde thiosemicarbazone | 386 |

TABLE 3-continued

| | Structure | Name | MH+ |
|---|---|---|---|
| 129 | 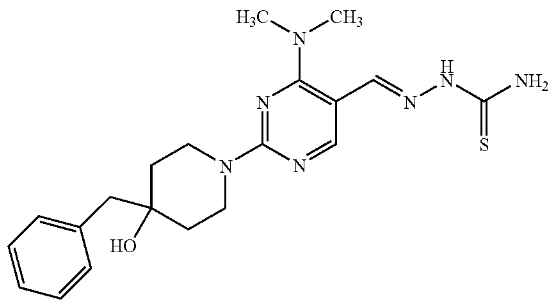 | 2-(4-benzyl-4-hydroxypiperidin-1-yl)-4-(dimethylamino)pyrimidine-5-carbaldehyde thiosemicarbazone | 415 |
| 130 | 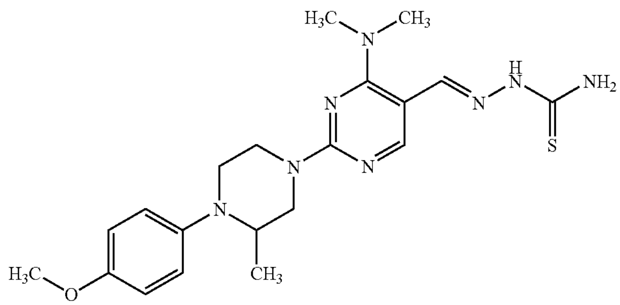 | 4-(dimethylamino)-2-[4-(4-methoxyphenyl)-3-methylpiperazin-1-yl]pyrimidine-5-carbaldehyde thiosemicarbazone | 430 |
| 131 | 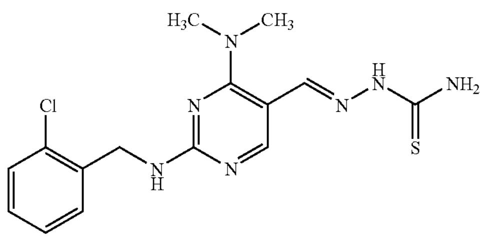 | 2-[(2-chlorobenzyl)amino]-4-(dimethylamino)pyrimidine-5-carbaldehyde thiosemicarbazone | 365 |
| 132 | 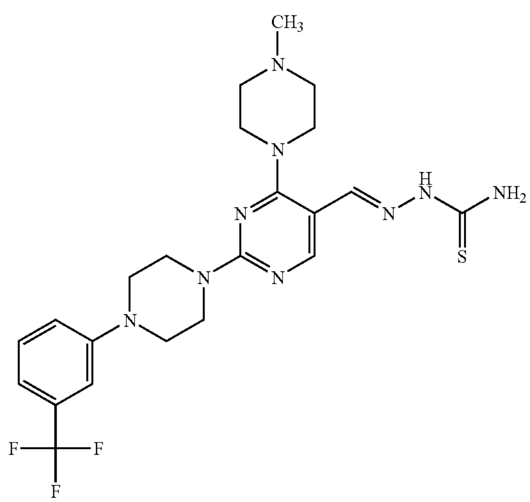 | 4-(4-methylpiperazin-1-yl)-2-{4-[3-(trifluoromethyl)phenyl]piperazin-1-yl}pyrimidine-5-carbaldehyde thiosemicarbazone | 509 |
| 133 | 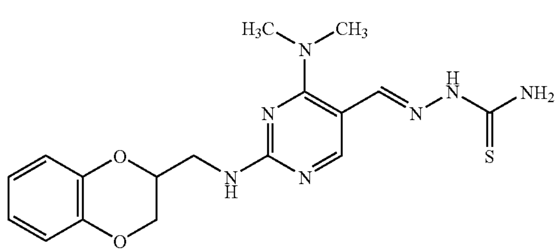 | 2-[(2,3-dihydro-1,4-benzodioxin-2-ylmethyl)amino]-4-dimethylamino)pyrimidine-5-carbaldehyde thiosemicarbazone | 388 |

TABLE 3-continued

| Structure | | Name | MH+ |
|---|---|---|---|
| 134 | | 4-(dimethylamino)-2-(4-pyridin-2-ylpiperazin-1-yl)pyrimidine-5-carbaldehyde thiosemicarbazone | 386 |
| 135 | | 2-[(1,3-benzodioxol-5-ylmethyl)amino]-4-(dimethylamino)pyrimidine-5-carbaldehyde thiosemicarbazone | 374 |
| 136 | | 4-(dimethylamino)-2-{[2-(2-methoxyphenyl)ethyl]amino)pyrimidine-5-carbaldehyde thiosemicarbazone | 374 |
| 137 | | 4-(dimethylamino)-2-[(2-morpholin-4-ylbenzyl)amino]pyrimidine-5-carbaldehyde thiosemicarbazone | 416 |
| 138 | | 4-(dimethylamino)-2-[4-(2-oxo-2,3-dihydro-1H-benzimidazol-1-yl)piperidin-1-yl]pyrimidine-5-carbaldehyde thiosemicarbazone | 360 |

TABLE 3-continued

| | Structure | Name | MH+ |
|---|---|---|---|
| 139 | 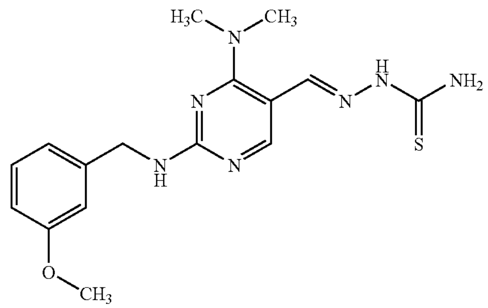 | 4-(dimethylamino)-2-[(3-methoxybenzyl)amino]pyrimidine-5-carbaldehyde thiosemicarbazone | 360 |
| 140 | 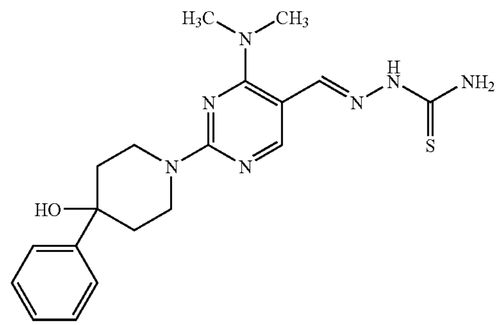 | 4-(dimethylamino)-2-(4-hydroxy-4-phenylpiperidin-1-yl)pyrimidine-5-carbaldehyde thiosemicarbazone | 401 |
| 141 | 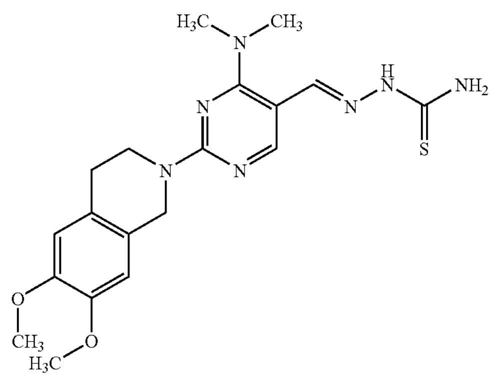 | 2-(6,7-dimethoxy-3,4-dihydroisoquinolin-2(1H)-yl)-4-(dimethylamino)pyrimidine-5-carbaldehyde thiosemicarbazone | 417 |
| 142 | 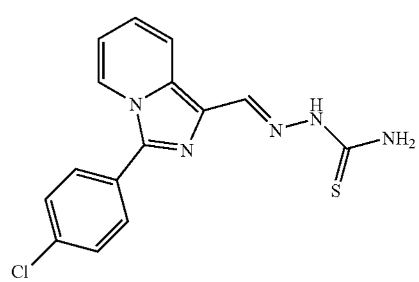 | 3-(4-chorophenyl)imidazo[1,5-a]pyridine-1-carbaldehyde thiosemicarbazone | 331 |
| 143 | 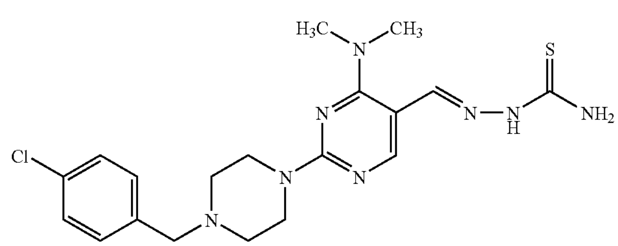 | 2-[4-(4-chlorobenzyl)piperazin-1-yl]-4-(dimethylamino)pyrimidine-5-carbaldehyde thiosemicarbazone | 434 |

TABLE 3-continued

| | Structure | Name | MH+ |
|---|---|---|---|
| 144 | 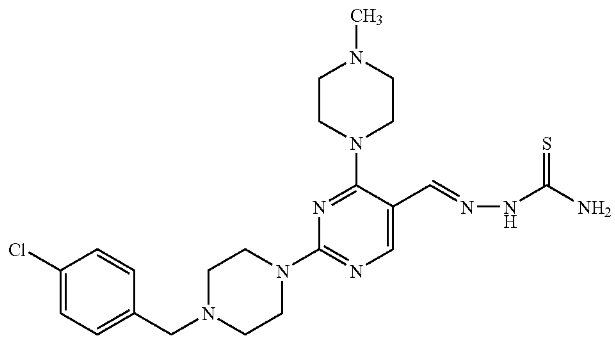 | 2-[4-(4-chlorobenzyl)piperazin-1-yl]-4-(4-methylpiperazin-1-yl)pyrimidine-5-carbaldehyde thiosemicarbazone | 489 |
| 145 | 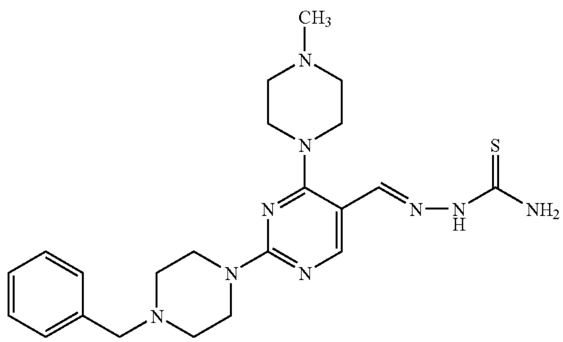 | 2-(4-benzylpiperazin-1-yl)-4-(4-methylpiperazin-1-yl)pyrimidine-5-carbaldehyde thiosemicarbazone | 455 |
| 146 | 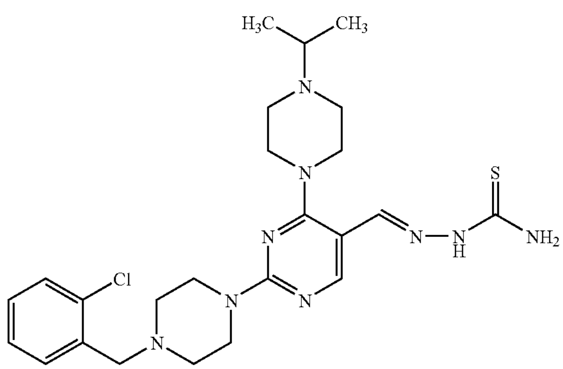 | 2-[4-(2-chlorobenzyl)piperazin-1-yl]-4-(4-isopropylpiperazin-1-yl)pyrimidine-5-carbaldehyde thiosemicarbazone | 517 |
| 147 | 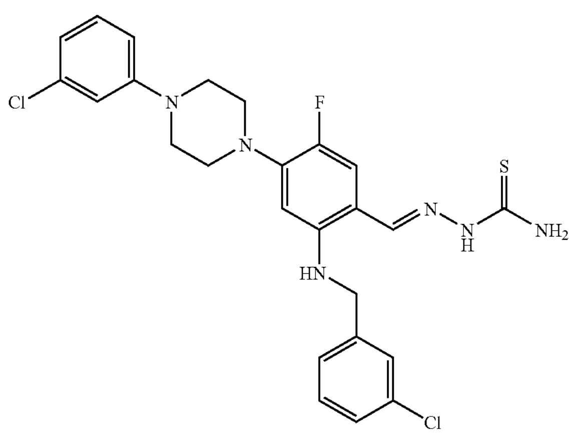 | 2-[(3-chlorobenzyl)amino]-4-[4-(3-chlorophenyl)piperazin-1-yl]-5-fluorobenzaldehyde thiosemicarbazone | 532 |

TABLE 3-continued

| Structure | Name | MH+ |
|---|---|---|
| 148 | 2-[(4-chlorobenzyl)amino]-4-[4-(3-chlorophenyl)piperazin-1-yl]-5-fluorobenzaldehyde thiosemicarbazone | 532 |
| 149 | 4-[(4-benzylpiperazin-1-yl)methyl]benzaldehyde thiosemicarbazone | 369 |
| 150 | 2,5-difluoro-4-[4-(3-methylbenzyl)piperazin-1-yl]benzaldehyde thiosemicarbazone | 404 |
| 151 | 2,5-difluoro-4-{4-[2-fluoro-4-(trifluoromethyl)benzyl]piperazin-1-yl}benzaldehyde thiosemicarbazone | 476 |
| 152 | 4-[4-(2,6-dichlorobenzyl)piperazin-1-yl]-2,5-difluorobenzaldehyde thiosemicarbazone | 459 |

TABLE 3-continued

| Structure | Name | MH+ |
|---|---|---|
| 153 | 4-[4-(2,4-difluorobenzyl)piperazin-1-yl]-2,5-difluorobenzaldehyde thiosemicarbazone | 426 |
| 154 | 4'-(trifluoromethyl)-1,1'-biphenyl-4-carbaldehyde thiosemicarbazone | 324 |
| 155 | 4-{[4-(2-chlorobenzyl)piperazin-1-yl]methyl)benzaldehyde thiosemicarbazone | 403 |
| 156 | 2,5-difluoro-4-[(3R,5S)-4-(4-fluorobenzyl)-3,5-dimethylpiperazin-1-yl]benzaldehyde thiosemicarbazone | 437 |
| 157 | 2,5-difluoro-4-[4-(3-fluorobenzyl)piperazin-1-yl]benzaldehyde thiosemicarbazone | 408 |

TABLE 3-continued

| | Structure | Name | MH+ |
|---|---|---|---|
| 158 | 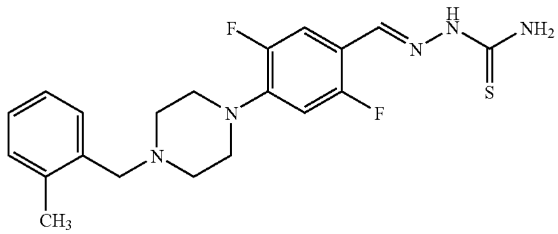 | 2,5-difluoro-4-[4-(2-methylbenzyl)piperazin-1-yl]benzaldehyde thiosemicarbazone | 404 |
| 159 | 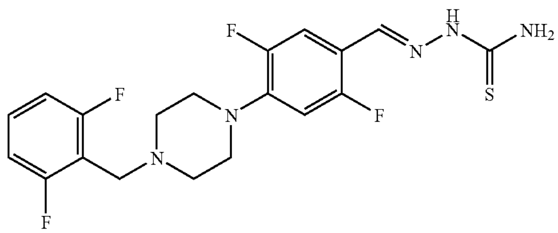 | 4-[4-(2,6-difluorobenzyl)piperazin-1-yl]-2,5-difluorobenzaldehyde thiosemicarbazone | 426 |
| 160 | 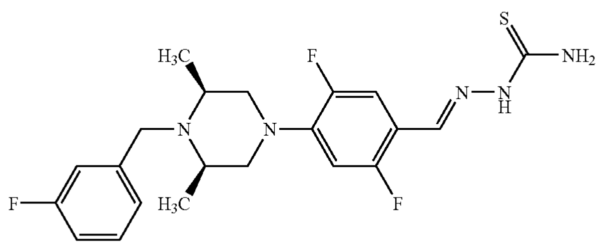 | 2,5-difluoro-4-[(3R,5S)-4-(3-fluorobenzyl)-3,5-dimethylpiperazin-1-yl]benzaldehyde thiosemicarbazone | 437 |
| 161 | 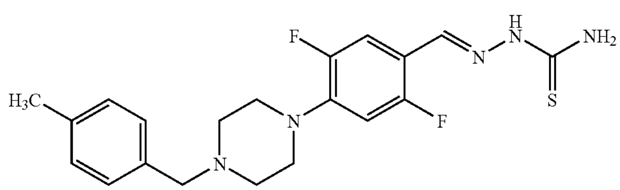 | 2,5-difluoro-4-[4-(4-methylbenzyl)piperazin-1-yl]benzaldehyde thiosemicarbazone | 404 |
| 162 | 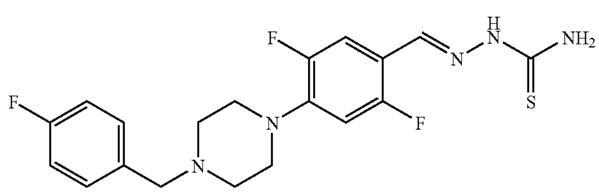 | 2,5-difluoro-4-[4-(4-fluorobenzyl)piperazin-1-yl]benzaldehyde thiosemicarbazone | 408 |
| 163 | 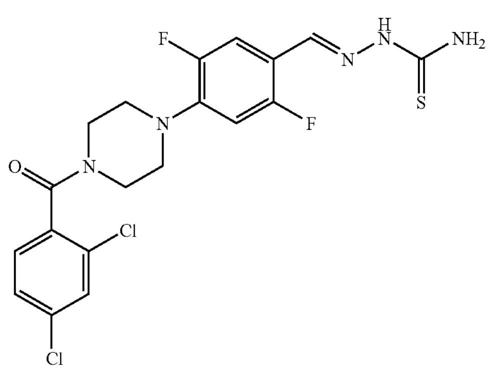 | 4-[4-(2,4-dichlorobenzoyl)piperazin-1-yl]-2,5-difluorobenzaldehyde thiosemicarbazone | 473 |

TABLE 3-continued

| | Structure | Name | MH+ |
|---|---|---|---|
| 164 | 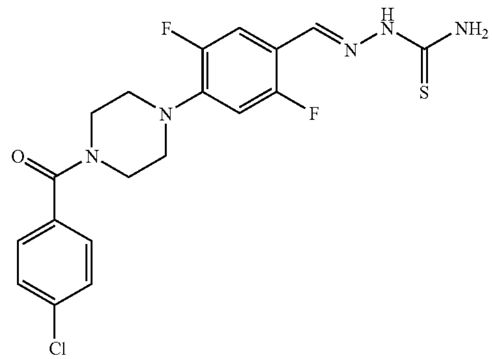 | 4-[4-(4-chlorobenzoyl)piperazin-1-yl]-2,5-difluorobenzaldehyde thiosemicarbazone | 439 |
| 165 | 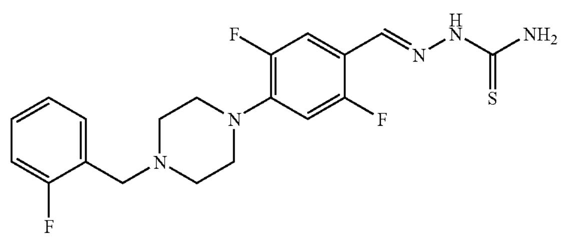 | 2,5-difluoro-4-[4-(2-fluorobenzyl)piperazin-1-yl]benzaldehyde thiosemicarbazone | 408 |
| 166 | 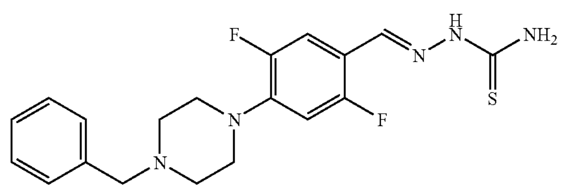 | 4-(4-benzylpiperazin-1-yl)-2,5-difluorobenzaldehyde thiosemicarbazone | 390 |
| 167 | 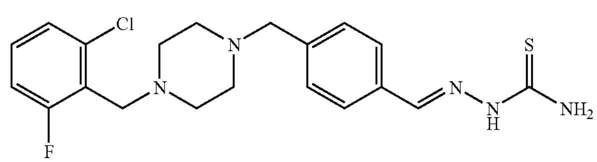 | 4-{[4-(2-chloro-6-fluorobenzyl)piperazin-1-yl]methyl}benzaldehyde thiosemicarbazone | 421 |
| 168 | 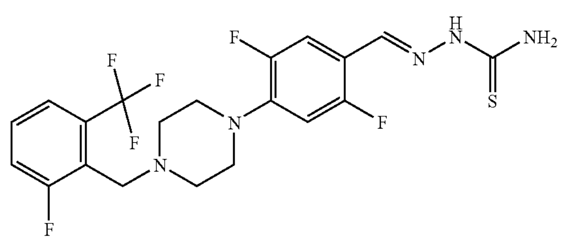 | 2,5-difluoro-4-{4-[2-fluoro-6-(trifluoromethyl)benzyl]piperazin-1-yl}benzaldehyde thiosemicarbazone | 476 |
| 169 | 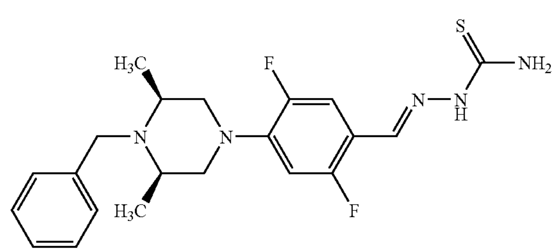 | 4-[(3R,5S)-4-benzyl-3,5-dimethylpiperazin-1-yl]-2,5-difluorobenzaldehyde thiosemicarbazone | 419 |

TABLE 3-continued

| Structure | Name | MH+ |
|---|---|---|
| 170 | 4-[4-(3,4-dichlorobenzoyl)piperazin-1-yl]-2,5-difluorobenzaldehyde thiosemicarbazone | 473 |
| 171 | 4-{4-[3-chloro-2-fluoro-6-(trifluoromethyl)benzyl]piperazin-1-yl}-2,5-difluorobenzaldehyde thiosemicarbazone | 511 |
| 172 | 2,5-difluoro-4-{4-[2-(trifluoromethoxy)benzyl]piperazin-1-yl}benzaldehyde thiosemicarbazone | 474 |
| 173 | 2,5-difluoro-4-{4-[2-(trifluoromethyl)benzyl]piperazin-1-yl}benzaldehyde thiosemicarbazone | 458 |
| 174 | 2,5-difluoro-4-[(3R,5S)-4-(2-fluorobenzyl)-3,5-dimethylpiperazin-1-yl]benzaldehyde thiosemicarbazone | 437 |

TABLE 3-continued

| Structure | Name | MH+ |
|---|---|---|
| 175 | 2,5-difluoro-4-{4-(2-(1H-pyrrol-1-yl)ethyl]piperazin-1-yl)benzaldehyde thiosemicarbazone | 393 |
| 176 | 4-[4-(2-chlorobenzyl)piperazin-1-yl]-2,5-difluorobenzaldehyde thiosemicarbazone | 425 |
| 177 | 4-[4-(2-chloro-4-fluorobenzyl)piperazin-1-yl]-2,5-difluorobenzaldehyde thiosemicarbazone | 443 |
| 178 | 4-[(3R,5S)-4-(2-chlorobenzyl)-3,5-dimethylpiperazin-1-yl]-2,5-difluorobenzaldehyde thiosemicarbazone | 453 |
| 179 | 4-{(3R,5S)-3,5-dimethyl-4-[3-(trifluoromethyl)benzyl]piperazin-1-yl}-2,5-difluorobenzaldehyde thiosemicarbazone | 487 |
| 180 | 4-[(3R,5S)-4-(4-chlorobenzoyl)-3,5-dimethylpiperazin-1-yl]-2,5-difluorobenzaldehyde thiosemicarbazone | 467 |

TABLE 3-continued

| | Structure | Name | MH+ |
|---|---|---|---|
| 181 | 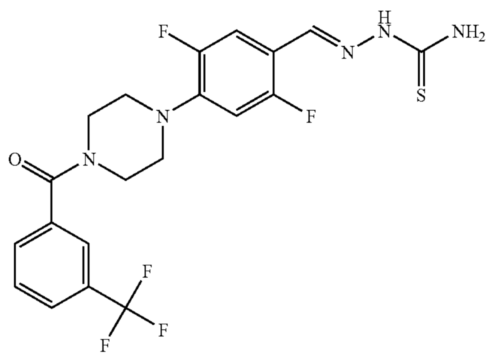 | 2,5-difluoro-4-{4-[3-(trifluoromethyl)benzoyl]piperazin-1-yl}benzaldehyde thiosemicarbazone | 472 |
| 182 | 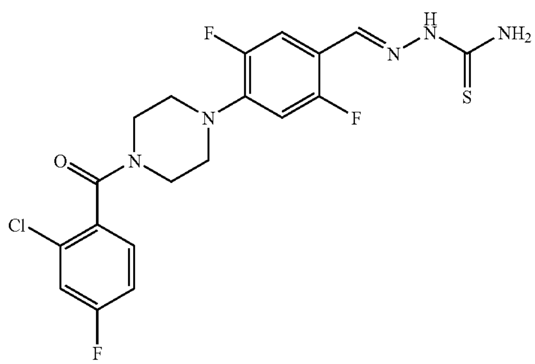 | 4-[4-(2-chtoro-4-fluorobenzoyl)piperazin-1-yl]-2,5-difluorobenzaldehyde thiosemicarbazone | 457 |
| 183 | 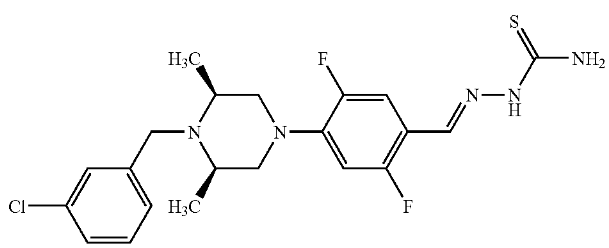 | 4-[(3R,5S)-4-(3-chlorobenzyl)-3,5-dimethylpiperazin-1-yl]-2,5-difluorobenzaldehyde thiosemicarbazone | 453 |
| 184 | 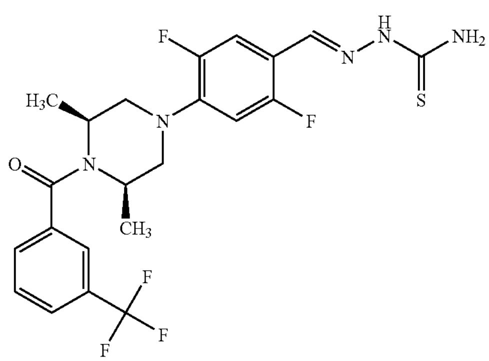 | 4-{(3R,5S)-3,5-dimethyl-4-[3-(trifluoromethyl)benzoyl]piperazin-1-yl}-2,5-difluorobenzaldehyde thiosemicarbazone | 501 |
| 185 | 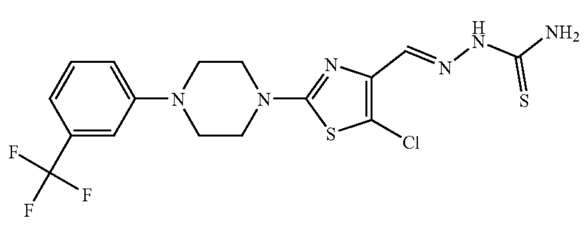 | 5-chloro-2-{4-[3-(trifluoromethyl)phenyl]piperazin-1-yl}-1,3-thiazole-4-carbaldehyde thiosemicarbazone | 450 |

TABLE 3-continued

| Structure | Name | MH+ |
|---|---|---|
| 186 | 2,5-difluoro-4-[4-(4-fluorobenzoyl)piperazin-1-yl]benzaldehyde thiosemicarbazone | 422 |
| 187 | 4-[4-(2-bromobenzoyl)piperazin-1-yl]-2,5-difluorobenzaldehyde thiosemicarbazone | 483 |
| 188 | 2,5-difluoro-4-{4-[4-fluoro-2-(trifluoromethyl)benzoyl]piperazin-1-yl}benzaldehyde thiosemicarbazone | 490 |
| 189 | 4-(4-(2,6-dichlorobenzoyl)piperazin-1-yl]-2,5-difluorobenzaldehyde thiosemicarbazone | 473 |

TABLE 3-continued

| Structure | Name | MH+ |
|---|---|---|
| 190 | 2,5-difluoro-4-{(3R,5S)-4-[4-fluoro-2-(trifluoromethyl)benzoyl]-3,5-dimethylpiperazin-1-yl}benzaldehyde thiosemicarbazone | 518 |
| 191 | 4-[(3R,5S)-4-(3-bromobenzoyl)-3,5-dimethylpiperazin-1-yl]-2,5-difluorobenzaldehyde thiosemicarbazone | 511 |
| 192 | 4-{[4-(2-chlorobenzyl)piperazin-1-yl]carbonyl}benzaldehyde thiosemicarbazone | 417 |
| 193 | 3-[5-(3-chlorophenyl)-2-furyl]-4,5-dihydro-1H-pyrazole-1-carbothioamide | 307 |
| 194 | 4-{(3R,5S)-3,5-dimethyl-4-[4-(trifluoromethyl)benzoyl]piperazin-1-yl}-2,5-difluorobenzaldehyde thiosemicarbazone | 501 |

TABLE 3-continued

| Structure | Name | MH+ |
|---|---|---|
| 195 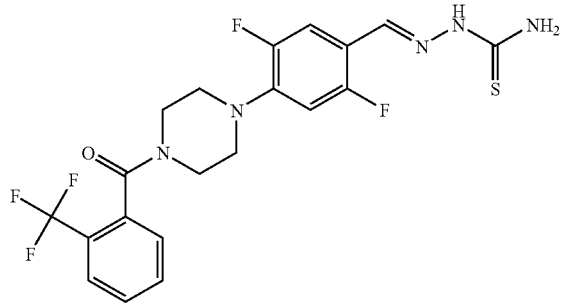 | 2,5-difluoro-4-{4-[2-(trifluoromethyl)benzoyl]piperazin-1-yl}benzaldehyde thiosemicarbazone | 472 |
| 196 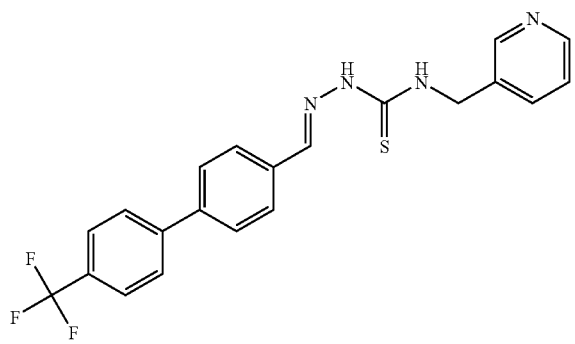 | 4'-(trifluoromethyl)-1,1'-biphenyl-4-carbaldehyde N-(pyridin-3-ylmethyl)thiosemicarbazone | 415 |
| 197 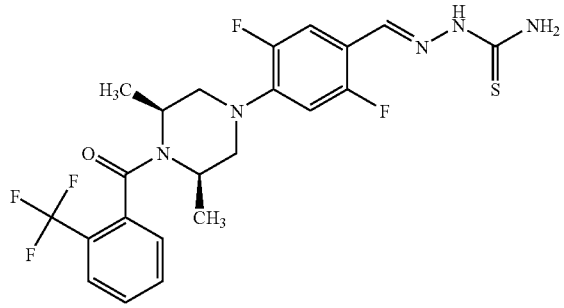 | 4-{(3R,5S)-3,5-dimethyl-4-[2-(trifluoromethyl)benzoyl]piperazin-1-yl}-2,5-difluorobenzaldehyde thiosemicarbazone | 501 |
| 198 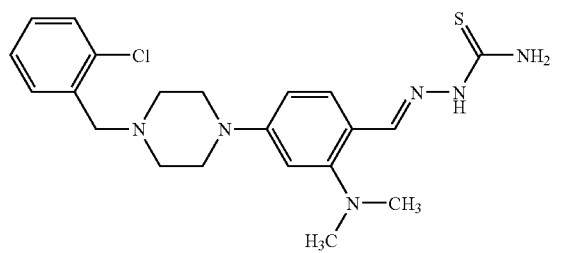 | 4-[4-(2-chlorobenzyl)piperazin-1-yl]-2-(dimethylamino)benzaldehyde thiosemicarbazone | 432 |
| 199 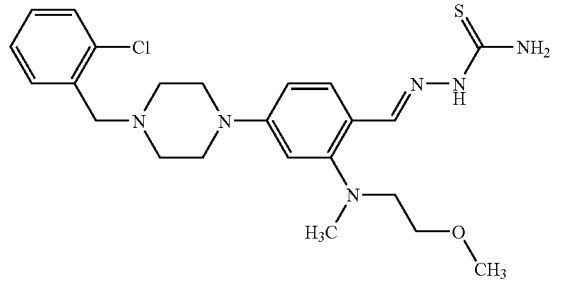 | 4-[4-(2-chlorobenzyl)piperazin-1-yl]-2-[(2-methoxyethyl)(methyl)amino]benzaldehyde thiosemicarbazone | 476 |

TABLE 3-continued

| | Structure | Name | MH+ |
|---|---|---|---|
| 200 | 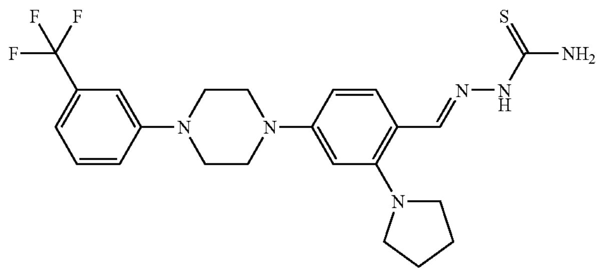 | 2-pyrrolidin-1-yl-4-{4-[3-(trifluoromethyl)phenyl]piperazin-1-yl}benzaldehyde thiosemicarbazone | 478 |
| 201 | 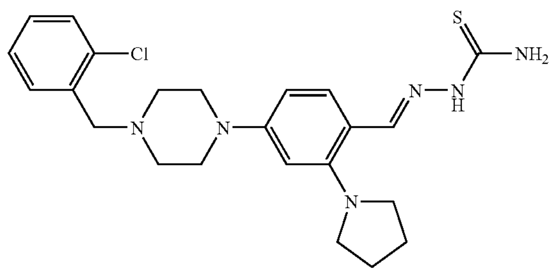 | 4-[4-(2-chlorobenzyl)piperazin-1-yl]-2-pyrrolidin-1-ylbenzaldehyde thiosemicarbazone | 458 |
| 202 | Chiral | 2-[(3S)-3-(dimethylamino)pyrrolidin-1-yl]-4-{4-[3-(trifluoromethyl)phenyl]piperazin-1-yl}benzaldehyde thiosemicarbazone | 521 |
| 203 | 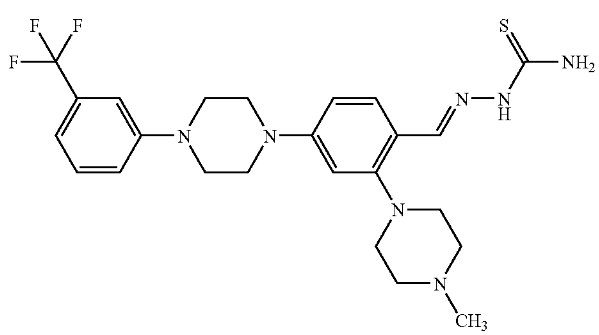 | 2-(4-methylpiperazin-1-yl)-4-{4-[3-(trifluoromethyl)phenyl]piperazin-1-yl}benzaldehyde thiosemicarbazone | 507 |
| 204 | 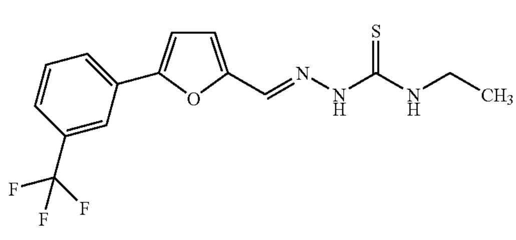 | 5-(3-(trifluoromethyl)phenyl]-2-furaldehyde-N-ethylthiosemicarbazone | 342 |

TABLE 3-continued

| | Structure | Name | MH+ |
|---|---|---|---|
| 205 | 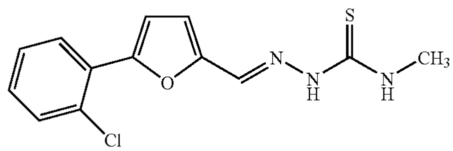 | 5-(2-chlorophenyl)-2-furaldehyde N-methylthiosemicarbazone | 295 |
| 206 | 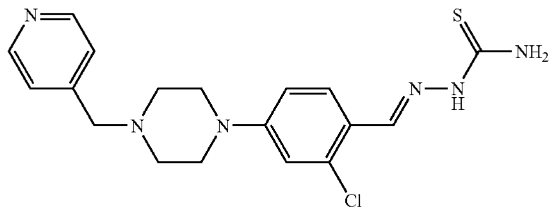 | 2-chloro-4-[4-(pyridin-4-ylmethyl)piperazin-1-yl]benzaldehyde thiosemicarbazone | 390 |
| 207 | 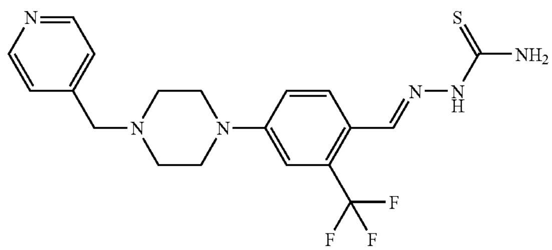 | 4-[4-(pyridin-4-ylmethyl)piperazin-1-yl]-2-(trifluoromethyl)benzaldehyde thiosemicarbazone | 423 |
| 208 | 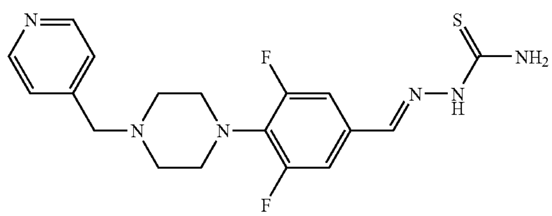 | 3,5-difluoro-4-[4-(pyridin-4-ylmethyl)piperazin-1-yl]benzaldehyde thiosemicarbazone | 391 |
| 209 | 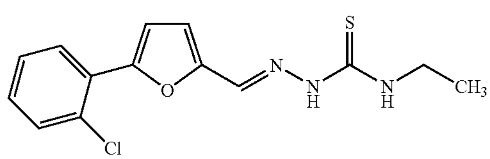 | 5-(2-chlorophenyl)-2-furaldehyde N-ethylthiosemicarbazone | 309 |
| 210 | 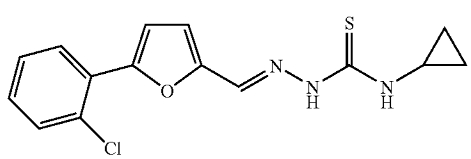 | 5-(3-chlorophenyl)-2-furaldehyde N-cyclopropylthiosemicarbazone | 321 |
| 211 | 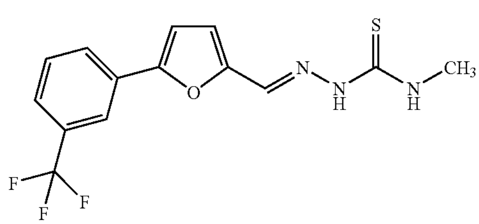 | 5-[3-(trifluoromethyl)phenyl]-2-furaldehyde N-methylthiosemicarbazone | 328 |

TABLE 3-continued

| | Structure | Name | MH+ |
|---|---|---|---|
| 212 | 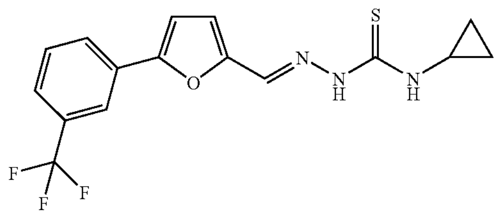 | 5-[3-(trifluoromethyl)phenyl]-2-furaldehyde N-cyclopropylthiosemicarbazone | 354 |
| 213 | 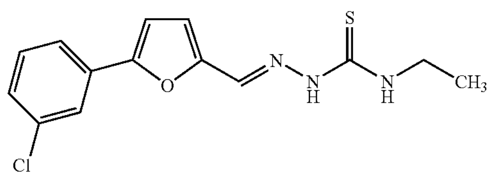 | 5-(3-chlorophenyl)-2-furaldehyde N-ethylthiosemicarbazone | 309 |
| 214 | 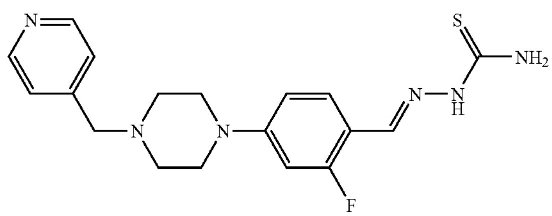 | 2-fluoro-4-[4-(pyridin-4-ylmethyl)piperazin-1-yl]benzaldehyde thiosemicarbazone | 373 |
| 215 | 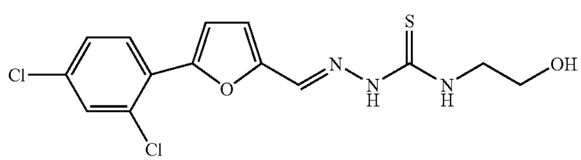 | 5-(2,4-dichlorophenyl)-2-furaldehyde N-(2-hydroxyethyl)thiosemicarbazone | 359 |
| 216 | 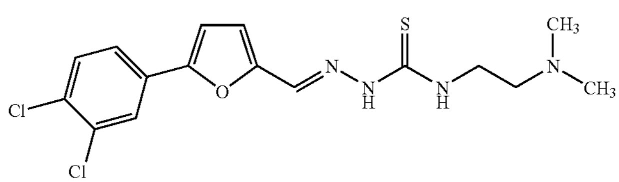 | 5-(3,4-dichlorophenyl)-2-furaldehyde N-[2-(dimethylamino)ethyl]thiosemicarbazone | 386 |
| 217 | 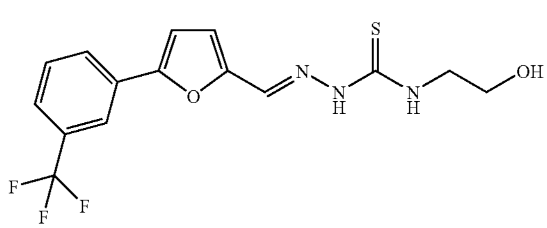 | 5-[3-(trifluoromethyl)phenyl]-2-furaldehyde N-(2-hydroxyethyl)thiosemicarbazone | 358 |
| 218 | 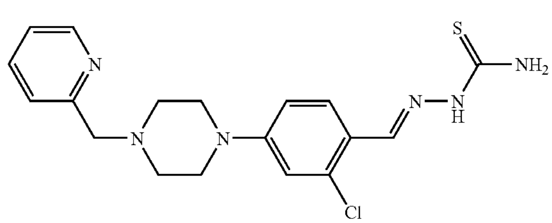 | 2-chloro-4-[4-(pyridin-2-ylmethyl)piperazin-1-yl]benzaldehyde thiosemicarbazone | 390 |

TABLE 3-continued

| | Structure | Name | MH+ |
|---|---|---|---|
| 219 | 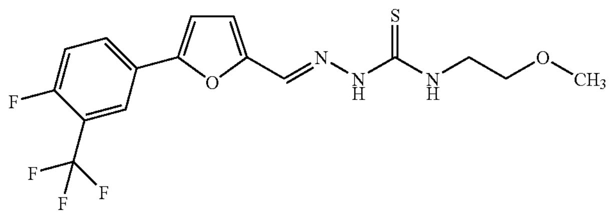 | 5-[4-fluoro-3-(trifluoromethyl) phenyl]-2-furaldehyde N-(2-methoxyethyl)thiosemicarbazone | 390 |
| 220 | 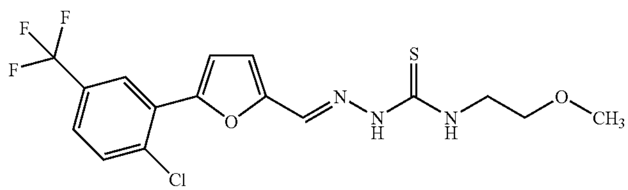 | 5-[2-chloro-5-(trifluoromethyl) phenyl]-2-furaldehyde N-(2-methoxyethyl)thiosemicarbazone | 407 |
| 221 | 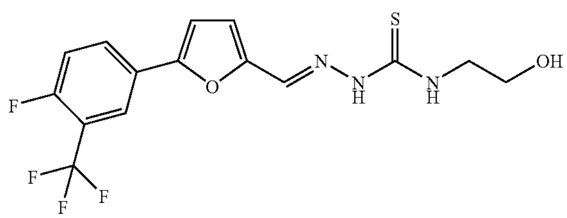 | 5-[4-fluoro-3-(trifluoromethyl) phenyl]-2-furaldehyde N-(2-hydroxyethyl)thiosemicarbazone | 376 |
| 222 | 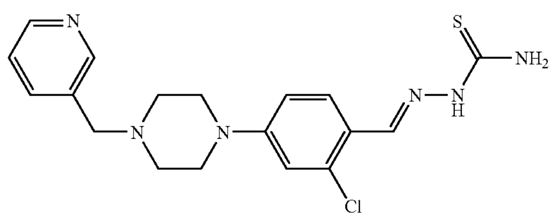 | 2-chloro-4-[4-(pyridin-3-ylmethyl) piperazin-1-yl] benzaldehyde thiosemicarbazone | 390 |
| 223 | 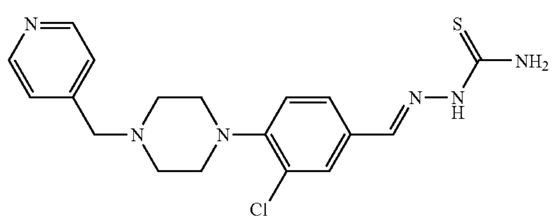 | 3-chloro-4-[4-(pyridin-4-ylmethyl) piperazin-1-yl] benzaldehyde thiosemicarbazone | 390 |
| 224 | 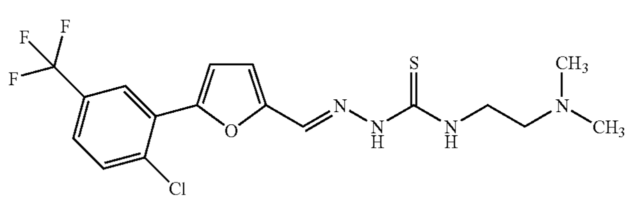 | 5-[2-chloro-5-(trifluoromethyl) phenyl]-2-furaldehyde N-[2-(dimethylamino)ethyl] thiosemicarbazone | 420 |
| 225 | 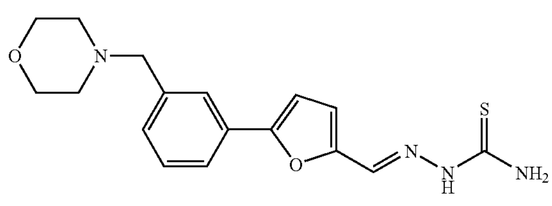 | 5-[3-(morpholin-4-ylmethyl) phenyl]-2-furaldehyde thiosemicarbazone | 345 |

TABLE 3-continued

| | Structure | Name | MH+ |
|---|---|---|---|
| 226 | 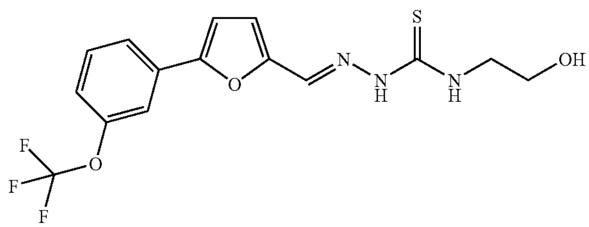 | 5-[3-(trifluoromethoxy)phenyl]-2-furaldehyde N-(2-hydroxyethyl)thiosemicarbazone | 374 |
| 227 | 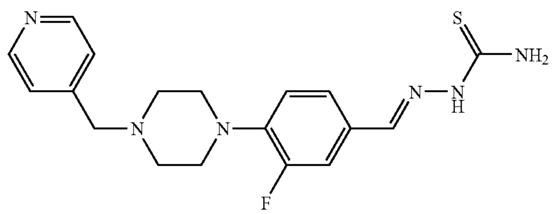 | 3-fluoro-4-[4-(pyridin-4-ylmethyl)piperazin-1-yl]benzaldehyde thiosemicarbazone | 373 |
| 228 | 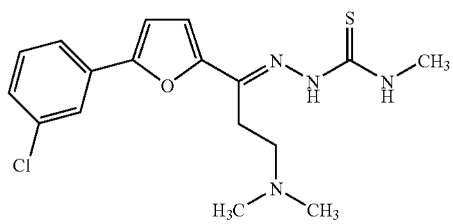 | (1E)-1-[5-(3-chlorophenyl)-2-furyl]-3-(dimethylamino)propan-1-one N-methylthiosemicarbazone | 366 |
| 229 | 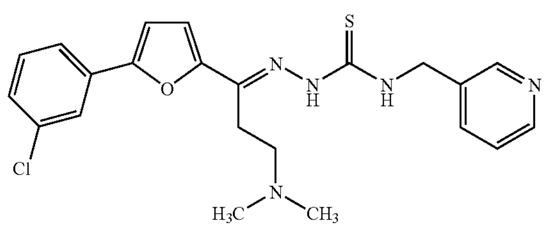 | (1E)-1-[5-(3-chlorophenyl)-2-furyl]-3-(dimethylamino)propan-1-one N-(pyridin-3-ylmethyl)thiosemicarbazone | 443 |
| 230 | 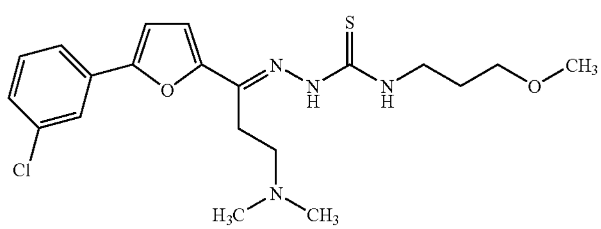 | (1E)-1-[5-(3-chlorophenyl)-2-furyl]-3-(dimethylamino)propan-1-one N-(3-methoxypropyl)thiosemicarbazone | 424 |
| 231 | 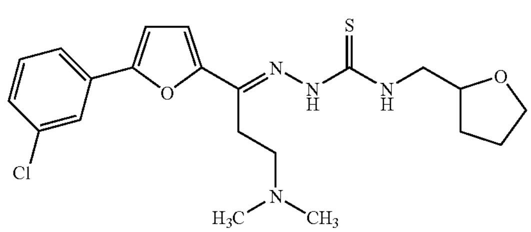 | (1E)-1-[5-(3-chlorophenyl)-2-furyl]-3-(dimethylamino)propan-1-one N-(tetrahydrofuran-2-ylmethyl)thiosemicarbazone | 436 |
| 232 | 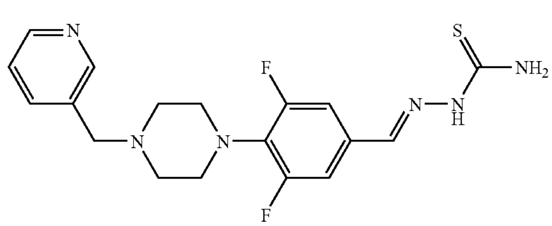 | 3,5-difluoro-4-[4-(pyridin-3-ylmethyl)piperazin-1-yl]benzaldehyde thiosemicarbazone | 391 |

TABLE 3-continued

| | Structure | Name | MH+ |
|---|---|---|---|
| 233 | 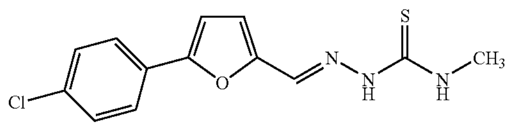 | 5-(4-chlorophenyl)-2-furaldehyde N-methylthiosemicarbazone | 295 |
| 234 | 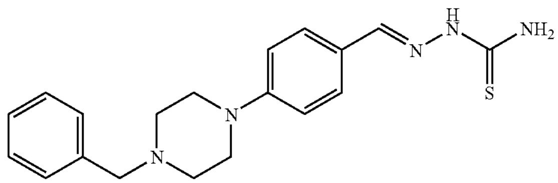 | 4-(4-benzyl-2-oxopiperazin-1-yl)benzaldehyde thiosemicarbazone | 368 |
| 235 | 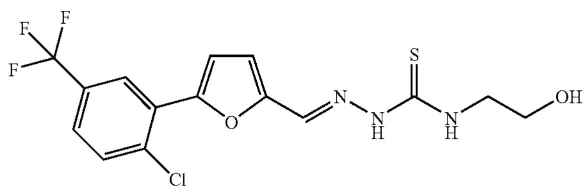 | 5-[2-chloro-5-(trifluoromethyl)phenyl]-2-furaldehyde N-(2-hydroxyethyl)thiosemicarbazone | 393 |
| 236 | 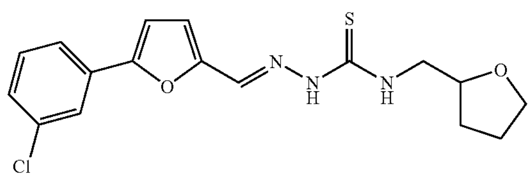 | 5-(3-chlorophenyl)-2-furaldehyde N-(tetrahydrofuran-2-ylmethyl)thiosemicarbazone | 365 |
| 237 | 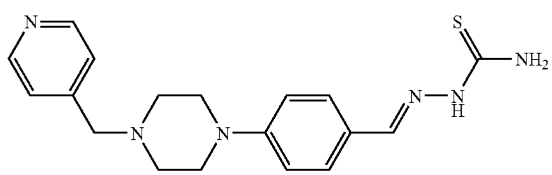 | 4-[4-(pyridin-4-ylmethyl)piperazin-1-yl]benzaldehyde thiosemicarbazone | 355 |
| 238 | 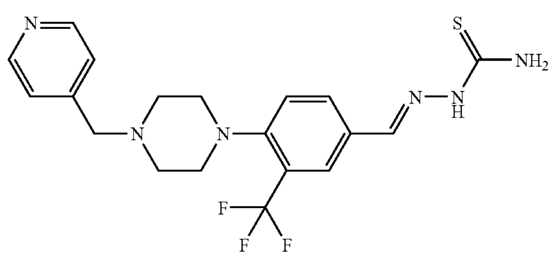 | 4-[4-(pyridin-4-ylmethyl)piperazin-1-yl]-3-(trifluoromethyl)benzaldehyde thiosemicarbazone | 423 |
| 239 | 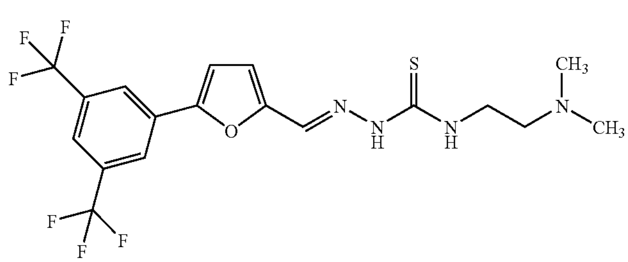 | 5-[3,5-bis(trifluoromethyl)phenyl]-2-furaldehyde N-[2-(dimethylamino)ethyl]thiosemicarbazone | 453 |

TABLE 3-continued

| | Structure | Name | MH+ |
|---|---|---|---|
| 240 | 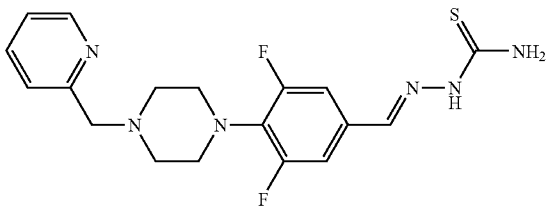 | 3,5-difluoro-4-[4-(pyridin-2-ylmethyl)piperazin-1-yl]benzaldehyde thiosemicarbazone | 391 |
| 241 | 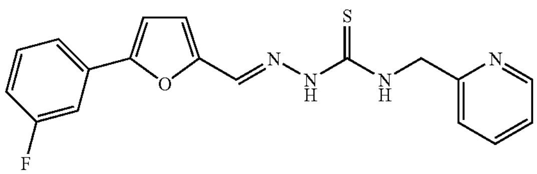 | 5-(3-fluorophenyl)-2-furaldehyde N-(pyridin-2-ylmethyl)thiosemicarbazone | 355 |
| 242 | 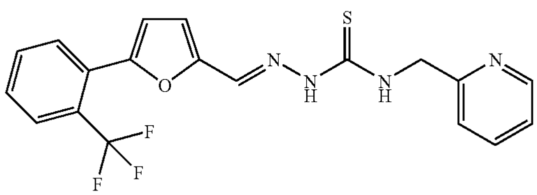 | 5-[2-(trifluoromethyl)phenyl]-2-furaldehyde N-(pyridin-2-ylmethyl)thiosemicarbazone | 405 |
| 243 | 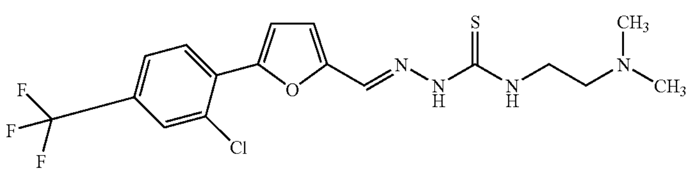 | 5-[2-chloro-4-(trifluoromethyl)phenyl]-2-furaldehyde N-[2-(dimethylamino)ethyl]thiosemicarbazone | 420 |
| 244 | 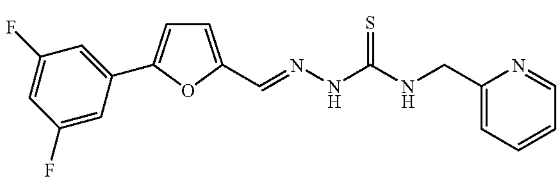 | 5-(3,5-difluorophenyl)-2-furaldehyde N-(pyridin-2-ylmethyl)thiosemicarbazone | 373 |
| 245 | 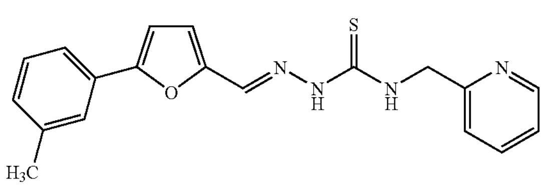 | 5-(3-methylphenyl)-2-furaldehyde N-(pyridin-2-ylmethyl)thiosemicarbazone | 351 |
| 246 | 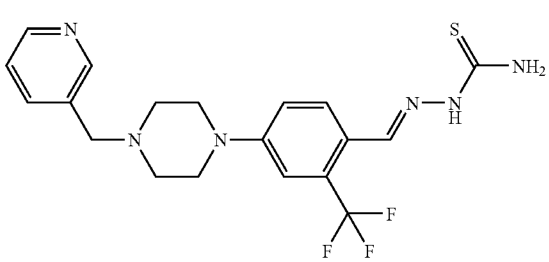 | 4-[4-(pyridin-3-ylmethyl)piperazin-1-yl]-2-(trifluoromethyl)benzaldehyde thiosemicarbazone | 423 |

TABLE 3-continued

| | Structure | Name | MH+ |
|---|---|---|---|
| 247 | 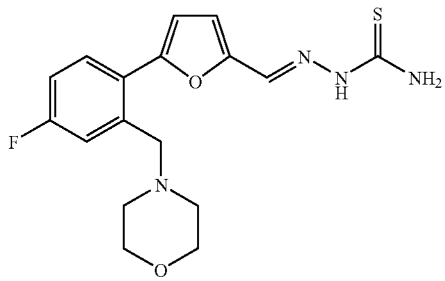 | 5-[4-fluoro-2-(morpholin-4-ylmethyl)phenyl]-2-furaldehyde thiosemicarbazone | 363 |
| 248 | 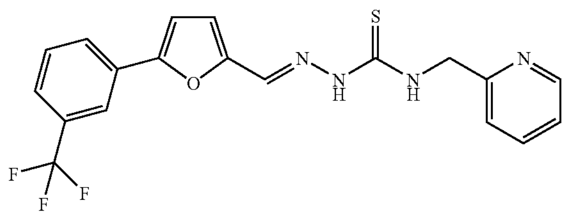 | 5-[3-(trifluoromethyl)phenyl]-2-furaldehyde N-(pyridin-2-ylmethyl)thiosemicarbazone | 405 |
| 249 | 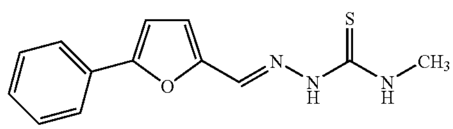 | 5-phenyl-2-furaldehyde N-methylthiosemicarbazone | 260 |
| 250 | 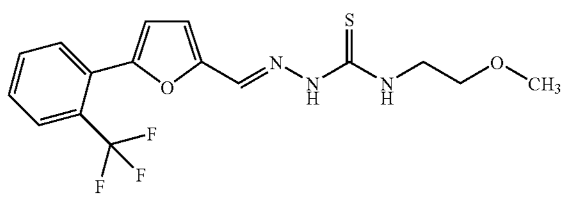 | 5-[2-(trifluoromethyl)phenyl]-2-furaldehyde N-(2-methoxyethyl)thiosemicarbazone | 372 |
| 251 | 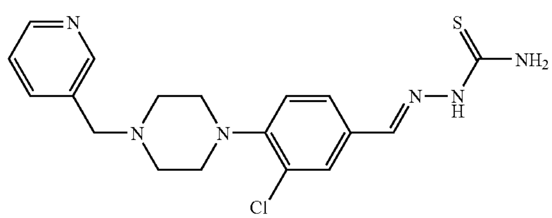 | 3-chloro-4-[4-(pyridin-3-ylmethyl)piperazin-1-yl]benzaldehyde thiosemicarbazone | 390 |
| 252 | 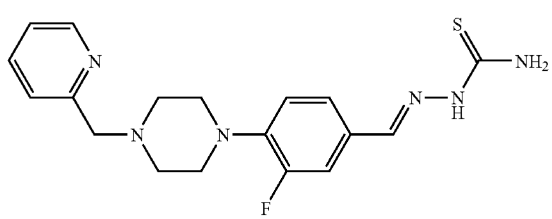 | 3-fluoro-4-[4-(pyridin-2-ylmethyl)piperazin-1-yl]benzaldehyde thiosemicarbazone | 373 |
| 253 | 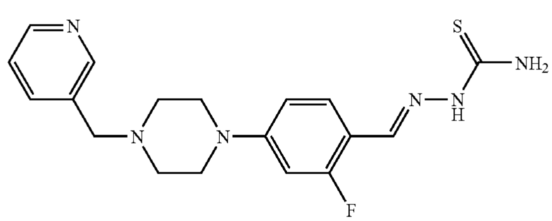 | 2-fluoro-4-[4-(pyridin-3-ylmethyl)piperazin-1-yl]benzaldehyde thiosemicarbazone | 373 |

TABLE 3-continued

| Structure | Name | MH+ |
|---|---|---|
| 254 | 4-[4-(pyridin-3-ylmethyl)piperazin-1-yl]-3-(trifluoromethyl)benzaldehyde thiosemicarbazone | 423 |
| 255 | 5-(2-methoxyphenyl)-2-furaldehyde N-(pyridin-2-ylmethyl)thiosemicarbazone | 367 |
| 256 | 3-fluoro-4-[4-(pyridin-3-ylmethyl)piperazin-1-yl]benzaldehyde thiosemicarbazone | 373 |
| 257 | 5-(2,5-difluorophenyl)-2-furaldehyde N-(pyridin-2-ylmethyl)thiosemicarbazone | 373 |
| 258 | 3-chloro-4-[4-(pyridin-2-ylmethyl)piperazin-1-yl]benzaldehyde thiosemicarbazone | 390 |
| 259 | 5-(4-chlorophenyl)-2-furaldehyde N-cyclopropylthiosemicarbazone | 321 |
| 260 | 5-[2-fluoro-5-(morpholin-4-ylmethyl)phenyl]-2-furaldehyde N-methylthiosemicarbazone | 377 |

TABLE 3-continued

| | Structure | Name | MH+ |
|---|---|---|---|
| 261 | 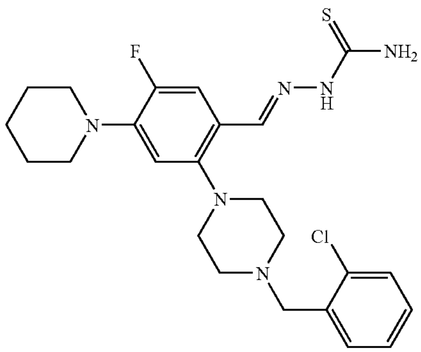 | 2-[4-(2-chlorobenzyl)piperazin-1-yl]-5-fluoro-4-piperidin-1-ylbenzaldehyde thiosemicarbazone | 490 |
| 262 | 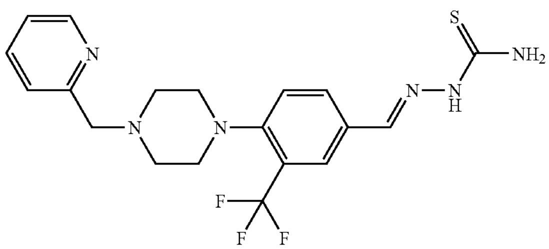 | 4-[4-(pyridin-2-ylmethyl)piperazin-1-yl]-3-(trifluoromethyl)benzaldehyde thiosemicarbazone | 423 |
| 263 | 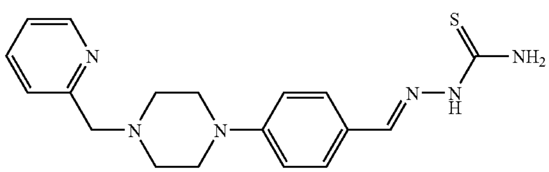 | 4-[4-(pyridin-2-ylmethyl)piperazin-1-yl]benzaldehyde thiosemicarbazone | 355 |
| 264 | 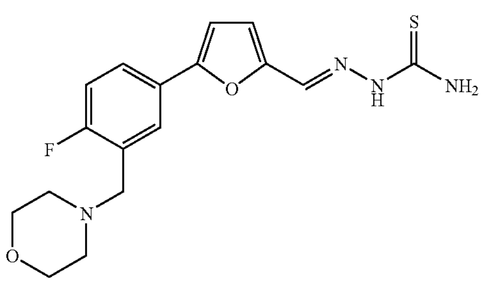 | 5-[4-fluoro-3-(morpholin-4-ylmethyl)phenyl]-2-furaldehyde thiosemicarbazone | 363 |
| 265 | 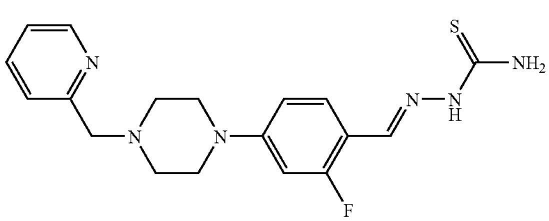 | 2-fluoro-4-[4-(pyridin-2-ylmethyl)piperazin-1-yl]benzaldehyde thiosemicarbazone | 373 |
| 266 | 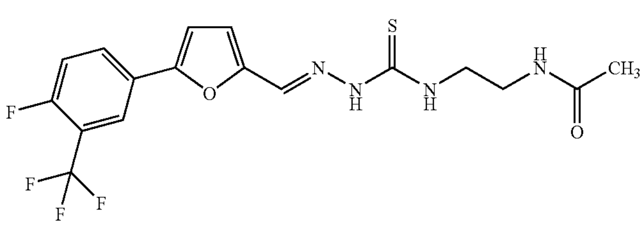 | N-[2-({[(2E)-2-({5-[4-fluoro-3-(trifluoromethyl)phenyl]-2-furyl}methylene)hydrazino]carbonothioyl}amino)ethyl]acetamide | 417 |

TABLE 3-continued

| Structure | Name | MH+ |
|---|---|---|
| 267 | 5-(4-chlorophenyl)-2-furaldehyde N-(tetrahydrofuran-2-ylmethyl)thiosemicarbazone | 365 |
| 268 | 5-(2,4-difluorophenyl)-2-furaldehyde N-(pyridin-2-ylmethyl)thiosemicarbazone | 373 |
| 269 | 5-(2-methylphenyl)-2-furaldehyde N-(pyridin-2-ylmethyl)thiosemicarbazone | 351 |
| 270 | 5-(3,4-dichlorophenyl)-2-furaldehyde N-(2-hydroxyethyl)thiosemicarbazone | 359 |
| 271 | 5-phenyl-2-furaldehyde N-(tetrahydrofuran-2-ylmethyl)thiosemicarbazone | 330 |
| 272 | 4-[(3R,5S)-4-benzoyl-3,5-dimethylpiperazin-1-yl]-2,5-difluorobenzaldehyde thiosemicarbazone | 433 |
| 273 | 2,5-difluoro-4-[(3R,5S)-4-(2-fluorobenzoyl)-3,5-dimethylpiperazin-1-yl] benzaldehyde thiosemicarbazone | 450 |

US 7,521,062 B2

149             150

TABLE 3-continued

| Structure | Name | MH+ |
|---|---|---|
| 274 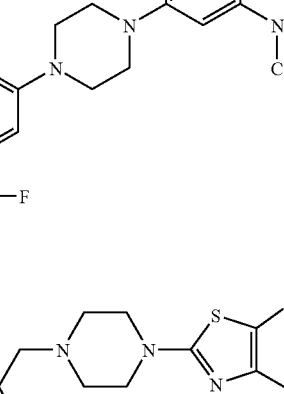 | N-{3-[(2-{(E)-[(aminocarbonothioyl)hydrazono]methyl}-4-fluoro-5-{4-[3-(trifluoromethyl)phenyl]piperazin-1-yl}phenyl)(methyl)amino]propyl}acetamide | 555 |
| 275  | 2-(4-benzylpiperazin-1-yl)-5-chloro-1,3-thiazole-4-carbaldehyde thiosemicarbazone | 396 |
| 276  | 4-[4-(3-chlorophenyl)piperazin-1-yl]-5-fluoro-2-(4-methylpiperazin-1-yl)benzaldehyde thiosemicarbazone | 491 |
| 277  | 4-[(3R,5S)-4-(2-bromobenzoyl)-3,5-dimethylpiperazin-1-yl]-2,5-difluorobenzaldehyde thiosemicarbazone | 511 |
| 278  | 4-[4-(2-chloro-6-fluorobenzyl)piperazin-1-yl]-3,5-difluorobenzaldehyde thiosemicarbazane | 443 |

TABLE 3-continued

| | Structure | Name | MH+ |
|---|---|---|---|
| 279 | 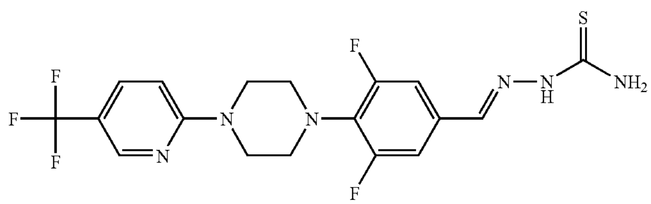 | 3,5-difluoro-4-{4-[5-(trifluoromethyl)pyridin-2-yl]piperazin-1-yl} benzaldehyde thiosemicarbazone | 445 |
| 280 | 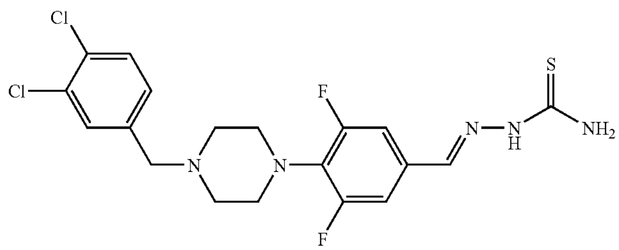 | 4-[4-(3,4-dichlorobenzyl)piperazin-1-yl]-3,5-difluorobenzaldehyde thiosemicarbazone | 459 |
| 281 | 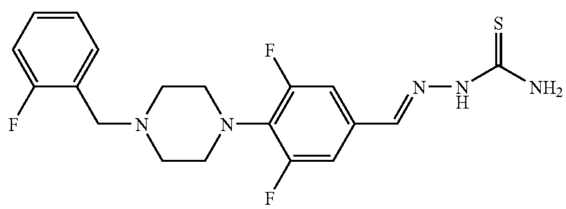 | 3,5-difluoro-4-[4-(2-fluorobenzyl) piperazin-1-yl] benzaldehyde thiosemicarbazone | 408 |
| 282 | 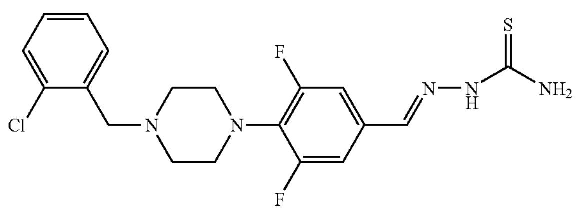 | 4-[4-(2-chlorobenzyl)piperazin-1-yl]-3,5-difluorobenzaldehyde thiosemicarbazone | 425 |
| 283 | 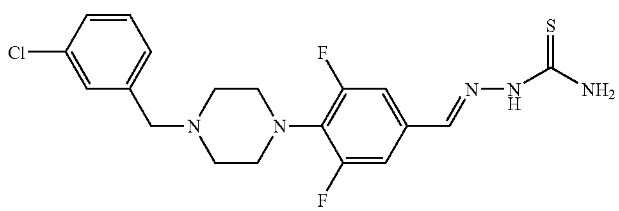 | 4-[4-(3-chlorobenzyl)piperazin-1-yl]-3,5-difluorobenzaldehyde thiosemicarbazone | 425 |
| 284 | 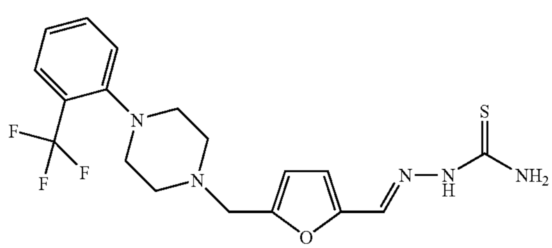 | 5-({4-[2-(trifluoromethyl) phenyl]piperazin-1-yl}methyl)-2-furaldehyde thiosemicarbazone | 412 |
| 285 | 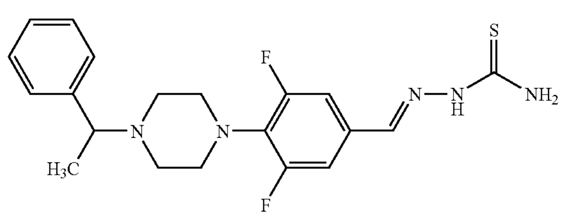 | 3,5-difluoro-4-[4-(1-phenylethyl) piperazin-1-yl] benzaldehyde thiosemicarbazone | 404 |

TABLE 3-continued

| Structure | Name | MH+ |
|---|---|---|
| 286 | 2,3-difluoro-4-[4-(4-fluorobenzyl)piperazin-1-yl]benzaldehyde thiosemicarbazone | 408 |
| 287 | 4-[4-(1,3-benzodioxol-5-ylmethyl)piperazin-1-yl]-3,5-difluorobenzaldehyde thiosemicarbazone | 434 |
| 288 | 3,5-difluoro-4-[4-(4-methylbenzyl)piperazin-1-yl]benzaldehyde thiosemicarbazone | 404 |
| 289 | 4-{4-(4-chlorobenzyl)piperazin-1-yl}-2,3-difluorobenzaldehyde thiosemicarbazone | 425 |
| 290 | 4-[4-(cyclohexylmethyl)piperazin-1-yl]-3,5-difluorobenzaldehyde thiosemicarbazone | 397 |
| 291 | 3,5-difluoro-4-[4-(4-fluorobenzyl)-1,4-diazepan-1-yl]benzaldehyde thiosemicarbazone | 422 |

TABLE 3-continued

| | Structure | Name | MH+ |
|---|---|---|---|
| 292 | 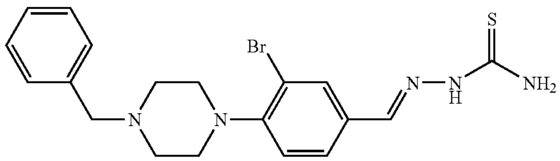 | 4-(4-benzylpiperazin-1-yl)-3-bromobenzaldehyde thiosemicarbazone | 433 |
| 293 | 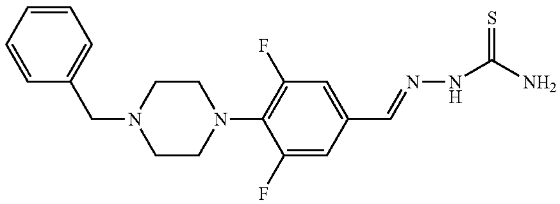 | 4-(4-benzylpiperazin-1-yl)-3,5-difluorobnzaldehyde thiosemicarbazone | 390 |
| 294 | 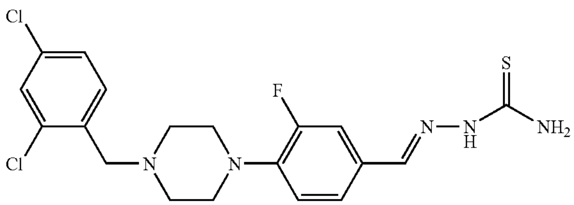 | 4-[4-(2,4-dichlorobenzyl)piperazin-1-yl]-3-fluorobenzaldehyde thiosemicarbazone | 441 |
| 295 | 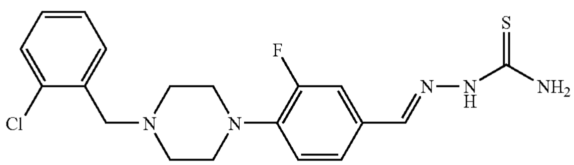 | 4-[4-(2-chlorobenzyl)piperazin-1-yl]-3-fluorobenzaldehyde thiosemicarbazone | 407 |
| 296 | 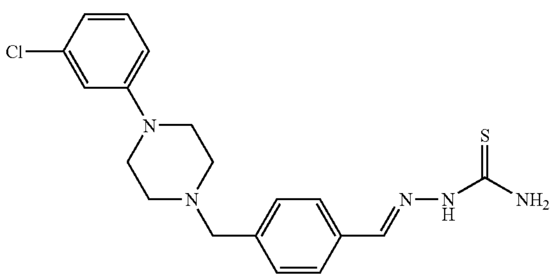 | 4-[4-(3-chlorophenyl)piperazin-1-yl]methyl} benzaldehyde thiosemicarbazone | 389 |
| 297 | 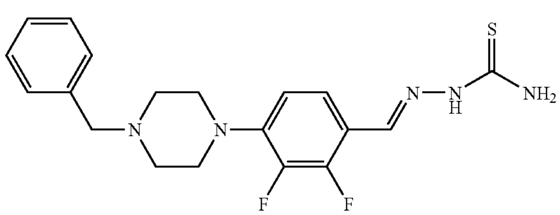 | 4-(4-benzylpiperazin-1-yl)-2,3-difluorobenzaldehyde thiosemicarbazone | 390 |
| 298 | 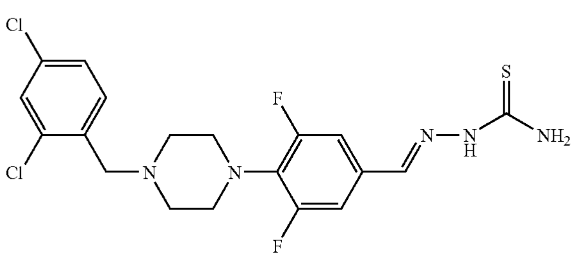 | 4-[4-(2,4-dichlorobenzyl)piperazin-1-yl]-3,5-difluorobenzaldehyde thiosemicarbazone | 459 |

TABLE 3-continued

| | Structure | Name | MH+ |
|---|---|---|---|
| 299 | 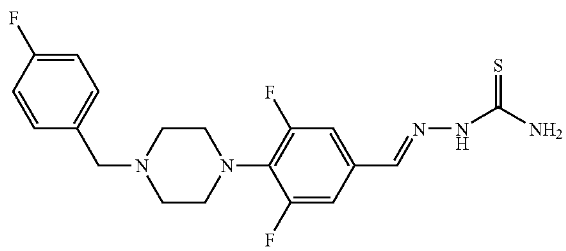 | 3,5-difluoro-4-[4-(4-fluorobenzyl)piperazin-1-yl]benzaldehyde thiosemicarbazone | 408 |
| 300 | 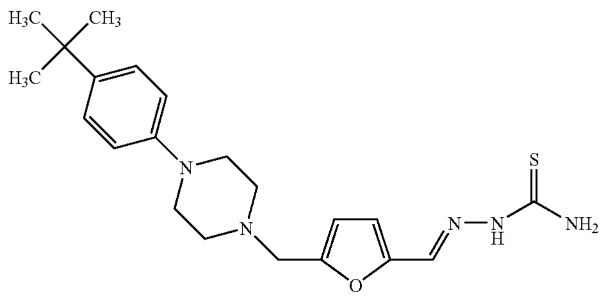 | 5-{[4-(4-tert-butylphenyl)piperazin-1-yl]methyl}-2-furaldehyde thiosemicarbazone | 401 |
| 301 | 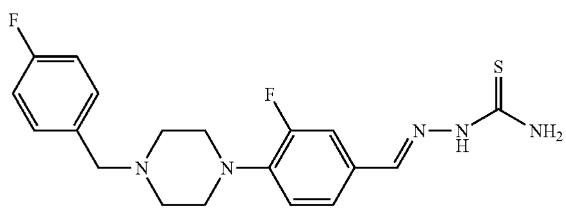 | 3--fluoro-4-[4-(4-fluorobenzyl)piperazin-1-yl]benzaldehyde thiosemicarbazone | 390 |
| 302 | 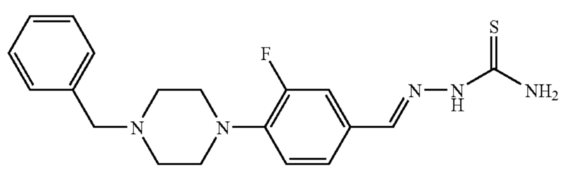 | 4-(4-benzylpiperazin-1-yl)-3-fluorobenzaldehyde thiosemicarbazone | 372 |
| 303 | 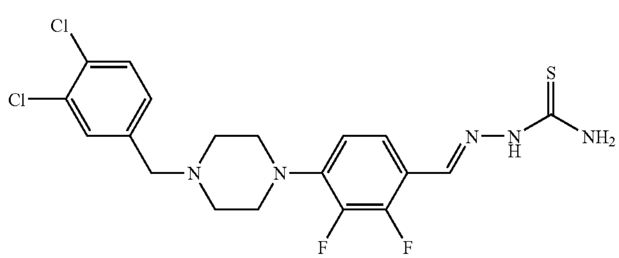 | 4-[4-(3,4-dichlorobenzyl)piperazin-1-yl]-2,3-difluorobenzaldehyde thiosemicarbazone | 459 |
| 304 | 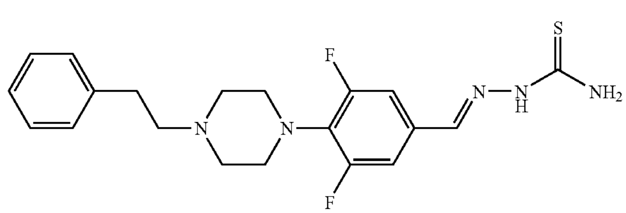 | 3,5-difluoro-4-[4-(2-phenylethyl)piperazin-1-yl]benzaldehyde thiosemicarbazone | 404 |

TABLE 3-continued

| | Structure | Name | MH+ |
|---|---|---|---|
| 305 | 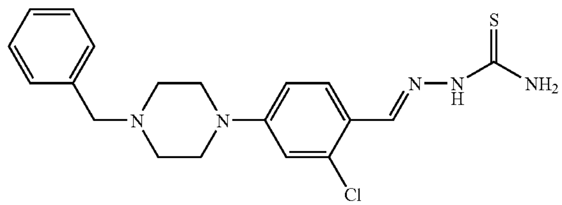 | 4-(4-benzylpiperazin-1-yl)-2-chlorobenzaldehyde thiosemicarbazone | 389 |
| 306 | 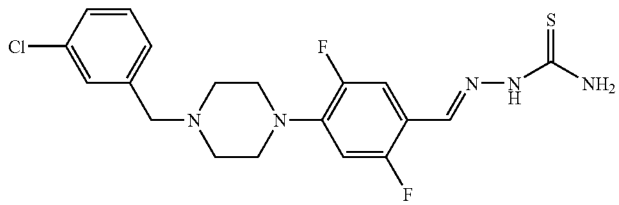 | 4-[4-(3-chlorobenzyl)piperazin-1-yl]-2,5-difluorobenzaldehyde thiosemicarbazone | 425 |
| 307 | 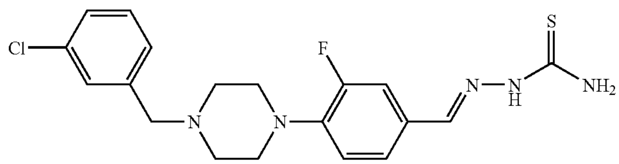 | 4-[4-(3-chlorobenzyl)piperazin-1-yl]-3-fluorobenzaldehyde thiosemicarbazone | 407 |
| 308 | 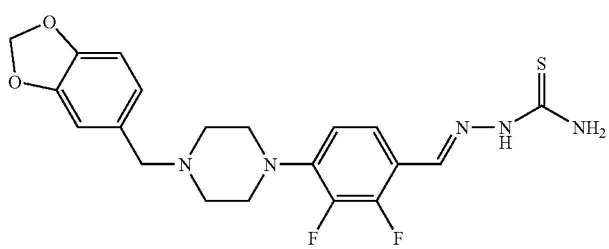 | 4-[4-(1,3-benzodioxol-5-ylmethyl)piperazin-1-yl]-2,3-difluorobenzaldehyde thiosemicarbazone | 434 |
| 309 | 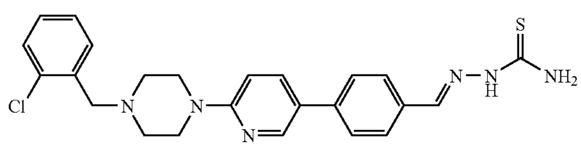 | 4-{6-(4-(2-chlorobenzyl)piperazin-1-yl]pyridin-3-yl}benzaldehyde thiosemicarbazone | 466 |
| 310 | 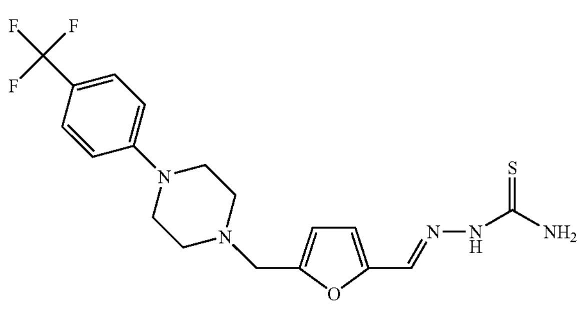 | 5-({4-[4-(trifluoromethyl)phenyl]piperazin-1-yl}methyl)-2-furaldehyde thiosemicarbazone | 412 |
| 311 | 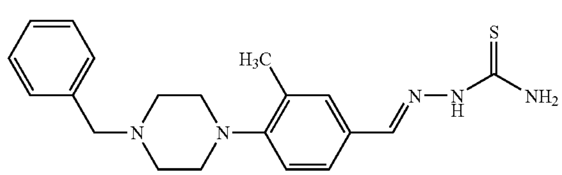 | 4-(4-benzylpiperazin-1-yl)-3-methylbenzaldehyde thiosemicarbazone | 369 |

TABLE 3-continued

| | Structure | Name | MH+ |
|---|---|---|---|
| 312 | | 2,3-difluoro-4-[4-(2-fluorobenzyl)piperazin-1-yl]benzaldehyde thiosemicarbazone | 408 |
| 313 | | 3-fluoro-4-[4-(4-methylbenzyl)piperazin-1-yl]benzaldehyde thiosemicarbazone | 387 |
| 314 | | 5-{[4-(2-chlorophenyl)piperazin-1-yl]methyl}-2-furaldehyde thiosemicarbazone | 379 |
| 315 | | 4-[4-(4-fluorobenzyl)piperazin-1-yl]-3-(trifluoromethyl)benzaldehyde thiosemicarbazone | 440 |
| 316 | | 4-[6-(4-benzylpiperazin-1-yl)pyridin-3-yl]benzaldehyde thiosemicarbazone | 432 |
| 317 | | 4-[4-(2-chloro-6-fluorobenzyl)-1,4-diazepan-1-yl]-3,5-difluorobenzaldehyde thiosemicarbazone | 457 |
| 318 | | 4-[4-(2-chloro-6-fluorobenzyl)-1,4-diazepan-1-yl]-2,3-difluorobenzaldehyde thiosemicarbazone | 457 |

TABLE 3-continued

| | Name | MH+ |
|---|---|---|
| 319 | 4-[4-(3,4-dichlorobenzyl)piperazin-1-yl]benzaldehyde thiosemicarbazone | 423 |
| 320 | 4-[4-(cyclohexylmethyl)piperazin-1-yl]-2,3-difluorobenzaldehyde thiosemicarbazone | 397 |
| 321 | 4-(4-benzylpiperazin-1-yl)-3-(trifluoromethyl)benzaldehyde thiosemicarbazone | 422 |
| 322 | 4-{6-[4-(cyclohexylmethyl)piperazin-1-yl]pyridin-3-yl}benzaldehyde thiosemicarbazone | 438 |
| 323 | 3-fluoro-4-(4-(2-methoxybenzyl)piperazin-1-yl]benzaldehyde thiosemicarbazone | 403 |
| 324 | 2,3-difluoro-4-[4-(4-methylbenzyl)piperazin-1-yl]benzaldehyde thiosemicarbazone | 404 |
| 325 | 3,5-difluoro-4-[4-(2-methylbenzyl)piperazin-1-yl]benzaldehyde thiosemicarbazone | 404 |

TABLE 3-continued

| | Structure | Name | MH+ |
|---|---|---|---|
| 326 | 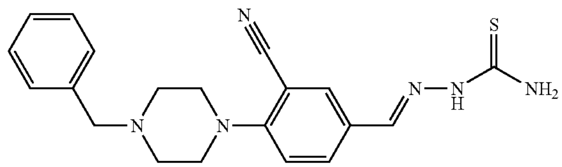 | 5-{(E)-[(aminocarbonothioyl)hydrazono]methyl}-2-(4-benzylpiperazin-1-yl)benzonitrile | 380 |
| 327 | 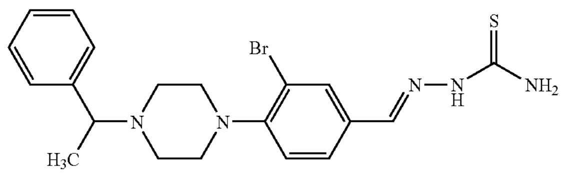 | 3-bromo-4-[4-(1-phenylethyl)piperazin-1-yl]benzaldehyde thiosemicarbazone | 447 |
| 328 | Chiral | 4-{(3S)-3-[(2-chloro-6-fluorobenzyl)amino]pyrrolidin-1-yl}-2,5-difluorobenzaldehyde thiosemicarbazone | 443 |
| 329 | 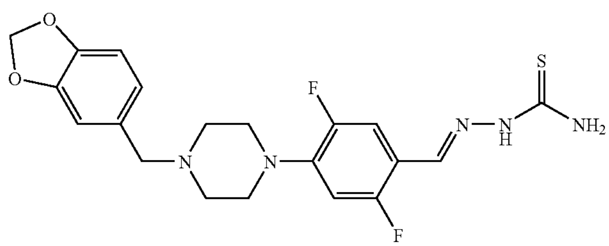 | 4-[4-(1,3-benzodioxol-5-ylmethyl)piperazin-1-yl]-2,5-difluorobenzaldehyde thiosemicarbazone | 434 |
| 330 | 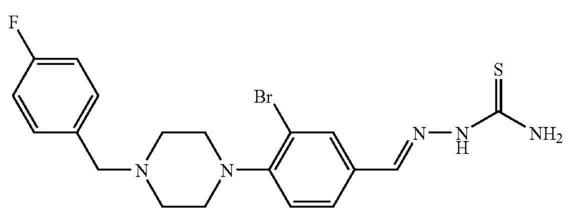 | 3-bromo-4-[4-(4-fluorobenzyl)piperazin-1-yl]benzaldehyde thiosemicarbazone | 451 |
| 331 | 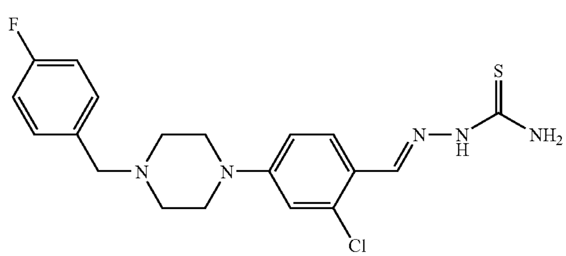 | 2-chloro-4-[4-(4-fluorobenzyl)piperazin-1-yl]benzaldehyde thiosemicarbazone | 407 |
| 332 | 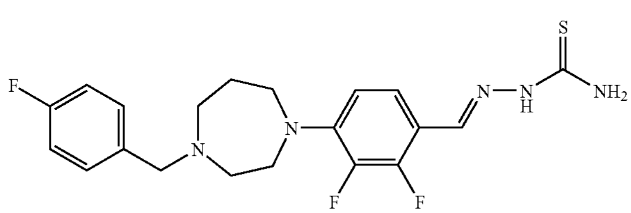 | 2,3-difluoro-4-[4-(4-fluorobenzyl)-1,4-diazepan-1-yl]benzaldehyde thiosemicarbazone | 422 |

TABLE 3-continued

| Structure | | Name | MH+ |
|---|---|---|---|
| 333 | | 4-[4-(3-chlorobenzyl)piperazin-1-yl]-2,3-difluorobenzaldehyde thiosemicarbazone | 425 |
| 334 | | 4-[4-(2-chloro-6-fluorobenzyl)piperazin-1-yl]-2,3-difluorobenzaldehyde thiosemicarbazone | 443 |
| 335 | Chiral | 4-{(3R)-4-benzyl-3-[(benzyloxy)methyl]piperazin-1-yl}-2,5-difluorobenzaldehyde thiosemicarbazone | 511 |
| 336 | | 5-{[4-(4-chlorophenyl)piperazin-1-yl]methyl}-2-furaldehyde thiosemicarbazone | 379 |
| 337 | | 2-chloro-4-[4-(2-fluorobenzyl)piperazin-1-yl]benzaldehyde thiosemicarbazone | 407 |
| 338 | | 4-[4-(2,4-dichlorobenzyl)piperazin-1-yl]-2,3-difluorobenzaldehyde thiosemicarbazone | 459 |

TABLE 3-continued

| | Structure | Name | MH+ |
|---|---|---|---|
| 339 | 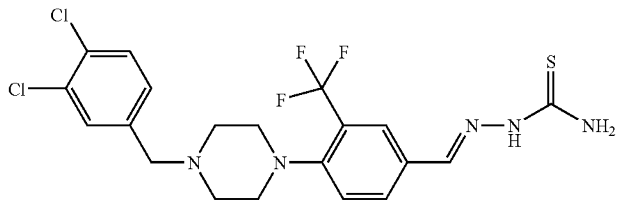 | 4-[4-(3,4-dichlorobenzyl)piperazin-1-yl]-3-(trifluoromethyl)benzaldehyde thiosemicarbazone | 491 |
| 340 | Chiral | 4-{[(3R)-1-benzylpyrrolidin-3-yl]amino}-2,5-difluorobenzaldehyde thiosemicarbazone | 390 |
| 341 | 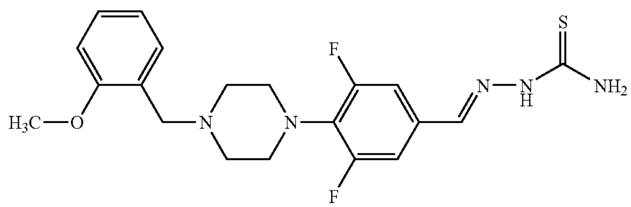 | 3,5-difluoro-4-[4-(2-methoxybenzyl)piperazin-1-yl]benzaldehyde thiosemicarbazone | 420 |
| 342 | 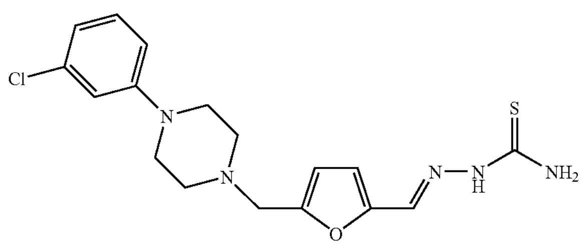 | 5-{[4-(3-chlorophenyl)piperazin-1-yl]methyl}-2-furaldehyde thiosemicarbazone | 379 |
| 343 | Chiral | 4-[(1S,4S)-5-benzyl-2,5-diazabicyclo[2.2.1]hept-2-yl]-3,5-difluorobenzaldehyde thiosemicarbazone | 402 |
| 344 | 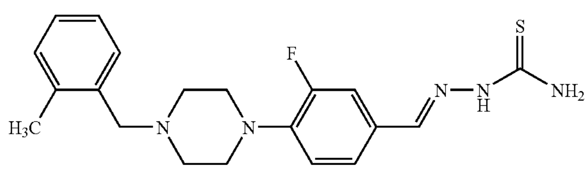 | 3-fluoro-4-[4-(2-methylbenzyl)piperazin-1-yl]benzaldehyde thiosemicarbazone | 387 |

TABLE 3-continued

| Structure | Name | MH+ |
|---|---|---|
| 345 | 5-{(E)-[(aminocarbonothioyl)hydrazono]methyl}-2-[4-(cyclohexylmethyl)piperazin-1-yl]benzonitrile | 386 |
| 346 | 2,5-difluoro-4-[4-(2-methoxybenzyl)piperazin-1-yl]benzaldehyde thiosemicarbazone | 420 |
| 347 | 4-[4-(4-fluorobenzyl)piperazin-1-yl]benzaldehyde thiosemicarbazone | 372 |
| 348 | 4-[4-(2-chlorobenzyl)piperazin-1-yl]-2,3-difluorobenzaldehyde thiosemicarbazone | 425 |
| 349 | 4-[4-(3-chlorobenzyl)piperazin-1-yl]benzaldehyde thiosemicarbazone | 389 |
| 350 | 4-[4-(4-tert-butylbenzyl)piperazin-1-yl]benzaldehyde thiosemicarbazone | 411 |
| 351 Chiral | 4-{[(3S)-1-benzylpiperidin-3-yl]amino}-3,5-difluorobenzaldehyde thiosemicarbazone | 404 |

TABLE 3-continued

| | Structure | Name | MH+ |
|---|---|---|---|
| 352 | 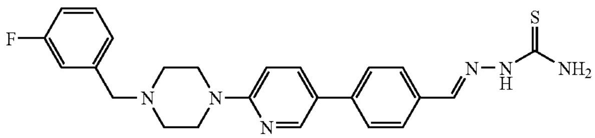 | 4-{6-[4-(3-fluorobenzyl)piperazin-1-yl]pyridin-3-yl}benzaldehyde thiosemicarbazone | 450 |
| 353 | 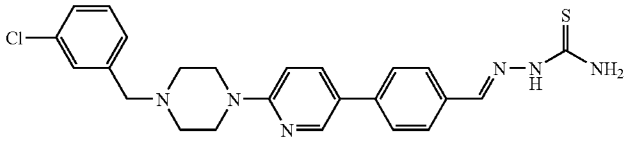 | 4-{6-[4-(3-chlorobenzyl)piperazin-1-yl]pyridin-3-yl}benzaldehyde thiosemicarbazone | 466 |
| 354 | 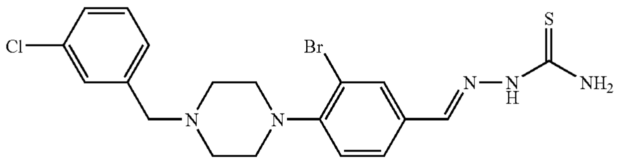 | 3-bromo-4-[4-(3-chlorobenzyl)piperazin-1-yl]benzaldehyde thiosemicarbazone | 468 |
| 355 | 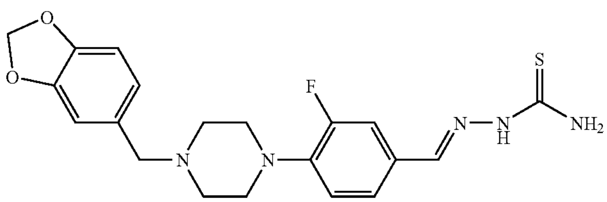 | 4-[4-(1,3-benzodioxol-5-ylmethyl)piperazin-1-yl]-3-fluorobenzaldehyde thiosemicarbazone | 416 |
| 356 | 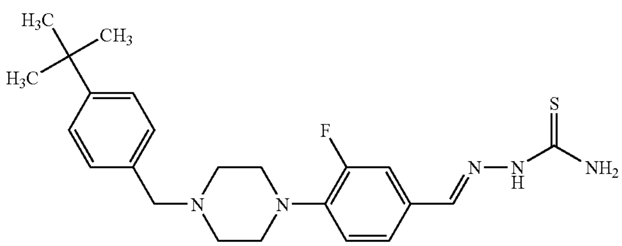 | 4-[4-(4-tert-butylbenzyl)piperazin-1-yl]-3-fluorobenzaldehyde thiosemicarbazone | 429 |
| 357 | 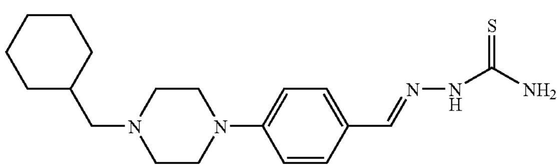 | 4-[4-(cyclohexylmethyl)piperazin-1-yl]benzaldehyde thiosemicarbazone | 361 |
| 358 | 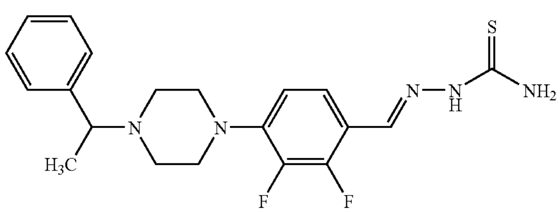 | 2,3-difluoro-4-[4-(1-phenylethyl)piperazin-1-yl]benzaldehyde thiosemicarbazone | 404 |
| 359 | 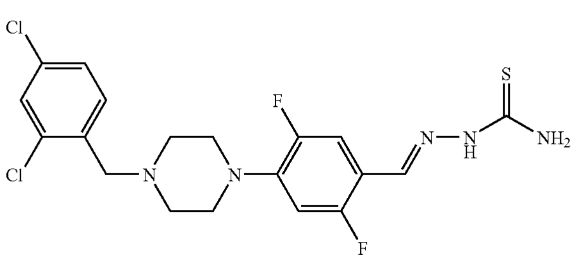 | 4-[4-(2,4-dichlorobenzyl)piperazin-1-yl]-2,5-difluorobenzaldehyde thiosemicarbazone | 459 |

TABLE 3-continued

| | Structure | Name | MH+ |
|---|---|---|---|
| 360 | 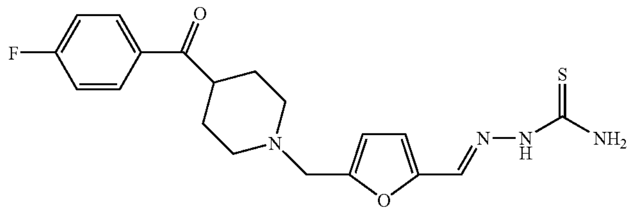 | 5-{[4-(4-fluorobenzoyl)piperidin-1-yl]methyl}-2-furaldehyde thiosemicarbazone | 389 |
| 361 | 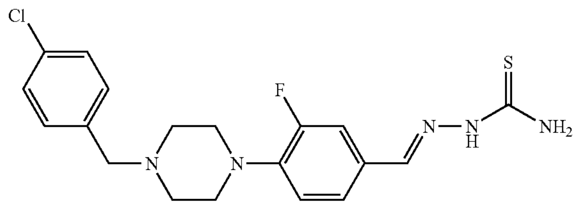 | 4-[4-(4-chlorobenzyl)piperazin-1-yl]-3-fluorobenzaldehyde thiosemicarbazone | 407 |
| 362 | 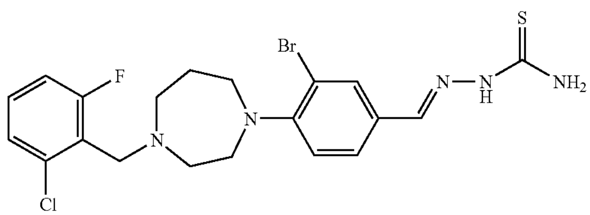 | 3-bromo-4-[4-(2-chloro-6-fluorobenzyl)-1,4-diazepan-1-yl]benzaldehyde thiosemicarbazone | 500 |
| 363 | Chiral | 2,5-difluoro-4-[(3S)-4-(2-fluorobenzyl)-3-isopropylpiperazin-1-yl]benzaldehyde thiosemicarbazone | 451 |
| 364 | 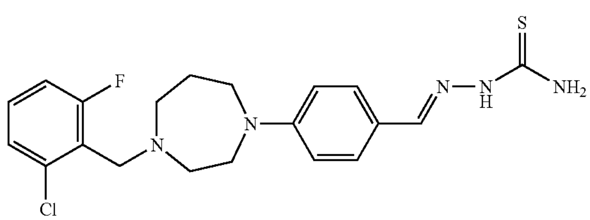 | 4-[4-(2-chloro-6-fluorobenzyl)-1,4-diazepan-1-yl]benzaldehyde thiosemicarbazone | 421 |
| 365 | 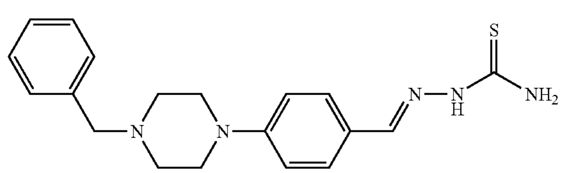 | 4-(4-benzylpiperazin-1-yl)benzaldehyde thiosemicarbazone | 354 |
| 366 | 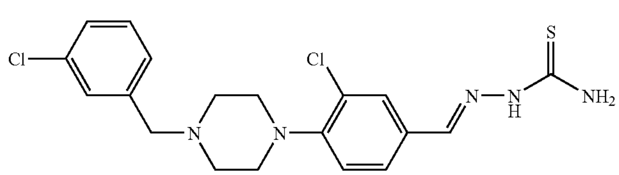 | 3-chloro-4-[4-(3-chlorobenzyl)piperazin-1-yl]benzaldehyde thiosemicarbazone | 423 |

TABLE 3-continued

| | Structure | Name | MH+ |
|---|---|---|---|
| 367 | 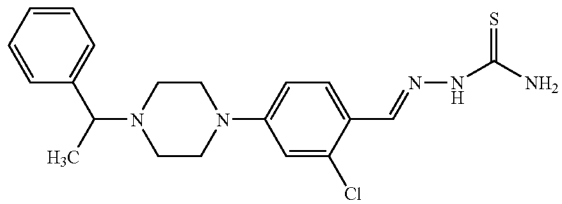 | 2-chloro-4-[4-(1-phenylethyl)piperazin-1-yl]benzaldehyde thiosemicarbazone | 403 |
| 368 | Chiral | 4-[(2S)-4-benzyl-2-isopropylpiperazin-1-yl]-2,5-difluorobenzaldehyde thiosemicarbazone | 433 |
| 369 | 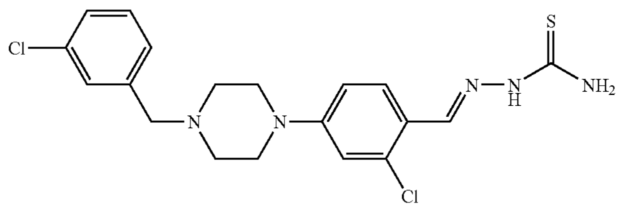 | 2-chloro-4-[4-(3-chlorobenzyl)piperazin-1-yl]benzaldehyde thiosemicarbazone | 423 |
| 370 | Chiral | 4-[(2S)-4-benzyl-2-isopropylpiperazin-1-yl]-3,5-difluorobenzaldehyde thiosemicarbazone | 433 |
| 371 | 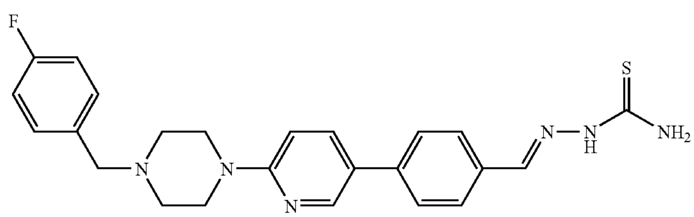 | 4-{6-[4-(4-fluorobenzyl)piperazin-1-yl]pyridin-3-yl)benzaldehyde thiosemicarbazone | 450 |
| 372 | 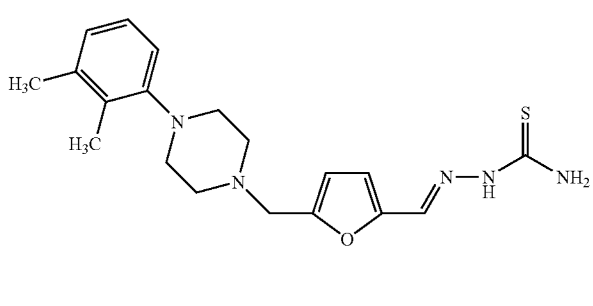 | 5-{[4-(2,3-dimethylphenyl)piperazin-1-yl]methyl}-2-furaldehyde thiosemicarbazone | 373 |

TABLE 3-continued

| Structure | | Name | MH+ |
|---|---|---|---|
| 373 | Chiral | 4-{(3S)-3-[(3,4-dichlorobenzyl)amino]pyrrolidin-1-yl}-2,5-difluorobenzaldehyde thiosemicarbazone | 459 |
| 374 | Chiral | 4-[(3R)-3-[(benzyloxy)methyl]-4-(2-chlorobenzyl)piperazin-1-yl]-2,5-difluorobenzaldehyde thiosemicarbazone | 545 |
| 375 | Chiral | 4-{[(3S)-1-benzylpyrrolidin-3-yl]amino)-2,5-difluorobenzaldehyde thiosemicarbazone | 390 |
| 376 | | 3-bromo-4-[4-(2-fluorobenzyl)piperazin-1-yl]benzaldehyde thiosemicarbazone | 451 |
| 377 | | 5-[(3,4-dichlorophenoxy)methyl]-2-furaldehyde thiosemicarbazone | 345 |

TABLE 3-continued

| Structure | | Name | MH+ |
|---|---|---|---|
| 378 | Chiral | 4-{[(3S)-1-benzylpyrrolidin-3-yl]amino}-3,5-difluorobenzaldehyde thiosemicarbazone | 390 |
| 379 | | 3-chloro-4-[4-(cyclohexylmethyl)piperazin-1-yl]benzaldehyde thiosemicarbazone | 395 |
| 380 | Chiral | 2-[(3R)-3-(dimethylamino)pyrrolidin-1-yl]-5-fluoro-4-[4-(3-fluorophenyl)piperidin-1-yl]benzaldehyde thiosemicarbazone | 488 |
| 381 | | 3-[4-(2-chloro-6-fluorobenzyl)-1,4-diazepan-1-yl]-2,5-difluorobenzaldehyde thiosemicarbazone | 457 |
| 382 | | 5-{(E)-[(aminocarbonothioyl)hydrazono]methyl}-2-(4-cyclohexylpiperazin-1-yl)benzonitrile | 372 |
| 383 | Chiral | 4-[(3S)-3,4-dibenzylpiperazin-1-yl]-2,5-difluorobenzaldehyde thiosemicarbazone | 481 |

TABLE 3-continued

| Structure | Name | MH+ |
|---|---|---|
| 384 | 4-[4-(cyclohexylmethyl)piperazin-1-yl]-2-(trifluoromethyl)benzaldehyde thiosemicarbazone | 429 |
| 385 | 5-(2,4-difluorophenyl)-2-furaldehyde thiosemicarbazone | 282 |
| 386 | 4-[4-(2-chlorophenyl)piperazin-1-yl]-3-fluorobenzaldehyde thiosemicarbazone | 393 |
| 387 | 2-chloro-4-[4-(3,4-dichlorobenzyl)piperazin-1-yl]benzaldehyde thiosemicarbazone | 458 |
| 388 Chiral | 2,5-difluoro-4-[(3S)-4-(3-fluorobenzyl)-3-isopropylpiperazin-1-yl]benzaldehyde thiosemicarbazone | 451 |
| 389 Chiral | 4-{(3S)-3-[(2,6-dichlorobenzyl)amino]pyrrolidin-1-yl}-2,5-difluorobenzaldehyde thiosemicarbazone | 459 |

TABLE 3-continued

| Structure | Name | MH+ |
|---|---|---|
| 390 | 2,5-difluoro-4-[(3S)-4-(4-fluorobenzyl)-3-isopropylpiperazin-1-yl]benzaldehyde thiosemicarbazone | 451 |
| 391 | 5-[6-(4-phenylpiperidin-1-yl)pyridin-3-yl]-2-furaldehyde thiosemicarbazone | 407 |
| 392 | 4-(4-benzyl-1,4-diazepan-1-yl)benzaldehyde thiosemicarbazone | 369 |
| 393 | 3-fluoro-4-(4-phenylpiperidin-1-yl)benzaldehyde thiosemicarbazone | 357 |
| 394 | 5-[4-fluoro-3-(trifluoromethyl)phenyl]-2-furaldehyde thiosemicarbazone | 332 |
| 395 | 4-[(3R)-3-[(benzyloxy)methyl]-4-(4-fluorobenzyl)piperazin-1-yl]-2,5-difluorobenzaldehyde thiosemicarbazone | 529 |

TABLE 3-continued

| Structure | Name | MH+ |
|---|---|---|
| 396 (Chiral) | 4-{[(3R)-1-benzylpyrrolidin-3-yl]amino}-3,5-difluorobenzaldehyde thiosemicarbazone | 390 |
| 397 | 5-fluoro-2-pyrrolidin-1-yl-4-{4-[3-(trifluoromethyl)phenyl]piperazin-1-yl}benzaldehyde thiosemicarbazone | 496 |
| 398 | 3-chloro-4-[4-(4-fluorobenzyl)piperazin-1-yl]benzaldehyde thiosemicarbazone | 407 |
| 399 (Chiral) | 4-[(3S)-3-benzyl-4-(2-chlorobenzyl)piperazin-1-yl]-2,5-difluorobenzaldehyde thiosemicarbazone | 515 |
| 400 | 4-[(1-benzylpiperidin-4-yl)amino]-2,5-difluorobenzaldehyde thiosemicarbazone | 404 |

TABLE 3-continued

| | Structure | Name | MH+ |
|---|---|---|---|
| 401 | 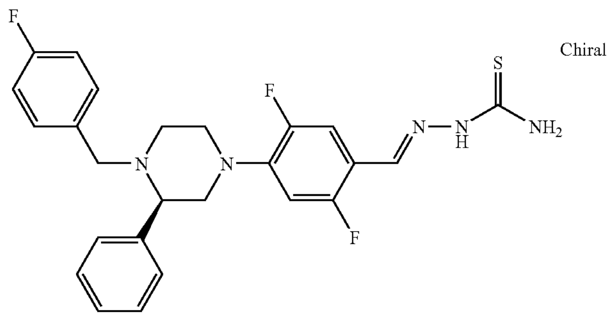 | 2,5-difluoro-4-[(3R)-4-(4-fluorobenzyl)-3-phenylpiperazin-1-yl]benzaldehyde thiosemicarbazone | 485 |
| 402 | 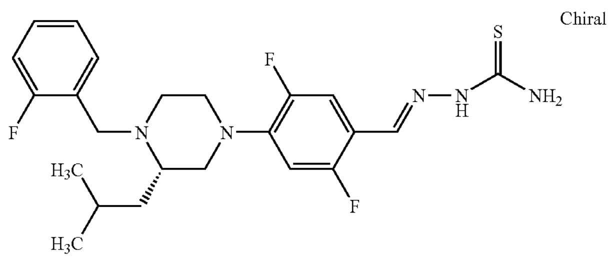 | 2,5-difluoro-4-[(3S)-4-(2-fluorobenzyl)-3-isobutylpiperazin-1-yl]benzaldehyde thiosemicarbazone | 465 |
| 403 | 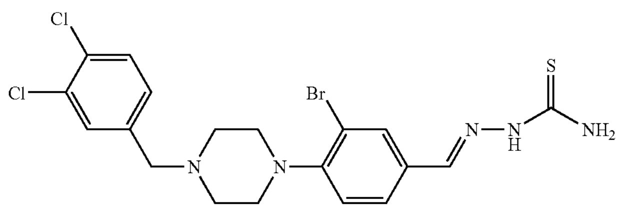 | 3-bromo-4-[4-(3,4-dichlorobenzyl)piperazin-1-yl]benzaldehyde thiosemicarbazone | 502 |
| 404 | 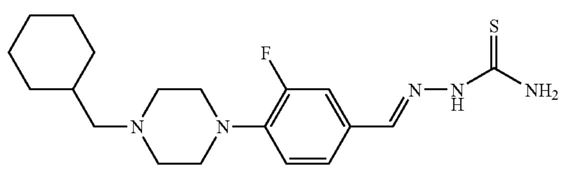 | 4-[4-(cyclohexylmethyl)piperazin-1-yl]-3-fluorobenzaldehyde thiosemicarbazone | 379 |
| 405 | 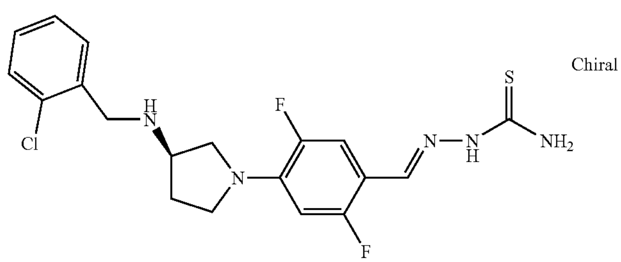 | 4-{(3R)-3-[(2-chlorobenzyl)amino]pyrrolidin-1-yl}-2,5-difluorobenzaldehyde thiosemicarbazone | 425 |
| 406 | 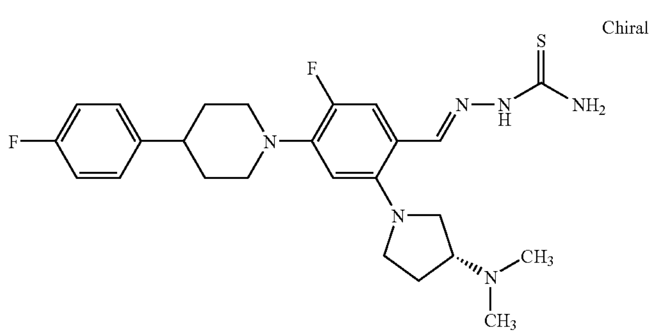 | 2-[(3R)-3-(dimethylamino)pyrrolidin-1-yl]-5-fluoro-4-[4-(4-fluorophenyl)piperidin-1-yl]benzaldehyde thiosemicarbazone | 488 |

TABLE 3-continued

| Structure | Name | MH+ |
|---|---|---|
| 407 | 4-{(3S)-3-[(2-chlorobenzyl)amino]pyrrolidin-1-yl]-2,5-difluorobenzaldehyde thiosemicarbazone | 425 |
| 408 | 2,3-difluoro-4-[4-(2-phenylethyl)piperazin-1-yl]benzaldehyde thiosemicarbazone | 404 |
| 409 | 4-[4-(3-chlorophenyl)piperazin-1-yl]-3-fluorobenzaldehyde thiosemicarbazone | 393 |
| 410 | 4-{(3R)-3-[(2-chloro-6-fluorobenzyl)amino]pyrrolidin-1-yl}-2,5-difluorobenzaldehyde thiosemicarbazone | 443 |
| 411 | 5-(3,4-dichlorophenyl)-2-furaldehyde thiosemicarbazone | 315 |
| 412 | 2,5-difluoro-4-{4-[5-(trifluoromethyl)pyridin-2-yl]piperazin-1-yl}benzaldehyde thiosemicarbazone | 445 |

TABLE 3-continued

| | Structure | Name | MH+ |
|---|---|---|---|
| 413 | (Chiral) | 2,5-difluoro-4-[(3S)-4-(3-fluorobenzyl)-3-isobutylpiperazin-1-yl]benzaldehyde thiosemicarbazone | 465 |
| 414 | 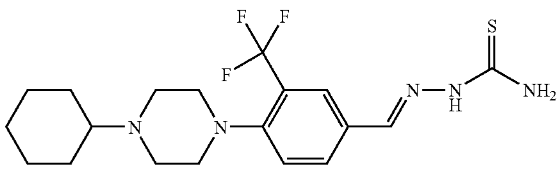 | 4-(4-cyclohexylpiperazin-1-yl)-3-(trifluoromethyl)benzaldehyde thiosemicarbazone | 415 |
| 415 | 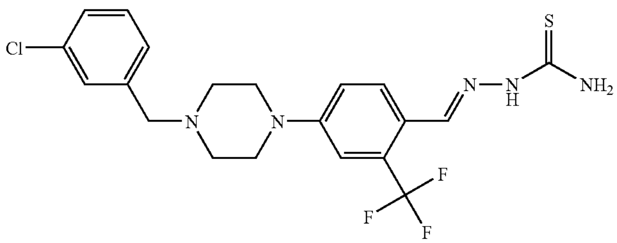 | 5-[4-(3-chlorobenzyl)piperazin-1-yl]-2-(trifluoromethyl)benzaldehyde thiosemicarbazone | 457 |
| 416 | 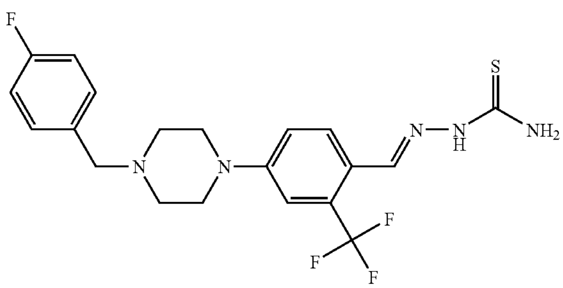 | 4-[4-(4-fluorobenzyl)piperazin-1-yl]-2-(trifluoromethyl)benzaldehyde thiosemicarbazone | 440 |
| 417 | 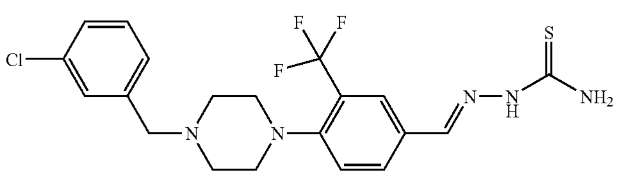 | 4-[4-(3-chlorobenzyl)piperazin-1-yl]-3-(trifluoromethyl)benzaldehyde thiosemicarbazone | 457 |
| 418 | 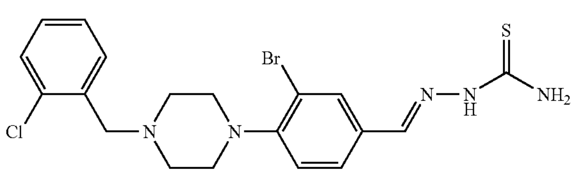 | 3-bromo-4-[4-(2-chlorobenzyl)piperazin-1-yl]benzaldehyde thiosemicarbazone | 468 |
| 419 | 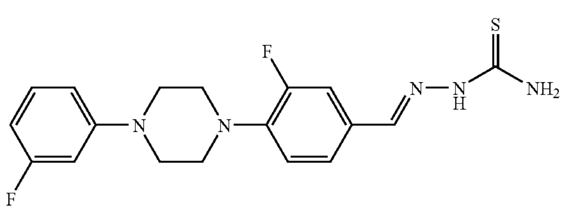 | 3-fluoro-4-[4-(3-fluorophenyl)piperazin-1-yl]benzaldehyde thiosemicarbazone | 376 |

TABLE 3-continued

| | Structure | Name | MH+ |
|---|---|---|---|
| 420 | 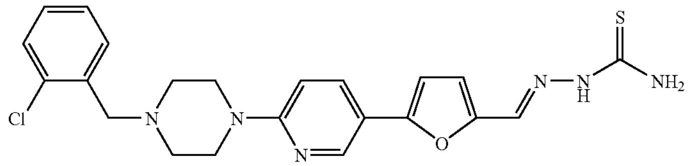 | 5-{6-[4-(2-chlorobenzyl)piperazin-1-yl]pyridin-3-yl}-2-furaldehyde thiosemicarbazone | 456 |
| 421 | 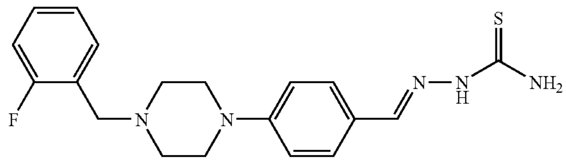 | 4-[4-(2-fluorobenzyl)piperazin-1-yl]benzaldehyde thiosemicarbazone | 372 |
| 422 | 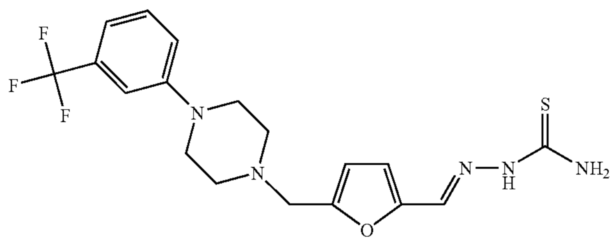 | 5-({4-[3-(trifluoromethyl)phenyl]piperazin-1-yl}methyl)-2-furaldehyde thiosemicarbazone | 412 |
| 423 | 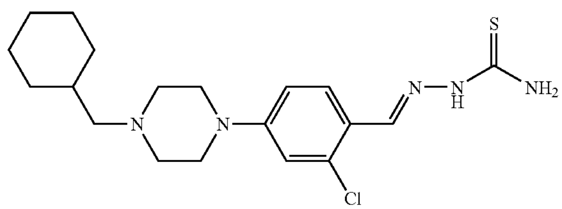 | 2-chloro-4-[4-(cyclohexylmethyl)piperazin-1-yl]benzaldehyde thiosemicarbazone | 395 |
| 424 | 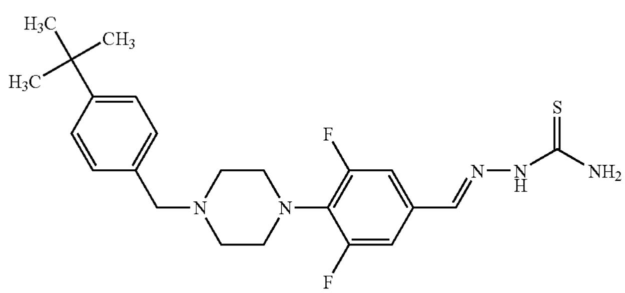 | 4-[4-(4-tert-butylbenzyl)piperazin-1-yl]-3,5-difluorobenzaldehyde thiosemicarbazone | 447 |
| 425 | 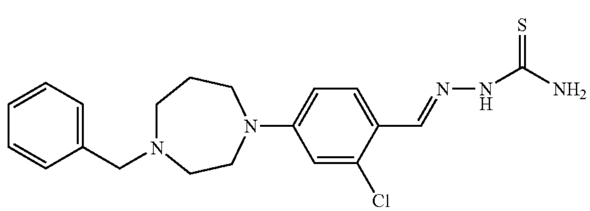 | 4-(4-benzyl-1,4-diazepan-1-yl)-2-chlorobenzaldehyde thiosemicarbazone | 403 |
| 426 | 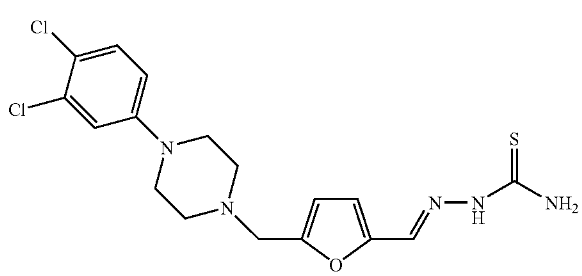 | 5-{[4-(3,4-dichlorophenyl)piperazin-1-yl]methyl)-2-furaldehyde thiosemicarbazone | 413 |

TABLE 3-continued

| | Structure | Name | MH+ |
|---|---|---|---|
| 427 | 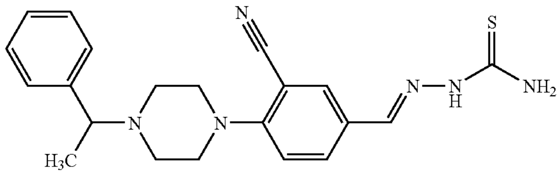 | 5-{(E)-[(aminocarbonothioyl)hydrazono]methyl}-2-[4-(1-phenylethyl)piperazin-1-yl]benzonitrile | 394 |
| 428 | Chiral | 4-[(3S)-3-benzyl-4-(2-fluorobenzyl)piperazin-1-yl]-2,5-difluorobenzaldehyde thiosemicarbazone | 499 |
| 429 | 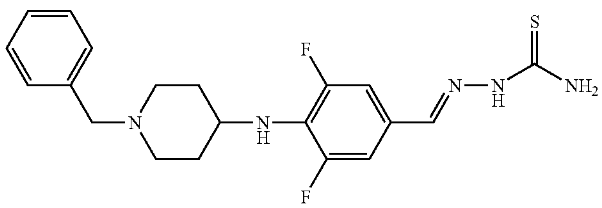 | 4-[(1-benzylpiperidin-4-yl)amino]-3,5-difluorobenzaldehyde thiosemicarbazone | 404 |
| 430 | Chiral | 4-{(3R)-3-[(2-chloro-5-fluorobenzyl)amino]pyrrolidin-1-yl}-2,5-difluorobenzaldehyde thiosemicarbazone | 443 |
| 431 | 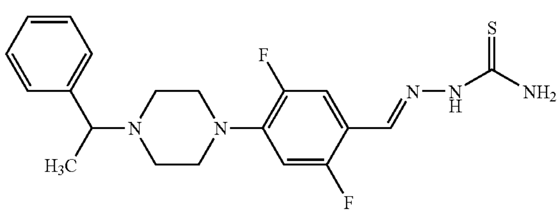 | 2,5-difluoro-4-[4-(1-phenylethyl)piperazin-1-yl]benzaldehyde thiosemicarbazone | 404 |
| 432 | 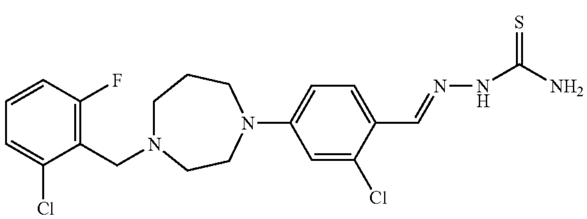 | 2-chloro-4-[4-(2-chloro-6-fluorobenzyl)-1,4-diazepan-1-yl]benzaldehyde thiosemicarbazone | 455 |

TABLE 3-continued

| Structure | Name | MH+ |
|---|---|---|
| 433 (Chiral) | 4-[4-(3-chlorophenyl)piperazin-1-yl]-2-[(3R)-3-(dimethylamino)pyrrolidin-1-yl]-5-fluorobenzaldehyde thiosemicarbazone | 505 |
| 434 (Chiral) | 2,5-difluoro-4-{(3S)-3-[(2-fluorobenzyl)amino]pyrrolidin-1-yl}benzaldehyde thiosemicarbazone | 408 |
| 435 | 4-[4-(1-phenylethyl)piperazin-1-yl]benzaldehyde thiosemicarbazone | 369 |
| 436 (Chiral) | 4-[(3R)-3-[(benzyloxy)methyl]-4-(2-fluorobenzyl)piperazin-1-yl]-2,5-fluorobenzaldehyde thiosemicarbazone | 529 |
| 437 (Chiral) | 2,5-difluoro-4-[(3S)-3-isobutyl-4-(3-methylbenzyl)piperazin-1-yl]benzaldehyde thiosemicarbazone | 461 |

TABLE 3-continued

| Structure | Name | MH+ |
|---|---|---|
| 438 | 5-fluoro-2-(4-methylpiperazin-1-yl)-4-{4-[3-(trifluoromethyl)phenyl]piperidin-1-yl}benzaldehyde thiosemicarbazone | 524 |
| 439 | 5-{(E)-[(aminocarbonothioyl)hydrazono]methyl}-2-[4-(4-fluorobenzyl)piperazin-1-yl]benzonitrile | 397 |
| 440 | 5-{(E)-[(aminocarbonothioyl)hydrazono]methyl}-2-[4-(3-chlorobenzyl)piperazin-1-yl]benzonitrile | 414 |
| 441 | 3-chloro-4-[4-(1-phenylethyl)piperazin-1-yl]benzaldehyde thiosemicarbazone | 403 |
| 442 | 4-[4-(1-phenylethyl)piperazin-1-yl]-3-(trifluoromethyl)benzaldehyde thiosemicarbazone | 437 |
| 443 | 5-fluoro-2-piperidin-1-yl-4-{4-[3-(trifluoromethyl)phenyl]piperazin-1-yl}benzaldehyde thiosemicarbazone | 510 |
| 444 | 4-chloro-4-[4-(2,4-dichlorobenzyl)piperazin-1-yl]benzaldehyde thiosemicarbazone | 458 |

TABLE 3-continued

| | Structure | Name | MH+ |
|---|---|---|---|
| 445 | Chiral | 5-{[(2S)-2-(anilinomethyl)pyrrolidin-1-yl]methyl}-2-furaldehyde thiosemicarbazone | 358 |
| 446 | 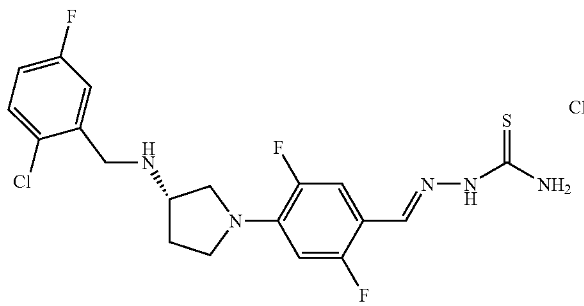 | 4-{(3S)-3-[(2-chloro-5-fluorobenzyl)amino]pyrrolidin-1-yl}-2,5-difluorobenzaldehyde thiosemicarbazone | 443 |
| 447 | Chiral | 2-[(3R)-3-(dimethylamino)pyrrolidin-1-yl]-5-fluoro-4-{4-[3-(trifluoromethyl)phenyl]piperidin-1-yl}benzaldehyde thiosemicarbazone | 538 |
| 448 | 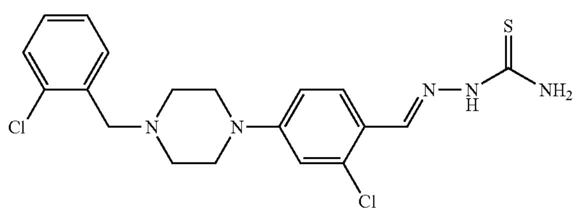 | 2-chloro-4-[4-(2-chlorobenzyl)piperazin-1-yl]benzaldehyde thiosemicarbazone | 423 |
| 449 | 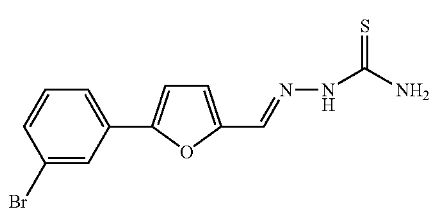 | 5-(3-bromophenyl)-2-furaldehyde thiosemicarbazone | 325 |
| 450 | 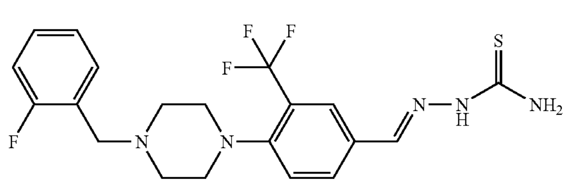 | 4-[4-(2-fluorobenzyl)piperazin-1-yl]-3-(trifluoromethyl)benzaldehyde thiosemicarbazone | 440 |

TABLE 3-continued

| Structure | Name | MH+ |
|---|---|---|
| 451 (Chiral) | 2,5-difluoro-4-[(3S)-3-isopropyl-4-(3-methylbenzyl)piperazin-1-yl]benzaldehyde thiosemicarbazone | 447 |
| 452 (Chiral) | 2-[(2S)-4-benzyl-2-isobutylpiperazin-1-yl]-3,5-difluorobenzaldehyde thiosemicarbazone | 447 |
| 453 | 2,3-difluoro-4-[4-(2-methylbenzyl)piperazin-1-yl]benzaldehyde thiosemicarbazone | 404 |
| 454 | 5-{[4-(3,5-dichlorophenyl)piperazin-1-yl]methyl}-2-furaldehyde thiosemicarbazone | 413 |
| 455 | 4-(4-benzyl-1,4-diazepan-1-yl)-2,3-difluorobenzaldehyde thiosemicarbazone | 404 |
| 456 | 3-chloro-4-[4-(2-chlorobenzyl)piperazin-1-yl]benzaldehyde thiosemicarbazone | 423 |

TABLE 3-continued

| Structure | Name | MH+ |
|---|---|---|
| 457 (Chiral) | 2,5-difluoro-4-{(3S)-3-[(3-fluorobenzyl)amino]pyrrolidin-1-yl}benzaldehyde thiosemicarbazone | 408 |
| 458 | 5-(2-bromophenyl)-2-furaldehyde thiosemicarbazone | 325 |
| 459 (Chiral) | 4-{(3S)-3-[(2-chloro-6-fluorobenzyl)(methyl)amino]pyrrolidin-1-yl}-2,5-difluorobenzaldehyde thiosemicarbazone | 457 |
| 460 | 4-(4-benzyl-1,4-diazepan-1-yl)-3,5-difluorobenzaldehyde thiosemicarbazone | 404 |
| 461 (Chiral) | 4-[(3R)-3-[(benzyloxy)methyl]-4-(3-fluorobenzyl)piperazin-1-yl]-2,5-difluorobenzaldehyde thiosemicarbazone | 529 |
| 462 | 4-(4-cyclopentylpiperazin-1-yl)-3,5-difluorobenzaldehyde thiosemicarbazone | 368 |

TABLE 3-continued

| | Structure | Name | MH+ |
|---|---|---|---|
| 463 | 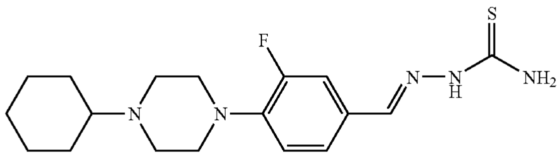 | 4-(4-cyclohexylpiperazin-1-yl)-3-fluorobenzaldehyde thiosemicarbazone | 365 |
| 464 | 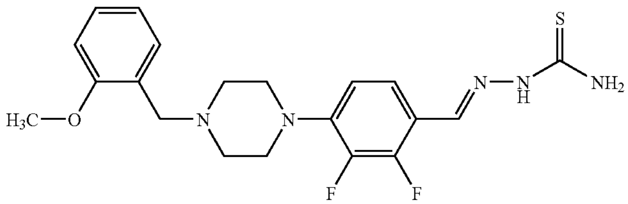 | 2,3-difluoro-4-[4-(2-methoxybenzyl)piperazin-1-yl]benzaldehyde thiosemicarbazone | 420 |
| 465 | 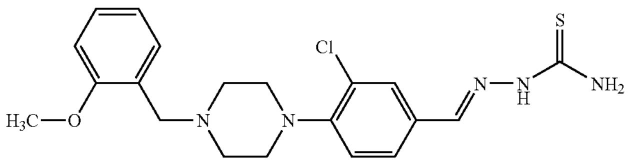 | 3-chloro-4-[4-(2-methoxybenzyl)piperazin-1-yl]benzaldehyde thiosemicarbazone | 419 |
| 466 | 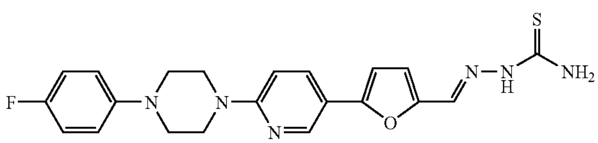 | 5-{6-[4-(4-fluorophenyl)piperazin-1-yl]pyridin-3-yl}-2-furaldehyde thiosemicarbazone | 426 |
| 467 | Chiral | 2,5-difluoro-4-((3R)-3-{[2-(trifluoromethyl)benzyl]amino}pyrrolidin-1-yl)benzaldehyde thiosemicarbazone | 458 |
| 468 | Chiral | 4-[4-(3-chlorophenyl)piperidin-1-yl]-2-[(3R)-3-(dimethylamino)pyrrolidin-1-yl]-5-fluorobenzaldehyde thiosemicarbazone | 504 |
| 469 | 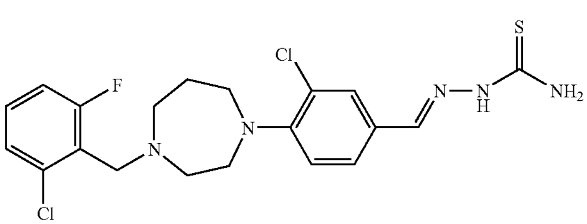 | 3-chloro-4-[4-(2-chloro-6-fluorobenzyl)-1,4-diazepan-1-yl]benzaldehyde thiosemicarbazone | 455 |

TABLE 3-continued

| | Structure | Name | MH+ |
|---|---|---|---|
| 470 | (Chiral) | 4-[(3S)-4-(2-chlorobenzyl)-3-isopropylpiperazin-1-yl]-2,5-difluorobenzaldehyde thiosemicarbazone | 467 |
| 471 | 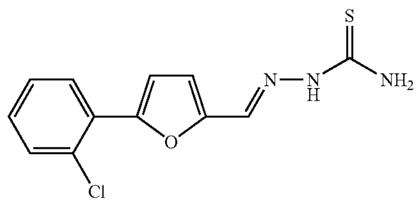 | 5-(2-chlorophenyl)-2-furaldehyde thiosemicarbazone | 281 |
| 472 | 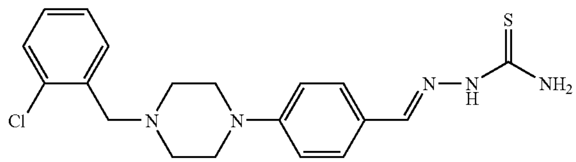 | 4-[4-(2-chlorobenzyl)piperazin-1-yl]benzaldehyde thiosemicarbazone | 389 |
| 473 | (Chiral) | 2,5-difluoro-4-{(3R)-3-[(3-fluorobenzyl)amino]pyrrolidin-1-yl}benzaldehyde thiosemicarbazone | 408 |
| 474 | 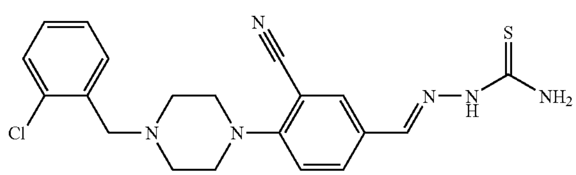 | 5-{(E)-](aminocarbonothioyl)hydrazonolmethyl}-2-[4-(2-chlorobenzyl)piperazin-1-yl]benzonitrile | 414 |
| 475 | (Chiral) | 2,5-difluoro-4-((3S)-3-{[2-(trifluoromethoxy)benzyl]amino}pyrrolidin-1-yl)benzaldehyde thiosemicarbazone | 474 |

TABLE 3-continued

| Structure | | Name | MH+ |
|---|---|---|---|
| 476 | Chiral | 4-[(3S)-3-benzyl-4-(3-fluorobenzyl)piperazin-1-yl]-2,5-difluorobenzaldehyde thiosemicarbazone | 499 |
| 477 | | 4-[4-(2-chloro-6-fluorobenzyl)piperazin-1-yl]-2,5-difluorobenzaldehyde thiosemicarbazone | 443 |
| 478 | | 4-[4-(3,4-dichlorobenzyl)piperazin-1-yl]-3-fluorobenzaldehyde thiosemicarbazone | 441 |
| 479 | Chiral | 2,5-difluoro-4-((3S)-3-{[2-(trifluoromethyl)benzyl]amino}pyrrolidin-1-yl)benzaldehyde thiosemicarbazone | 458 |
| 480 | | 5-[2-(trifluoromethyl)phenyl]-2-furaldehyde thiosemicarbazone | 314 |
| 481 | | 4-[4-(cyclohexylmethyl)piperazin-1-yl]-3-(trifluoromethyl)benzaldehyde thiosemicarbazone | 429 |

TABLE 3-continued

| Structure | | Name | MH+ |
|---|---|---|---|
| 482 | Chiral | 2,5-difluoro-4-((3R)-3-{[2-(trifluoromethoxy)benzyl]amino}pyrrolidin-1-yl)benzaldehyde thiosemicarbazone | 474 |
| 483 | Chiral | 4-{[(3S)-1-benzylpiperidin-3-yl]amino)-2,5-difluorobenzaldehyde thiosemicarbazone | 404 |
| 484 | | 5-[4-(2,3-dichlorophenyl)piperazin-1-yl]methyl}-2-furaldehyde thiosemicarbazone | 413 |
| 485 | Chiral | 4-[(2S)-4-benzyl-2-isobutylpiperazin-1-yl]-2,5-difluorobenzaldehyde thiosemicarbazone | 447 |
| 486 | | 4-(4-cyclohexylpiperazin-1-yl)-3,5-difluorobenzaldehyde thiosemicarbazone | 382 |

TABLE 3-continued

| | Structure | Name | MH+ |
|---|---|---|---|
| 487 | 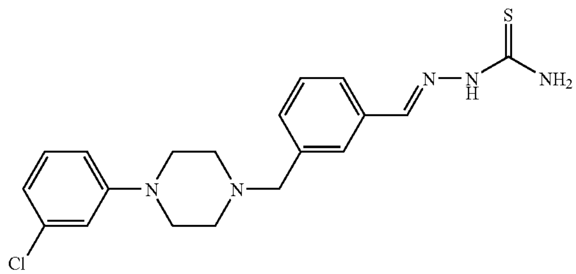 | 3-{[4-(3-chlorophenyl)piperazin-1-yl]methyl}benzaldehyde thiosemicarbazone | 389 |
| 488 | Chiral | 4-{(3S)-3-[(2-chlorobenzyl)(methyl)amino]pyrrolidin-1-yl}-2,5-difluorobenzaldehyde thiosemicarbazone | 439 |
| 489 | 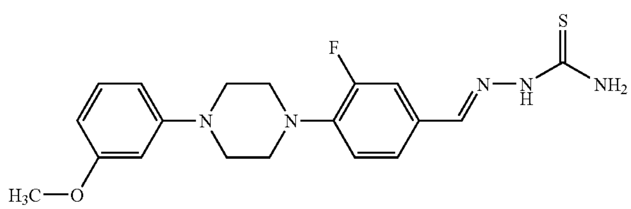 | 3-fluoro-4-[4-(3-methoxyphenyl)piperazin-1-yl]benzaldehyde thiosemicarbazone | 388 |
| 490 | Chiral | 4-[(3S)-4-benzyl-3-isobutylpiperazin-1-yl]-2,5-difluorobenzaldehyde thiosemicarbazone | 447 |
| 491 | 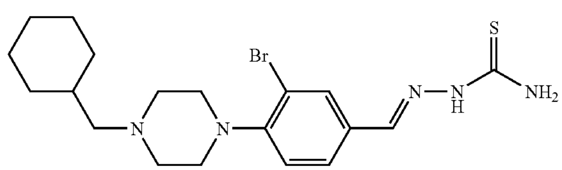 | 3-bromo-4-[4-(cyclohexylmethyl)piperazin-1-yl]benzaldehyde thiosemicarbazone | 439 |
| 492 | 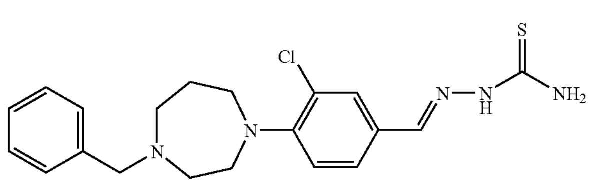 | 4-(4-benzyl-1,4-diazepan-1-yl)-3-chlorobenzaldehyde thiosemicarbazone | 403 |
| 493 | 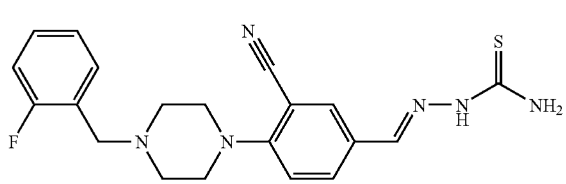 | 5-{(E)-[(aminocarbonothioyl)hydrazono]methyl}-2-[4-(2-fluorobenzyl)piperazin-1-yl]benzonitrile | 397 |

TABLE 3-continued

| | Structure | Name | MH+ |
|---|---|---|---|
| 494 | 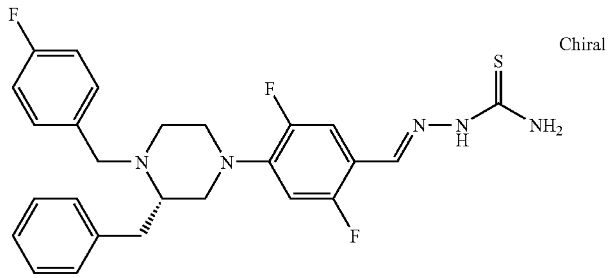 | 4-[(3S)-3-benzyl-4-(4-fluorobenzyl)piperazin-1-yl]-2,5-difluorobenzaldehyde thiosemicarbazone | 499 |
| 495 | 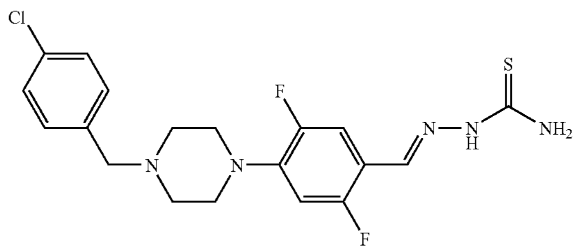 | 4-[4-(4-chlorobenzyl)piperazin-1-yl]-2,5-difluorobenzaldehyde thiosemicarbazone | 425 |
| 496 | 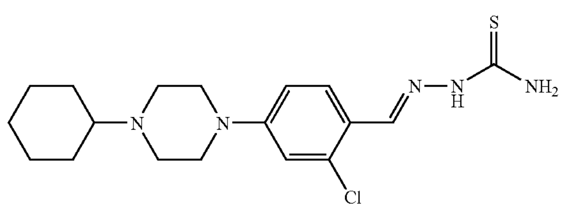 | 2-chloro-4-(4-cyclohexylpiperazin-1-yl)benzaldehyde thiosemicarbazone | 381 |
| 497 | 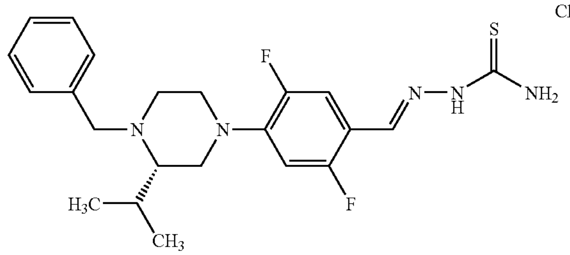 | 4-[(3S)-4-benzyl-3-isopropylpiperazin-1-yl]-2,5-difluorobenzaldehyde thiosemicarbazone | 433 |
| 498 | 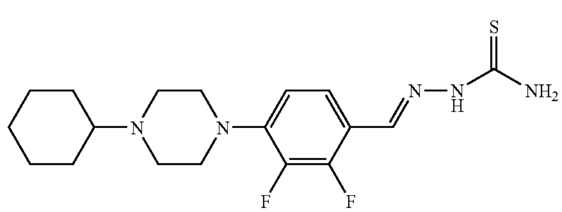 | 4-(4-cyclohexylpiperazin-1-yl)-2,3-difluorobenzaldehyde thiosemicarbazone | 382 |

TABLE 3-continued

| | Structure | Name | MH+ |
|---|---|---|---|
| 499 | 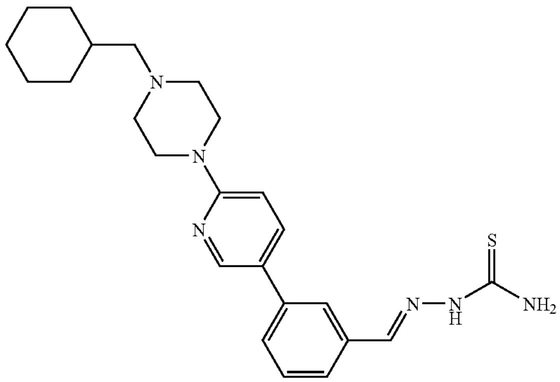 | 3-{6-[4-(cyclohexylmethyl)piperazin-1-yl]pyridin-3-yl}benzaldehyde thiosemicarbazone | 438 |
| 500 | 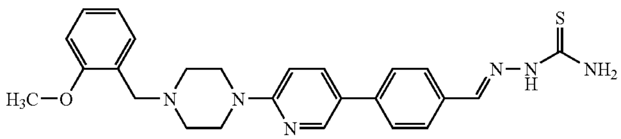 | 4-{6-[4-(2-methoxybenzyl)piperazin-1-yl]pyridin-3-yl}benzaldehyde thiosemicarbazone | 462 |
| 501 | Chiral | 4-[(1S,4S)-5-benzyl-2,5-diazabicyclo[2.2.1]hept-2-yl]-2,3-difluorobenzaldehyde thiosemicarbazone | 402 |
| 502 | 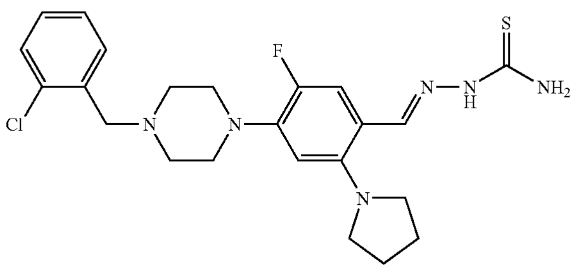 | 4-[4-(2-chlorobenzyl)piperazin-1-yl]-5-fluoro-2-pyrrolidin-1-ylbenzaldehyde thiosemicarbazone | 476 |
| 503 | Chiral | 4-[4-(2-chlorobenzyl)piperazin-1-yl]-5-fluoro-2-[(4aS,8aS)-octahydroisoquinolin-2(1H)-yl]benzaldehyde thiosemicarbazone | 544 |

TABLE 3-continued

| | Structure | Name | MH+ |
|---|---|---|---|
| 504 | 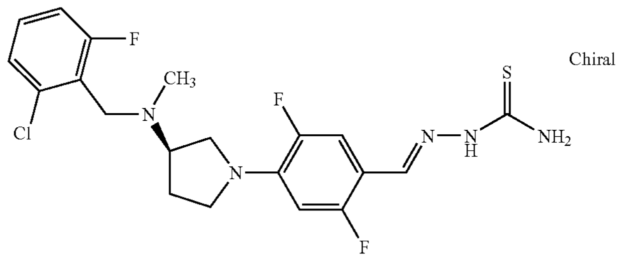 | 4-{(3R)-3-[(2-chloro-6-fluorobenzyl)(methyl)amino]pyrrolidin-1-2,5-difluorobenzaldehyde thiosemicarbazone | 457 |
| 505 | 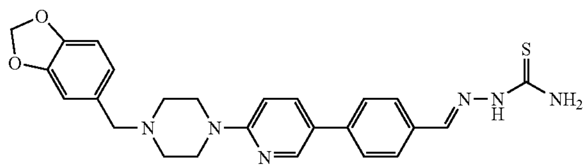 | 4-{6-[4-(1,3-benzodioxol-5-ylmethyl)piperazin-1-yl]pyridin-3-yl}benzaldehyde thiosemicarbazone | 476 |
| 506 | 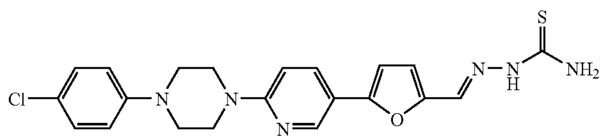 | 5-{6-[4-(4-chlorophenyl)piperazin-1-yl]pyridin-3-yl}-2-furaldehyde thiosemicarbazone | 442 |
| 507 | 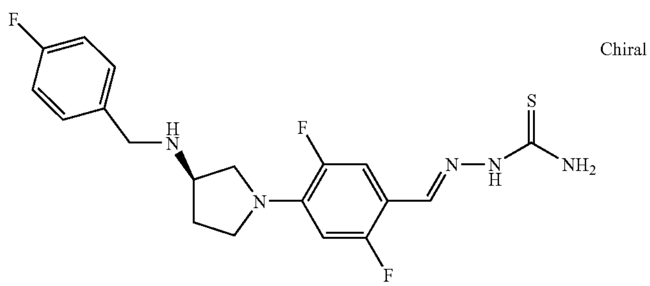 | 2,5-difluoro-4-{(3R)-3-[(4-fluorobenzyl)amino]pyrrolidin-1-yl})benzaldehyde thiosemicarbazone | 408 |
| 508 | 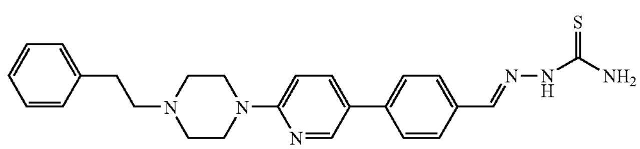 | 4-{6-[4-(2-phenylethyl)piperazin-1-yl]pyridin-3-yl}benzaldehyde thiosemicarbazone | 446 |
| 509 | 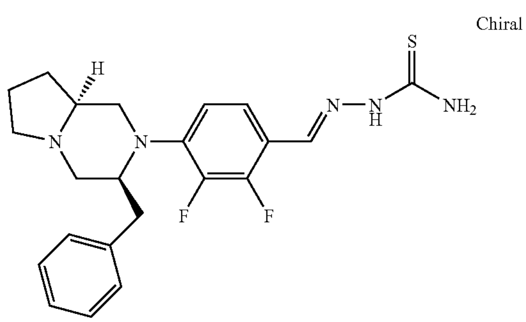 | 4-[(3S,8aS)-3-benzylhexahydro-pyrrolo[1,2-a]pyrazin-2(1H)-yl]-2,3-difluorobenzaldehyde thiosemicarbazone | 431 |
| 510 | 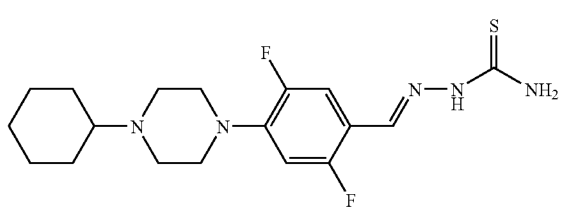 | 4-(4-cyclohexylpiperazin-1-yl)-2,5-difluorobenzaldehyde thiosemicarbazone | 382 |

Entries 504, 507, 509 are marked Chiral.

TABLE 3-continued

| Structure | | Name | MH+ |
|---|---|---|---|
| 511 | 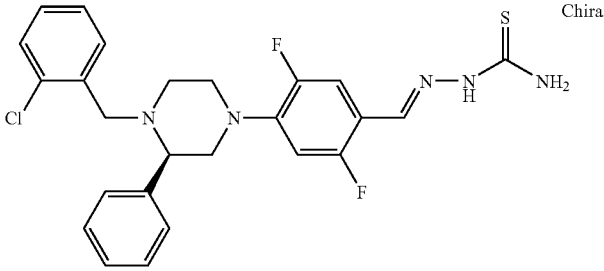 Chiral | 4-[(3R)-4-(2-chlorobenzyl)-3-phenylpiperazin-1-yl]-2,5-difluorobenzaldehyde thiosemicarbazone | 501 |
| 512 | 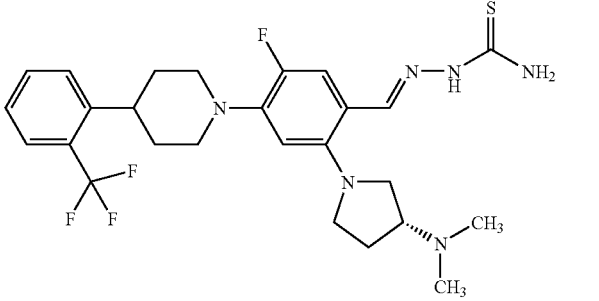 Chiral | 2-[(3R)-3-(dimethylamino)pyrrolidin-1-yl]-5-fluoro-4-{4-[2-(trifluoromethyl)phenyl]piperidin-1-yl}benzaldehyde thiosemicarbazone | 538 |
| 513 | 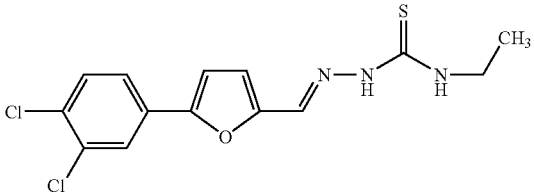 | 5-(3,4-dichlorophenyl)-2-furaldehyde N-ethylthiosemicarbazone | 343 |
| 514 | 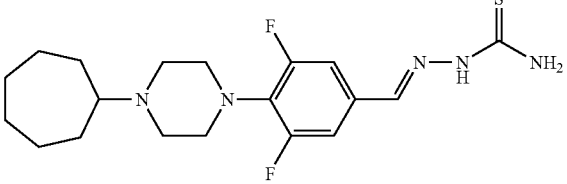 | 4-(4-cycloheptylpiperazin-1-yl)-3,5-difluorobenzaldehyde thiosemicarbazone | 397 |
| 515 | 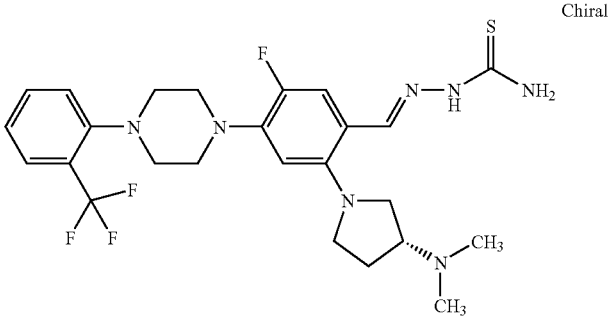 Chiral | 2-[(3R)-3-(dimethylamino)pyrrolidin-1-yl]-5-fluoro-4-{4-[2-(trifluoromethyl)phenyl]piperazin-1-yl}benzaldehyde thiosemicarbazone | 539 |

TABLE 3-continued

| Structure | Name | MH+ |
|---|---|---|
| 516 | 4-[4-(2-chloro-6-fluorobenzyl)-1,4-diazepan-1-yl]-2-(trifluoromethyl)benzaldehyde thiosemicarbazone | 489 |
| 517 | 4-[4-(2,4-dichlorobenzyl)piperazin-1-yl]-2-(trifluoromethyl) benzaldehyde thiosemicarbazone | 491 |
| 518 | 4-(4-benzyl-1,4-diazepan-1-yl)-3-(trifluoromethyl)benzaldehyde thiosemicarbazone | 437 |
| 519 | 3-{6-[4-(1-ethylpropyl)piperazin-1-yl]pyridin-3-yl}benzaldehyde thiosemicarbazone | 412 |
| 520 Chiral | 2-[(3R)-3-(dimethylamino)pyrrolidin-1-yl]-5-fluoro-4-{4-[5-(trifluoromethyl)pyridin-2-yl]-1,4-diazepan-1-yl}benzaldehyde thiosemicarbazone | 554 |

TABLE 3-continued

| Structure | Name | MH+ |
|---|---|---|
| 521 | 3-{6-[4-(3-chlorobenzyl)piperazin-1-yl]pyridin-3-yl}benzaldehyde thiosemicarbazone | 466 |
| 522 | 5-[4-(trifluoromethoxy)phenyl]-2-furaldehyde thiosemicarbazone | 330 |
| 523 | 4-(4-cyctoheptylpiperazin-1-yl)-3-fluorobenzaldehyde thiosemicarbazone | 379 |
| 524 | 4-[4-(3,4-dichlorobenzyl)piperazin-1-yl]-2,5-difluorobenzaldehyde thiosemicarbazone | 459 |
| 525 | 4-[4-(2-chlorobenzyl)piperazin-1-yl]-3-(trifluoromethyl)benzaldehyde thiosemicarbazone | 457 |
| 526 Chiral | 2,5-difluoro-4-{(3R)-3-[(2-fluorobenzyl)amino]pyrrolidin-1-yl}benzaldehyde thiosemicarbazone | 408 |

TABLE 3-continued

| | Structure | | Name | MH+ |
|---|---|---|---|---|
| 527 | 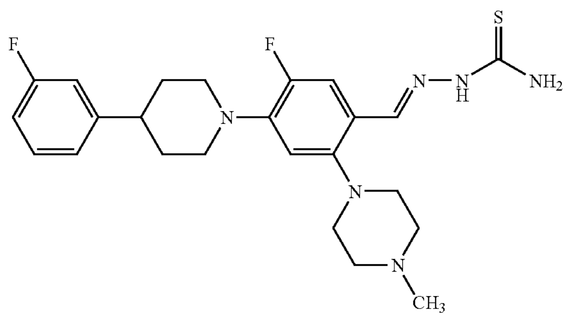 | | 5-fluoro-4-[4-(3-fluorophenyl)piperidin-1-yl]-2-(4-methylpiperazin-1-yl)benzaldehyde thiosemicarbazone | 474 |
| 528 | 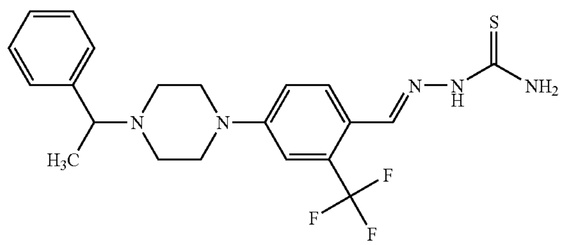 | | 4-[4-(1-phenylethyl)piperazin-1-yl]-2-(trifluoromethyl)benzaldehyde thiosemicarbazone | 437 |
| 529 | 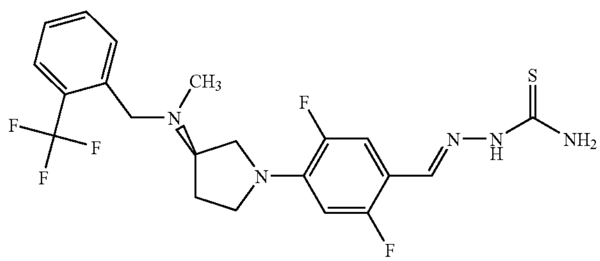 | Chiral | 2,5-difluoro-4-((3R)-3-{methyl[2-(trifluoromethyl)benzyl]amino}pyrrolidin-1-yl)benzaldehyde thiosemicarbazone | 472 |
| 530 | 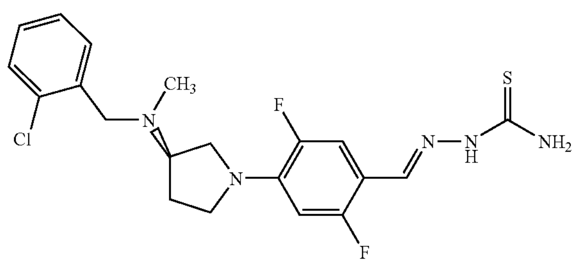 | Chiral | 4-{(3R)-3-[(2-chlorobenzyl)(methyl)amino]pyrrolidin-1-yl}-2,5-difluorobenzaldehyde thiosemicarbazone | 439 |
| 531 | 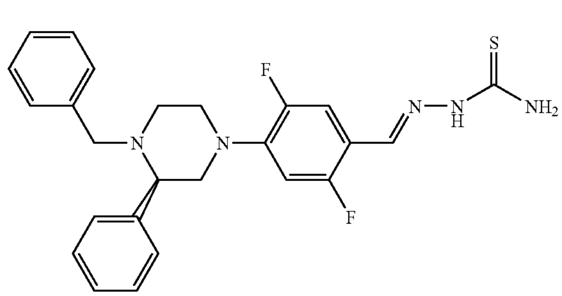 | Chiral | 4-[(3R)-4-benzyl-3-phenylpiperazin-1-yl]-2,5-difluorobenzaldehyde thiosemicarbazone | 467 |
| 532 | 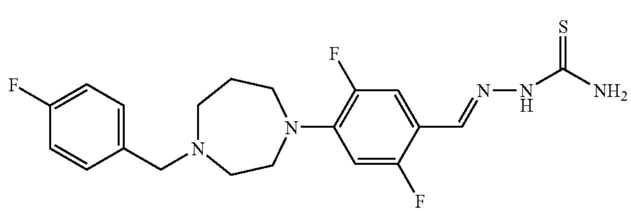 | | 2,5-difluoro-4-[4-(4-fluorobenzyl)-1,4-diazepan-1-yl]benzaldehyde thiosemicarbazone | 422 |

TABLE 3-continued

| | Structure | Name | MH+ |
|---|---|---|---|
| 533 | 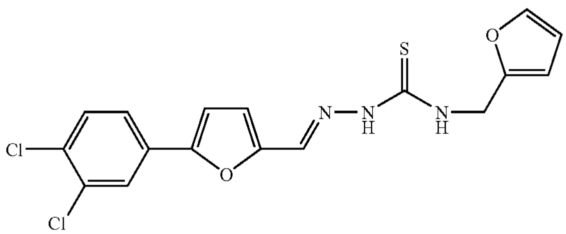 | 5-(3,4-dichlorophenyl)-2-furaldehyde N-(2-furylmethyl)thiosemicarbazone | 395 |
| 534 | 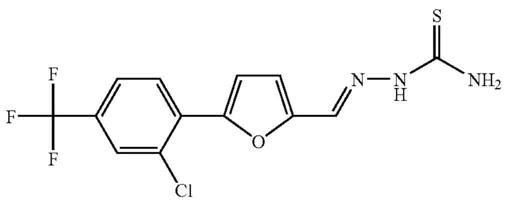 | 5-[2-chloro-4-(trifluoromethyl)phenyl]-2-furaldehyde thiosemicarbazone | 349 |
| 535 | 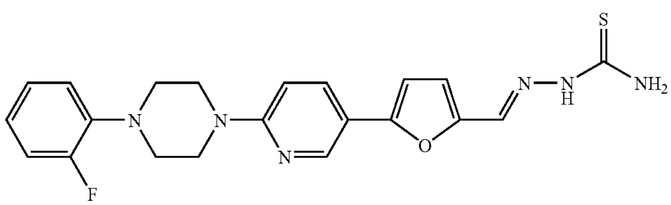 | 5-{6-[4-(2-fluorophenyl)piperazin-1-yl]pyridin-3-yl}-2-furaldehyde thiosemicarbazone | 426 |
| 536 | 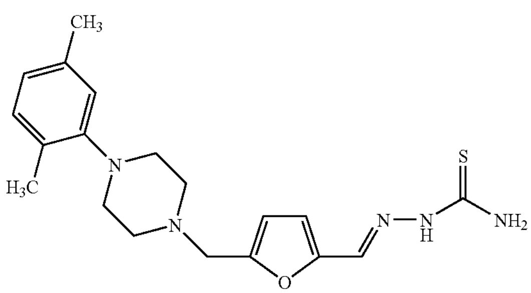 | 5-{[4-(2,5-dimethylphenyl)piperazin-1-yl]methyl}-2-furaldehyde thiosemicarbazone | 373 |
| 537 | Chiral | 4-[(3S)-3-(benzylamino)pyrrolidin-1-yl]-2,5-difluorobenzaldehyde thiosemicarbazone | 390 |
| 538 | 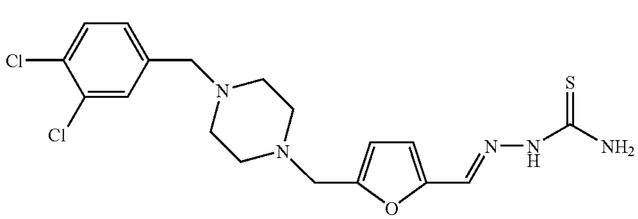 | 5-{[4-(3,4-dichlorobenzyl)piperazin-1-yl]methyl}-2-furaldehyde thiosemicarbazone | 427 |

TABLE 3-continued

| | Structure | Name | MH+ |
|---|---|---|---|
| 539 | 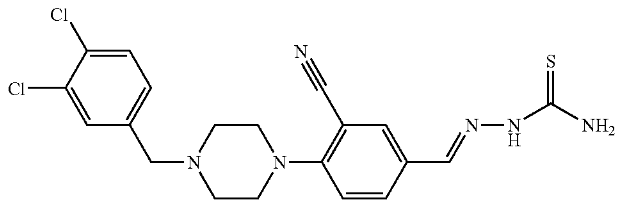 | 5-{(E)-[(aminocarbonothioyl)hydrazono]methyl}-2-[4-(3,4-dichlorobenzyl)piperazin-1-yl]benzonitrile | 448 |
| 540 | 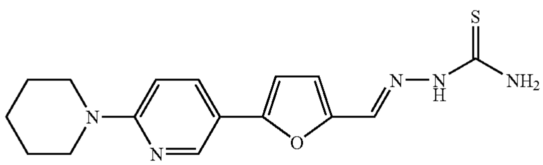 | 5-(6-piperidin-1-ylpyridin-3-yl)-2-furaldehyde thiosemicarbazone | 330 |
| 541 | 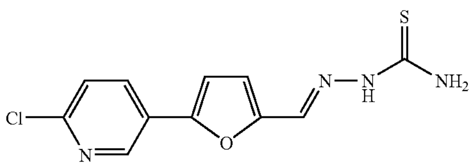 | 5-(6-chloropyridin-3-yl)-2-furaldehyde thiosemicarbazone | 282 |
| 542 | 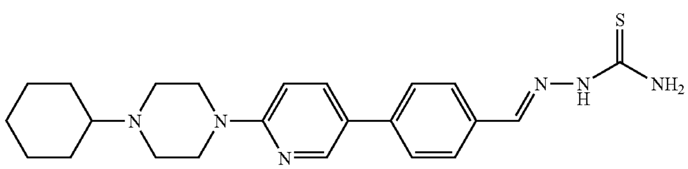 | 4-[6-(4-cyclohexylpiperazin-1-yl)pyridin-3-yl]benzaldehyde thiosemicarbazone | 424 |
| 543 | 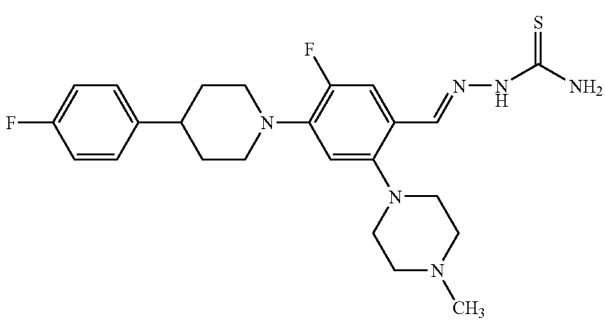 | 5-fluoro-4-[4-(4-fluorophenyl)piperidin-1-yl]-2-(4-methylpiperazin-1-yl)benzaldehyde thiosemicarbazone | 474 |
| 544 | 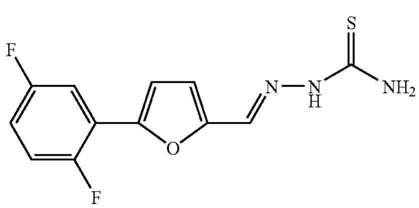 | 5-(2,5-difluorophenyl)-2-furaldehyde thiosemicarbazone | 282 |
| 545 | 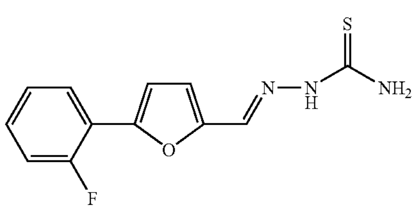 | 5-(2-fluorophenyl)-2-furaldehyde thiosemicarbazone | 264 |

TABLE 3-continued

| Structure | Name | MH+ |
|---|---|---|
| 546 | 5-[4-(2-chloro-6-fluorobenzyl)piperazin-1-yl]methyl}-2-furaldehyde thiosemicarbazone | 411 |
| 547 | 1H-indole-2-carbaldehyde N-(tetrahydrofuran-2-ylmethyl)thiosemicarbazone | 303 |
| 548 | 5-[4-(trifluoromethyl)phenyl]-2-furaldehyde thiosemicarbazone | 314 |
| 549 | 4-[4-(cyclohexylmethyl)piperazin-1-yl]-2,5-difluorobenzaldehyde thiosemicarbazone | 397 |
| 550 | 4-[4-(2-chloro-6-fluorobenzyl)-1,4-diazepan-1-yl]-3-(trifluoromethyl)benzaldehyde thiosemicarbazone | 489 |
| 551 Chiral | 2-[(3R)-3-(dimethylamino)pyrrolidin-1-yl]-5-fluoro-4-{4-[3-(trifluoromethyl)phenyl]piperazin-1-yl}benzaldehyde thiosemicarbazone | 539 |
| 552 | 3-bromo-4-(4-cyclohexylpiperazin-1-yl)benzaldehyde thiosemicarbazone | 425 |

TABLE 3-continued

| Structure | | Name | MH+ |
|---|---|---|---|
| 553 | | 5-{(E)-[(aminocarbonothioyl)hydrazono]methyl}-2-[4-(2-chloro-6-fluorobenzyl)-1,4-diazepan-1-yl]benzonitrile | 446 |
| 554 | | 4-[4-(1-ethylpropyl)piperazin-1-yl]-3,5-difluorobenzaldehyde thiosemicarbazone | 370 |
| 555 | | 4-{6-[4-(1-ethylpropyl)piperazin-1-yl]pyridin-3-yl}benzaldehyde thiosemicarbazone | 412 |
| 556 | Chiral | 4-[4-(4-chlorophenyl)piperidin-1-yl]-2-[(3R)-3-(dimethylamino)pyrrolidin-1-yl]-5-fluorobenzaldehyde thiosemicarbazone | 504 |
| 557 | | 4-(4-cyclopentylpiperazin-1-yl)-2,5-difluorobenzaldehyde thiosemicarbazone | 368 |
| 558 | Chiral | 4-[(3S)-3-benzyl-4-isopropyl-piperazin-1-yl]-2,5-difluorobenzaldehyde thiosemicarbazone | 433 |

TABLE 3-continued

| Structure | Name | MH+ |
|---|---|---|
| 559 | 4-(4-benzyl-1,4-diazepan-1-yl)-2-(trifluoromethyl)benzaldehyde thiosemicarbazone | 437 |
| 560 | 5-(3,4-difluorophenyl)-2-furaldehyde thiosemicarbazone | 282 |
| 561 | 4-[4-(2-chlorobenzyl)piperazin-1-yl]-2-(trifluoromethyl)benzaldehyde thiosemicarbazone | 457 |
| 562 Chiral | 2,5-difluoro-4-[(3R)-4-isopropyl-3-phenylpiperazin-1-yl]benzaldehyde thiosemicarbazone | 419 |
| 563 Chiral | 2,5-difluoro-4-{(3S)-3-[(4-fluorobenzyl)amino]pyrrolidin-1-yl}benzaldehyde thiosemicarbazone | 408 |

TABLE 3-continued

| Structure | | Name | MH+ |
|---|---|---|---|
| 564 | Chiral | 2-[(3R)-3-(dimethylamino)pyrrolidin-1-yl]-5-fluoro-4-(4-phenoxypiperidin-1-yl)benzaldehyde thiosemicarbazone | 486 |
| 565 | | 5-(4-bromophenyl)-2-furaldehyde thiosemicarbazone | 325 |
| 566 | | 5-{[4-(4-methoxyphenyl)piperazin-1-yl]methyl}-2-furaldehyde thiosemicarbazone | 374 |
| 567 | Chiral | 2-[(3R)-3-(dimethylamino)pyrrolidin-1-yl]-5-fluoro-4-{4-[5-(trifluoromethyl)pyridin-2-yl]piperazin-1-yl)benzaldehyde thiosemicarbazone | 540 |
| 568 | Chiral | 4-[(3S)-4-(2,5-dichlorobenzyl)-3-isobutylpiperazin-1-yl]-2,5-difluorobenzaldehyde thiosemicarbazone | 515 |
| 569 | | 4-[4-(2-methoxybenzyl)piperazin-1-yl]-2-(trifluoromethyl)benzaldehyde thiosemicarbazone | 453 |

TABLE 3-continued

| Structure | | Name | MH+ |
|---|---|---|---|
| 570 | | 1H-indole-2-carbaldehyde N'-methylthiosemicarbazone | 233 |
| 571 | | 5-[4-(4-fluorophenyl)piperazin-1-yl]-2-furaldehyde thiosemicarbazone | 348 |
| 572 | Chiral | 4-{(3R)-3-[(benzyloxy)methyl]-4-methylpiperazin-1-yl}-2,5-difluorobenzaldehyde thiosemicarbazone | 435 |
| 573 | | 3-{6[4-(2-phenylethyl)piperazin-1-yl]pyridin-3-yl} benzaldehyde thiosemicarbazone | 446 |
| 574 | Chiral | 2-[(3R)-3-(dimethylamino)pyrrolidin-1-yl]-5-fluoro-4-[4-(4-fluorobenzyl)piperidin-1-yl]benzaldehyde thiosemicarbazone | 502 |

TABLE 3-continued

| | Structure | Name | MH+ |
|---|---|---|---|
| 575 | Chiral | 2,5-difluoro-4-((3S)-3-{methyl[2-(trifluoromethoxy)benzyl]amino}pyrrolidin-1-yl)benzaldehyde thiosemicarbazone | 488 |
| 576 | Chiral | 2,5-difluoro-4-[(3S)-4-(4-fluorobenzyl)-3-isobutylpiperazin-1-yl]benzaldehyde thiosemicarbazone | 465 |
| 577 | Chiral | 4-[(3S)-3-benzyl-4-ethylpiperazin-1-yl]-2,5-difluorobenzaldehyde thiosemicarbazone | 419 |
| 578 | 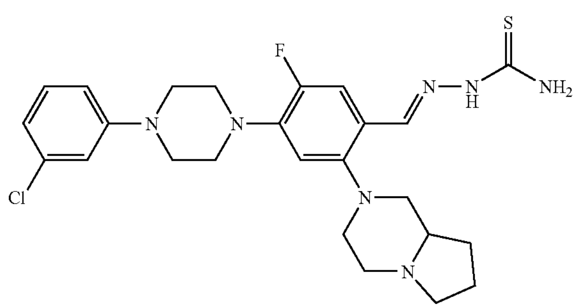 | 4-[4-(3-chlorophenyl)piperazin-1-yl]-5-fluoro-2-hexahydropyrrolo[1,2-a]pyrazin-2(1H)-ylbenzaldehyde thiosemicarbazone | 517 |
| 579 | 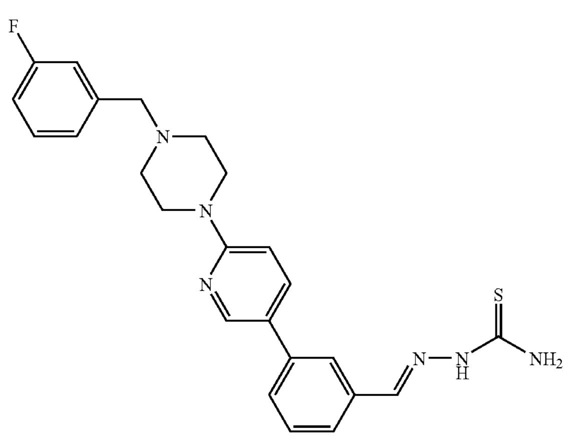 | 3-{6-[4-(3-fluorobenzyl)piperazin-1-yl]pyridin-3-yl}benzaldehyde thiosemicarbazone | 450 |

TABLE 3-continued

| Structure | Name | MH+ |
|---|---|---|
| 580 Chiral | 4-[(3R)-3-(benzylamino)pyrrolidin-1-yl]-2,5-difluorobenzaldehyde thiosemicarbazone | 390 |
| 581 | 5-(3-methylphenyl)-2-furaldehyde thiosemicarbazone | 260 |
| 582 | 5-[6-(4-benzylpiperazin-1-yl)pyridin-3-yl]-2-furaldehyde thiosemicarbazone | 422 |
| 583 | 4-(4-cycloheptylpiperazin-1-yl)benzaldehyde thiosemicarbazone | 361 |
| 584 Chiral | 2,5-difluoro-4-((3R)-3-{methyl[2-(trifluoromethoxy)benzyl]amino}pyrrolidin-1-yl)benzaldehyde thiosemicarbazone | 488 |
| 585 | 5-(4-butylphenyl)-2-furaldehyde thiosemicarbazone | 302 |
| 586 | 4-(4-benzyl-1,4-diazepan-1-yl)-3-fluorobenzaldehyde thiosemicarbazone | 387 |

TABLE 3-continued

| | Structure | Name | MH+ |
|---|---|---|---|
| 587 | 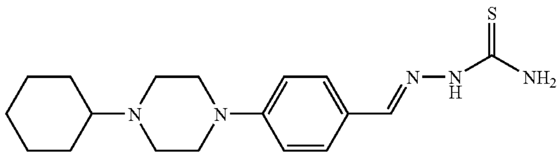 | 4-(4-cyclohexylpiperazin-1-yl) benzaldehyde thiosemicarbazone | 347 |
| 588 | 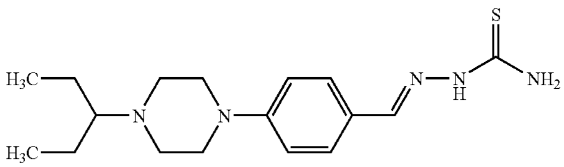 | 4-[4-(1-ethylpropyl)piperazin-1-yl]benzaldehyde thiosemicarbazone | 335 |
| 589 | Chiral | 4-(4-benzylpiperidin-1-yl)-2-[(3R)-3-(dimethylamino)pyrrolidin-1-yl]-5-fluorobenzaldehyde thiosemicarbazone | 484 |
| 590 | 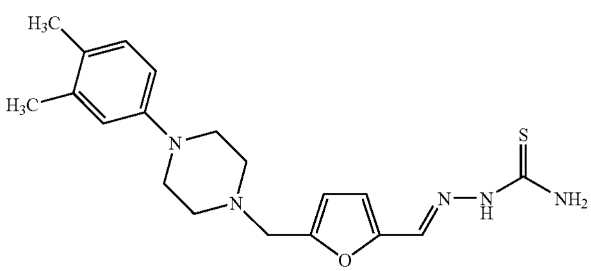 | 5-{[4-(3,4-dimethylphenyl)piperazin-1-yl]methyl}-2-furaldehyde thiosemicarbazone | 373 |
| 591 | Chiral | 4-[(1S,4S)-5-benzyl-2,5-diazabicyclo[2.2.1]hept-2-yl]-3-fluorobenzaldehyde thiosemicarbazone | 384 |
| 592 | Chiral | 4-(3-benzylpyrrolidin-1-yl)-2-[(3R)-3-(dimethylamino)pyrrolidin-1-yl]-5-fluorobenzaldehyde thiosemicarbazone | 470 |

TABLE 3-continued

| Structure | Name | MH+ |
|---|---|---|
| 593 Chiral | 4-[(1S,4S)-5-benzyl-2,5-diazabicyclo[2.2.1]hept-2-yl]-3-chlorobenzaldehyde thiosemicarbazone | |
| 594 | 5-(3,5-difluorophenyl)-2-furaldehyde thiosemicarbazone | 282 |
| 595 | 4-(4-cycloheptylpiperazin-1-yl)-2,5-difluorobenzaldehyde thiosemicarbazone | 397 |
| 596 Chiral | 2-[(3R)-3-(dimethylamino)pyrrolidin-1-yl]-5-fluoro-4-(4-(2-methylphenyl)piperazin-1-yl]benzaldehyde thiosemicarbazone | 485 |
| 597 | 4-[4-(3,4-dichlorophenyl)piperazin-1-yl]-5-fluoro-2-(4-methylpiperazin-3-yl)benzaldehyde thiosemicarbazone | 525 |
| 598 | 3-chloro-4-(4-cyclohexylpiperazin-1-yl)benzaldehyde thiosemicarbazone | 381 |

TABLE 3-continued

| | Structure | Name | MH+ |
|---|---|---|---|
| 599 | 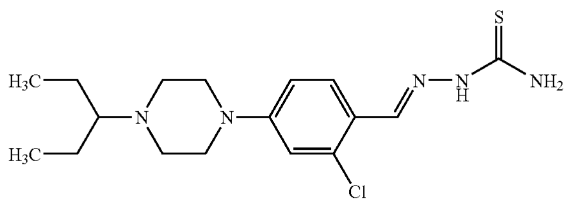 | 2-chloro-4-[4-(1-ethylpropyl)piperazin-1-yl]benzaldehyde thiosemicarbazone | 369 |
| 600 | 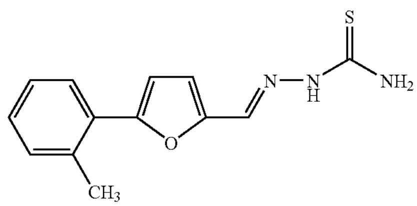 | 5-(2-methylphenyl)-2-furaldehyde thiosemicarbazone | 260 |
| 601 | 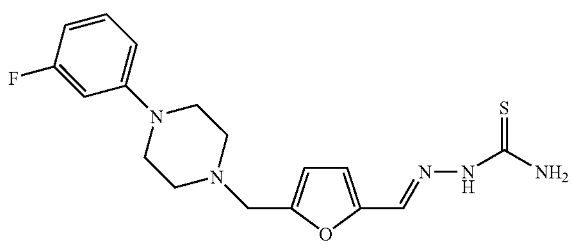 | 5-{[4-(3-fluorophenyl)piperazin-1-yl]methyl}-2-furaldehyde thiosemicarbazone | 362 |
| 602 | Chiral | 2-[(3R)-3-(dimethylamino)pyrrolidin-1-yl]-5-fluoro-4-{4-[4-(trifluoromethyl)phenyl]piperidin-1-yl}benzaldehyde thiosemicarbazone | 538 |
| 603 | 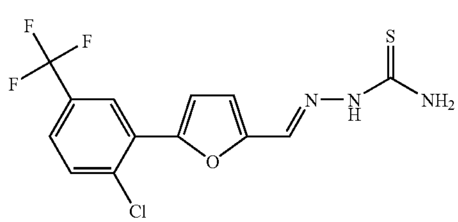 | 5-[2-chloro-5-(trifluoromethyl)phenyl]-2-furaldehyde thiosemicarbazone | 349 |
| 604 | 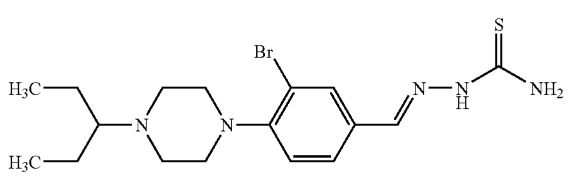 | 3-bromo-4-[4-(1-ethylpropyl)piperazin-1-yl]benzaldehyde thiosemicarbazone | 413 |

TABLE 3-continued

| Structure | Name | MH+ |
|---|---|---|
| 605 | 5-{[4-(2-methylphenyl)piperazin-1-yl]methyl}-2-furaldehyde thiosemicarbazone | 358 |
| 606 | 5-(2'-bromo-1,1'-biphenyl-2-yl)-2-furaldehyde thiosemicarbazone | 401 |
| 607 | 3-{6-[4-(2-chlorobenzyl)piperazin-1-yl]pyridin-3-yl}benzaldehyde thiosemicarbazone | 466 |
| 608 | 5-({4-[5-(trifluoromethyl)pyridin-2-yl]piperazin-1-yl}methyl)-2-furaldehyde thiosemicarbazone | 413 |

| Structure | Name | MH+ |
|---|---|---|
| 609 Chiral | 4-[4-(cyclohexylmethyl)piperazin-1-yl]-5-fluoro-2-[(4aS,8aS)-actahydroisoquinolin-2(1H)-yl]benzaldehyde thiosemicarbazone | 516 |
| 610 | 4-(4-benzyl-1,4-diazepan-1-yl)-2,5-difluorobenzaldehyde thiosemicarbazone | 404 |
| 611 | 4-[4-(1-ethylpropyl)piperazin-1-yl]-3-(trifluoromethyl)benzaldehyde thiosemicarbazone | 402 |
| 612 Chiral | 4-[(3S)-3-benzyl-4-methylpiperazin-1-yl]-2,5-difluorobenzaldehyde thiosemicarbazone | 404 |
| 613 | 5-(2-chloro-4-methoxyphenyl)-2-furaldehyde thiosemicarbazone | 311 |
| 614 | 5-(1,3-benzodioxol-5-yl)-2-furaldehyde thiosemicarbazone | 290 |
| 615 | 3-fluoro-4-[4-(2-phenylethyl)piperazin-1-yl]benzaldehyde thiosemicarbazone | 387 |

TABLE 3-continued

| Structure | Name | MH+ |
|---|---|---|
| 616 | 4-[4-(2-chlorobenzyl)piperazin-1-yl]-5-fluoro-2-piperidin-1-ylbenzaldehyde thiosemicarbazone | 490 |
| 617 | 4-(4-benzyl-1,4-diazepan-1-yl)-3-bromobenzaldehyde thiosemicarbazone | 447 |
| 618 Chiral | 2-[(3R)-3-(dimethylamino)pyrrolidin-1-yl]-4-[4-(2,3-dimethylphenyl)piperazin-1-yl]-5-fluorobenzaldehyde thiosemicarbazone | 499 |
| 619 | 4-(4-cyclopentylpiperazin-1-yl)-3-fluorobenzaldehyde thiosemicarbazone | 350 |
| 620 Chiral | 2,5-difluoro-4-((3S)-3-{methyl[2-(trifluoromethyl)benzyl]amino}pyrrolidin-1-yl)benzaldehyde thiosemicarbazone | 472 |
| 621 | 5-fluoro-2-(4-methylpiperazin-1-yl)-4-{4-[4-(trifluoromethyl)phenyl]piperazin-1-yl}benzaldehyde thiosemicarbazone | 525 |

TABLE 3-continued

| Structure | | Name | MH+ |
|---|---|---|---|
| 622 | | 4-[4-(1-ethylpropyl)piperazin-1-yl]-2,5-difluorobenzaldehyde thiosemicarbazone | 370 |
| 623 | Chiral | 2-[(3R)-3-(dimethylamino)pyrrolidin-1-yl]-5-fluoro-4-{4-[3-(trifluoromethyl)pyridin-2-yl]piperazin-1-yl}benzaldehyde thiosemicarbazone | 540 |
| 624 | | 4-[4-(4-chlorophenyl)piperidin-1-yl]-5-fluoro-2-(4-methylpiperazin-1-yl)benzaldehyde thiosemicarbazone | 490 |
| 625 | | 5-{6-[(2-phenylethyl)amino]pyridin-3-yl}-2-furaldehyde thiosemicarbazone | 366 |
| 626 | Chiral | 2,5-difluoro-4-[(3R)-4-(3-fluorobenzyl)-3-phenylpiperazin-1-yl]benzaldehyde thiosemicarbazone | 485 |

TABLE 3-continued

| Structure | | Name | MH+ |
|---|---|---|---|
| 627 | 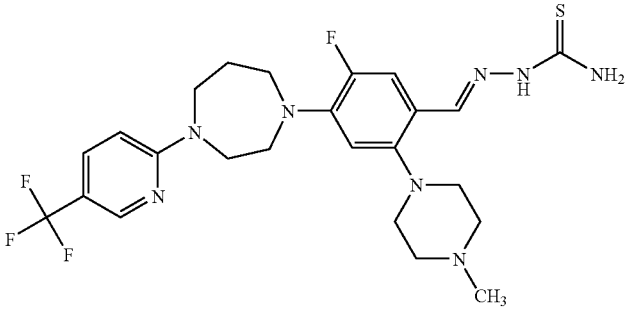 | 5-fluoro-2-(4-methylpiperazin-1-yl)-4-{4-[5-(trifluoromethyl)pyridin-2-yl]-1,4-diazepan-1-yl}benzaldehyde thiosemicarbazone | 540 |
| 628 | 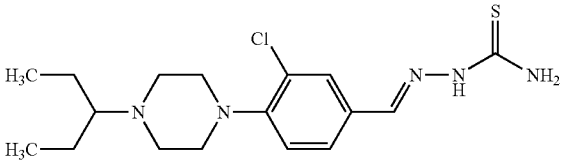 | 3-chloro-4-[4-(1-ethylpropyl)piperazin-1-yl]benzaldehyde thiosemicarbazone | 369 |
| 629 | Chiral 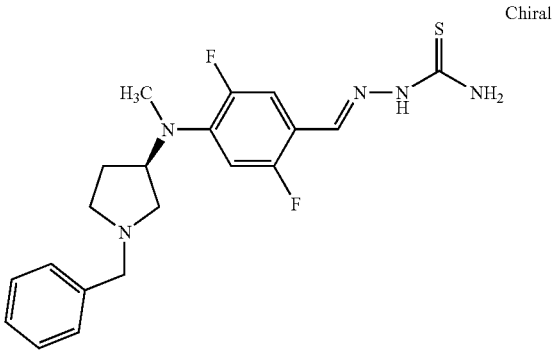 | 4-[[(3R)-1-benzylpyrrolidin-3-yl](methyl)amino]-2,5-difluorobenzaldehyde thiosemicarbazone | 404 |
| 630 | Chiral 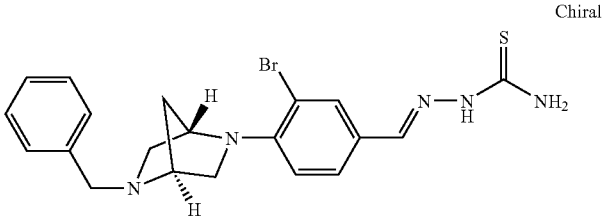 | 4-[(1S,4S)-5-benzyl-2,5-diazabicyclo[2.2.1]hept-2-yl]-3-bromobenzaldehyde thiosemicarbazone | 445 |
| 631 | 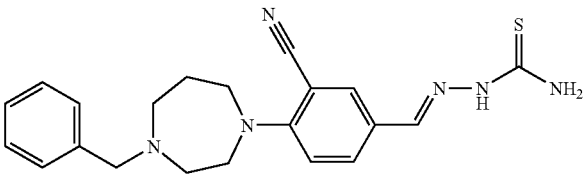 | 5-[(E)-[(aminocarbonothioyl)hydrazono]methyl}-2-(4-benzyl-1,4-diazepan-1-yl)benzonitrile | 394 |

TABLE 3-continued

| Structure | Name | MH+ |
|---|---|---|
| 632 (Chiral) | 4-[[(3S)-1-benzylpyrrolidin-3-yl](methyl)amino]-2,5-difluorobenzaldehyde thiosemicarbazone | 404 |
| 633 | 5-(3,4-dichlorophenyl)-2-furaldehyde N-methylthiosemicarbazone | 329 |
| 634 (Chiral) | 4-[4-(4-chlorophenyl)piperazin-1-yl]-2-[(3R)-3-(dimethylamino)pyrrolidin-1-yl]-5-fluorobenzaldehyde thiosemicarbazone | 505 |
| 635 (Chiral) | 4-[4-(2,3-dichlorophenyl)piperazin-1-yl]-2-[(3R)-3-(dimethylamino)pyrrolidin-1-yl]-5-fluorobenzaldehyde thiosemicarbazone | 540 |
| 636 | 5-[4-(methyhthio)phenyl]-2-furaldehyde thiosemicarbazone | 292 |

TABLE 3-continued

| Structure | | Name | MH+ |
|---|---|---|---|
| 637 | Chiral | 2-[(3R)-3-(dimethylamino) pyrrolidin-1-yl]-5-fluoro-4-(4-phenylpiperidin-1-yl)benzaldehyde thiosemicarbazone | 470 |
| 638 | | 5-fluoro-2-(4-methylpiperazin-1-yl)-4-{4-[5-(trifluoromethyl) pyridin-2-yl]piperazin-1-yl}benzaldehyde thiosemicarbazone | 526 |
| 639 | Chiral | 2-[(3S)-3-(dimethylamino)pyrrolidin-1-yl]-5-fluoro-4-{4-[3-(trifluoromethyl)phenyl]piperazin-1-yl}benzaldehyde thiosemicarbazone | 539 |
| 640 | | 3-{6-[4-(4-fluorobenzyl)piperazin-1-yl]pyridin-3-yl}benzaldehyde thiosemicarbazone | 450 |

TABLE 3-continued

| Structure | Name | MH+ |
|---|---|---|
| 641 Chiral | 4-[4-(3,4-dichlorophenyl)piperazin-1-yl]-2-[(3R)-3-(dimethylamino)pyrrolidin-1-yl]-5-fluorobenzaldehyde thiosemicarbazone | 540 |
| 642 | 5-(3-fluorophenyl)-2-furaldehyde thiosemicarbazone | 264 |
| 643 | 5-[4-chloro-3-methylphenoxy)methyl]-2-furaldehyde thiosemicarbazone | 325 |
| 644 | 5-[3-(trifluoromethoxy)phenyl]-2-furaldehyde thiosemicarbazone | 330 |
| 645 | 5-{[4-(2-fluorobenzyl)piperazin-1-yl]methyl}-2-furaldehyde thiosemicarbazone | 376 |
| 646 Chiral | 5-fluoro-2-(4-methylpiperazin-1-yl)-4-[(4aS,8aS)-octahydroisoquinolin-2(1H)-yl]benzaldehyde thiosemicarbazone | 434 |

TABLE 3-continued

| | Structure | | Name | MH+ |
|---|---|---|---|---|
| 647 | 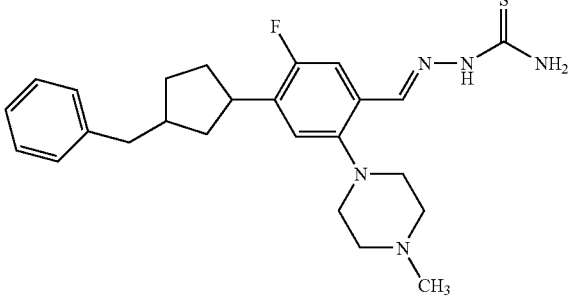 | | 4-(3-benzylpyrrolidin-1-yl)-5-fluoro-2-(4-methylpiperazin-1-yl)benzaldehyde thiosemicarbazone | 456 |
| 648 | 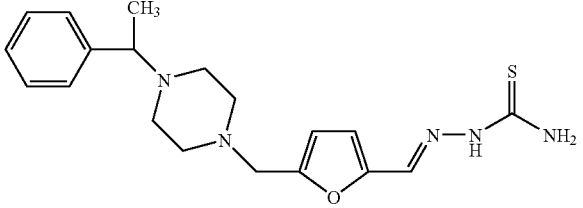 | | 5-{[4-(1-phenylethyl)piperazin-1-yl]methyl}-2-furaldehyde thiosemicarbazone | 373 |
| 649 | 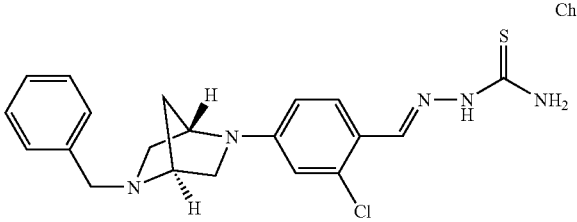 | Chiral | 4-[(1S,4S)-5-benzyl-2,5-diazabicyclo[2.2.1]hept-2-yl]-2-chlorobenzaldehyde thiosemicarbazone | 401 |
| 650 | 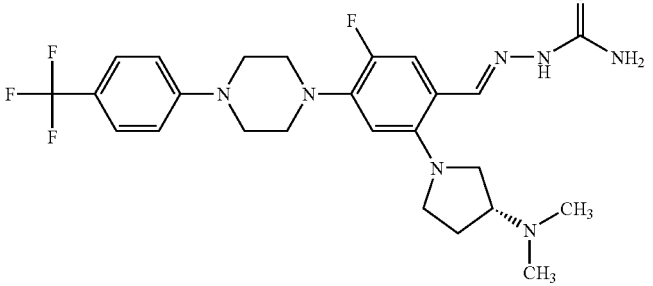 | Chiral | 2-[(3R)-3-(dimethylamino)pyrrolidin-1-yl]-5-fluoro-4-{4-[4-(trifluoromethyl)phenyl]piperazin-1-yl}benzaldehyde thiosemicarbazone | 539 |
| 651 | 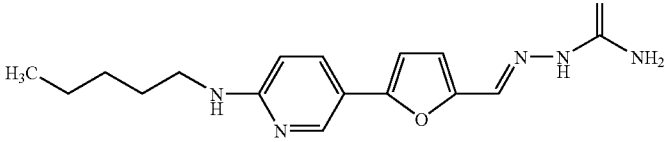 | | 5-[6-(pentylamino)pyridin-3-yl]-2-furaldehyde thiosemicarbazone | 332 |
| 652 | 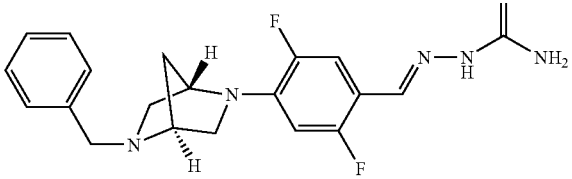 | Chiral | 4-[(1S,4S)-5-benzyl-2,5-diazabicyclo[2.2.1]hept-2-yl]-2,5-difluorobenzaldehyde thiosemicarbazone | 402 |

TABLE 3-continued

| Structure | Name | MH+ |
|---|---|---|
| 653 | 4-(4-cyclopentylpiperazin-1-yl)benzaldehyde thiosemicarbazone | 332 |
| 654 | 4-[4-(3-chlorophenyl)piperidin-1-yl]-5-fluoro-2-(4-methylpiperazin-1-yl)benzaldehyde thiosemicarbazone | 490 |
| 655 | 5-fluoro-4-[4-(2-methylphenyl)piperazin-1-yl]-2-(4-methylpiperazin-1-yl)benzaldehyde thiosemicarbazone | 471 |
| 656 | 3-fluoro-4-[4-(2-fluorobenzyl)piperazin-1-yl]benzaldehyde thiosemicarbazone | 390 |
| 657 | 4-[4-(2-chloro-6-fluorobenzyl)piperazin-1-yl]-3-fluorobenzaldehyde thiosemicarbazone | 425 |
| 658 | 4-[4-(4-tert-butylbenzyl)piperazin-1-yl]-2,5-difluorobenzaldehyde thiosemicarbazone | 447 |

TABLE 3-continued

| Structure | Name | MH+ |
|---|---|---|
| 659 | 4-[4-(2,4-dichlorobenzoyl)piperazin-1-yl]-5-fluoro-2-piperidin-1-ylbenzaldehyde thiosemicarbazone | 538 |
| 660 Chiral | 4-[(2R)-2-(anilinomethyl)pyrrolidin-1-yl]-2,5-difluorobenzaldehyde thiosemicarbazone | 390 |
| 661 Chiral | 4-[4-(2-chlorophenyl)piperazin-1-yl]-2-[(3R)-3-(dimethylamino)pyrrolidin-1-yl]-5-fluorobenzaldehyde thiosemicarbazone | 505 |
| 662 | 5-{[4-(2-fluorophenyl)piperazin-1-yl]methyl}-2-furaldehyde thiosemicarbazone | 362 |
| 663 Chiral | 4-[(3R,5S)-4-(4-chlorobenzoyl)-3,5-dimethylpiperazin-1-yl]-5-fluoro-2-piperidin-1-ylbenzaldehyde thiosemicarbazone | 532 |

TABLE 3-continued

| | Structure | Name | MH+ |
|---|---|---|---|
| 664 | 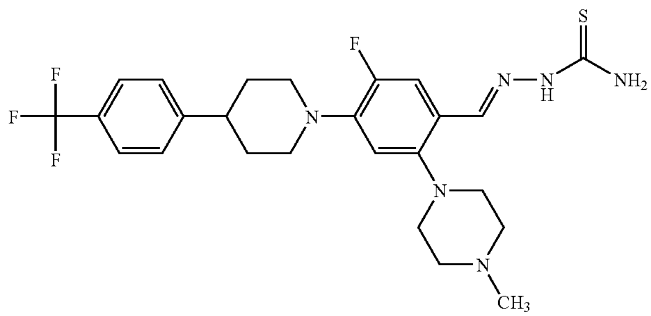 | 5-fluoro-2-(4-methylpiperazin-1-yl)-4-{4-[4-(trifluoromethyl)phenyl]piperidin-1-yl}benzaldehyde thiosemicarbazone | 524 |
| 665 | 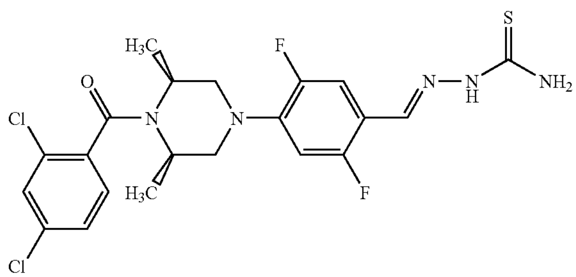 | 4-[(3R,5S)-4-(2,4-dichlorobenzoyl)-3,5-dimethylpiperazin-1-yl]-2,5-difluorobenzaldehyde thiosemicarbazone | 501 |
| 666 | Chiral | 4-[(3R,5S)-4-(4-chlorobenzoyl)-3,5-dimethylpiperazin-1-yl]-5-fluoro-2-pyrrolidin-1-ylbenzaldehyde thiosemicarbazone | 518 |
| 667 | 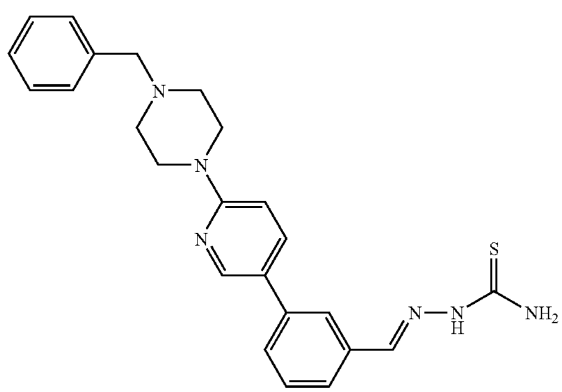 | 3-[6-(4-benzylpiperazin-1-yl)pyridin-3-yl]benzaldehyde thiosemicarbazone | 432 |
| 668 | 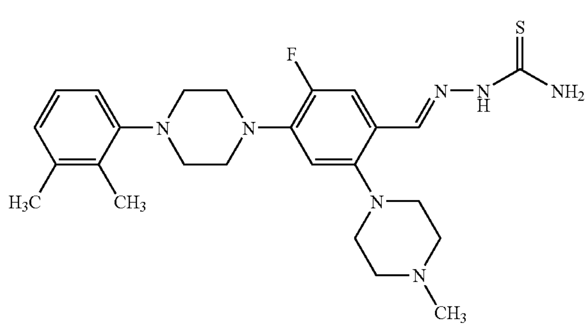 | 4-[4-(2,3-dimethylphenyl)piperazin-1-yl]-5-fluoro-2-(4-methylpiperazin-1-yl)benzaldehyde thiosemicarbazone | 485 |

TABLE 3-continued

| Structure | Name | MH+ |
|---|---|---|
| 669 (Chiral) | 4-[(3S,8aS)-3-benzylhexahydro-pyrrolo[1,2-a]pyrazin-2(1H)-yl]-2,5-difluorobenzaldehyde thiosemicarbazone | 431 |
| 670 | 5-fluoro-2-(4-methylpiperazin-1-yl)-4-(4-phenylpiperidin-1-yl)benzaldehyde thiosemicarbazone | 456 |
| 671 | 5-{[4-(4-methylphenyl)piperazin-1-yl]methyl)-2-furaldehyde thiosemicarbazone | 358 |
| 672 | 5-{[4-(4-fluorophenyl)piperazin-1-yl]methyl}-2-furaldehyde thiosemicarbazone | 362 |
| 673 | 4-[4-(4-chlorobenzoyl)piperazin-1-yl]-5-fluoro-2-piperidin-1-ylbenzaldehyde thiosemicarbazone | 504 |

TABLE 3-continued

| | Structure | Name | MH+ |
|---|---|---|---|
| 674 | 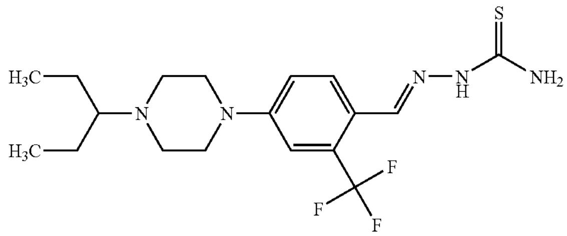 | 4-[4-(1-ethylpropyl)piperazin-1-yl]-2-(trifluoromethyl)benzaldehyde thiosemicarbazone | 402 |
| 675 | 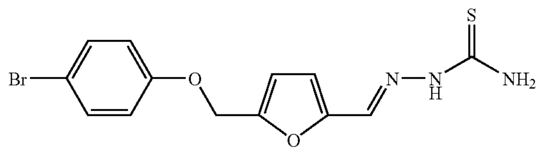 | 5-[(4-bromophenoxy)methyl]-2-furaldehyde thiosemicarbazone | 355 |
| 676 | Chiral | 4-[(2S)-2-(anilinomethyl)pyrrolidin-1-yl]-2,5-difluorobenzaldehyde thiosemicarbazone | 390 |
| 677 | Chiral | 2,5-difluoro-4-[(3R)-4-(2-fluorobenzyl)-3-phenylpiperazin-1-yl]benzaldehyde thiosemicarbazone | 485 |
| 678 | 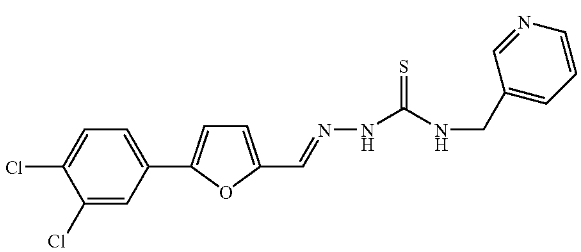 | 5-(3,4-dichlorophenyl)-2-furaldehyde N-(pyridin-3-ylmethyl)thiosemicarbazone | 406 |
| 679 | 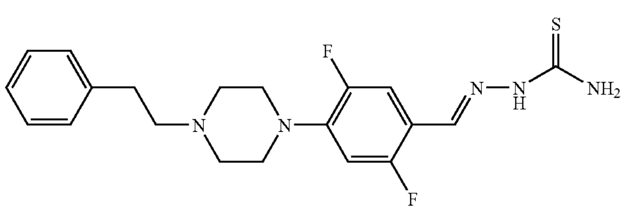 | 2,5-difluoro-4-[4-(2-phenylethyl)piperazin-1-yl]benzaldehyde thiosemicarbazone | 404 |
| 680 | 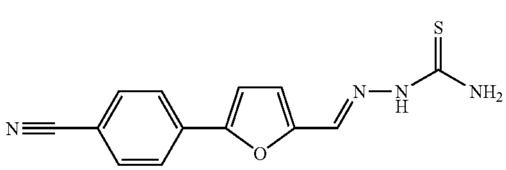 | 4-(5-{(E)-[(aminocarbonothioyl)hydrazono]methyl}-2-furyl)benzonitrile | 271 |

TABLE 3-continued

| | Structure | Name | MH+ |
|---|---|---|---|
| 681 | 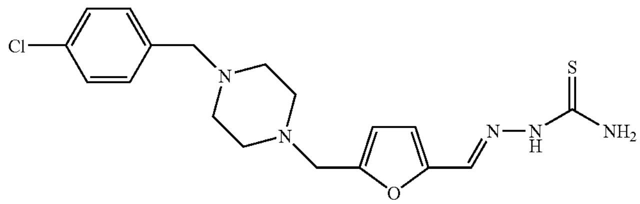 | 5-{[4-(4-chlorobenzyl)piperazin-1-yl]methyl}-2-furaldehyde thiosemicarbazone | 393 |
| 682 | 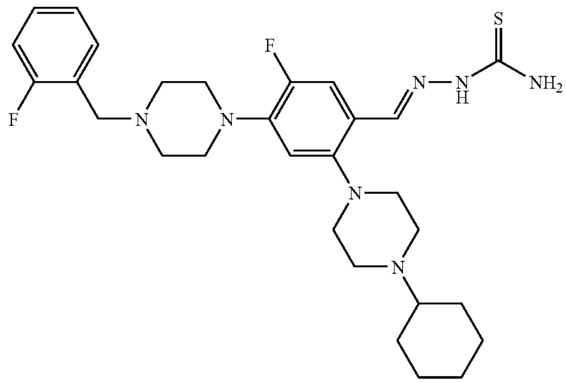 | 4-[4-(2-chlorobenzyl)piperazin-1-yl]-2-(4-cyclohexylpiperazin-1-yl)-5-fluorobenzaldehyde thiosemicarbazone | 573 |
| 683 | Chiral | 2-[(3R)-3-(dimethylamino)pyrrolidin-1-yl]-4-[4-(2,5-dimethylphenyl)piperazin-1-yl]-5-fluorobenzaldehyde thiosemicarbazone | 499 |
| 684 | Chiral | 4-[(3S)-4-(2-chlorobenzyl)-3-isobutylpiperazin-1-yl]-2,5-difluorobenzaldehyde thiosemicarbazone | 481 |
| 685 | Chiral | 2-[(3R)-3-(dimethylamino)pyrrolidin-1-yl]-5-fluoro-4-[4-(4-fluorophenyl)piperazin-1-yl]benzaldehyde thiosemicarbazone | 489 |

TABLE 3-continued

| | Structure | Name | MH+ |
|---|---|---|---|
| 686 | Chiral | 5-fluoro-4-[(3R,5S)-4-(2-fluorobenzoyl)-3,5-dimethylpiperazin-1-yl]-2-piperidin-1-ylbenzaldehyde thiosemicarbazone | 516 |
| 687 | Chiral | 4-[4-(1-ethylpropyl)piperazin-1-yl]-5-fluoro-2-[(4aS,8aS)-octahydroisoquinolin-2(1H)-yl]benzaldehyde thiosemicarbazone | 490 |
| 688 | Chiral | 5-{(E)-[(aminocarbonothioyl)hydrazono]methyl}-2-[(1S,4S)-5-benzyl-2,5-diazabicyclo[2.2.1]hept-2-yl]benzonitrile | 392 |
| 689 | 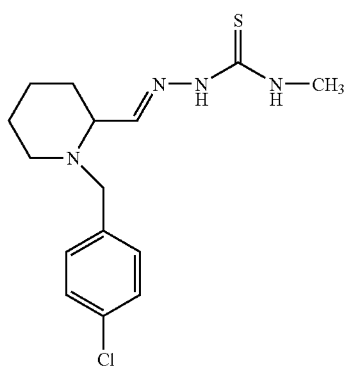 | 1-(4-chlorobenzyl)piperidine-2-carbaldehyde N-methylthiosemicarbazone | 326 |
| 690 | 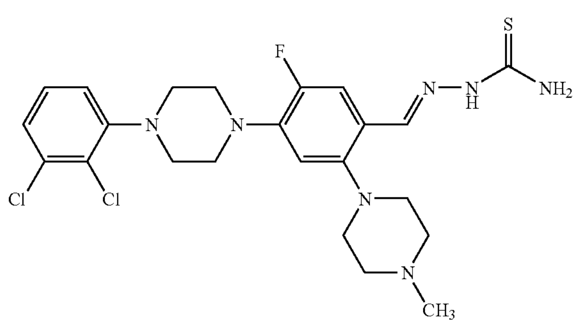 | 4-[4-(2,3-dichlorophenyl)piperazin-1-yl]-5-fluoro-2-(4-methylpiperazin-1-yl)benzaldehyde thiosemicarbazone | 525 |

TABLE 3-continued

| Structure | Name | MH+ |
|---|---|---|
| 691 | 5-(3,4-dichlorophenyl)-2-furaldehyde N-(tetrahydrofuran-2-ylmethyl)thiosemicarbazone | 399 |
| 692 | 5-(3,5-dimethylphenyl)-2-furaldehyde thiosemicarbazone | 274 |
| 693 | 4-(4-benzylpiperidin-1-yl)-5-fluoro-2-(4-methylpiperazin-1-yl)benzaldehyde thiosemicarbazone | 470 |
| 694 (Chiral) | 4-[(3S,8aS)-3-benzylhexahydro-pyrrolo[1,2-a]pyrazin-2(1H)-yl]-3-fluorobenzaldehyde thiosemicarbazone | 413 |
| 695 | 5-[(4-phenylpiperidin-1-yl)methyl]-2-furaldehyde thiosemicarbazone | 343 |
| 696 | 5-(3,4-dimethylphenyl)-2-furaldehyde thiosemicarbazone | 274 |

TABLE 3-continued

| Structure | Name | MH+ |
|---|---|---|
| 697 (Chiral) | 4-[(1S,4S)-5-benzyl-2,5-diazabicyclo[2.2.1]hept-2-yl]-3-(trifluoromethyl)benzaldehyde thiosemicarbazone | 435 |
| 698 | 5-(3-bromophenyl)-2-furaldehyde N-(pyridin-3-ylmethyl)thiosemicarbazone | 416 |
| 699 | 4-[(3R,5S)-4-(4-chloro-2-fluorobenzoyl)-3,5-dimethylpiperazin-1-yl]-2,5-difluorobenzaldehyde thiosemicarbazone | 485 |
| 700 | 5-fluoro-2-(4-methylpiperazin-1-yl)-4-{4-[2-(trifluoromethyl)phenyl]piperazin-1-yl}benzaldehyde thiosemicarbazone | 525 |
| 701 | 5-{(E)-[(aminocarbonothioyl)hydrazono]methyl}-2-[4-(1-ethylpropyl)piperazin-1-yl]benzonitrile | 360 |
| 702 (Chiral) | 4-[(3S)-3-benzyl-4-isobutylpiperazin-1-yl]-2,5-difluorobenzaldehyde thiosemicarbazone | 447 |

TABLE 3-continued

| Structure | Name | MH+ |
|---|---|---|
| 703 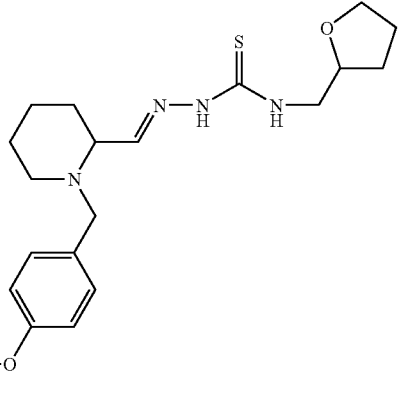 | 1-[4-(trifluoromethoxy)benzyl]piperidine-2-carbaldehyde N-(tetrahydrofuran-2-ylmethyl)thiosemicarbazone | 446 |
| 704 Chiral 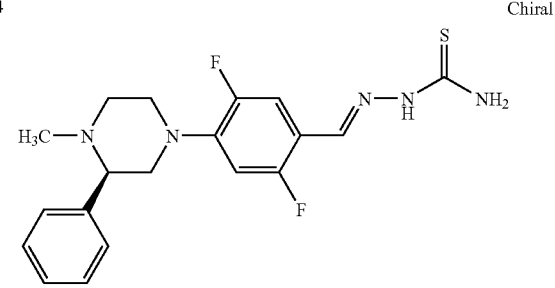 | 2,5-difluoro-4-[(3R)-4-methyl-3-phenylpiperazin-1-yl]benzaldehyde thiosemicarbazone | 390 |
| 705 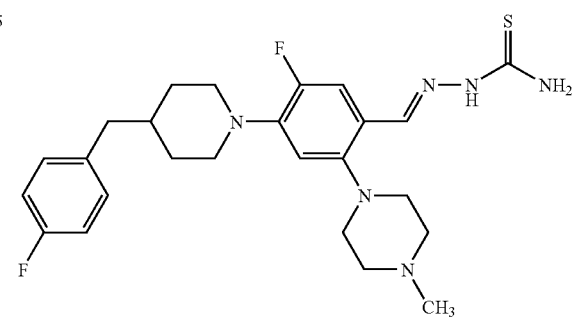 | 5-fluoro-4-[4-(4-fluorobenzyl)piperidin-1-yl]-2-(4-methylpiperazin-1-yl)benzaldehyde thiosemicarbazone | 488 |
| 706 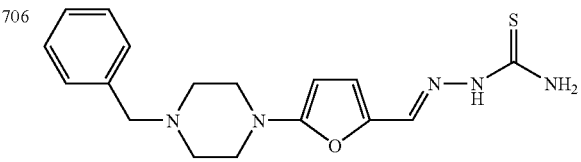 | 5-(4-benzylpiperazin-1-yl)-2-furaldehyde thiosemicarbazone | 344 |
| 707 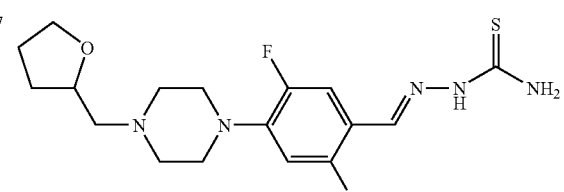 | 2,5-difluoro-4-[4-(tetrahydrofuran-2-ylmethyl)piperazin-1-yl]benzaldehyde thiosemicarbazone | 384 |

TABLE 3-continued

| Structure | Name | MH+ |
|---|---|---|
| 708 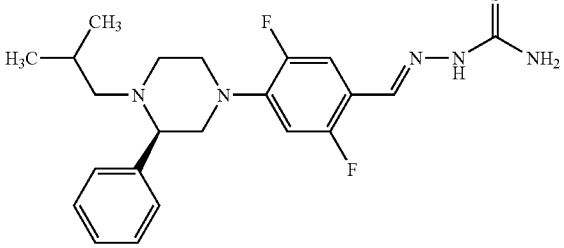 Chiral | 2,5-difluoro-4-[(3R)-4-isobutyl-3-phenylpiperazin-1-yl]benzaldehyde thiosemicarbazone | 433 |
| 709 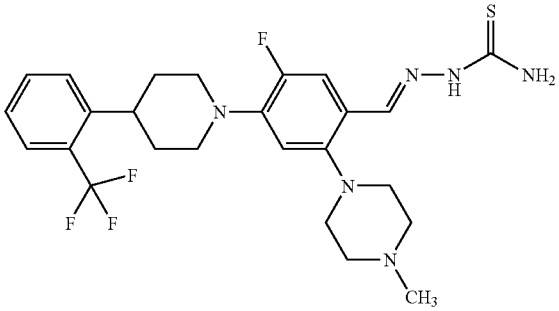 | 5-fluoro-2-(4-methylpiperazin-1-yl)-4-{4-[2-(trifluoromethyl)phenyl]piperidin-1-yl}benzaldehyde thiosemicarbazone | 524 |
| 710 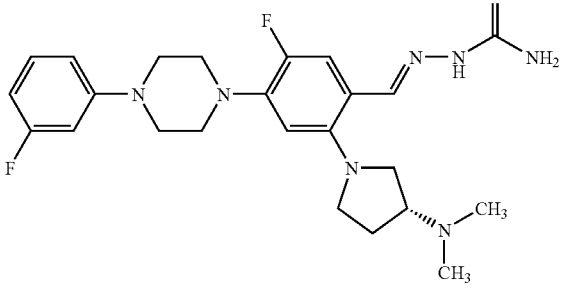 Chiral | 2-[(3R)-3-(dimethylamino)pyrrolidin-1-yl]-5-fluoro-4-[4-(3-fluorophenyl)piperazin-1-yl]benzaldehyde thiosemicarbazone | 489 |
| 711 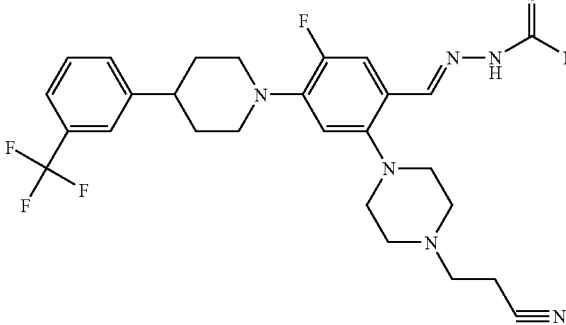 | 3-[4-(2-{(E)-[(aminocarbonothioyl)hydrazono]methyl}-4-fluoro-5-{4-[3-(trifluoromethyl)phenyl]piperazin-1-yl}phenyl)piperazin-1-yl]propanenitrile | 564 |

TABLE 3-continued

| Structure | | Name | MH+ |
|---|---|---|---|
| 712 | | 3-{6-[4-(1,3-benzodioxol-5-ylmethyl)piperazin-1-yl]pyridin-3-yl}benzaldehyde thiosemicarbazone | 476 |
| 713 | | 3,5-difluoro-4-[4-(tetrahydrofuran-2-ylmethyl)piperazin-1-yl]benzaldehyde thiosemicarbazone | 384 |
| 714 | Chiral | (2S)-1-(4-chlorobenzyl)pyrrolidine-2-carbaldehyde N-(2-furylmethyl)thiosemicarbazone | 378 |
| 715 | | 5-(2-methoxyphenyl)-2-furaldehyde thiosemicarbazone | 276 |
| 716 | Chiral | 4-[4-(3,5-dichlorophenyl)piperazin-1-yl]-2-[(3R)-3-(dimethylamino)pyrrolidin-1-yl]-5-fluorobenzaldehyde thiosemicarbazone | 540 |

TABLE 3-continued

| | Structure | Name | MH+ |
|---|---|---|---|
| 717 | 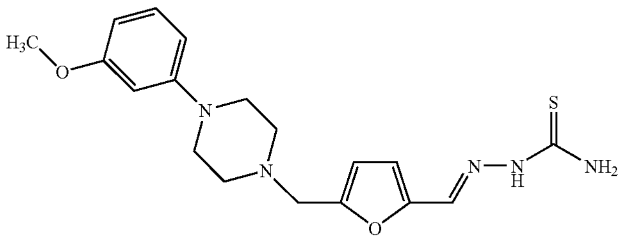 | 5-{[4-(3-methoxyphenyl)piperazin-1-yl]methyl}-2-furaldehyde thiosemicarbazone | 374 |
| 718 | 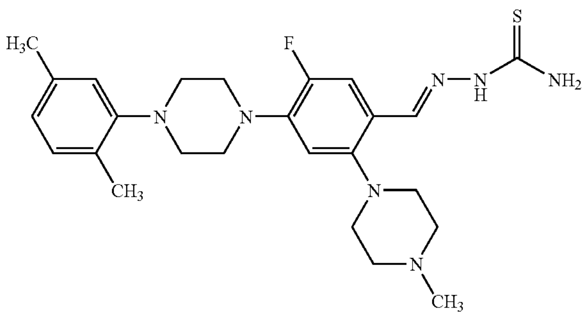 | 4-[4-(2,5-dimethylphenyl)piperazin-1-yl]-5-fluoro-2-(4-methylpiperazin-1-yl)benzaldehyde thiosemicarbazone | 485 |
| 719 | Chiral | 4-[(1S,4S)-5-benzyl-2,5-diazabicyclo[2.2.1]hept-2-yl]-2-(trifluoromethyl)benzaldehyde thiosemicarbazone | 435 |
| 720 | 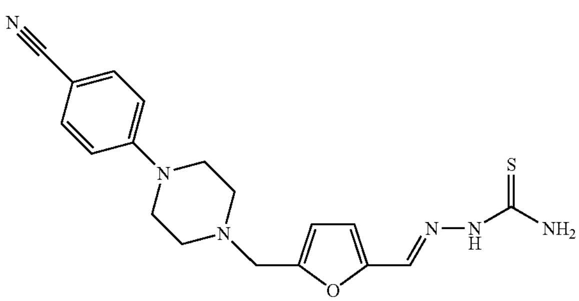 | 4-{4-[(5-{(E)-[(aminocarbonothioyl)hydrazono]methyl}-2-furyl)methyl]piperazin-1-yl}benzonitrile | 369 |
| 721 | 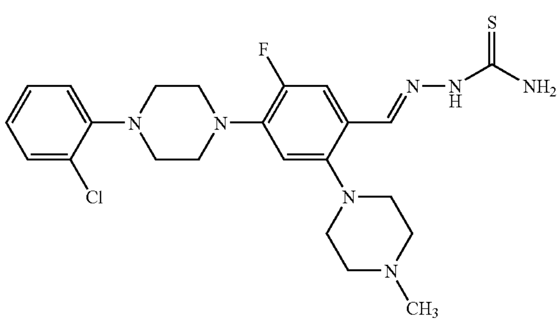 | 4-[4-(2-chlorophenyl)piperazin-1-yl]-5-fluoro-2-(4-methylpiperazin-1-yl)benzaldehyde thiosemicarbazone | 491 |

TABLE 3-continued

| | Structure | Name | MH+ |
|---|---|---|---|
| 722 | 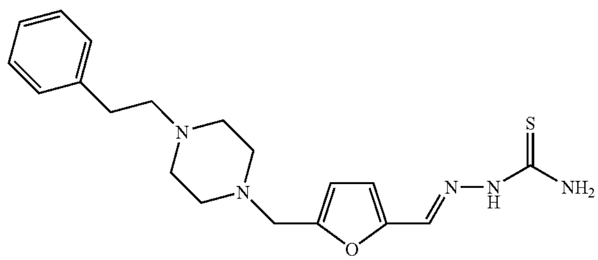 | 5-{[4-(2-phenylethyl)piperazin-1-yl]methyl}-2-furaldehyde thiosemicarbazone | 373 |
| 723 | 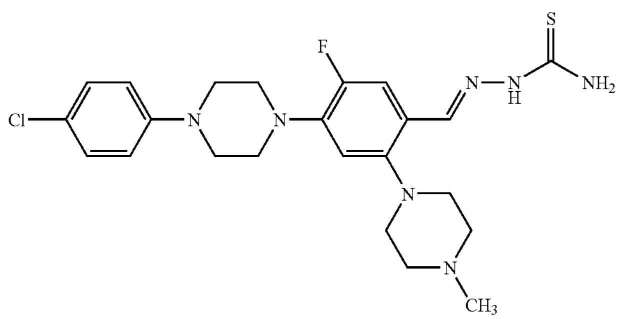 | 4-[4-(4-chlorophenyl)piperazin-1-yl]-5-fluoro-2-(4-methylpiperazin-1-yl)benzaldehyde thiosemicarbazone | 491 |
| 724 | 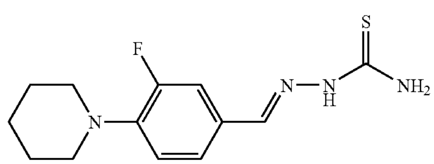 | 3-fluoro-4-piperidin-1-ylbenzaldehyde thiosemicarbazone | 281 |
| 725 | 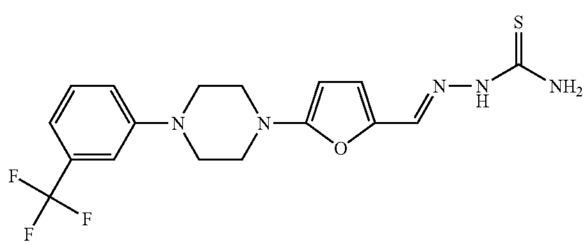 | 5-{4-[3-(trifluoromethyl)phenyl]piperazin-1-yl}-2-furaldehyde thiosemicarbazone | 398 |
| 726 | 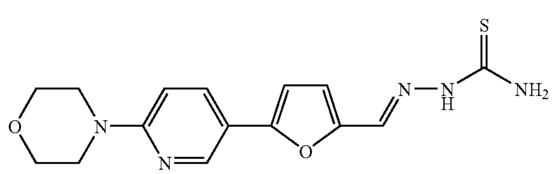 | 5-(6-morpholin-4-ylpyridin-3-yl)-2-furaldehyde thiosemicarbazone | 332 |
| 727 | 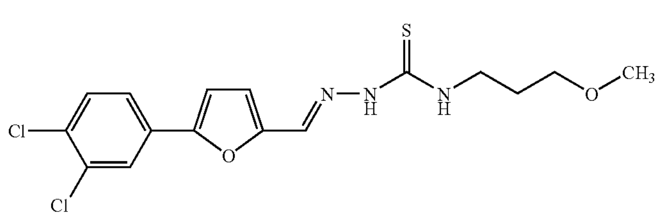 | 5-(3,4-dichlorophenyl)-2-furaldehyde N-(3-methoxypropyl)thiosemicarbazone | 387 |
| 728 | 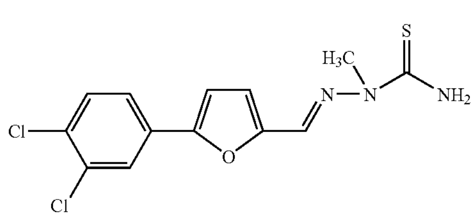 | 5-(3,4-dichlorophenyl)-2-furaldehyde N'-methylthiosemicarbazone | 329 |

TABLE 3-continued

| Structure | | Name | MH+ |
|---|---|---|---|
| 729 | | 5-[4-(dimethylamino)phenyl]-2-furaldehyde thiosemicarbazone | 289 |
| 730 | Chiral | 4-{(3R)-3-[(benzyloxy)methyl]piperazin-1-yl}-2,5-difluorobenzaldehyde thiosemicarbazone | 420 |
| 731 | | 3,5-difluoro-4-(4-isopropylpiperazin-1-yl)benzaldehyde thiosemicarbazone | 342 |
| 732 | | 3-(4-{2-{(E)-[(aminocarbonothioyl)hydrazono]methyl}-5-[4-(3-chlorophenyl)piperazin-1-yl]-4-fluorophenyl}piperazin-1-yl)propanenitrile | 530 |
| 733 | | 5-(2,4-dimethoxyphenyl)-2-furaldehyde thiosemicarbazone | 306 |

TABLE 3-continued

| Structure | Name | MH+ |
|---|---|---|
| 734 | 5-fluoro-2-(4-methylpiperazin-1-yl)-4-(4-phenoxypiperidin-1-yl)benzaldehyde thiosemicarbazone | 472 |
| 735 | 5-fluoro-2-(4-methylpiperazin-1-yl)-4-{4-[3-(trifluoromethyl)pyridin-2-yl]piperazin-1-yl}benzaldehyde thiosemicarbazone | 526 |
| 736 | 1-(2,6-dichlorobenzyl)piperidine-2-carbaldehyde N-(3-methoxypropyl)thiosemicarbazone | 418 |
| 737 | 4-(4-cyclohexylpiperazin-1-yl)-2-(trifluoromethyl)benzaldehyde thiosemicarbazone | 415 |
| 738 | 2,5-difluoro-4-[4-(2-fluorobenzoyl)piperazin-1-yl]benzaldehyde thiosemicarbazone | 422 |

TABLE 3-continued

| | Structure | Name | MH+ |
|---|---|---|---|
| 739 | Chiral | 2-[(3R)-3-(dimethylamino)pyrrolidin-1-yl]-5-fluoro-4-[4-(2-fluorophenyl)piperazin-1-yl]benzaldehyde thiosemicarbazone | 489 |
| 740 | Chiral | 2-({[(3S)-1-(4-{(E)-[(aminocarbonothioyl)hydrazono]methyl}-2,5-difluorophenyl)pyrrolidin-3-yl]amino}methyl)benzonitrile | 415 |
| 741 | 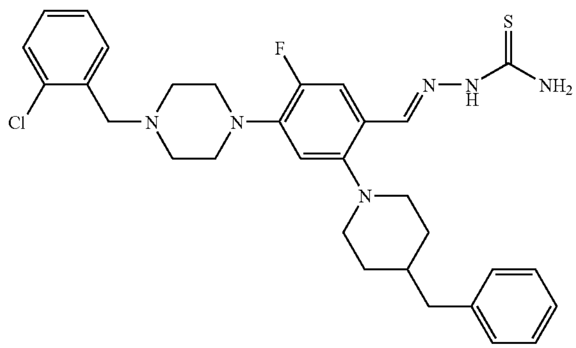 | 2-(4-benzylpiperidin-1-yl)-4-[4-(2-chlorobenzyl)piperazin-1-yl]-5-fluorobenzaldehyde thiosemicarbazone | 580 |
| 742 | Chiral | 5-{[(2R)-2-(anilinomethyl)pyrrolidin-1-yl]methyl}-2-furaldehyde thiosemicarbazone | 358 |
| 743 | 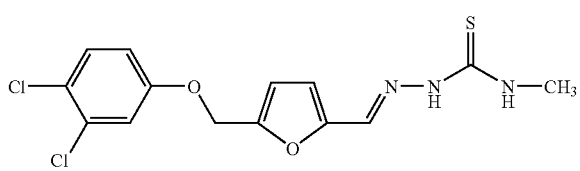 | 5-[(3,4-dichlorophenoxy)methyl]-2-furaldehyde N-methylthiosemicarbazone | 359 |
| 744 | 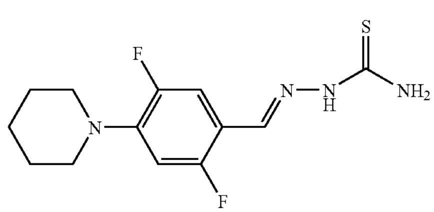 | 2,5-difluoro-4-piperidin-1-ylbenzaldehyde thiosemicarbazone | 299 |

TABLE 3-continued

| Structure | Name | MH+ |
|---|---|---|
| 745 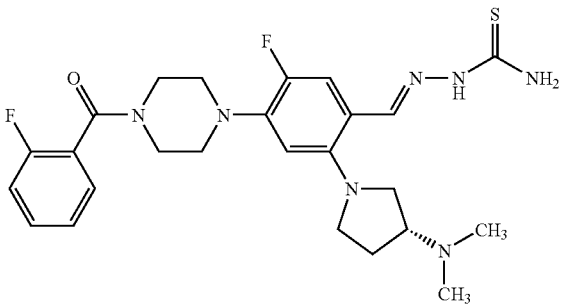 Chiral | 2-[(3R)-3-(dimethylamino)pyrrolidin-1-yl]-5-fluoro-4-[4-(2-fluorobenzoyl)piperazin-1-yl]benzaldehyde thiosemicarbazone | 517 |
| 746 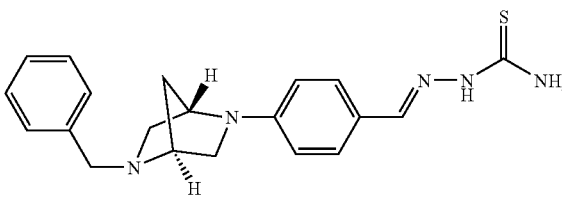 Chiral | 4-[(1S,4S)-5-benzyl-2,5-diazabicyclo[2.2.1]hept-2-yl]benzaldehyde thiosemicarbazone | 367 |
| 747 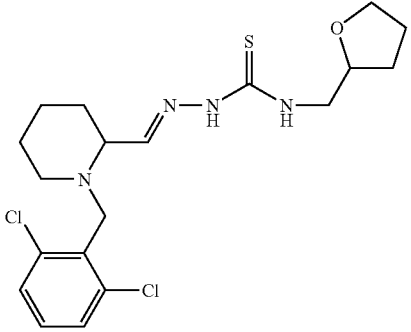 | 1-(2,6-dichlorobenzyl)piperidine-2-carbaldehyde N-(tetrahydrofuran-2-ylmethyl)thiosemicarbazone | 430 |
| 748 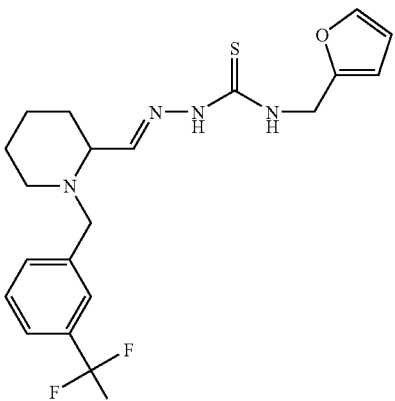 | 1-[3-(trifluoromethyl)benzyl]piperidine-2-carbaldehyde N-(2-furylmethyl)thiosemicarbazone | 425 |
| 749 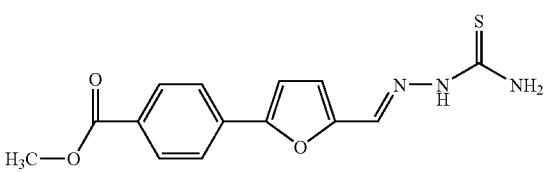 | methyl 4-(5-{(E)-[(aminocarbonothioyl)hydrazono]methyl}-2-furyl)benzoate | 304 |

TABLE 3-continued

| Structure | Name | MH+ |
|---|---|---|
| 750 | 4-(4-{4-{(E)-[(aminocarbonothioyl)hydrazono]methyl}-5-[(3R)-3-(dimethylamino)pyrrolidin-1-yl]-2-fluorophenyl)piperazin-1-yl)benzonitrile | 496 |
| 751 | 4-{6-[4-(2-methoxyethyl)piperazin-1-yl]pyridin-3-yl}benzaldehyde thiosemicarbazone | 400 |
| 752 | 5-[(3,4-dichlorophenoxy)methyl]-2-furaldehyde N-(2-furylmethyl)thiosemicarbazone | 425 |
| 753 | 4-[4-(3,4-dimethylphenyl)piperazin-1-yl]-5-fluoro-2-(4-methylpiperazin-1-yl)benzaldehyde thiosemicarbazone | 485 |
| 754 | 3-[6-(4-cyclohexylpiperazin-1-yl)pyridin-3-yl]benzaldehyde thiosemicarbazone | 424 |
| 755 | 5-{[benzyl(methyl)amino]methyl}-2-furaldehyde thiosemicarbazone | 303 |

TABLE 3-continued

| | Structure | Name | MH+ |
|---|---|---|---|
| 756 | | 1-[4-(trifluoromethyl)benzyl]piperidine-2-carbaldehyde N-(2-furylmethyl)thiosemicarbazone | 425 |
| 757 | | 5-(6-azepan-1-ylpyridin-3-yl)-2-furaldehyde thiosemicarbazone | 344 |
| 758 | | 5-[4-(2-fluorophenyl)piperazin-1-yl]-2-furaldehyde thiosemicarbazone | 348 |
| 759 | | 5-fluoro-4-[4-(2-fluorobenzoyl)piperazin-1-yl]2-piperidin-1-ylbenzaldehyde thiosemicarbazone | 488 |
| 760 | | 1-[4-(trifluoromethyl)benzyl]piperidine-2-carbaldehyde N-(tetrahydrofuran-2-ylmethyl)thiosemicarbazone | 430 |

TABLE 3-continued

| Structure | Name | MH+ |
|---|---|---|
| 761 | 2-{4-[(5-{(E)-[(aminocarbonothioyl) hydrazono]methyl}-2-furyl) methyl]piperazin-1-yl}benzonitrile | 369 |
| 762 | 5-(3-methoxyphenyl)-2-furaldehyde thiosemicarbazone | 276 |
| 763 | 4-[4-(2-chlorobenzyl)piperazin-1-yl]-2-[4-(1-ethylpropyl) piperazin-1-yl]-5-fluorobenzaldehyde thiosemicarbazone | 561 |
| 764 Chiral | 4-[(3S)-4-ethyl-3-isobutylpiperazin-1-yl]-2,5-difluorobenzaldehyde thiosemicarbazone | 385 |
| 765 Chiral | 2-[(3R)-3-(dimethylamino)pyrrolidin-1-yl]-5-fluoro-4-[4-(3-methylphenyl)piperazin-1-yl]benzaldehyde thiosemicarbazone | 485 |

TABLE 3-continued

| Structure | Name | MH+ |
|---|---|---|
| 766 | 1-(2,6-dichlorobenzyl)piperidine-2-carbaldehyde N-(2-furylmethyl)thiosemicarbazone | 426 |
| 767 (Chiral) | 2-[(3R)-3-(dimethylamino)pyrrolidin-1-yl]-5-fluoro-4-[(4aS,8aS)-octahydroisoquinolin-2(1H)-yl]benzaldehyde thiosemicarbazone | 448 |
| 768 | 3-fluoro-4-[4-(4-fluorobenzyl)-1,4-diazepan-1-yl]benzaldehyde thiosemicarbazone | 404 |
| 769 | 4-[4-(2-chloro-6-fluorobenzyl)-1,4-diazepan-1-yl]-3-fluorobenzaldehyde thiosemicarbazone | 439 |
| 770 | 3-fluoro-4-[4-(1-phenylethyl)piperazin-1-yl]benzaldehyde thiosemicarbazone | 387 |
| 771 | 4-[4-(4-chlorobenzyl)piperazin-1-yl]-3,5-difluorobenzaldehyde thiosemicarbazone | 425 |

TABLE 3-continued

| Structure | Name | MH+ |
|---|---|---|
| 772 | 1-(4-chlorobenzyl)piperidine-2-carbaldehyde N-(2-furylmethyl)thiosemicarbazone | 392 |
| 773 | 5-(6-piperidin-1-ylpyridin-3-yl)-2-furaldehyde N-(pyridin-3-ylmethyl)thiosemicarbazone | 422 |
| 774 | 5-fluoro-4-[4-(2-fluorophenyl)piperazin-1-yl]-2-(4-methylpiperazin-1-yl)benzaldehyde thiosemicarbazone | 475 |
| 775 Chiral | 5-{[(2S)-2-(hydroxymethyl)-2,3-dihydro-1H-indol-1-yl]methyl}-2-furaldehyde thiosemicarbazone | 331 |
| 776 Chiral | 4-[(3S)-3-benzylpiperazin-1-yl]-2,5-difluorobenzaldehyde thiosemicarbazone | 390 |

TABLE 3-continued

| | Structure | Name | MH+ |
|---|---|---|---|
| 777 | 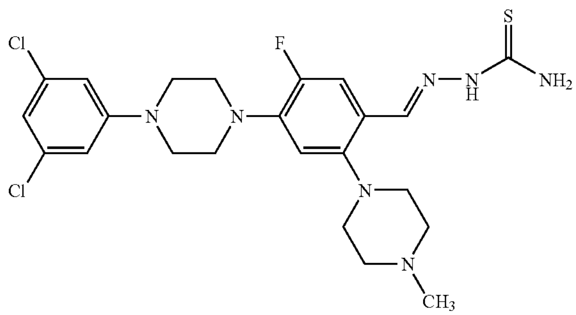 | 4-[4-(3,5-dichlorophenyl)piperazin-1-yl]-5-fluoro-2-(4-methylpiperazin-1-yl)benzaldehyde thiosemicarbazone | 525 |
| 778 | 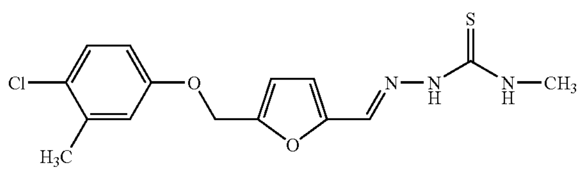 | 5-[(4-chloro-3-methylphenoxy)methyl]-2-furaldehyde N-methylthiosemicarbazone | 339 |
| 779 | 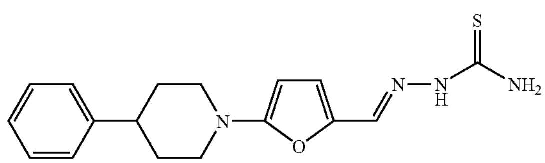 | 5-(4-phenylpiperidin-1-yl)-2-furaldehyde thiosemicarbazone | 329 |
| 780 | 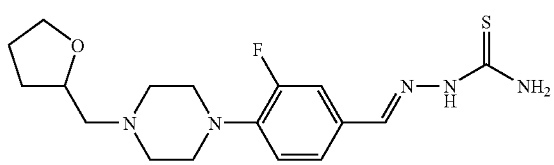 | 3-fluoro-4-[4-(tetrahydrofuran-2-ylmethyl)piperazin-1-yl]benzaldehyde thiosemicarbazone | 366 |
| 781 | Chiral | 4-[4-(3-chlorophenyl)piperazin-1-yl]-2-[(3S)-3-(dimethylamino)pyrrolidin-1-yl]-5-fluorobenzaldehyde thiosemicarbazone | 505 |
| 782 | Chiral | 2-[(3R)-3-(dimethylamino)pyrrolidin-1-yl]-5-fluoro-4-[4-(trifluoromethyl)piperidin-1-yl]benzaldehyde thiosemicarbazone | 462 |

TABLE 3-continued

| | Structure | Name | MH+ |
|---|---|---|---|
| 783 | 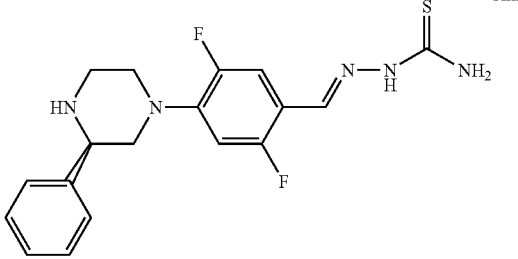 Chiral | 2,5-difluoro-4-[(3R)-3-phenylpiperazin-1-yl]benzaldehyde thiosemicarbazone | 376 |
| 784 | 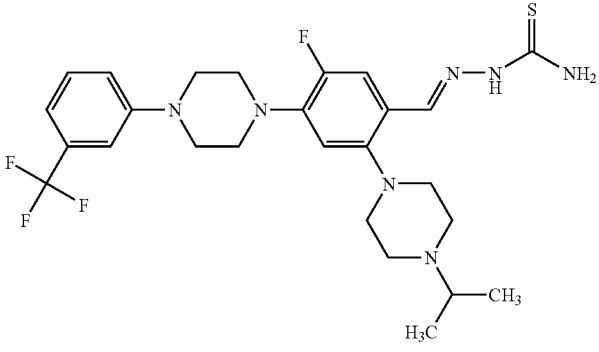 | 5-fluoro-2-(4-isopropylpiperazin-1-yl)-4-{4-[3-(trifluoromethyl)phenyl]piperazin-1-yl}benzaldehyde thiosemicarbazone | 553 |
| 785 | 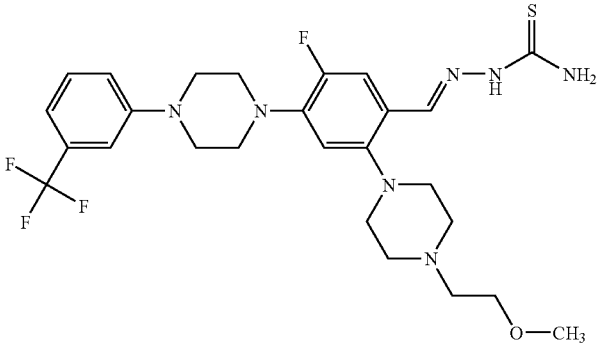 | 5-fluoro-2-[4-(2-methoxyethyl)piperazin-1-yl]-4-{4-[3-(trifluoromethyl)phenyl]piperazin-1-yl}benzaldehyde thiosemicarbazone | 569 |
| 786 | 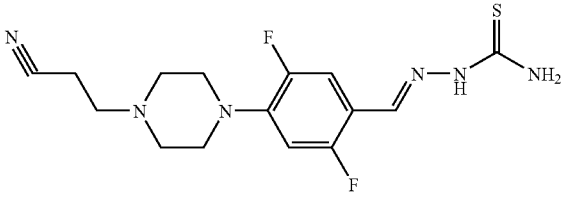 | 3-[4-(4-{(E)-[(aminocarbonothioyl)hydrazono]methyl}-2,5-difluorophenyl)piperazin-1-yl]propanenitrile | 353 |
| 787 | 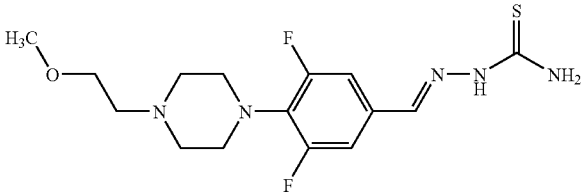 | 3,5-difluoro-4-[4-(2-methoxyethyl)piperazin-1-yl]benzaldehyde thiosemicarbazone | 358 |

TABLE 3-continued

| | Structure | Name | MH+ |
|---|---|---|---|
| 788 | Chiral | 2-[(3R)-3-(dimethylamino)pyrrolidin-1-yl]-5-fluoro-4-(4-phenylpiperazin-1-yl)benzaldehyde thiosemicarbazone | 471 |
| 789 | 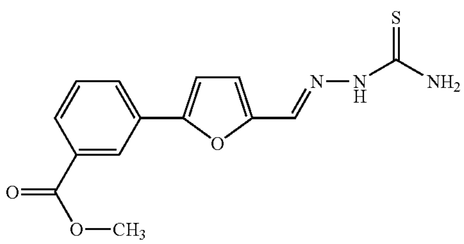 | methyl 3-(5-{(E)-[(aminocarbonothioyl)hydrazono]methyl}-2-furyl)benzoate | 304 |
| 790 | 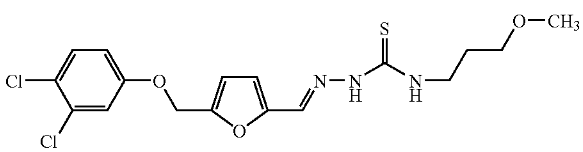 | 5-[(3,4-dichlorophenoxy)methyl]-2-furaldehyde N-(3-methoxypropyl)thiosemicarbazone | 417 |
| 791 | Chiral | 2,5-difluoro-4-[(3S)-3-isobutyl-4-isopropylpiperazin-1-yl]benzaldehyde thiosemicarbazone | 399 |
| 792 | 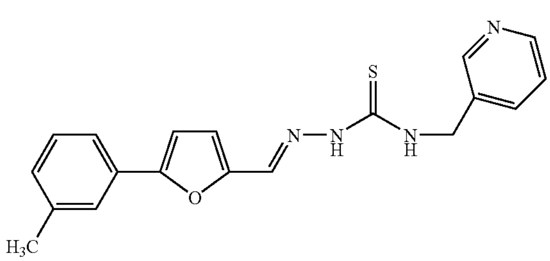 | 5-(3-methylpherlyl)-2-furaldehyde N-(pyridin-3-ylmethyl)thiosemicarbazone | 351 |
| 793 | 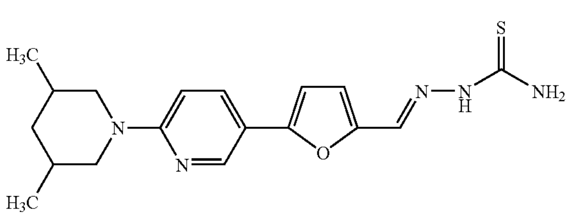 | 5-[6-(3,5-dimethylpiperidin-1-yl)pyridin-3-yl]-2-furaldehyde thiosemicarbazone | 358 |

TABLE 3-continued

| Structure | | Name | MH+ |
|---|---|---|---|
| 794 | Chiral | 5-{[(1S,4S)-5-(4-fluorophenyl)-2,5-diazabicyclo[2.2.1]hept-2-yl]methyl}-2-furaldehyde thiosemicarbazone | 374 |
| 795 | | methyl 2-(5-{(E)-[(aminocarbonothioyl)hydrazono]methyl}-2-furyl)benzoate | 304 |
| 796 | | 4-[4-(1-ethylpropyl)piperazin-1-yl]-5-fluoro-2-piperidin-1-ylbenzaldehyde thiosemicarbazone | 436 |
| 797 | | 2-[4-(cyclohexylmethyl)piperazin-1-yl]-5-fluoro-4-{4-[3-(trifluoromethyl)phenyl]piperazin-1-yl}benzaldehyde thiosemicarbazone | 607 |
| 798 | | 5-(2,5-dichlorophenyl)-2-furaldehyde N-(pyridin-3-ylmethyl)thiosemicarbazone | 406 |

TABLE 3-continued

| Structure | | Name | MH+ |
|---|---|---|---|
| 799 | 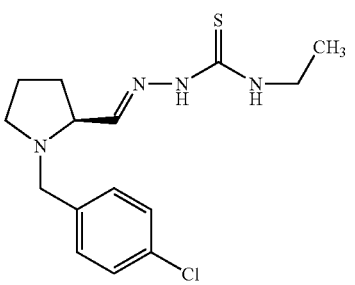 Chiral | (2S)-1-(4-chlorobenzyl)pyrrolidine-2-carbaldehyde N-ethylthiosemicarbazone | 326 |
| 800 | 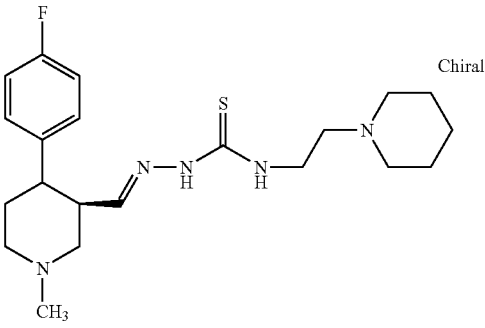 Chiral | (3S)-4-(4-fluorophenyl)-1-methyl-piperidine-3-carbaldehyde N-(2-piperidin-1-ylethyl)thiosemicarbazone | 407 |
| 801 | 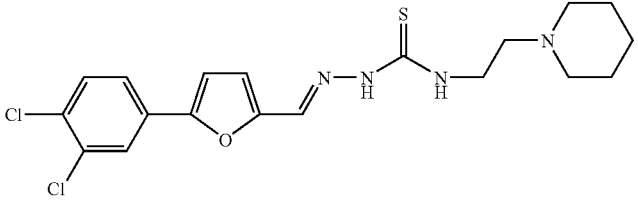 | 5-(3,4-dichlorophenyl)-2-furaldehyde N-(2-piperidin-1-ylethyl)thiosemicarbazone | 426 |
| 802 | 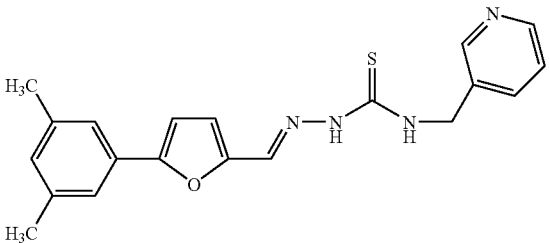 | 5-(3,5-dimethylphenyl)-2-furaldehyde N-(pyridin-3-ylmethyl)thiosemicarbazone | 365 |
| 803 | 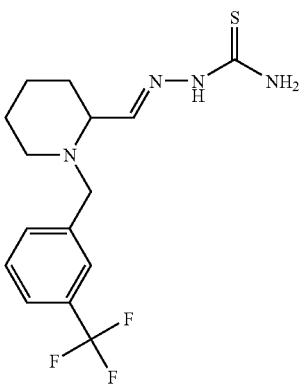 | 1-[3-(trifluoromethyl)benzyl]piperidine-2-carbaldehyde thiosemicarbazone | 345 |

TABLE 3-continued

| | Structure | Name | MH+ |
|---|---|---|---|
| 804 | 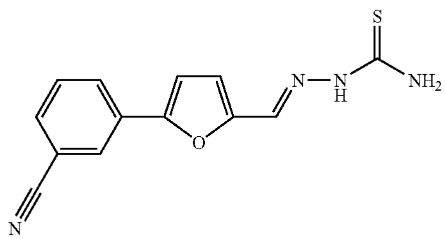 | 3-(5-{(E)-[(aminocarbonothioyl)hydrazono]methyl}-2-furyl)benzonitrile | 271 |
| 805 | 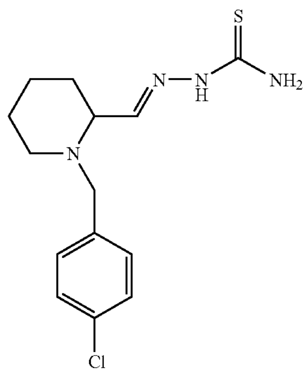 | 1-(4-chlorobenzyl)piperidine-2-carbaldehyde thiosemicarbazone | 312 |
| 806 | Chiral | (2S)-1-(2-chlorobenzyl)indoline-2-carbaldehyde thiosemicarbazone | 346 |
| 807 | 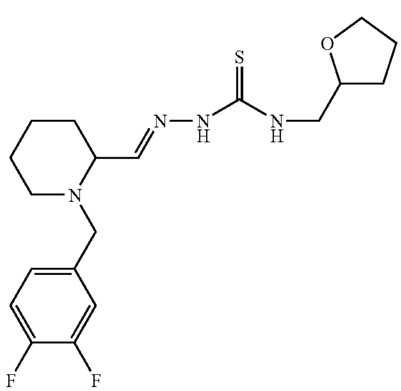 | 1-(3,4-difluorobenzyl)piperidine-2-carbaldehyde N-(tetrahydrofuran-2-ylmethyl)thiosemicarbazone | 398 |

TABLE 3-continued

| Structure | Name | MH+ |
|---|---|---|
| 808 (Chiral) | 2-[(3R)-3-(dimethylamino)pyrrolidin-1-yl]-4-[4-(3,4-dimethylphenyl)piperazin-1-yl]-5-fluorobenzaldehyde thiosemicarbazone | 499 |
| 809 | 1-(4-chlorobenzyl)piperidine-2-carbaldehyde N-(3-methoxypropyl)thiosemicarbazone | 384 |
| 810 (Chiral) | 4-(4-cyclohexypiperazin-1-yl)-5-fluoro-2-[(4aS,8aS)-octahydroisoquinolin-2(1H)-yl]benzaldehyde thiosemicarbazone | 502 |
| 811 | 1-(2,6-dichlorobenzyl)piperidine-2-carbaldehyde thiosemicarbazone | 346 |

TABLE 3-continued

| Structure | Name | MH+ |
|---|---|---|
| 812 | 1-(2,5-dichlorobenzyl)piperidine-2-carbaldehyde thiosemicarbazone | 346 |
| 813 | 1H-indole-2-carbaldehyde thiosemicarbazone | 219 |
| 814 (Chiral) | (2S)-1-(4-chlorobenzyl)indoline-2-carbaldehyde thiosemicarbazone | 346 |
| 815 | 5-pyridin-3-yl-2-furaldehyde thiosemicarbazone | 247 |
| 816 | 5-[(4-benzylpiperazin-1-yl)methyl]-2-furaldehyde thiosemicarbazone | 358 |
| 817 | 5-[benzyl(methyl)amino]-2-furaldehyde thiosemicarbazone | 289 |

TABLE 3-continued

| | Structure | Name | MH+ |
|---|---|---|---|
| 818 | | 1-(4-chlorobenzyl)piperidine-2-carbaldehyde N-(tetrahydrofuran-2-ylmethyl)thiosemicarbazone | 396 |
| 819 | | 2,3-difluoro-4-(4-isopropylpiperazin-1-yl)benzaldehyde thiosemicarbazone | 342 |
| 820 | | 5-fluoro-4-[4-(4-methylphenyl)piperazin-1-yl]-2-(4-methylpiperazin-1-yl)benzaldehyde thiosemicarbazone | 471 |
| 821 | Chiral | (2S)-1-(2-chlorobenzyl)indoline-2-carbaldehyde N-(2-morpholin-4-ylethyl)thiosemicarbazone | 459 |
| 822 | | 1-(3,4-dichlorobenzyl)piperidine-2-carbaldehyde thiosemicarbazone | 346 |

TABLE 3-continued

| | Structure | Name | MH+ |
|---|---|---|---|
| 823 | 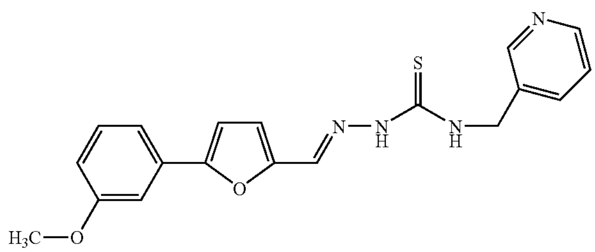 | 5-(3-methoxyphenyl)-2-furaldehyde N-(pyridin-3-ylmethyl)thiosemicarbazone | 367 |
| 824 | Chiral | (2S)-1-(4-chlorobenzyl)pyrrolidine-2-carbaldehyde thiosemicarbazone | 298 |
| 825 | 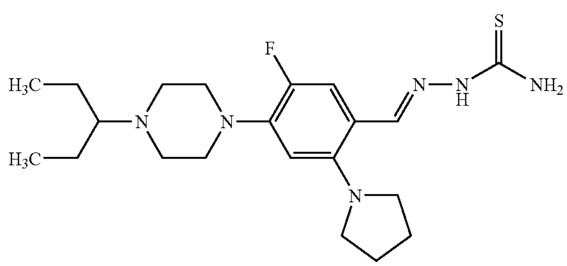 | 4-[4-(1-ethylpropyl)piperazin-1-yl]-5-fluoro-2-pyrrolidin-1-ylbenzaldehyde thiosemicarbazone | 422 |
| 826 | 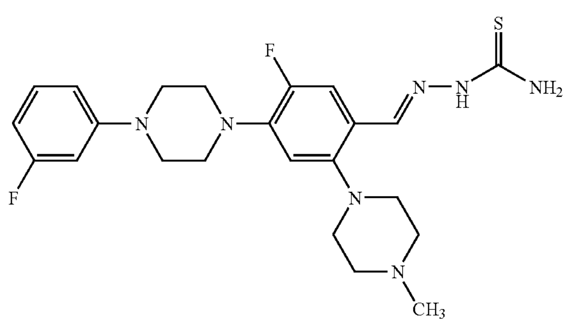 | 5-fluoro-4-[4-(3-fluorophenyl)piperazin-1-yl]-2-(4-methylpiperazin-1-yl)benzaldehyde thiosemicarbazone | 475 |
| 827 | Chiral | 2,5-difluoro-4-[(3S)-3-isobutyl-4-methylpiperazin-1-yl]benzaldehyde thiosemicarbazone | 370 |

TABLE 3-continued
| | Structure | Name | MH+ |
|---|---|---|---|
| 828 | 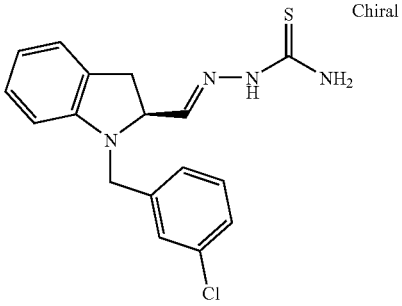 Chiral | (2S)-1-(3-chlorobenzyl)indoline-2-carbaldehyde thiosemicarbazone | 346 |
| 829 | 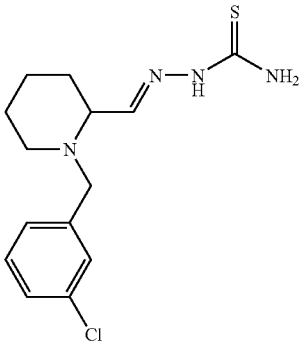 | 1-(3-chlorobenzyl)piperidine-2-carbaldehyde thiosemicarbazone | 312 |
| 830 | 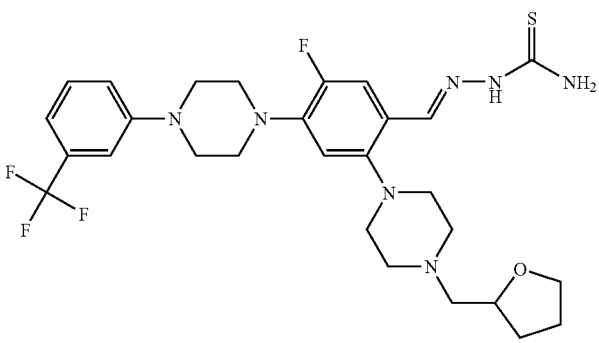 | 5-fluoro-2-[4-(tetrahydrofuran-2-ylmethyl)piperazin-1-yl]-4-{4-[3-(trifluoromethyl)phenyl]piperazin-1-yl}benzaldehyde thiosemicarbazone | 595 |
| 831 | 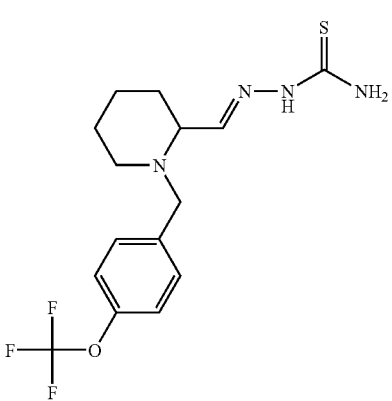 | 1-[4-(trifluoromethoxy)benzyl]piperidine-2-carbaldehyde thiosemicarbazone | 361 |

TABLE 3-continued

| Structure | Name | MH+ |
|---|---|---|
| 832 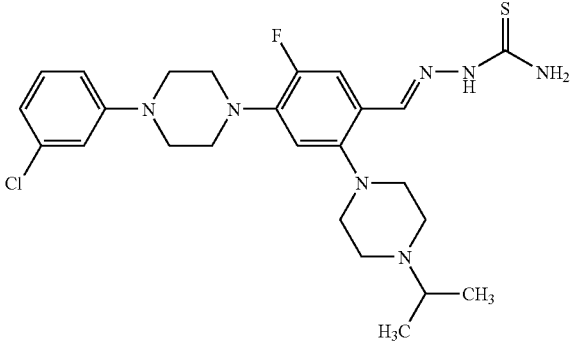 | 4-[4-(3-chlorophenyl)piperazin-1-yl]-5-fluoro-2-(4-isopropylpiperazin-1-yl)benzaldehyde thiosemicarbazone | 519 |
| 833 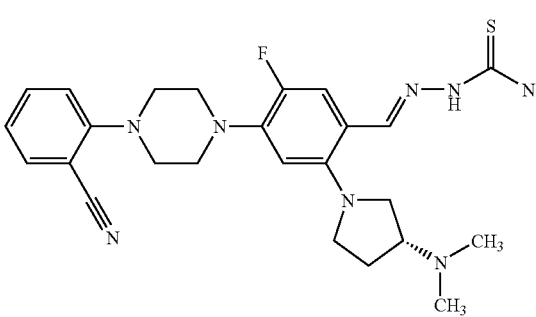 Chiral | 2-(4-{4-{(E)-[(aminocarbonothioyl)hydrazono]methyl)-5-[(3R)-3-(dimethylamino)pyrrolidin-1-yl]-2-fluorophenyl}piperazin-1-yl)benzonitrile | 496 |
| 834 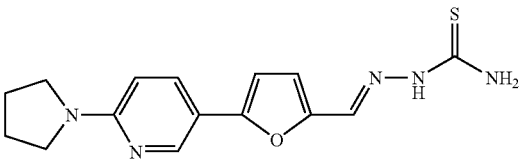 | 5-(6-pyrrolidin-1-ylpyridin-3-yl)-2-furaldehyde thiosemicarbazone | 316 |
| 835 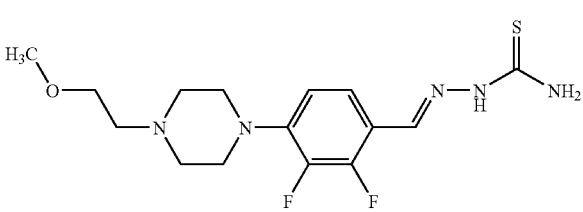 | 2,3-difluoro-4-[4-(2-methoxyethyl)piperazin-1-yl]benzaldehyde thiosemicarbazone | 358 |
| 836 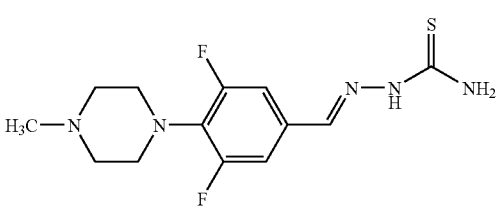 | 3,5-difluoro-4-(4-methylpiperazin-1-yl)benzaldehyde thiosemicarbazone | 314 |

TABLE 3-continued

| Structure | Name | MH+ |
|---|---|---|
| 837 (Chiral) | 2-[(3R)-3-(dimethylamino)pyrrolidin-1-yl]-5-fluoro-4-(3-phenylpyrrolidin-1-yl)benzaldehyde thiosemicarbazone | 456 |
| 838 | 5-(2,5-difluorophenyl)-2-furaldehyde N-(pyridin-3-ylmethyl)thiosemicarbazone | 373 |
| 839 | 5-fluoro-4-[4-(3-methylphenyl)piperazin-1-yl]-2-(4-methylpiperazin-1-yl)benzaldehyde thiosemicarbazone | 471 |
| 840 | 5-[(4-isopropylpiperazin-1-yl)methyl]-2-furaldehyde thiosemicarbazone | 310 |
| 841 | 5-{[4-(3,5-dimethoxyphenyl)piperazin-1-yl]methyl}-2-furaldehyde thiosemicarbazone | 405 |

TABLE 3-continued

| Structure | Name | MH+ |
|---|---|---|
| 842 | 4-{4-[4-{(E)-[(aminocarbonothioyl)hydrazono]methyl}-2-fluoro-5-(4-methylpiperazin-1-yl)phenyl]piperazin-1-yl}benzonitrile | 482 |
| 843 (Chiral) | 4-[(2S)-2-(anilinomethyl)pyrrolidin-1-yl]-5-fluoro-2-(4-methylpiperazin-1-yl)benzaldehyde | 471 |
| 844 (Chiral) | 2-[(3R)-3-(dimethylamino)pyrrolidin-1-yl]-5-fluoro-4-(2-phenylpyrrolidin-1-yl)benzaldehyde thiosemicarbazone | 456 |
| 845 | 2,5-difluoro-4-(4-{[2-(trifluoromethoxy)benzyl]amino}piperidin-1-yl)benzaldehyde thiosemicarbazone | 488 |
| 846 | 4-{4-[(2,6-dichlorobenzyl)(methyl)amino]piperidin-1-yl}-2,5-difluorobenzaldehyde thiosemicarbazone | 487 |

TABLE 3-continued

| Structure | Name | MH+ |
|---|---|---|
| 847 | 4-{4-[(4-chlorobenzyl)(methyl)amino]piperidin-1-yl}-2,5-difluorobenzaldehyde thiosemicarbazone | 453 |
| 848 | 4-{4-[(2,6-dichlorobenzyl)amino]piperidin-1-yl}-2,5-difluorobenzaldehyde thiosemicarbazone | 473 |
| 849 | 4-{4-[(3-chlorobenzyl)amino]piperidin-1-yl}-2,5-difluorobenzaldehyde thiosemicarbazone | 439 |
| 850 | 2,5-difluoro-4-(4-{methyl[2-(trifluoromethoxy)benzyl]amino}piperidin-1-yl)benzaldehyde thiosemicarbazone | 503 |
| 851 | 4-{4-[(3-chlorobenzyl)(methyl)amino]piperidin-1-yl}-2,5-difluorobenzaldehyde thiosemicarbazone | 453 |
| 852 | 2,5-difluoro-4-[4-(pyridin-4-ylmethyl)piperazin-1-yl]benzaldehyde thiosemicarbazone | 391 |
| 853 | 4-{4-[(4-chlorobenzyl)amino]piperidin-1-yl}-2,5-difluorobenzaldehyde thiosemicarbazone | 439 |

TABLE 3-continued

| Structure | Name | MH+ |
|---|---|---|
| 854 | 5-[3-(trifluoromethyl)phenyl]-2-furaldehyde N'-(2-hydroxyethyl)thiosemicarbazone | 358 |
| 855 | 4-{4-[(2-chlorobenzyl)amino]piperidin-1-yl}-2,5-difluorobenzaldehyde thiosemicarbazone | 439 |
| 856 | 2,5-difluoro-4-[4-(pyridin-2-ylmethyl)piperazin-1-yl]benzaldehyde thiosemicarbazone | 391 |
| 857 | 4-[4-(benzylamino)piperidin-1-yl]-2,5-difluorobenzaldehyde thiosemicarbazone | 404 |
| 858 | 2,5-difluoro-4-[4-(pyridin-3-ylmethyl)piperazin-1-yl]benzaldehyde thiosemicarbazone | 391 |
| 859 | 5-(2-chlorophenyl)-2-furaldehyde N'-(2-hydroxyethyl)thiosemicarbazone | 325 |

TABLE 3-continued

| | Structure | Name | MH+ |
|---|---|---|---|
| 860 | 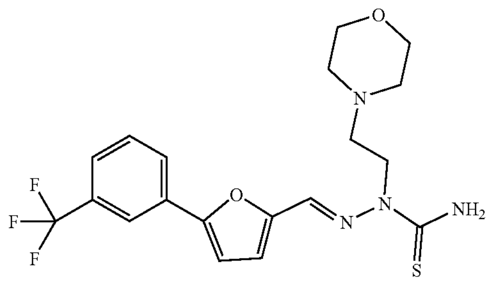 | 5-[3-(trifluoromethyl)phenyl]-2-furaldehyde N'-(2-morpholin-4-ylethyl)thiosemicarbazone | 427 |
| 861 | 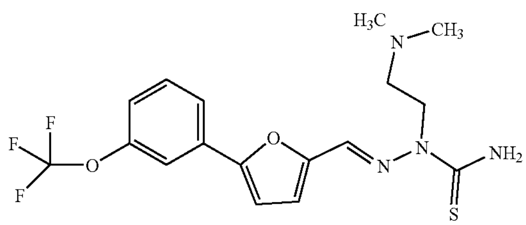 | 5-[3-(trifluoromethoxy)phenyl]-2-furaldehyde N'-(2-(dimethylamino)ethyl]thiosemicarbazone | 401 |
| 862 | 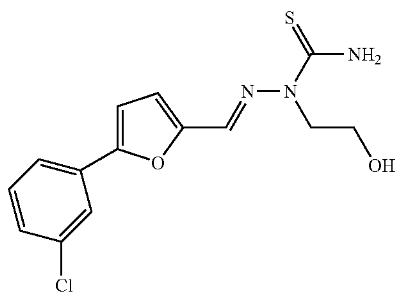 | 5-(3-chlorophenyl)-2-furaldehyde N'-(2-hydroxyethyl)thiosemicarbazone | 325 |
| 863 | 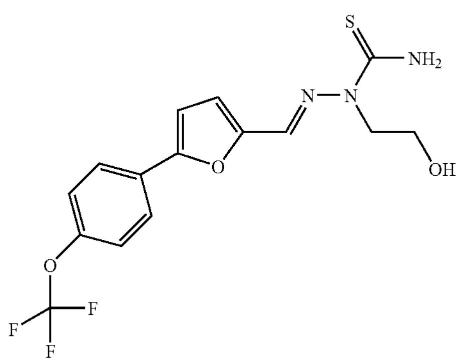 | 5-[4-(trifluoromethoxy)phenyl]-2-furaldehyde N'-(2-hydroxyethyl)thiosemscarbazone | 374 |
| 864 | 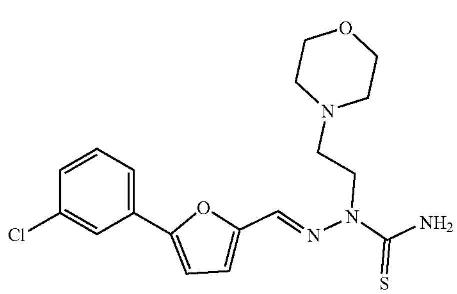 | 5-(3-chlorophenyl)-2-furaldehyde N'-(2-morpholin-4-ylethyl)thiosemicarbazone | 394 |

TABLE 3-continued

| Structure | Name | MH+ |
|---|---|---|
| 865 | 5-[3-(trifluoromethyl)phenyl]-2-furaldehyde N'-(2-pyrrolidin-1-ylethyl)thiosemicarbazone | 411 |
| 866 | 5-(3,4-dichlorophenyl)-2-furaldehyde N'-[2-(dimethylamino)ethyl]thiosemicarbazone | 386 |
| 867 | 5-(3,4-dichlorophenyl)-2-furaldehyde N'-(2-pyrrolidin-1-ylethyl)thiosemicarbazone | 412 |
| 868 | 5-[3-(trifluoromethoxy)phenyl]-2-furaldehyde N'-(2-pyrrolidin-1-ylethyl)thiosemicarbazone | 427 |

The compounds of Table 3 were assayed according to the procedures set forth with regard to Table 1. Each of these Example compounds displayed an $IC_{50}$ value of less than 10 µM with respect to HCV. Many of the compounds displayed an $IC_{50}$ value of less than or equal to 1 µM or less than or equal to 0.1 µM. Many of these compounds exhibited $IC_{50}$ values of less than or equal to 0.050 µM, less than or equal to 0.030 µM, less than or equal to 0.025 µM, or less than or equal to 0.010 µM. Thus, as described above, the compounds are well-suited for use in the methods described herein.

While the invention has been described with respect to specific examples including presently preferred modes of carrying out the invention, those skilled in the art will appreciate that there are numerous variations and permutations of the above described systems and techniques that fall within the spirit and scope of the invention.

ANTIGEN REFERENCES CITED

1. International patent application WO99/24578
2. International patent application WO99/36544.
3. International patent application WO99/57280.
4. International patent application WO00/22430.
5. Tettelin et al. (2000) Science 287:1809-1815.
6. International patent application WO96/29412.
7. Pizza et al. (2000) Science 287:1816-1820.
8. International patent application PCT/B01/0066.
9. Bjune et al. (1991) Lancet 338(8775).
10. Fuskasawa et al. (1999) Vaccine 17:2951-2958.
11. Rosenqist et al. (1998) Dev. Biol. Strand 92:323-333.
12. Constantino et al. (1992) Vaccine 10:691-698.
13. Constantino et al. (1999) Vaccine 17:1251-1263.
14. Watson (2000) Pediatr Infect Dis J 19:331-332.
15. Rubin (20000) Pediatr Clin North Am 47:269-285,v.
16. Jedrzejas (2001) Microbiol Mol Biol Rev 65:187-207.
17. International patent application filed on 3 Jul. 2001 claiming priority from GB-0016363.4].
18. Kalman et al. (1999) Nature Genetics 21:385-389.
19. Read et al. (2000) Nucleic Acids Res 28:1397406.
20. Shirai et al. (2000) J. Infect. Dis 181(Suppl 3):S524-S527.
21. International patent application WO99/27105.

22. International patent application WO00/27994.
23. International patent application WO00/37494.
24. International patent application WO99/28475.
25. Bell (2000) Pediatr Infect Dis J 19:1187-1188.
26. Iwarson (1995) APMIS 103:321-326.
27. Gerlich et al. (1990) Vaccine 8 Suppl:S63-68 & 79-80.
28. Hsu et al. (1999) Clin Liver Dis 3:901-915.
29. Gastofsson et al. (1996) N. Engl. J. Med. 334-:349-355.
30. Rappuoli et al. (1991) TIBTECH 9:232-238.
31. Vaccines (1988) eds. Plotkin & Mortimer. ISBN 0-7216-1946-0.
32. Del Guidice et al. (1998) Molecular Aspects of Medicine 19:1-70.
33. International patent application WO93/018150.
34. International patent application WO99/53310.
35. International patent application WO98/04702.
36. Ross et al. (2001) Vaccine 19:135-142.
37. Sutter et al. (2000) Pediatr Clin North Am 47:287-308.
38. Zimmerman & Spann (1999) Am Fan Physician 59:113-118, 125-126.
39. Dreensen (1997) Vaccine 15 Suppl"S2-6.
40. MMWR Morb Mortal Wkly rep 1998 Jan. 16:47(1):12, 9.
41. McMichael (2000) Vaccine19 Suppl 1:S101-107.
42. Schuchat (1999) Lancer 353(9146):51-6.
43. GB patnet applications 0026333.5, 0028727.6 & 0105640.7.
44. Dale (1999) Infect Disclin North Am 13:227-43, viii.
45. Ferretti et al. (2001) PNAS USA 98: 4658-4663.
46. Kuroda et al. (2001) Lancet 357(9264):1225-1240; see also pages 1218-1219.
47. Ramsay et al. (2001) Lancet 357(9251):195-196.
48. Lindberg (1999) Vaccine 17 Suppl 2:S28-36.
49. Buttery & Moxon (2000) J R Coil Physicians Long 34:163-168.
50. Ahmad & Chapnick (1999) Infect Dis Clin North Am 13:113-133, vii.
51. Goldblatt (1998) J. Med. Microbiol. 47:663-567.
52. European patent 0 477 508.
53. U.S. Pat. No. 5,306,492.
54. International patent application WO98/42721.
55. Conjugate Vaccines (eds. Cruse et al.) ISBN 3805549326, particularly vol. 10:48-114.
56. Hermanson (1996) Bioconjugate Techniques ISBN: 012323368 & 012342335X.
57. European patent application 0372501.
58. European patent application 0378881.
59. European patent application 0427347.
60. International patent application WO93/17712.
61. International patent application WO98/58668.
62. European patent application 0471177.
63. International patent application WO00/56360.
64. International patent application WO00/67161.

All US, foreign and international patents, patent applications, and other patent publications, articles, texts, references, and other publications cited throughout this specification are hereby incorporated by reference in their entirety for any purpose.

What is claimed is:
1. A composition comprising:
   a vaccine in an amount effective to stimulate a cell—mediated immune response; and
   a vaccine adjuvant comprising a thiosemicarbazone or derivative thereof, wherein the thiosemicarbazone is a compound of formula I:

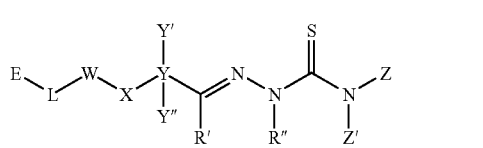

wherein:
E is absent or selected from the group consisting of alkyl, substituted alkyl, cycloalkyl, substituted cycloalkyl, aryl, substituted aryl, heterocyclyl, substituted heterocyclyl, heteroaryl, and substituted heteroaryl;

L is absent or is selected from the group consisting of oxo, amino, alkylene, substituted alkylene, alkoxy, alkylamino, aminoalkyl, heterocyclyl, carbocyclyl, and carbonyl;

W is absent or selected from the group consisting of cycloalkyl, substituted cycloalkyl, aryl, substituted aryl, heterocyclyl, substituted heterocyclyl, heteroaryl, and substituted heteroaryl;

X is a absent or is selected from the group consisting of oxo, amino, alkylene, substituted alkylene, alkoxy, alkylamino, aminoalkyl, heterocyclyl, carbocyclyl, and carbonyl;

Y is selected from the group consisting of cycloalkyl, substituted cycloalkyl, aryl, substituted aryl, heterocyclyl, substituted heterocyclyl, heteroaryl, and substituted heteroaryl;

Y' is absent or is selected from the group consisting of F, Cl, Br, I, nitro, alkyl, substituted alkyl, heterocyclyl, substituted heterocyclyl, amino, alkylamino, and dialkylamino;

Y" is absent or is selected from the group consisting of F, Cl, Br, I, nitro, alkyl, substituted alkyl, heterocyclyl, substituted heterocyclyl, amino, alkylamino, and dialkylamino;

R' is H, alkyl, or substituted alkyl;

R" is H, or

R' and R" are taken together to form a heterocyclic ring;

Z and Z' are independently selected from the group consisting of hydrogen, alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cycloamidino, cycloalkyl, cycloimido, arylsulfonyl and arylsulfonamido; or Z and Z' are taken together to form a heterocyclic group, which may be optionally substituted;

the tautomers and the pharmaceutically acceptable salts, esters, or prodrugs thereof.

2. The composition of claim 1 wherein R' is H.

3. The composition of claim 1 wherein the thiosemicarbazone is a compound of formula III,

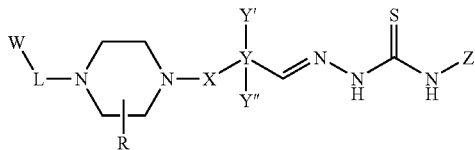

wherein:
- W is selected from the group consisting of substituted or unsubstituted alkyl, substituted or unsubstituted cycloalkyl, substituted or unsubstituted aryl, substituted or unsubstituted heterocyclyl, and substituted or unsubstituted heteroaryl groups;
- X and L are each independently absent or independently selected from the group consisting of lower alkyl and carbonyl;
- R is absent or selected from the group consisting of carbonyl, amino, alkyl, substituted alkyl, alkylamino, and dialkylamino;
- Y is an aryl or heteroaryl group;
- Y' is absent or selected from the group consisting of F, Cl, Br, I, alkyl, substituted alkyl, heterocyclyl, amino, alkylamino, dialkylamino, and nitro;
- Y" is absent or selected from the group consisting of F, Cl, Br, I, alkyl, substituted alkyl, heterocyclyl, amino, alkylamino, dialkylamino, and nitro;
- Z is hydrogen, or if Y is furanyl, then Z may be selected from the group consisting of alkyl, substituted alkyl, heterocyclyl, amino, alkylamino, dialkylamino, and nitro; and salts, prodrugs, or tautomers thereof.

4. The composition of claim 3 wherein W is an optionally substituted phenyl.

5. The composition of claim 3 wherein W is substituted with at least one member selected from the group consisting of Br, Cl, F, and CF$_3$.

6. The composition of claim 1 wherein Y is selected from the group consisting of phenyl, furanyl, pyridinyl, pyrrolyl, pyrazolyl, pyrazinyl, thiazolyl, imidazolyl and pyrimidinyl.

7. The composition of claim 6 wherein Y is phenyl, furanyl, or pyrimidinyl.

8. The composition of claim 3 wherein Z is hydrogen.

9. The composition of claim 3 wherein Y' is F or nitro.

10. The composition of claim 3 wherein W is phenyl optionally substituted with —CF$_3$ or Cl; Y is phenyl; Y' is F or nitro; and Z is H.

11. The composition of claim 1 wherein the thiosemicarbazone is a compound of formula IV,

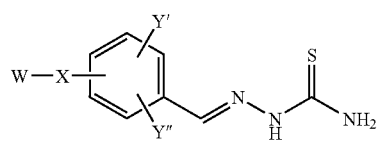

wherein:
- W is an optionally substituted phenyl or pyridinyl group;
- X is alkoxy or alkylamino;
- Y' is H or fluoro;
- Y" is dialkylamino, fluoro, or nitro; and salts, prodrugs, or tautomers thereof.

12. The composition of claim 11 wherein W is an optionally substituted phenyl.

13. The composition of claim 11 wherein W is an optionally substituted pyridinyl group.

14. The composition of claim 11 wherein W is substituted with at least one member selected from the group consisting of —Cl; —F; —Br; —CF$_3$; —OCH$_3$; —NO$_2$; —CH$_3$; —N(CH$_3$)$_2$; and —OCF$_3$.

15. The composition of claim 11 wherein the thiosemicarbazone is

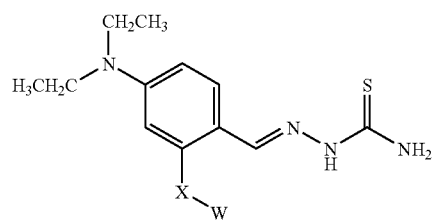

wherein:
- W is phenyl substituted with at least one member selected from the group consisting of —Cl; —F; —Br; —CF$_3$; —OCH$_3$; —NO$_2$; —CH$_3$; —N(CH$_3$)$_2$; and —OCF$_3$;
- X is alkoxy; and
- salts, prodrugs, or tautomers thereof.

16. The composition of claim 15 wherein X is —OCH$_2$—.

17. The composition of claim 15 wherein the compound is

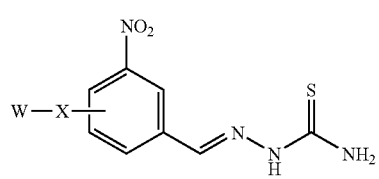

wherein:
- W is pyridinyl or is phenyl substituted with at least one member selected from the group consisting of Cl, F, and CF$_3$;
- X is alkylamino; and
- salts, prodrugs, or tautomers thereof.

18. The composition of claim 17 wherein X is —NHCH$_2$CH$_2$— or NHCH$_2$—.

19. The composition of claim 17 wherein W is pyridinyl.

20. The composition of claim 17 wherein W is phenyl substituted with Cl, F, and CF$_3$.

21. The composition of claim 1 wherein the thiosemicarbazone is a compound of Formula IVc

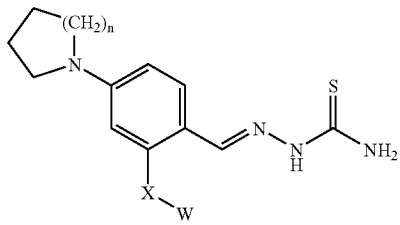

IVc wherein:
W is phenyl substituted with at least one member selected from the group consisting of —Cl; —F; —Br; —CF$_3$; —OCH$_3$; —NO$_2$; —CH$_3$; N(CH$_3$)$_2$; and —OCF$_3$;
X is alkoxy; and
n is an integer from 1 to 3.

22. The composition of claim 1 wherein the thiosemicarbazone is a compound of Formula V

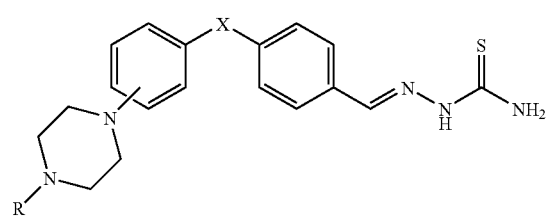

V wherein:
R is an alkyl group;
X is alkoxy; and
salts, prodrugs, or tautomers thereof.

23. The composition of claim 22 wherein R is methyl.

24. The composition of claim 22 wherein X is —OCH$_2$—; —OCH$_2$CH$_2$—; —CH$_2$O—; or —CH$_2$CH$_2$O—.

25. The composition of claim 1 wherein the thiosemicarbazone is a compound of Formula VI

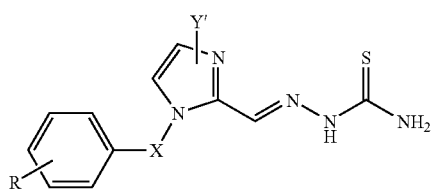

VI wherein:
X is absent or an alkylene;
Y' is absent or is an alkyl group; and
R is a halogen; and
salts, prodrugs, or tautomers thereof.

26. The composition of claim 25 wherein X is —CH$_2$CH$_2$—; Y' is absent or is methyl, and R is Cl.

27. The composition of claim 1 wherein the thiosemicarbazone is a compound of Formula VII

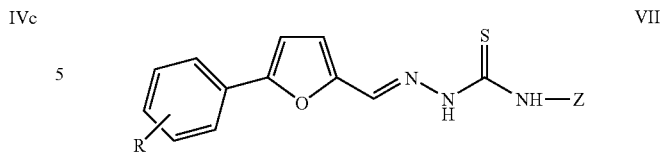

VII wherein:
R is nitro and Z is H; or
R is Cl and Z is selected from the group consisting of alkyl, pyridylalkylene, piperidinylalkylene, morpholinylalkylene, and piperazinylalkylene; and
salts, prodrugs, or tautomers thereof.

28. The composition of claim 27 wherein Z is methyl, pyridylmethylene, piperidinylethylene, morpholinylethylene, piperazinylmethylene, piperazinylethylene, and morpholinylbutylene.

29. The composition of claim 1 wherein the thiosemicarbazone is a compound of formula VIII and salts, prodrugs, or tautomers thereof:

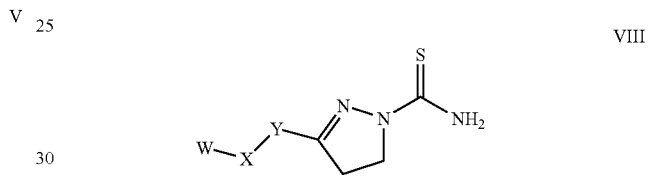

VIII wherein:
W is a phenyl, substituted phenyl, pyridinyl, or substituted pyridinyl group;
X is absent or is selected from the group consisting of oxo, amino, alkylene, and substituted alkylene; and
Y is an aryl or heteroaryl group.

30. The composition of claim 29 wherein Y is selected from the group consisting of phenyl, furanyl, pyridinyl, pyrrolyl, pyrazolyl, pyrazinyl, thiazolyl, and imidazolyl.

31. The composition of claim 29 wherein Y is furanyl.

32. The composition of claim 29 wherein X is absent.

33. The composition of claim 29 wherein W is substituted with at least one member selected from the group consisting of —Cl; —F; —Br; —CF$_3$; —OCH$_3$; —NO$_2$; —CH$_3$; —N(CH$_3$)$_2$; and —OCF$_3$.

34. The composition of claim 1 wherein the thiosemicarbazone is a compound of formula IX:

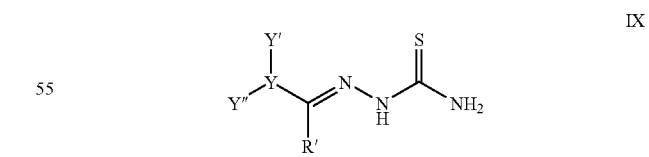

IX wherein:
R' is H or lower alkyl;
Y is an aryl or heteroaryl group having one ring or two fused rings;
Y' is selected from the group consisting of halo, nitro, alkyl, substituted alkyl, alkenyl, substituted alkenyl, alkynyl, substituted alkynyl, heterocyclyl, substituted heterocyclyl, amino, alkylamino, and dialkylamino; and Y" is absent or is selected from the group consisting of halo, nitro, alkyl, substituted alkyl, heterocyclyl, substituted heterocyclyl, amino, alkylamino, and dialkylamino.

35. The composition of claim 34 wherein Y is selected from the group consisting of phenyl, furanyl, pyrrolyl, pyrazolyl, pyrazinyl, thiazolyl, and imidazolyl.

36. A composition comprising:
   a vaccine in an amount effective to stimulate a cell—mediated immune response; and
   a vaccine adjuvant comprising a thiosemicarbazone or a derivative thereof, wherein the thiosemicarbazone is independently selected from Tables I, II, and III.

37. The composition of claim 36 wherein the thiosemicarbazone is selected from the group consisting of:

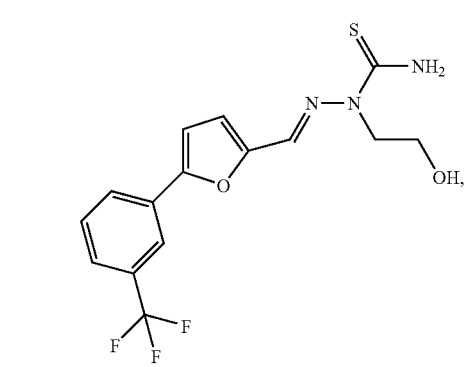

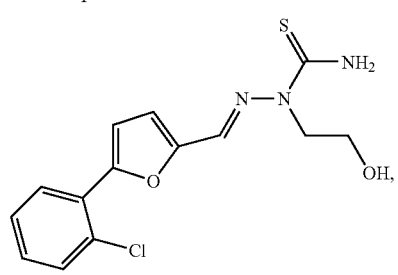

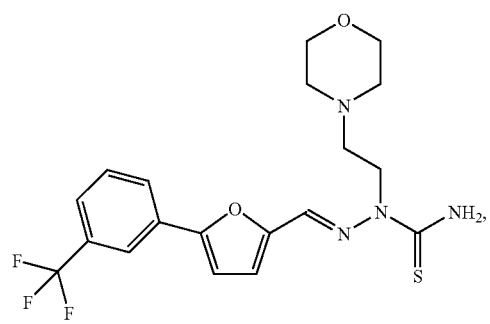

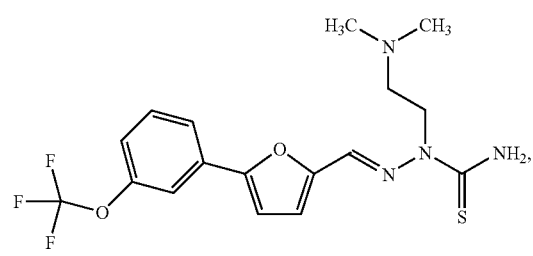

-continued

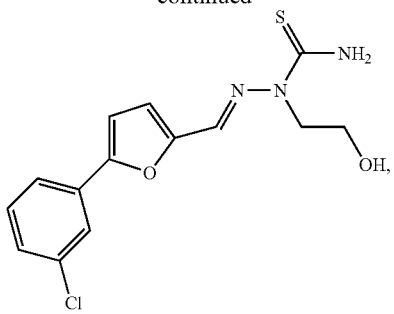

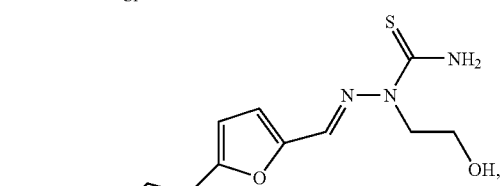

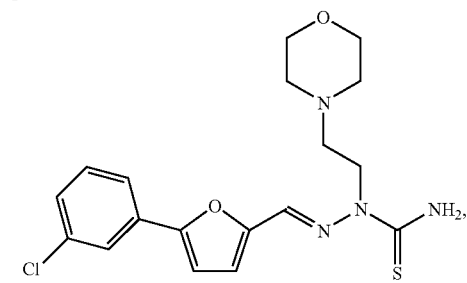

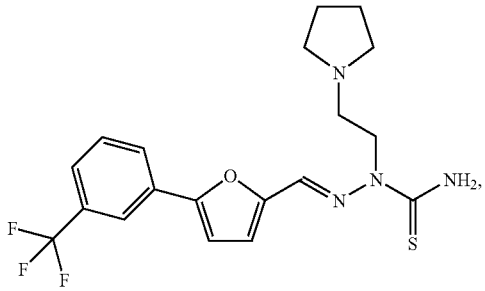

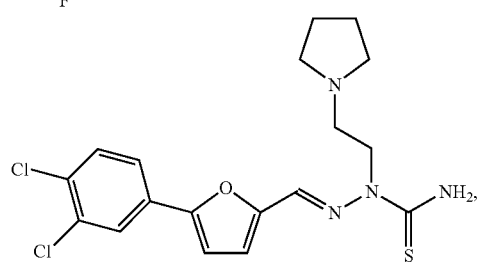

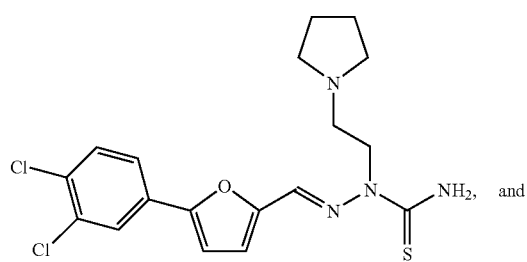

-continued

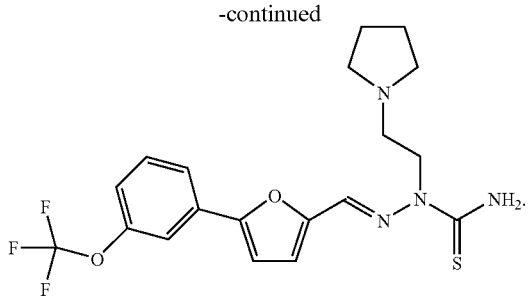

38. The composition of claim 36 wherein the thiosemicarbazone is pyridine-2-carbaldehyde thiosemicarbazone or a pharmaceutically acceptable salt thereof.

39. A method of administering a vaccine comprising simultaneously administering a vaccine in an amount effective to stimulate a cell—mediated immune response; and
   a vaccine adjuvant comprising a thiosemicarbazone or derivative thereof of claim 1 or 36.

40. A method of administering a vaccine comprising separately administering
   a vaccine in an amount effective to stimulate a cell—mediated immune response; and
   a vaccine adjuvant comprising a thiosemicarbazone or derivative thereof of claim 1 or 36,
   wherein said vaccine adjuvant is administered either prior to or subsequent to administration of the vaccine.

* * * * *